United States Patent
Guo et al.

(10) Patent No.: US 11,384,097 B2
(45) Date of Patent: Jul. 12, 2022

(54) TETRAHYDROISOQUINOLINE DERIVATIVE, PREPARATION METHOD THEREFOR AND USE THEREOF

(71) Applicant: ZHEJIANG HISUN PHARMACEUTICAL CO., LTD., Zhejiang (CN)

(72) Inventors: Yanghui Guo, Zhejiang (CN); Xiangui Huang, Zhejiang (CN); Weiwei Liao, Zhejiang (CN); Lichen Meng, Zhejiang (CN); Taishan Hu, Zhejiang (CN); Lei Chen, Zhejiang (CN); Guoping Jiang, Zhejiang (CN)

(73) Assignee: ZHEJIANG HISUN PHARMACEUTICAL CO., LTD., Zhejiang (CN)

( * ) Notice: Subject to any disclaimer, the term of this patent is extended or adjusted under 35 U.S.C. 154(b) by 4 days.

(21) Appl. No.: 17/254,273

(22) PCT Filed: Jun. 18, 2019

(86) PCT No.: PCT/CN2019/091669
§ 371 (c)(1),
(2) Date: Dec. 19, 2020

(87) PCT Pub. No.: WO2019/242599
PCT Pub. Date: Dec. 26, 2019

(65) Prior Publication Data
US 2021/0277021 A1    Sep. 9, 2021

(30) Foreign Application Priority Data

Jun. 19, 2018 (CN) .......... 201810631646.8
Jan. 31, 2019 (CN) .......... 201910098344.3

(51) Int. Cl.
| C07D 498/04 | (2006.01) |
|---|---|
| C07D 401/04 | (2006.01) |
| C07D 413/04 | (2006.01) |
| C07D 413/14 | (2006.01) |
| C07D 417/04 | (2006.01) |

(52) U.S. Cl.
CPC ......... *C07D 498/04* (2013.01); *C07D 401/04* (2013.01); *C07D 413/04* (2013.01); *C07D 413/14* (2013.01); *C07D 417/04* (2013.01)

(58) Field of Classification Search
CPC .. C07D 498/04; C07D 413/14; C07D 401/04; C07D 417/04

USPC .......................................................... 514/302
See application file for complete search history.

(56) References Cited

U.S. PATENT DOCUMENTS

| 2015/0218180 A1 | 8/2015 | McCarthy et al. |
| 2016/0145213 A1 | 5/2016 | McCarthy et al. |

FOREIGN PATENT DOCUMENTS

| CN | 104470930 A | 3/2015 | |
| CN | 105358532 A | 2/2016 | |
| WO | 9323378 A1 | 11/1993 | |
| WO | WO-9323378 A1 * | 11/1993 | ........... C07C 205/38 |
| WO | 2013110135 A1 | 8/2013 | |
| WO | 2015003223 A1 | 1/2015 | |
| WO | 2016113668 A1 | 7/2016 | |

OTHER PUBLICATIONS

International Search Report for PCT/CN2019/091669 dated Sep. 18, 2019, ISA/CN.

* cited by examiner

*Primary Examiner* — Kahsay Habte
(74) *Attorney, Agent, or Firm* — Yue Robert Xu; Apex Attorneys at Law, LLP

(57) ABSTRACT

Provided are a tetrahydroisoquinoline derivative, a preparation method therefor and an application thereof in medicine. In particular, provided are a tetrahydroisoquinoline derivative represented by general formula (I), a preparation method therefor and a pharmaceutically acceptable salt thereof as well as use thereof as a therapeutic agent, in particular as an angiotensin II type 2 receptor ($AT_2R$) antagonist, wherein definitions of substituent groups in the general formula (I) are the same as definitions in the description.

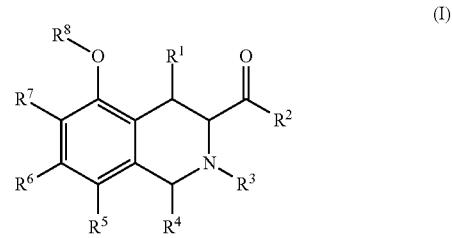

(I)

19 Claims, No Drawings

TETRAHYDROISOQUINOLINE DERIVATIVE, PREPARATION METHOD THEREFOR AND USE THEREOF

CROSS REFERENCE TO RELATED APPLICATIONS

The present application is the national phase of International Application No. PCT/CN2019/091669, titled "TETRAHYDROISOQUINOLINE DERIVATIVE, PREPARATION METHOD THEREFOR AND USE THEREOF", which claims the priority to Chinese Patent Application No. 201810631646.8, titled "TETRAHYDROISOQUINOLINE DERIVATIVE, PREPARATION METHOD THEREFOR AND USE THEREOF", filed on Jun. 19, 2018 with the Chinese Patent Office, and the priority to Chinese Patent Application No. 201910098344.3, titled "TETRAHYDROISOQUINOLINE DERIVATIVE, PREPARATION METHOD THEREFOR AND USE THEREOF", filed on Jan. 31, 2019 with the Chinese Patent Office, the entire disclosures thereof are incorporated herein by reference.

FIELD

The present invention relates to a new tetrahydroisoquinoline derivative, preparation method thereof, pharmaceutical composition comprising the derivative, and use of the derivative as a therapeutic agent, particularly an angiotensin II type 2 receptor ($AT_2R$) antagonist.

BACKGROUND

Neuropathic pain is a chronic pain disease caused by primary injury or dysfunction of the nervous system. According to the location of the lesion, it can be divided into peripheral neuropathic pain and central neuropathic pain. Trauma, inflammation, infection or compression can cause neuropathic pain, such as diabetic neuralgia (DNP), postherpetic neuralgia (PHN), primary neuropathy, secondary neuropathy, peripheral neuropathy, neurological diseases caused by mechanical nerve injury or biochemical nerve injury. At present, the drugs used clinically to treat neuropathic pain mainly include antiepileptic drugs, antidepressants and narcotic analgesics, such as gabapentin, pregabalin, tricyclic antidepressants, etc. However, these drugs lack specificity to diseases, and they have very limited therapeutic effects, and have serious side effects, including cognitive changes, sedation, nausea, and tolerability and dependence, which are far from meeting the needs of clinical medication. Therefore, it is necessary to study the pathogenesis of neuropathic pain, find a clear target of drug action, and develop new drugs that can effectively treat neuropathic pain with fewer adverse reactions.

Angiotensin II receptor is a G protein-coupled receptor with angiotensin II as a ligand. It is an important part of the renin-angiotensin system. The main subtypes of angiotensin II receptors include type 1 receptor ($AT_1R$) and type 2 receptor ($AT_2R$). $AT_1R$ and $AT_2R$ share only about 30% of the amino acid sequences, but angiotensin II, as their main ligand, has similar affinity to the two receptors.

$AT_1R$ is the most clearly studied angiotensin receptor. $AT_1R$ receptor activation can cause smooth muscle contraction, aldosterone and vasopressin secretion, increased renal tubular reabsorption of sodium, central and peripheral sympathetic nerve activation, and myocardial hypertrophy. Therefore, antagonizing angiotensin II at the receptor level has become a research hotspot of finding a new type of antihypertensive drugs, and a series of sartan antihypertensive drugs were born.

$AT_2R$ is abundantly expressed in various embryonic tissues, and less distributed in adult normal tissues, but its expression increases after tissue injury. $AT_2R$ is related to blood pressure regulation, nerve growth, pain control and myocardial regeneration. Drugs targeting $AT_2R$ can improve cardiovascular function and relieve neuropathic pain. The compound olodanrigan (EMA401) developed by Spinifex in Australia is a highly selective $AT_2R$ antagonist and is currently in clinical phase II. This candidate drug has a good therapeutic effect on neuropathic pain such as diabetic neuralgia and postherpetic neuralgia. At the same time, Spinifex is also developing the $AT_2R$ antagonist EMA-400. Olodanrigan and EMA-400 are both prepared according to WO 93/23378, and their structures are as follows:

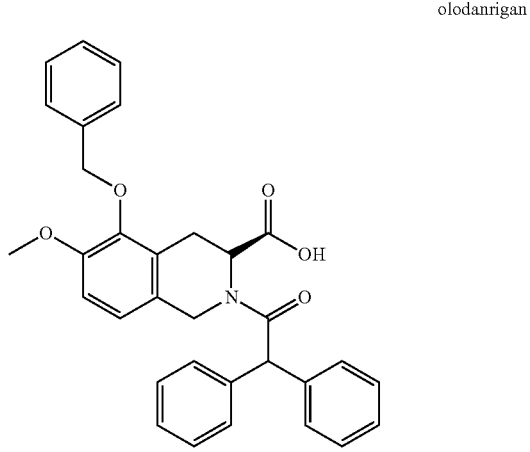

olodanrigan

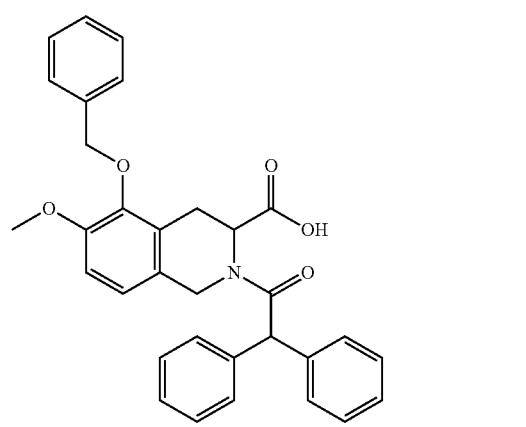

EMA-400

At present, there are a series of patent application publications involving $AT_2R$ antagonist, including WO2016113668, WO2015003223 and WO2013110135. The research and application of $AT_2R$ antagonists have made certain progress, but there is still huge room for improvement. It is still necessary to continue research and development of new $AT_2R$ antagonists.

SUMMARY

The purpose of the present disclosure is to provide a new type of tetrahydroisoquinoline derivatives represented by general formula (I), or a stereoisomer, a tautomer, or a pharmaceutically acceptable salt thereof:

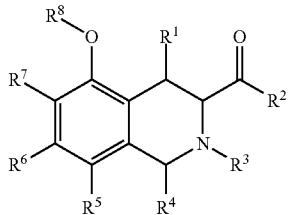

wherein $R^1$, $R^4$, $R^5$ and $R^6$ are each independently selected from hydrogen, hydroxyl, halogen, nitro, cyano, alkyl, alkoxy, cycloalkyl, heterocyclyl, aryl and heteroaryl, wherein the alkyl, alkoxy, cycloalkyl, heterocyclyl, aryl or heteroaryl is optionally further substituted by one or more substituents selected from hydroxyl, halogen, nitro, cyano, alkyl, alkoxy, cycloalkyl, heterocyclyl, aryl, heteroaryl, —C(O)$R^9$, —C(O)O$R^9$, —OC(O)$R^9$, —N$R^{10}R^{11}$, —C(O)N$R^{10}R^{11}$, —S(O)$_n$N$R^{10}R^{11}$ and —N$R^{10}$C(O)$R^{11}$; preferably, $R^1$, $R^4$, $R^5$ and $R^6$ are each independently selected from hydrogen, alkyl, halogen and cyano;

$R^2$ is selected from —O$R^a$ and —N$R^b$S(O)$_n R^c$;

$R^a$ is selected from hydrogen and alkyl;

$R^b$ is selected from hydrogen and alkyl;

$R^c$ is selected from hydrogen, alkyl, cycloalkyl and —N$R^d R^e$;

$R^d$ is selected from hydrogen and alkyl;

$R^e$ is selected from alkyl, wherein the alkyl is optionally further substituted by one or more substituents selected from hydroxyl, halogen, nitro, cyano, alkoxy, cycloalkyl, heterocyclyl, aryl, heteroaryl, —C(O)$R^9$, —C(O)O$R^9$, —OC(O)$R^9$, —N$R^{10}R^{11}$, —C(O)N$R^{10}R^{11}$, —S(O)$_n$N$R^{10}R^{11}$ and —N$R^{10}$C(O)$R^n$;

or, $R^d$ and $R^e$ together with the N atom to which they are attached form a 4 to 8-membered heterocyclyl, wherein the 4 to 8-membered heterocyclyl contains one or more N, O or S(O)$_n$, and the 4 to 8-membered heterocyclyl is optionally further substituted by one or more substituents selected from hydroxyl, halogen, nitro, cyano, alkyl, alkoxy, cycloalkyl, heterocyclyl, aryl, heteroaryl, =O, —C(O)$R^{12}$, —C(O)O$R^{12}$, —OC(O)$R^{12}$, —N$R^{13}R^{14}$, —C(O)N$R^{13}R^{14}$, —S(O)$_n$N$R^{13}R^{14}$ and —N$R^{13}$C(O)$R^{14}$;

$R^3$ is selected from heteroaryl, wherein the heteroaryl is optionally further substituted by one or more substituents selected from $R^f$; preferably, $R^3$ is selected from a 5 to 6-membered heteroaryl and an 8 to 10-membered heteroaryl;

$R^f$ is selected from hydroxyl, halogen, nitro, cyano, alkyl, alkoxy, cycloalkyl, heterocyclyl, aryl, heteroaryl, —C(O)$R^9$, —C(O)O$R^9$, —OC(O)$R^9$, —N$R^{10}R^{11}$, —C(O)N$R^{10}R^{11}$, —S(O)$_n$N$R^{10}R^{11}$ and —N$R^{10}$C(O)$R^n$, wherein the alkyl, alkoxy, cycloalkyl, heterocyclyl, aryl or heteroaryl is optionally further substituted by one or more substituents selected from hydroxyl, halogen, nitro, cyano, alkoxy, cycloalkyl, heterocyclyl, aryl, heteroaryl, —C(O)$R^9$, —C(O)O$R^9$, —OC(O)$R^9$, —N$R^{10}R^{11}$, —C(O)N$R^{10}R^{11}$, —S(O)$_n$N$R^{10}R^{11}$ and —N$R^{10}$C(O)$R^n$;

$R^7$ is selected from hydrogen, halogen, alkyl, cycloalkyl, cyano and —O$R^g$, wherein the alkyl or cycloalkyl is optionally further substituted by one or more substituents selected from hydroxyl, halogen, nitro and cyano;

$R^g$ is selected from alkyl, cycloalkyl, heterocyclyl, aryl and heteroaryl, wherein the alkyl, cycloalkyl, heterocyclyl, aryl or heteroaryl is optionally further substituted by one or more substituents selected from hydroxyl, halogen, nitro, cyano, alkyl, alkoxy, cycloalkyl, heterocyclyl, aryl, heteroaryl, —C(O)$R^9$, —C(O)O$R^9$, —OC(O)$R^9$, —N$R^{10}R^{11}$, —C(O)N$R^{10}R^{11}$, —S(O)$_n$N$R^{10}R^{11}$ and —N$R^{10}$C(O)$R^{11}$; preferably, $R^g$ is methyl;

$R^8$ is alkyl, wherein the alkyl is further substituted by aryl or heteroaryl, wherein the aryl or heteroaryl is optionally further substituted by one or more substituents selected from $R^h$; the aryl is preferably $C_6$-$C_{10}$ aryl; the heteroaryl is preferably 5 to 6-membered heteroaryl;

$R^h$ is selected from hydroxyl, halogen, nitro, cyano, alkyl, alkoxy, cycloalkyl, heterocyclyl, aryl, heteroaryl, —C(O)$R^9$, —C(O)O$R^9$, —OC(O)$R^9$, —N$R^{10}R^{11}$, —C(O)N$R^{10}R^{11}$, —S(O)$_n$N$R^{10}R^{11}$ and —N$R^{10}$C(O)$R^{11}$; wherein the alkyl, alkoxy, cycloalkyl, heterocyclyl, aryl or heteroaryl is optionally further substituted by one or more substituents selected from hydroxyl, halogen, nitro, cyano, alkoxy, cycloalkyl, heterocyclyl, aryl, heteroaryl, —C(O)$R^9$, —C(O)O$R^9$, —OC(O)$R^9$, —N$R^{10}R^{11}$, —C(O)N$R^{10}R^{11}$, —S(O)$_n$N$R^{10}R^{11}$ and —N$R^{10}$C(O)$R^n$;

preferably, $R^8$ is selected from benzyl, pyridylmethylene, pyrimidylmethylene and pyridazinylmethylene, wherein the benzyl, pyridylmethylene, pyrimidylmethylene or pyridazinylmethylene is optionally further substituted by one or more substituents selected from fluorine, chlorine, cyano, methyl, trifluoromethyl, methoxy and trifluoromethoxy;

$R^9$, $R^{10}$ and $R^{11}$ are each independently selected from hydrogen, hydroxyl, halogen, nitro, cyano, alkyl, alkoxy, cycloalkyl, heterocyclyl, aryl and heteroaryl, wherein the alkyl, alkoxy, cycloalkyl, heterocyclyl, aryl or heteroaryl is optionally further substituted by one or more substituents selected from hydroxyl, halogen, nitro, cyano, alkyl, alkoxy, cycloalkyl, heterocyclyl, aryl, heteroaryl, —C(O)$R^{12}$, —C(O)O$R^{12}$, —OC(O)$R^{12}$, —N$R^{13}R^{14}$, —C(O)N$R^{13}R^{14}$, —S(O)$_n$N$R^{13}R^{14}$ and —N$R^{13}$C(O)$R^{14}$;

or, $R^{10}$ and $R^{11}$ together with the N atom to which they are attached form a 4 to 8-membered heterocyclyl, wherein the 4 to 8-membered heterocyclyl contains one or more N, O or S(O)$_n$, and the 4 to 8-membered heterocyclyl is optionally further substituted by one or more substituents selected from hydroxyl, halogen, nitro, cyano, alkyl, alkoxy, cycloalkyl, heterocyclyl, aryl, heteroaryl, =O, —C(O)$R^{12}$, —C(O)O$R^{12}$, —OC(O)$R^{12}$, —N$R^{13}R^{14}$, —C(O)N$R^{13}R^{14}$, —S(O)$_n$N$R^{13}R^{14}$ and —N$R^{13}$C(O)$R^{14}$;

$R^{12}$, $R^{13}$ and $R^{14}$ are each independently selected from hydrogen, alkyl, cycloalkyl, heterocyclyl, aryl and heteroaryl, wherein the alkyl, cycloalkyl, heterocyclyl, aryl or heteroaryl is optionally further substituted by one or more substituents selected from hydroxyl, halogen, nitro, cyano, alkyl, alkoxy, cycloalkyl, heterocyclyl, aryl, heteroaryl, carboxyl and carboxylate group; and n is selected from 0, 1 and 2.

In a preferred embodiment, the present disclosure provides a compound represented by general formula (I) or a stereoisomer, a tautomer, or a pharmaceutically acceptable salt thereof, which is a compound of general formula (II) or a stereoisomer, a tautomer, or a pharmaceutically acceptable salt thereof

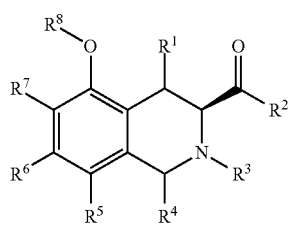

(II)

wherein $R^1$ to $R^8$ are as defined in general formula (I).

In a preferred embodiment, the present disclosure provides a compound represented by general formula (I) or a stereoisomer, a tautomer, or a pharmaceutically acceptable salt thereof, which is a compound of general formula (III) or a stereoisomer, a tautomer, or a pharmaceutically acceptable salt thereof

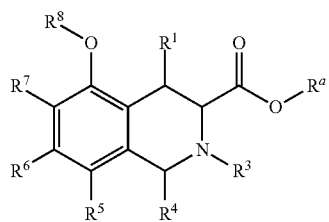

(III)

wherein $R^1$, $R^3$ to $R^8$ and $R^a$ are as defined in general formula (I).

In a preferred embodiment, the present disclosure provides a compound represented by general formula (I) or a stereoisomer, a tautomer, or a pharmaceutically acceptable salt thereof, which is a compound of general formula (IV) or a stereoisomer, a tautomer, or a pharmaceutically acceptable salt thereof.

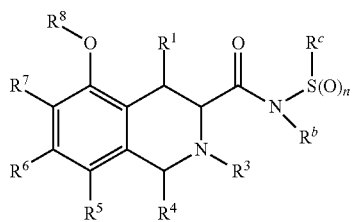

(IV)

wherein $R^1$, $R^3$ to $R^8$, $R^b$, $R^c$ and n are as defined in general formula (I).

In a preferred embodiment, the present disclosure provides a compound represented by general formula (I) or a stereoisomer, a tautomer, or a pharmaceutically acceptable salt thereof, which is a compound of general formula (V) or a stereoisomer, a tautomer, or a pharmaceutically acceptable salt thereof

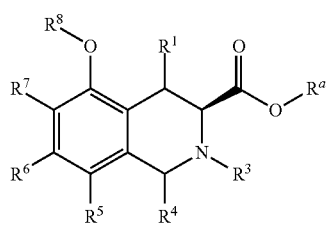

(V)

wherein $R^1$, $R^3$ to $R^8$ and $R^a$ are as defined in general formula (I).

In a preferred embodiment, the present disclosure provides a compound represented by general formula (I) or a stereoisomer, a tautomer, or a pharmaceutically acceptable salt thereof, which is a compound of general formula (VI) or a stereoisomer, a tautomer, or a pharmaceutically acceptable salt thereof.

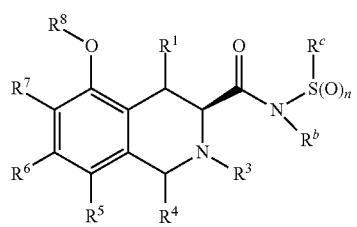

(VI)

wherein $R^1$, $R^3$ to $R^8$, $R^b$, $R^c$ and n are as defined in general formula (I).

In a preferred embodiment, the present disclosure provides a compound of general formula (I), (II), (III), (IV), (V) or (VI), or a stereoisomer, a tautomer, or a pharmaceutically acceptable salt thereof, wherein $R^3$ is selected from

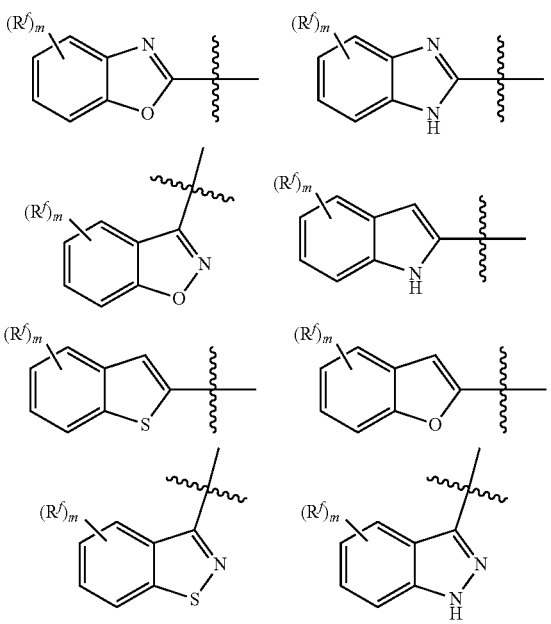

-continued

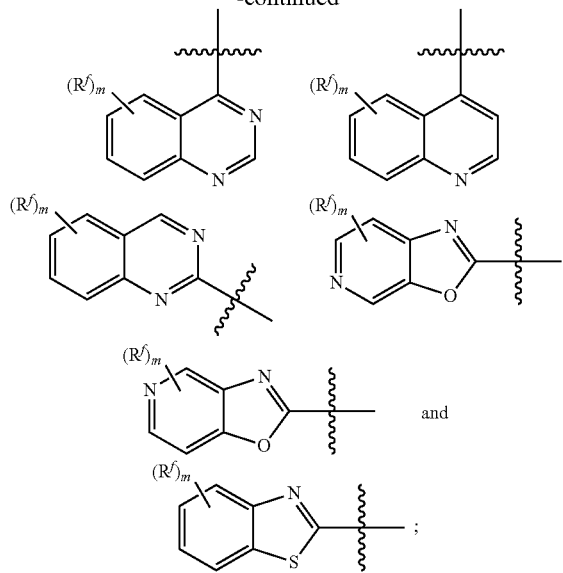

m is 0, 1, 2, 3 or 4; and $R^f$ is selected from $C_{1-6}$ alkyl, $C_{1-6}$ alkoxy, halogen and cyano, wherein $C_{1-6}$ alkyl or $C_{1-6}$ alkoxy is optionally further substituted by one or more halogens.

In a preferred embodiment, the present disclosure provides a compound of general formula (I), (II), (III), (IV), (V) or (VI), or a stereoisomer, a tautomer, or a pharmaceutically acceptable salt thereof, wherein $R^3$ is selected from

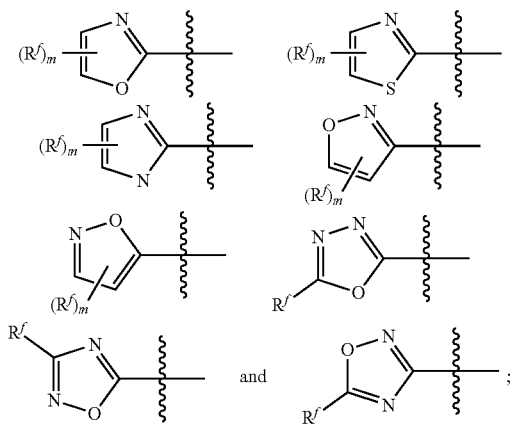

m is 0, 1 or 2; and $R^f$ is selected from $C_{1-6}$ alkyl, $C_{1-6}$ alkoxy, halogen and cyano, wherein $C_{1-6}$ alkyl or $C_{1-6}$ alkoxy is optionally further substituted by one or more halogens.

In a preferred embodiment, the present disclosure provides a compound of general formula (I), (II), (III), (IV), (V) or (VI), or a stereoisomer, a tautomer, or a pharmaceutically acceptable salt thereof, wherein $R^3$ is selected from

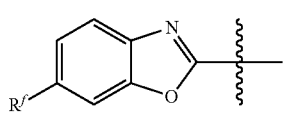

-continued

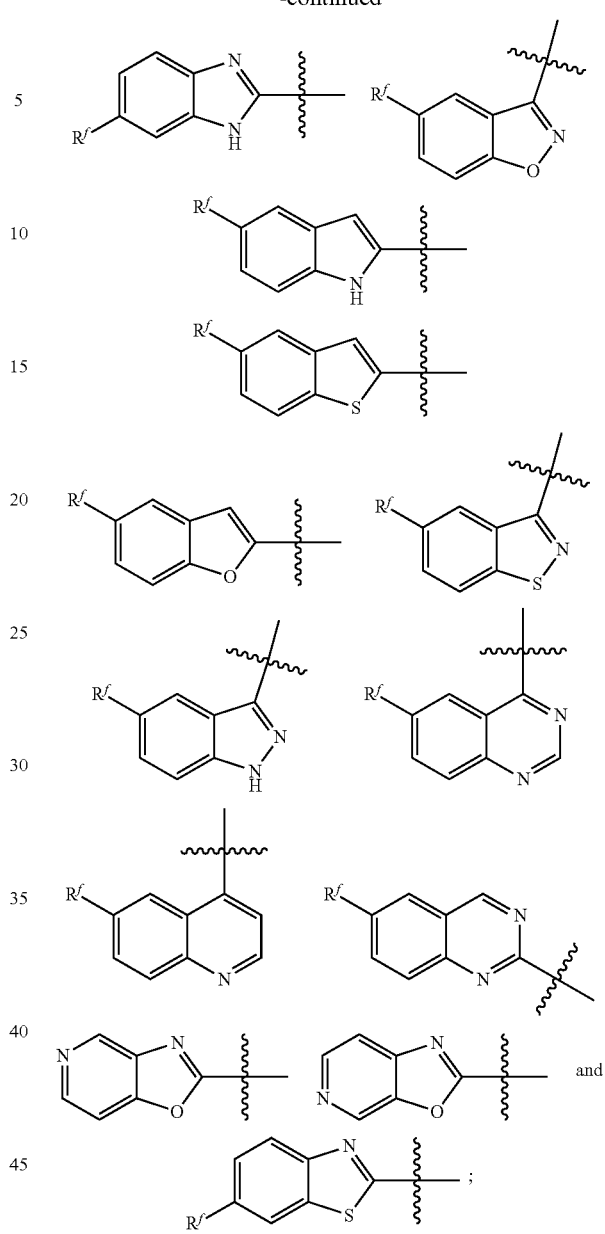

$R^f$ is selected from fluorine, chlorine, cyano, methyl, methoxy, ethyl, isopropyl, difluoromethyl, trifluoromethyl and trifluoromethoxy.

In a preferred embodiment, the present disclosure provides a compound of general formula (I), (II), (III), (IV), (V) or (VI), or a stereoisomer, a tautomer, or a pharmaceutically acceptable salt thereof, wherein $R^8$ is selected from

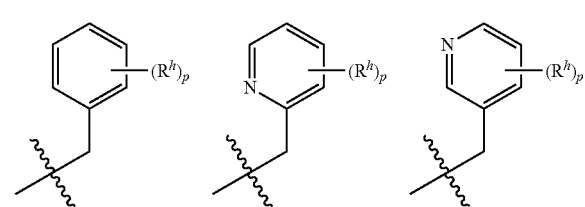

-continued

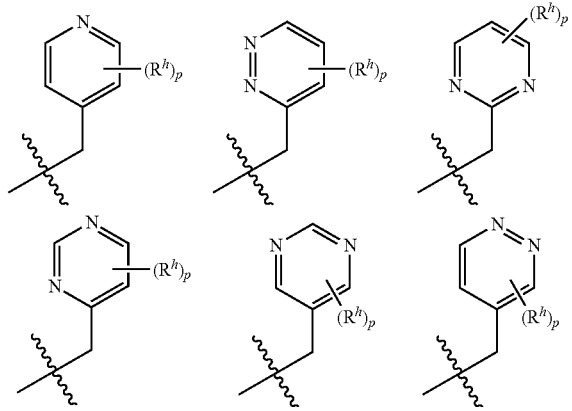

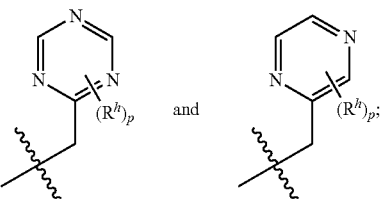

p is 0, 1, 2, 3 or 4; and $R^h$ is selected from $C_{1-6}$ alkyl, $C_{1-6}$ alkoxy, halogen and cyano, wherein $C_{1-6}$ alkyl or $C_{1-6}$ alkoxy is optionally further substituted by one or more halogens.

Typical compounds of the present disclosure include, but are not limited to:

| Example No. | Structure | Name |
|---|---|---|
| 1 | 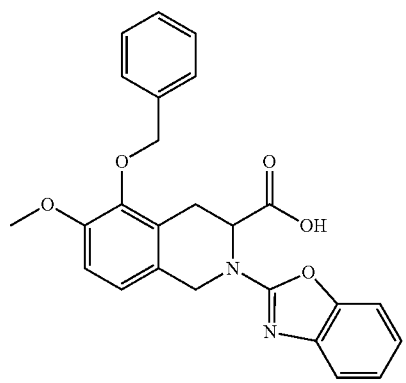 [SMILES: COc1ccc2c(c1OCc1ccccc1)CC(C(=O)O)N(c1nc3ccccc3o1)C2] | 2-(benzo[d]oxazol-2-yl)-5-(benzyloxy)-6-methoxy-1,2,3,4-tetrahydroisoquinoline-3-carboxylic acid |
| 2 | 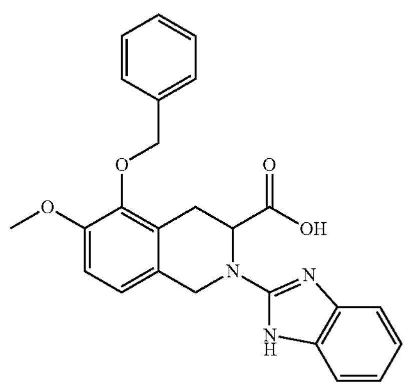 [SMILES: COc1ccc2c(c1OCc1ccccc1)CC(C(=O)O)N(c1nc3ccccc3[nH]1)C2] | 2-(1H-benzo[d]imidazol-2-yl)-5-(benzyl-oxy)-6-methoxy-1,2,3,4-tetrahydroiso-quinoline-3-carboxylic acid |

-continued

| Example No. | Structure | Name |
|---|---|---|
| 3 | 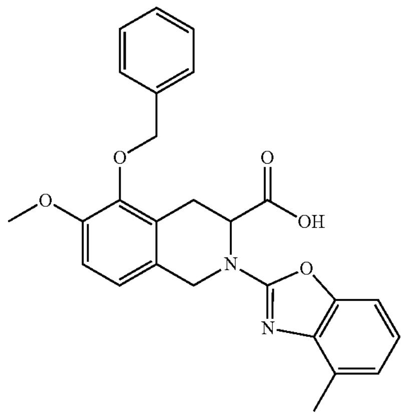 [SMILES: COc1ccc2c(c1OCc1ccccc1)CC(C(=O)O)N(c1nc3c(C)cccc3o1)C2] | 5-(benzyloxy)-6-methoxy-2-(4-methyl-benzo[d]oxazol-2-yl)-1,2,3,4-tetrahydro-isoquinoline-3-carboxylic acid |
| 4 | 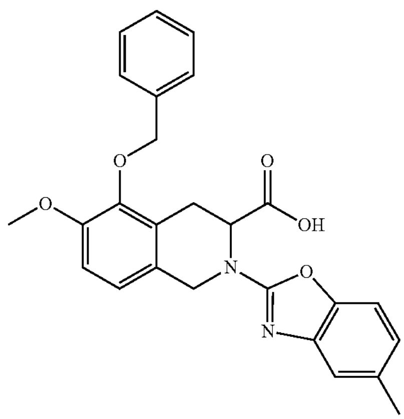 | 5-(benzyloxy)-6-methoxy-2-(5-methyl-benzo[d]oxazol-2-yl)-1,2,3,4-tetrahydro-isoquinoline-3-carboxylic acid |
| 5 | 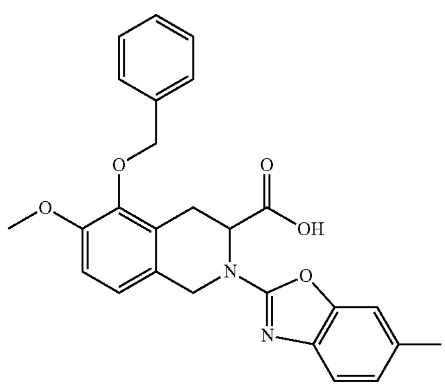 | 5-(benzyloxy)-6-methoxy-2-(6-methyl-benzo[d]oxazol-2-yl)-1,2,3,4-tetrahydro-isoquinoline-3-carboxylic acid |
| 6 | 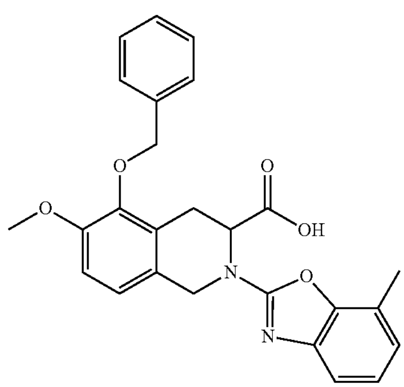 | 5-(benzyloxy)-6-methoxy-2-(7-methyl-benzo[d]oxazol-2-yl)-1,2,3,4-tetrahydro-isoquinoline-3-carboxylic acid |

| Example No. | Structure | Name |
|---|---|---|
| 7 | 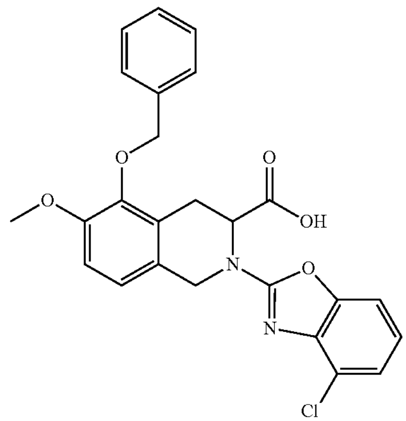 [SMILES: COc1ccc2c(c1OCc1ccccc1)CC(C(=O)O)N(c1nc3c(Cl)cccc3o1)C2] | 5-(benzyloxy)-2-(4-chlorobenzo[d]oxazol-2-yl)-6-methoxy-1,2,3,4-tetrahydroisoquinoline-3-carboxylic acid |
| 8 | 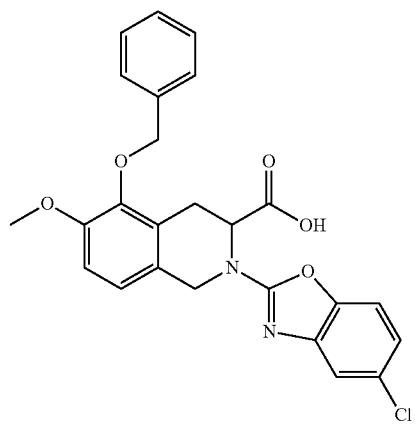 [SMILES: COc1ccc2c(c1OCc1ccccc1)CC(C(=O)O)N(c1nc3cc(Cl)ccc3o1)C2] | 5-(benzyloxy)-2-(5-chlorobenzo[d]oxazol-2-yl)-6-methoxy-1,2,3,4-tetrahydroisoquinoline-3-carboxylic acid |
| 9 | 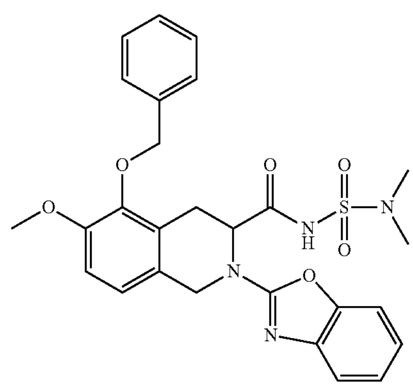 | 2-(benzo[d]oxazol-2-yl)-5-(benzyloxy)-N-(N,N-dimethylsulfonyl)-6-methoxy-1,2,3,4-tetrahydroisoquinoline-3-carboxamide |

-continued

| Example No. | Structure | Name |
|---|---|---|
| 10 | 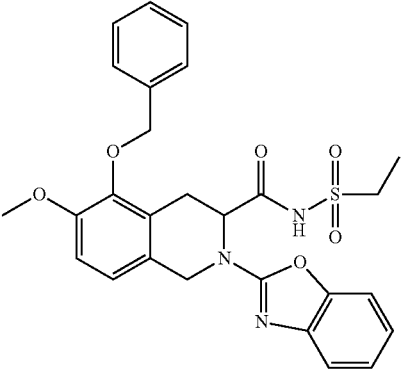 [SMILES: CCS(=O)(=O)NC(=O)C1Cc2c(ccc(OC)c2OCc2ccccc2)CN1c1nc2ccccc2o1] | 2-(benzo[d]oxazol-2-yl)-5-(benzyloxy)-N-(ethylsulfonyl)-6-methoxy-1,2,3,4-tetrahydroisoquinoline-3-carboxamide |
| 11 | 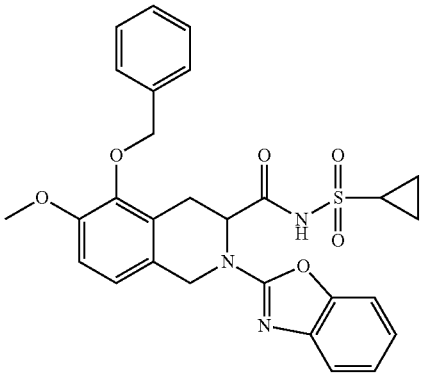 [SMILES: COc1ccc2c(c1OCc1ccccc1)CC(C(=O)NS(=O)(=O)C1CC1)N(c1nc3ccccc3o1)C2] | 2-(benzo[d]oxazol-2-yl)-5-(benzyloxy)-N-(cyclopropylsulfonyl)-6-methoxy-1,2,3,4-tetrahydroisoquinoline-3-carboxamide |
| 12 | 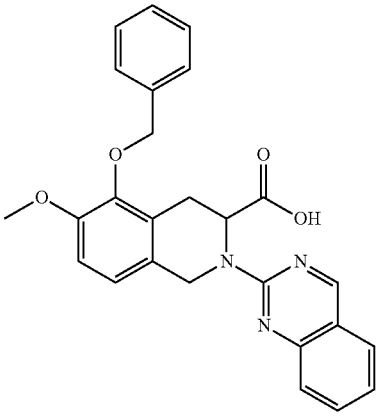 [SMILES: COc1ccc2c(c1OCc1ccccc1)CC(C(=O)O)N(c1ncc3ccccc3n1)C2] | 5-(benzyloxy)-6-methoxy-2-(quinazolin-2-yl)-1,2,3,4-tetrahydroisoquinoline-3-carboxylic acid |
| 13 | 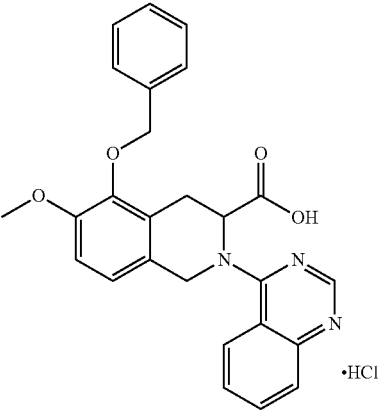 [SMILES: COc1ccc2c(c1OCc1ccccc1)CC(C(=O)O)N(c1ncnc3ccccc13)C2 ; Cl] | 5-(benzyloxy)-6-methoxy-2-(quinazolin-4-yl)-1,2,3,4-tetrahydroisoquinoline-3-carboxylic acid hydrochloride |

-continued

| Example No. | Structure | Name |
|---|---|---|
| 13' | 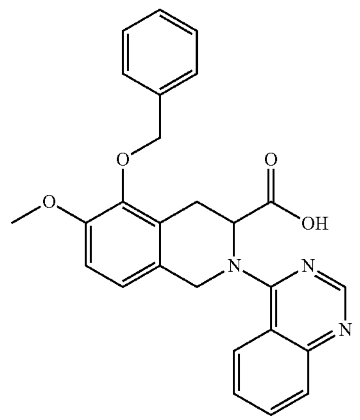 [SMILES: COc1ccc2c(c1OCc1ccccc1)CC(C(=O)O)N(c1ncnc3ccccc13)C2] | 5-(benzyloxy)-6-methoxy-2-(quinazolin-4-yl)-1,2,3,4-tetrahydroisoquinoline-3-carboxylic acid |
| 14 | 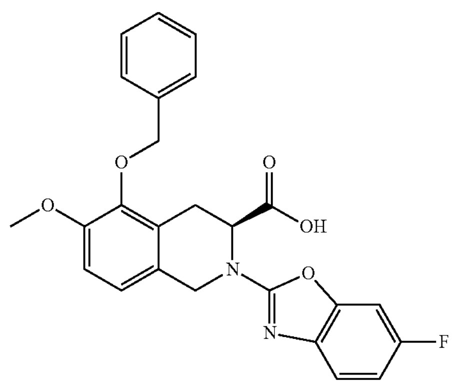 [SMILES: COc1ccc2c(c1OCc1ccccc1)C[C@@H](C(=O)O)N(c1nc3ccc(F)cc3o1)C2] | (S)-5-(benzyloxy)-2-(6-fluorobenzo[d]oxazol-2-yl)-6-methoxy-1,2,3,4-tetrahydroisoquinoline-3-carboxylic acid |
| 15 | 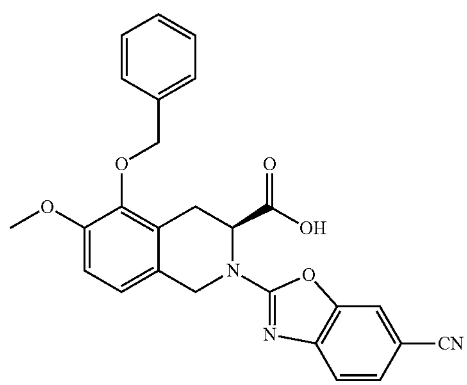 [SMILES: COc1ccc2c(c1OCc1ccccc1)C[C@@H](C(=O)O)N(c1nc3ccc(C#N)cc3o1)C2] | (S)-5-(benzyloxy)-2-(6-cyanobenzo[d]oxazol-2-yl)-6-methoxy-1,2,3,4-tetrahydroisoquinoline-3-carboxylic acid |
| 16 | 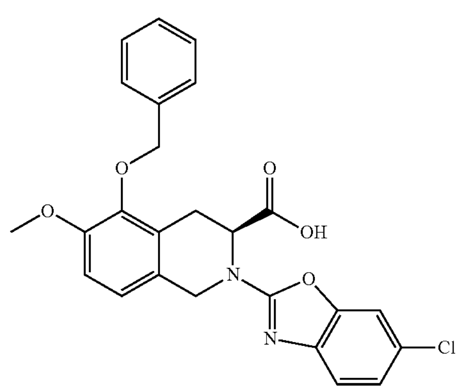 [SMILES: COc1ccc2c(c1OCc1ccccc1)C[C@@H](C(=O)O)N(c1nc3ccc(Cl)cc3o1)C2] | (S)-5-(benzyloxy)-2-(6-chlorobenzo[d]oxazol-2-yl)-6-methoxy-1,2,3,4-tetrahydroisoquinoline-3-carboxylic acid |

| Example No. | Structure | Name |
|---|---|---|
| 17 | 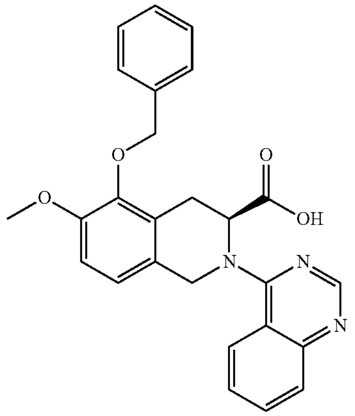 [SMILES: COc1ccc2c(c1OCc1ccccc1)C[C@@H](C(=O)O)N(c1ncnc3ccccc13)C2] | (S)-5-(benzyloxy)-6-methoxy-2-(quinazolin-4-yl)-1,2,3,4-tetrahydroisoquinoline-3-carboxylic acid |
| 18 | 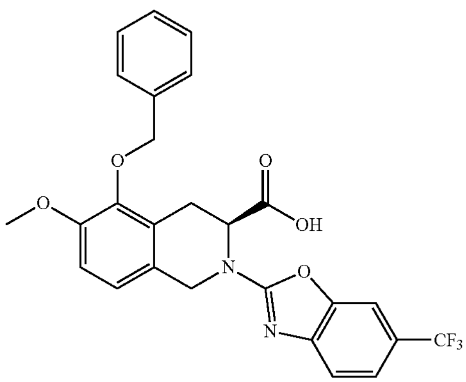 [SMILES: COc1ccc2c(c1OCc1ccccc1)C[C@@H](C(=O)O)N(c1nc3ccc(C(F)(F)F)cc3o1)C2] | (S)-5-(benzyloxy)-6-methoxy-2-(6-(trifluoromethyl)benzo[d]oxazol-2-yl)-1,2,3,4-tetrahydroisoquinoline-3-carboxylic acid |
| 19 | 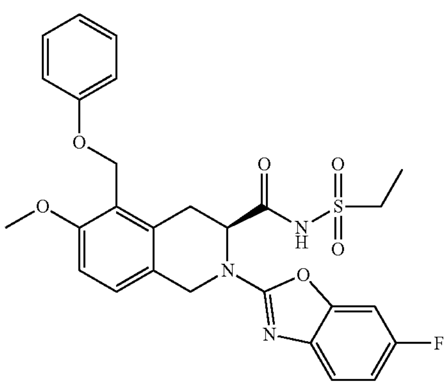 [SMILES: CCS(=O)(=O)NC(=O)[C@@H]1Cc2c(ccc(OC)c2COc2ccccc2)CN1c1nc2ccc(F)cc2o1] | (S)-N-(ethylsulfonyl)-2-(6-fluorobenzo[d]oxazol-2-yl)-6-methoxy-5-(phenoxymethyl)-1,2,3,4-tetrahydroisoquinoline-3-carboxamide |
| 20 | 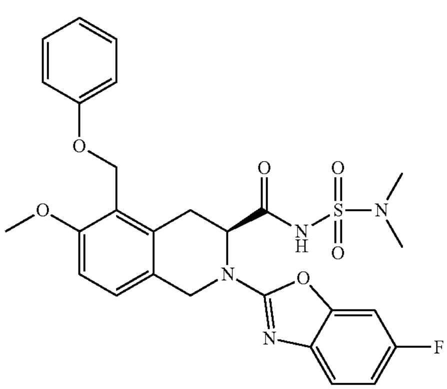 [SMILES: COc1ccc2c(c1COc1ccccc1)C[C@@H](C(=O)NS(=O)(=O)N(C)C)N(c1nc3ccc(F)cc3o1)C2] | (S)-N-(N,N-dimethylaminosulfonyl)-2-(6-fluorobenzo[d]oxazol-2-yl)-6-methoxy-5-(phenoxymethyl)-1,2,3,4-tetrahydroisoquinoline-3-carboxamide |

-continued

| Example No. | Structure | Name |
|---|---|---|
| 21 | 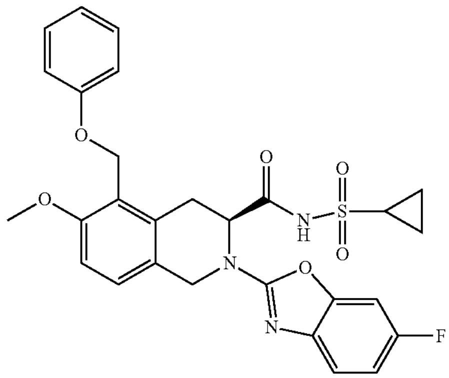 [SMILES: COc1ccc2c(c1COc1ccccc1)C[C@@H](C(=O)NS(=O)(=O)C1CC1)N(c1nc3ccc(F)cc3o1)C2] | (S)-N-(cyclopropylsulfonyl)-2-(6-fluoro-benzo[d]oxazol-2-yl)-6-methoxy-5-(phenoxymethyl)-1,2,3,4-tetrahydroiso-quinoline-3-carboxamide |
| 22 | 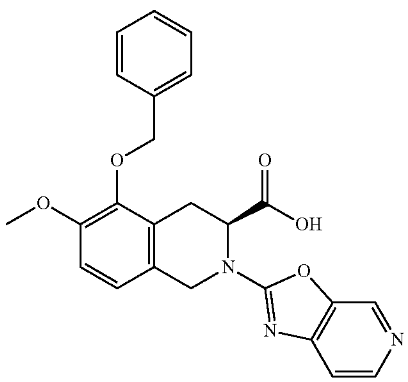 [SMILES: COc1ccc2c(c1OCc1ccccc1)C[C@@H](C(=O)O)N(c1nc3ccncc3o1)C2] | (S)-5-(benzyloxy)-6-methoxy-2-(oxazolo[5,4-c]pyridin-2-yl)-1,2,3,4-tetrahydroiso-quinoline-3-carboxylic acid |
| 23 | 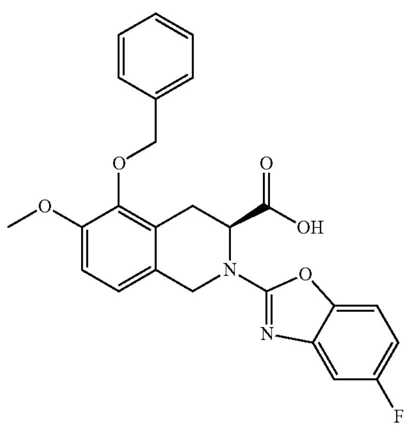 [SMILES: COc1ccc2c(c1OCc1ccccc1)C[C@@H](C(=O)O)N(c1nc3cc(F)ccc3o1)C2] | (S)-5-(benzyloxy)-2-(5-fluorobenzo[d]oxazol-2-yl)-6-methoxy-1,2,3,4-tetrahydroisoquinoline-3-carboxylic acid |
| 24 | 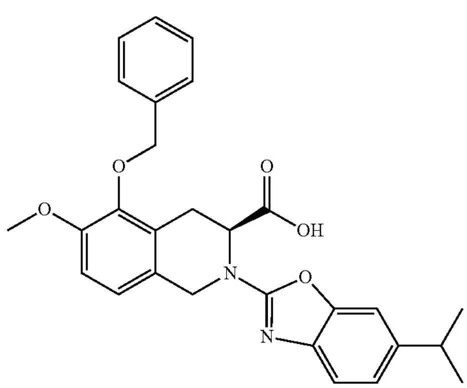 [SMILES: COc1ccc2c(c1OCc1ccccc1)C[C@@H](C(=O)O)N(c1nc3ccc(C(C)C)cc3o1)C2] | (S)-5-(benzyloxy)-2-(6-isopropylbenzo[d]oxazol-2-yl)-6-methoxy-1,2,3,4-tetra-hydroisoquinoline-3-carboxylic acid |

-continued

| Example No. | Structure | Name |
|---|---|---|
| 25 | 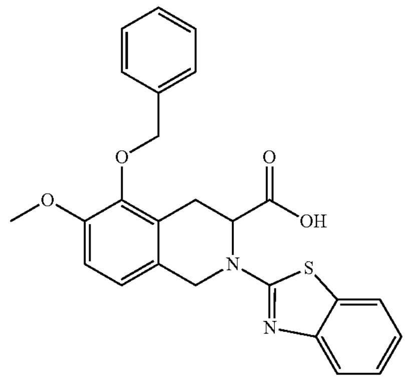 [SMILES: COc1ccc2c(c1OCc1ccccc1)CC(C(=O)O)N(c1nc3ccccc3s1)C2] | 2-(benzo[d]thiazol-2-yl)-5-(benzyloxy)-6-methoxy-1,2,3,4-tetrahydroisoquinoline-3-carboxylic acid |
| 26 | 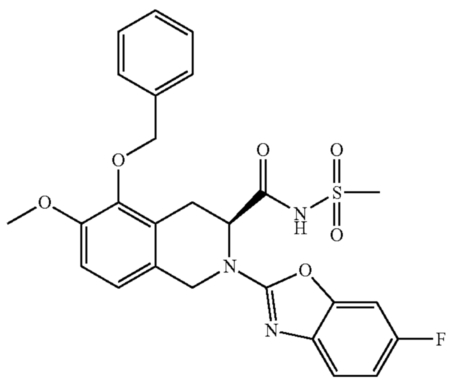 [SMILES: COc1ccc2c(c1OCc1ccccc1)C[C@@H](C(=O)NS(C)(=O)=O)N(c1nc3ccc(F)cc3o1)C2] | (S)-5-(benzyloxy)-2-(6-fluorobenzo[d]oxazol-2-yl)-6-methoxy-N-(methylsulfonyl)-1,2,3,4-tetrahydroisoquinoline-3-carboxamide |
| 27 | 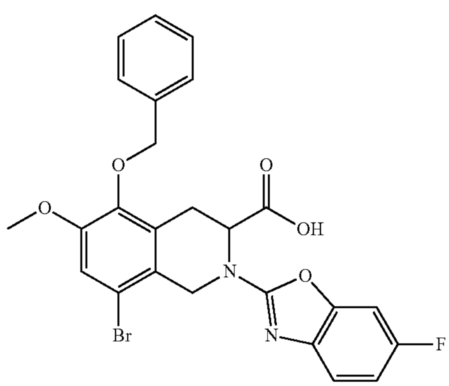 [SMILES: COc1cc(Br)c2c(c1OCc1ccccc1)CC(C(=O)O)N(c1nc3ccc(F)cc3o1)C2] | 5-(benzyloxy)-8-bromo-2-(6-fluorobenzo[d]oxazol-2-yl)-6-methoxy-1,2,3,4-tetrahydroisoquinoline-3-carboxylic acid |
| 1d | 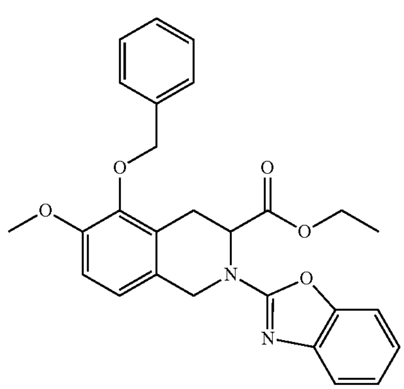 [SMILES: CCOC(=O)C1Cc2c(ccc(OC)c2OCc2ccccc2)CN1c1nc2ccccc2o1] | ethyl 2-(benzo[d]oxazol-2-yl)-5-(benzyloxy)-6-methoxy-1,2,3,4-tetrahydroisoquinoline-3-carboxylate |

-continued

| Example No. | Structure | Name |
|---|---|---|
| 2d | 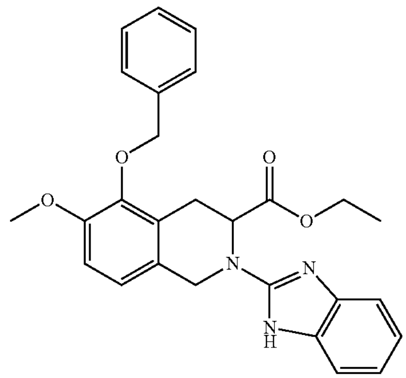 [SMILES: CCOC(=O)C1Cc2c(ccc(OC)c2OCc2ccccc2)CN1c1nc2ccccc2[nH]1] | ethyl 2-(1H-benzo[d]imidazol-2-yl)-5-(benzyloxy)-6-methoxy-1,2,3,4-tetrahydroisoquinoline-3-carboxylate |
| 3c | 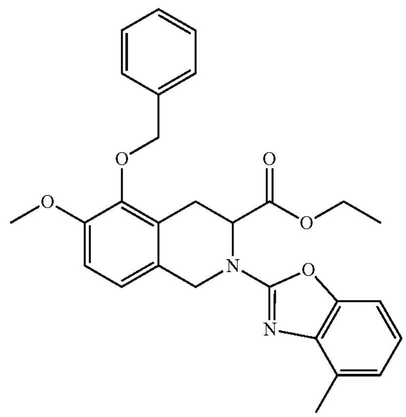 [SMILES: CCOC(=O)C1Cc2c(ccc(OC)c2OCc2ccccc2)CN1c1nc2c(C)cccc2o1] | ethyl 5-(benzyloxy)-6-methoxy-2-(4-methylbenzo[d]oxazol-2-yl)-1,2,3,4-tetrahydroisoquinoline-3-carboxylate |
| 4b | 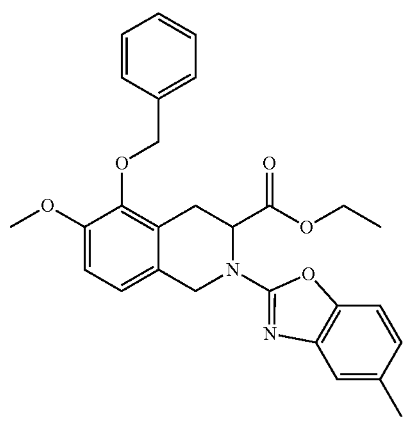 | ethyl 5-(benzyloxy)-6-methoxy-2-(5-methylbenzo[d]oxazol-2-yl)-1,2,3,4-tetrahydroisoquinoline-3-carboxylate |
| 5b | 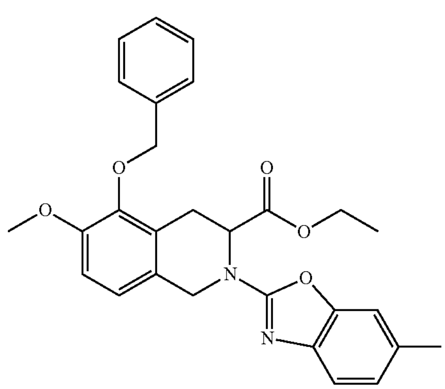 | ethyl 5-(benzyloxy)-6-methoxy-2-(6-methylbenzo[d]oxazol-2-yl)-1,2,3,4-tetrahydroisoquinoline-3-carboxylate |

-continued

| Example No. | Structure | Name |
|---|---|---|
| 6b | 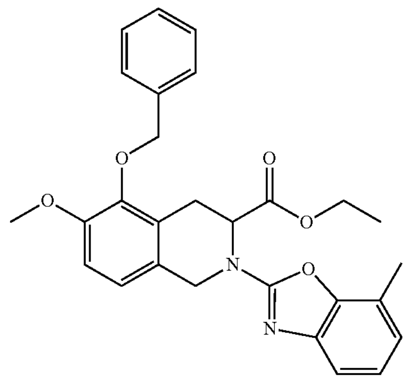 | ethyl 5-(benzyloxy)-6-methoxy-2-(7-methyl-benzo[d]oxazol-2-yl)-1,2,3,4-tetrahydro-isoquinoline-3-carboxylate |
| 7b | 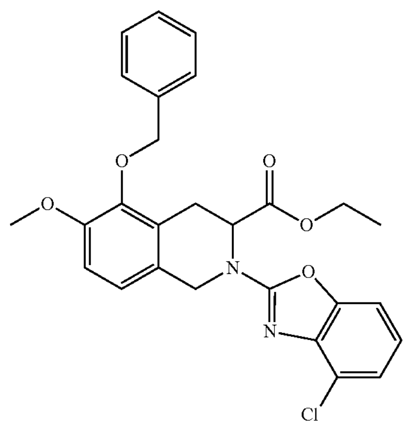 [SMILES: CCOC(=O)C1Cc2c(ccc(OC)c2OCc2ccccc2)CN1c1nc2c(Cl)cccc2o1] | ethyl 5-(benzyloxy)-2-(4-chlorobenzo[d]oxazol-2-yl)-6-methoxy-1,2,3,4-tetrahydroiso-quinoline-3-carboxylate |
| 8b | 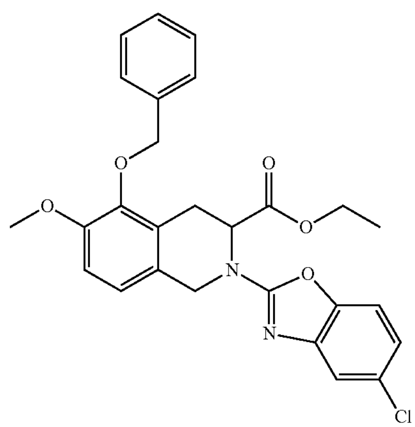 [SMILES: CCOC(=O)C1Cc2c(ccc(OC)c2OCc2ccccc2)CN1c1nc2cc(Cl)ccc2o1] | ethyl 5-(benzyloxy)-2-(5-chlorobenzo[d]oxazol-2-yl)-6-methoxy-1,2,3,4-tetrahydroiso-quinoline-3-carboxylate |

| Example No. | Structure | Name |
|---|---|---|
| 12b | 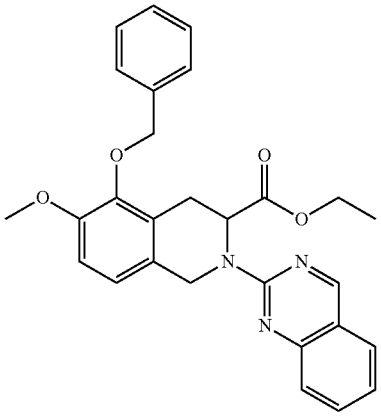 [SMILES: CCOC(=O)C1Cc2c(ccc(OC)c2OCc2ccccc2)CN1c1ncc2ccccc2n1] | ethyl 5-(benzyloxy)-6-methoxy-2-(quinazolin-2-yl)-1,2,3,4-tetrahydroisoquinoline-3-carboxylate |
| 13b | 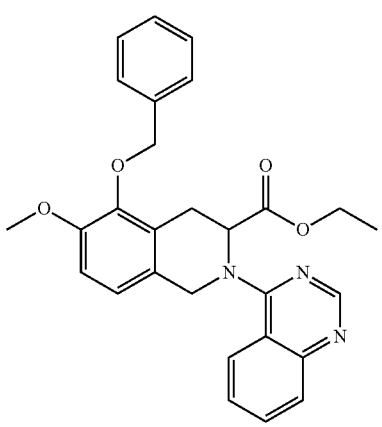 [SMILES: CCOC(=O)C1Cc2c(ccc(OC)c2OCc2ccccc2)CN1c1ncnc2ccccc12] | ethyl 5-(benzyloxy)-6-methoxy-2-(quinazolin-4-yl)-1,2,3,4-tetrahydroisoquinoline-3-carboxylate |
| 14h | 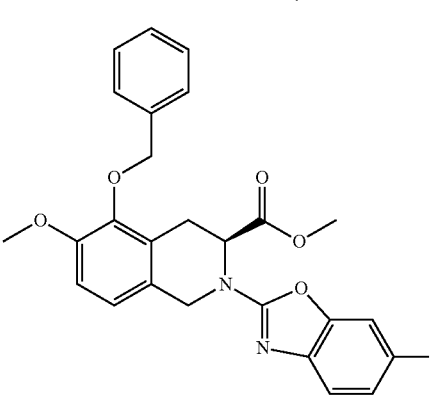 | methyl (S)-5-(benzyloxy)-2-(6-fluorobenzo[d]oxazol-2-yl)-6-methoxy-1,2,3,4-tetrahydroisoquinoline-3-carboxylate |
| 15d | 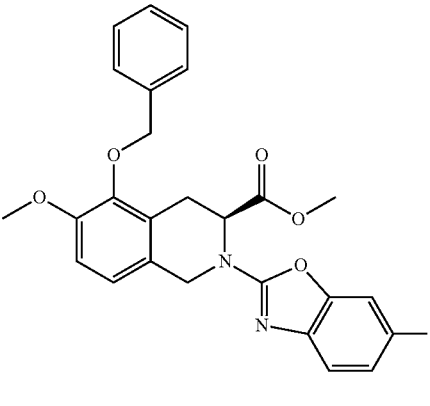 | methyl (S)-5-(benzyloxy)-2-(6-cyanobenzo[d]oxazol-2-yl)-6-methoxy-1,2,3,4-tetrahydroisoquinoline-3-carboxylate |

-continued

| Example No. | Structure | Name |
|---|---|---|
| 16b | 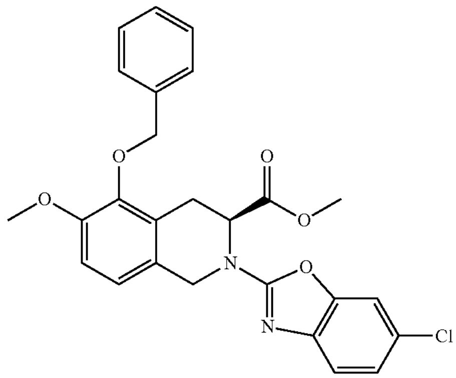 [SMILES: COC(=O)[C@@H]1Cc2c(ccc(OC)c2OCc2ccccc2)CN1c1nc2ccc(Cl)cc2o1] | methyl (S)-5-(benzyloxy)-2-(6-chlorobenzo[d]oxazol-2-yl)-6-methoxy-1,2,3,4-tetrahydroisoquinoline-3-carboxylate |
| 17a | 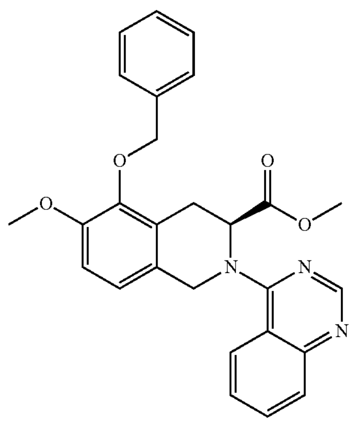 [SMILES: COC(=O)[C@@H]1Cc2c(ccc(OC)c2OCc2ccccc2)CN1c1ncnc2ccccc12] | methyl (S)-5-(benzyloxy)-6-methoxy-2-(quinazolin-4-yl)-1,2,3,4-tetrahydroisoquinoline-3-carboxylate |
| 18b | 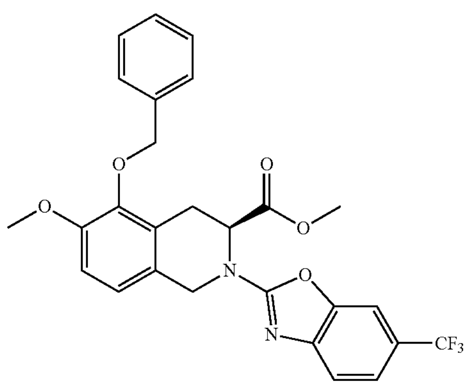 [SMILES: COC(=O)[C@@H]1Cc2c(ccc(OC)c2OCc2ccccc2)CN1c1nc2ccc(C(F)(F)F)cc2o1] | methyl (S)-5-(benzyloxy)-6-methoxy-2-(6-(trifluoromethyl)benzo[d]oxazol-2-yl)-1,2,3,4-tetrahydroisoquinoline-3-carboxylate |
| 22b | 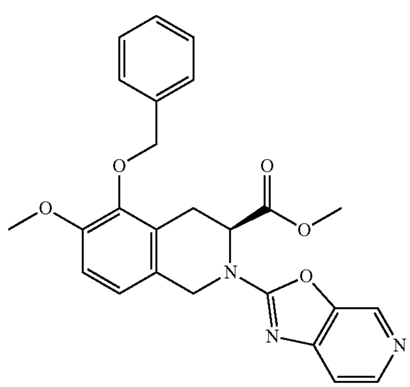 [SMILES: COC(=O)[C@@H]1Cc2c(ccc(OC)c2OCc2ccccc2)CN1c1nc2ccncc2o1] | methyl (S)-5-(benzyloxy)-6-methoxy-2-(oxazolo[5,4-c]pyridin-2-yl)-1,2,3,4-tetrahydroisoquinoline-3-carboxylate |

-continued

| Example No. | Structure | Name |
|---|---|---|
| 23b | 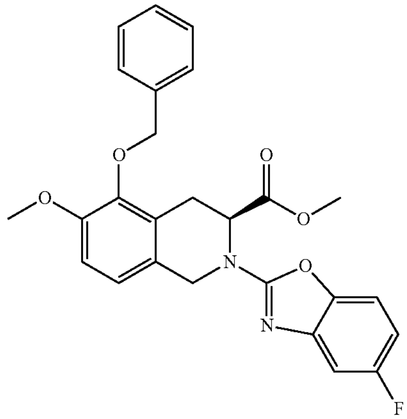 [SMILES: COC(=O)[C@@H]1Cc2c(ccc(OC)c2OCc2ccccc2)CN1c1nc2cc(F)ccc2o1] | methyl (S)-5-(benzyloxy)-2-(5-fluorobenzo[d]oxazol-2-yl)-6-methoxy-1,2,3,4-tetrahydroisoquinoline-3-carboxylate |
| 24d | 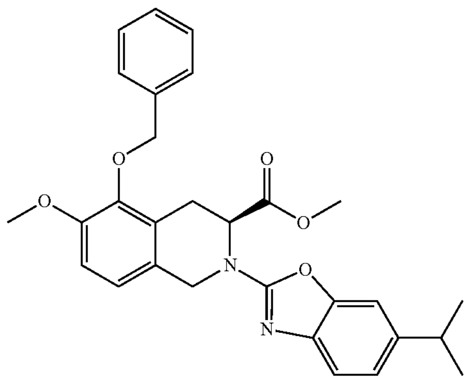 [SMILES: COC(=O)[C@@H]1Cc2c(ccc(OC)c2OCc2ccccc2)CN1c1nc2ccc(C(C)C)cc2o1] | methyl (S)-5-(benzyloxy)-2-(6-isopropylbenzo[d]oxazol-2-yl)-6-methoxy-1,2,3,4-tetrahydroisoquinoline-3-carboxylate |
| 25b | 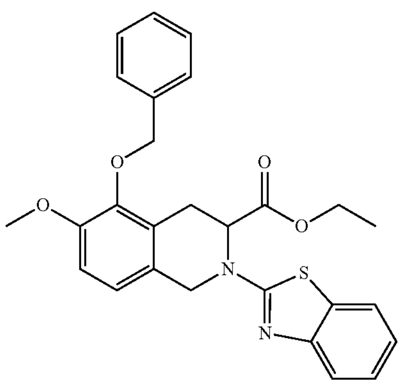 [SMILES: CCOC(=O)C1Cc2c(ccc(OC)c2OCc2ccccc2)CN1c1nc2ccccc2s1] | methyl 2-(benzo[d]thiazol-2-yl)-5-(benzyloxy)-6-methoxy-1,2,3,4-tetrahydroisoquinoline-3-carboxylate |
| 27i | 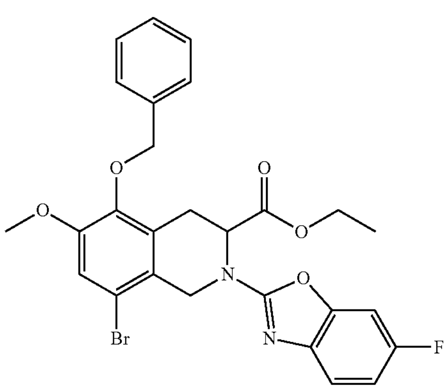 [SMILES: CCOC(=O)C1Cc2c(c(Br)cc(OC)c2OCc2ccccc2)CN1c1nc2ccc(F)cc2o1] | ethyl 5-(benzyloxy)-8-bromo-2-(6-fluorobenzo[d]oxazol-2-yl)-6-methoxy-1,2,3,4-tetrahydroisoquinoline-3-carboxylate |

| Example No. | Structure | Name |
|---|---|---|
| 28 | 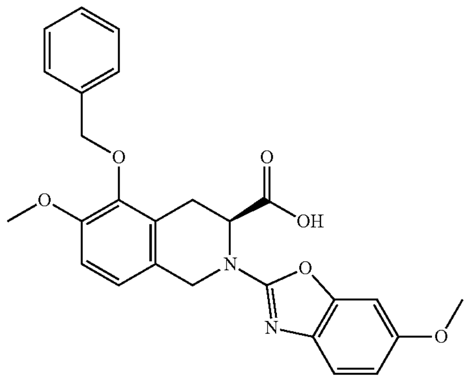 | (S)-5-(benzyloxy)-6-methoxy-2-(6-methoxybenzo[d]oxazol-2-yl)-1,2,3,4-tetrahydroisoquinoline-3-carboxylic acid |
| 29 | 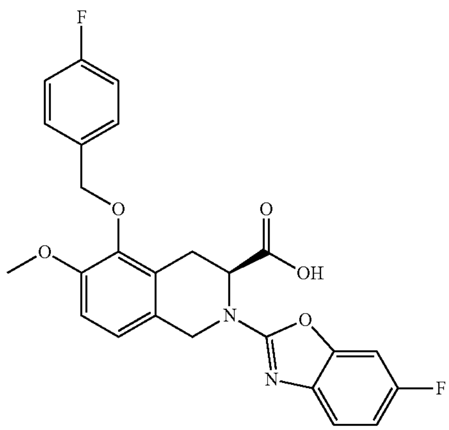 [SMILES: COc1ccc2c(c1OCc1ccc(F)cc1)C[C@@H](C(=O)O)N(c1nc3ccc(F)cc3o1)C2] | (S)-2-(6-fluorobenzo[d]oxazol-2-yl)-5-((4-fluorobenzyl)oxy)-6-methoxy-1,2,3,4-tetrahydroisoquinoline-3-carboxylic acid |
| 30 | 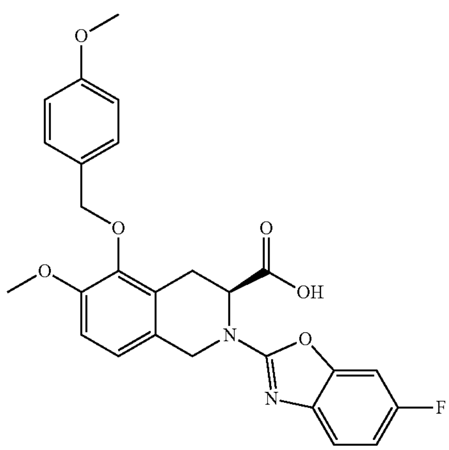 [SMILES: COc1ccc(COc2c(OC)ccc3c2C[C@@H](C(=O)O)N(c2nc4ccc(F)cc4o2)C3)cc1] | (S)-2-(6-fluorobenzo[d]oxazol-2-yl)-6-methoxy-5-((4-methoxybenzyl)oxy)-1,2,3,4-tetrahydroisoquinoline-3-carboxylic acid |

-continued

| Example No. | Structure | Name |
|---|---|---|
| 31 | 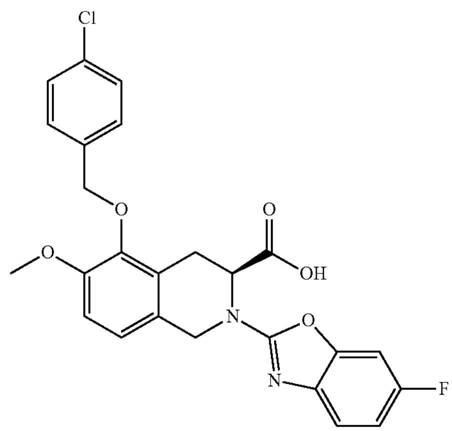 | (S)-5-((4-chlorobenzyl)oxy)-2-(6-fluoro-benzo[d]oxazol-2-yl)-6-methoxy-1,2,3,4-tetrahydroisoquinoline-3-carboxylic acid |
| 32 | 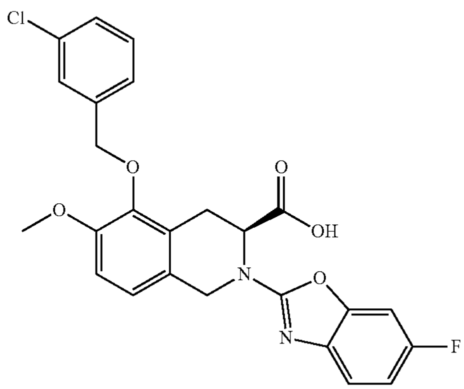 [SMILES: COc1ccc2c(c1OCc1cccc(Cl)c1)C[C@@H](C(=O)O)N(c1nc3ccc(F)cc3o1)C2] | (S)-5-((3-chlorobenzyl)oxy)-2-(6-fluoro-benzo[d]oxazol-2-yl)-6-methoxy-1,2,3,4-tetrahydroisoquinoline-3-carboxylic acid |
| 33 | 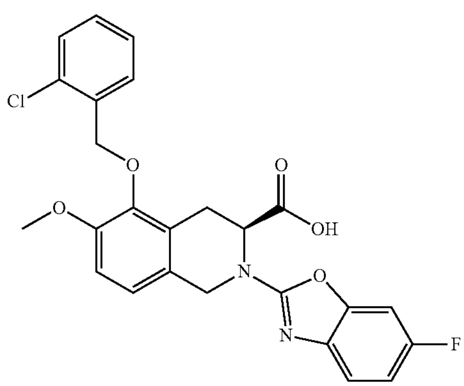 [SMILES: COc1ccc2c(c1OCc1ccccc1Cl)C[C@@H](C(=O)O)N(c1nc3ccc(F)cc3o1)C2] | (S)-5-((2-chlorobenzyl)oxy)-2-(6-fluoro-benzo[d]oxazol-2-yl)-6-methoxy-1,2,3,4-tetrahydroisoquinoline-3-carboxylic acid |
| 34 | 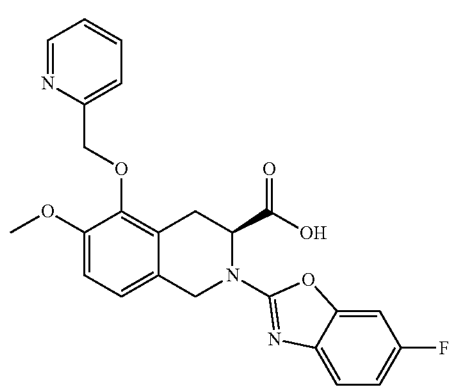 [SMILES: COc1ccc2c(c1OCc1ccccn1)C[C@@H](C(=O)O)N(c1nc3ccc(F)cc3o1)C2] | (S)-2-(6-fluorobenzo[d]oxazol-2-yl)-6-methoxy-5-(pyridin-2-ylmethoxy)-1,2,3,4-tetrahydroisoquinoline-3-carboxylic acid |

-continued

| Example No. | Structure | Name |
|---|---|---|
| 35 | 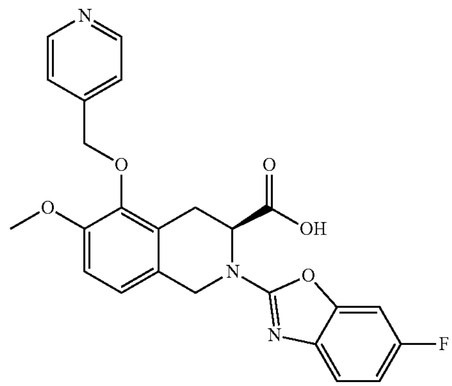 [SMILES: COc1ccc2c(c1OCc1ccncc1)C[C@@H](C(=O)O)N(c1nc3ccc(F)cc3o1)C2] | (S)-2-(6-fluorobenzo[d]oxazol-2-yl)-6-methoxy-5-(pyridin-4-ylmethoxy)-1,2,3,4-tetrahydroisoquinoline-3-carboxylic acid |
| 36 | 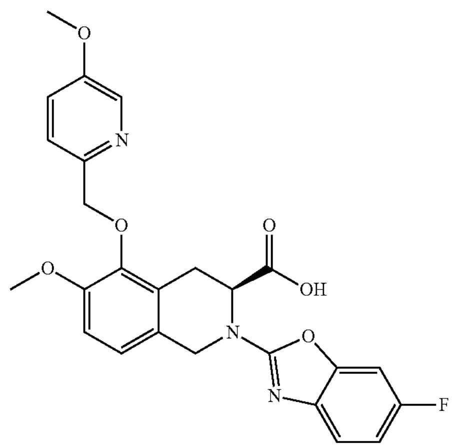 [SMILES: COc1ccc(COc2c(OC)ccc3c2C[C@@H](C(=O)O)N(c2nc4ccc(F)cc4o2)C3)nc1] | (S)-2-(6-fluorobenzo[d]oxazol-2-yl)-6-methoxy-5-((5-methoxypyridin-2-yl)methoxy)-1,2,3,4-tetrahydroisoquinoline-3-carboxylic acid |
| 37 | 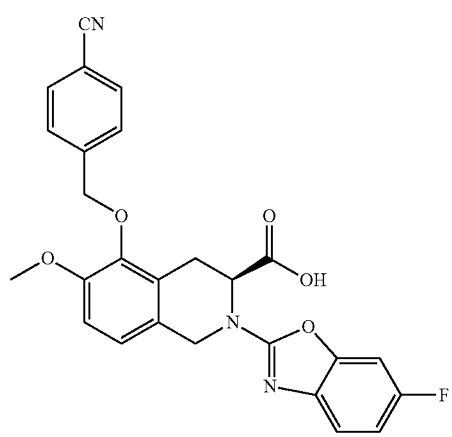 [SMILES: COc1ccc2c(c1OCc1ccc(C#N)cc1)C[C@@H](C(=O)O)N(c1nc3ccc(F)cc3o1)C2] | (S)-5-((4-cyanobenzyl)oxy)-2-(6-fluorobenzo[d]oxazol-2-yl)-6-methoxy-1,2,3,4-tetrahydroisoquinoline-3-carboxylic acid |

| Example No. | Structure | Name |
|---|---|---|
| 38 | 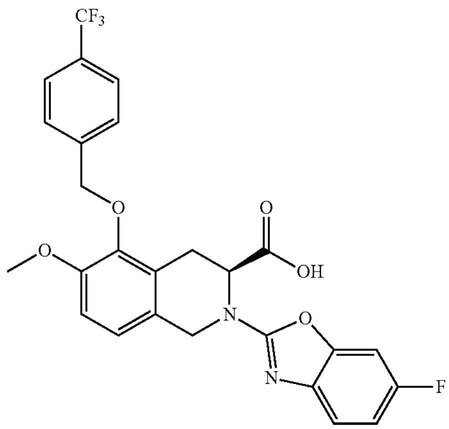 [SMILES: COc1ccc2c(c1OCc1ccc(C(F)(F)F)cc1)C[C@@H](C(=O)O)N(c1nc3ccc(F)cc3o1)C2] | (S)-2-(6-fluorobenzo[d]oxazol-2-yl)-6-methoxy-5-((4-(trifluoromethyl)benzyl)oxy)-1,2,3,4-tetrahydroisoquinoline-3-carboxylic acid |
| 39 | 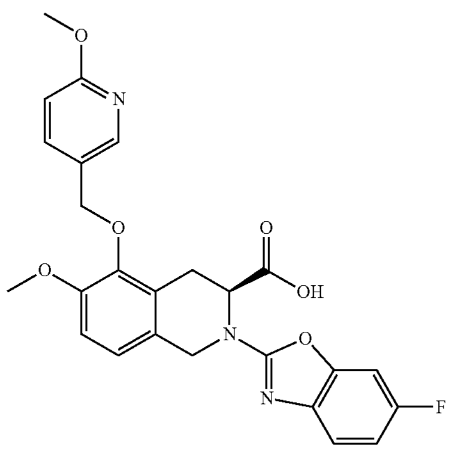 [SMILES: COc1ccc(COc2c(OC)ccc3c2C[C@@H](C(=O)O)N(c2nc4ccc(F)cc4o2)C3)cn1] | (S)-2-(6-fluorobenzo[d]oxazol-2-yl)-6-methoxy-5-((6-methoxypyridin-2-yl)methoxy)-1,2,3,4-tetrahydroisoquinoline-3-carboxylic acid |
| 40 | 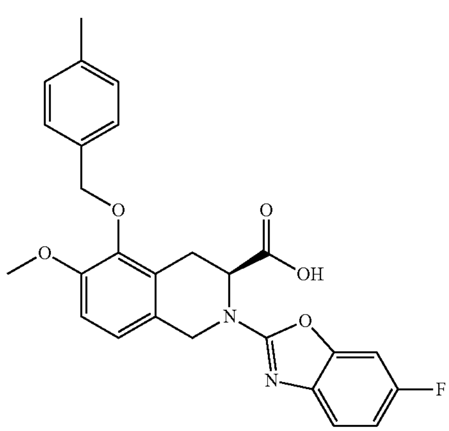 [SMILES: COc1ccc2c(c1OCc1ccc(C)cc1)C[C@@H](C(=O)O)N(c1nc3ccc(F)cc3o1)C2] | (S)-2-(6-fluorobenzo[d]oxazol-2-yl)-6-methoxy-5-((4-methylbenzyl)oxy)-1,2,3,4-tetrahydroisoquinoline-3-carboxylic acid |

| Example No. | Structure | Name |
|---|---|---|
| 41 | 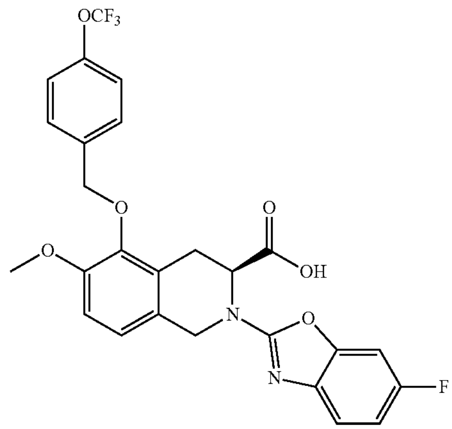 [SMILES: COc1ccc2c(c1OCc1ccc(OC(F)(F)F)cc1)C[C@@H](C(=O)O)N(c1nc3ccc(F)cc3o1)C2] | (S)-2-(6-fluorobenzo[d]oxazol-2-yl)-6-methoxy-5-((4-trifluoromethoxy)benzyl)oxy)-1,2,3,4-tetrahydroisoquinoline-3-carboxylic acid |
| 42 | 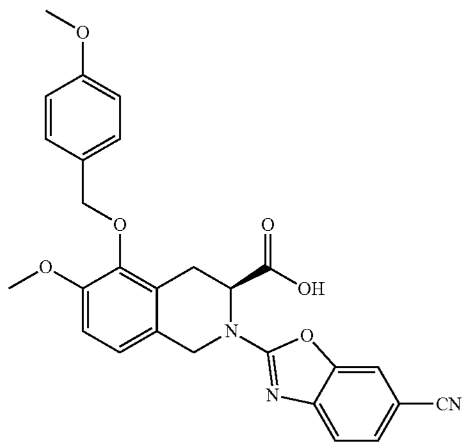 [SMILES: COc1ccc(COc2c(OC)ccc3c2C[C@@H](C(=O)O)N(c2nc4ccc(C#N)cc4o2)C3)cc1] | (S)-2-(6-cyanobenzo[d]oxazol-2-yl)-6-methoxy-5-((4-methoxybenzyl)oxy)-1,2,3,4-tetrahydroisoquinoline-3-carboxylic acid |
| 43 | 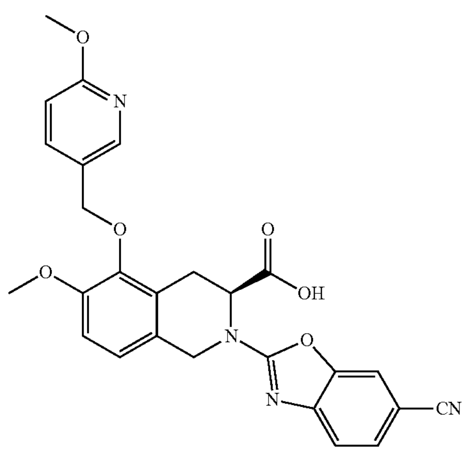 [SMILES: COc1ccc(COc2c(OC)ccc3c2C[C@@H](C(=O)O)N(c2nc4ccc(C#N)cc4o2)C3)cn1] | (S)-2-(6-cyanobenzo[d]oxazol-2-yl)-6-methoxy-5-((6-methoxypyridin-3-yl)methoxy)-1,2,3,4-tetrahydroisoquinoline-3-carboxylic acid |

| Example No. | Structure | Name |
|---|---|---|
| 44 | 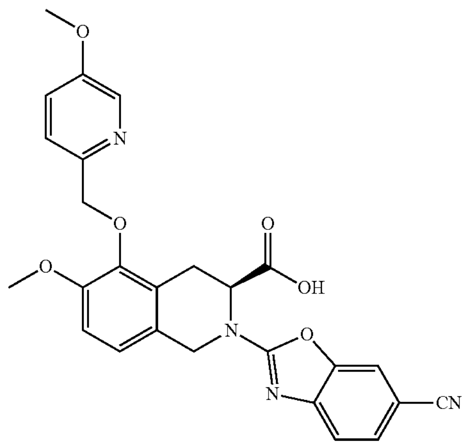 [SMILES: COc1ccc(COc2c(OC)ccc3c2C[C@@H](C(=O)O)N(c2nc4ccc(C#N)cc4o2)C3)nc1] | (S)-2-(6-cyanobenzo[d]oxazol-2-yl)-6-methoxy-5-((5-methoxypyridin-2-yl)methoxy)-1,2,3,4-tetrahydroisoquinoline-3-carboxylic acid |
| 45 | 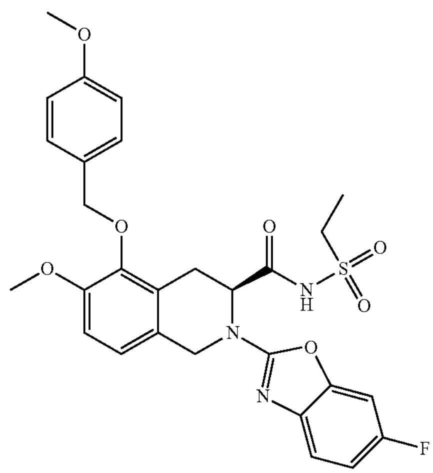 [SMILES: CCS(=O)(=O)NC(=O)[C@@H]1Cc2c(ccc(OC)c2OCc2ccc(OC)cc2)CN1c1nc2ccc(F)cc2o1] | (S)-N-(ethylsulfonyl)-2-(6-fluorobenzo[d]oxazol-2-yl)-6-methoxy-5-((4-methoxybenzyl)oxy)-1,2,3,4-tetrahydroisoquinoline-3-carboxamide |
| 46 | 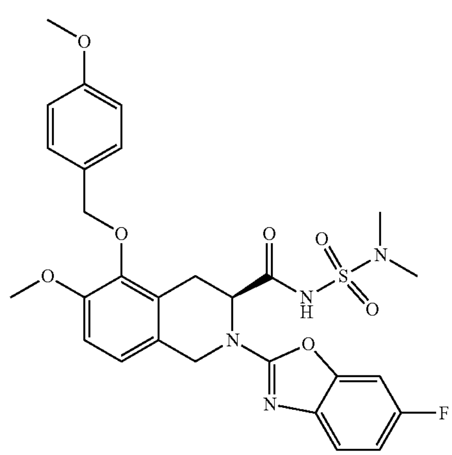 [SMILES: COc1ccc(COc2c(OC)ccc3c2C[C@@H](C(=O)NS(=O)(=O)N(C)C)N(c2nc4ccc(F)cc4o2)C3)cc1] | (S)-N-(N,N-dimethylamino)-2-(6-fluorobenzo[d]oxazol-2-yl)-6-methoxy-5-((4-methoxybenzyl)oxy)-1,2,3,4-tetrahydroisoquinoline-3-carboxamide |

| Example No. | Structure | Name |
|---|---|---|
| 28h | 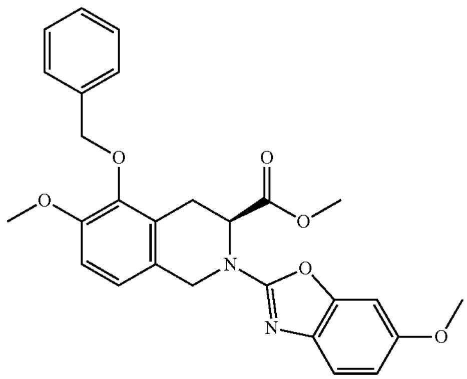 | methyl (S)-5-(benzyloxy)-6-methoxy-2-(6-methoxybenzo[d]oxazol-2-yl)-1,2,3,4-tetrahydroisoquinoline-3-carboxylate |
| 29e | 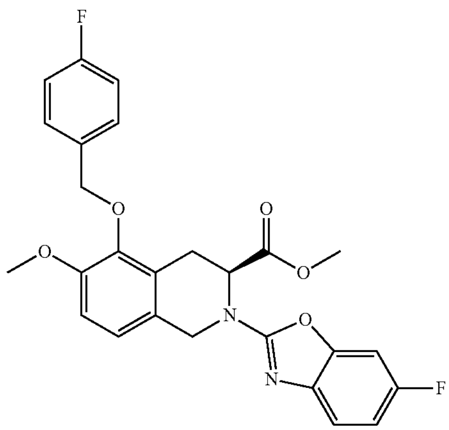 [SMILES: COC(=O)[C@@H]1Cc2c(ccc(OC)c2OCc2ccc(F)cc2)CN1c1nc2ccc(F)cc2o1] | methyl (S)-2-(6-fluorobenzo[d]oxazol-2-yl)-5-((4-fluorobenzyl)oxy)-6-methoxy-1,2,3,4-tetrahydroisoquinoline-3-carboxylate |
| 30b | 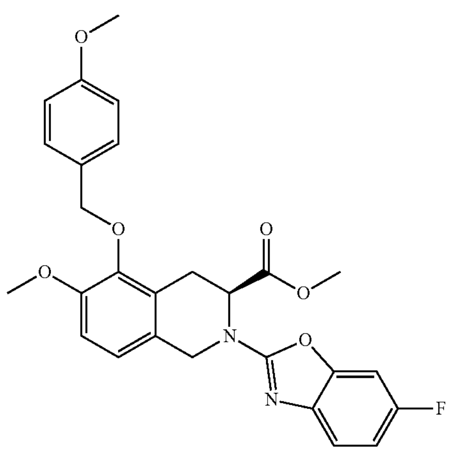 [SMILES: COC(=O)[C@@H]1Cc2c(ccc(OC)c2OCc2ccc(OC)cc2)CN1c1nc2ccc(F)cc2o1] | methyl (S)-2-(6-fluorobenzo[d]oxazol-2-yl)-6-methoxy-5-((4-methoxybenzyl)oxy)-1,2,3,4-tetrahydroisoquinoline-3-carboxylate |

| Example No. | Structure | Name |
|---|---|---|
| 31b | 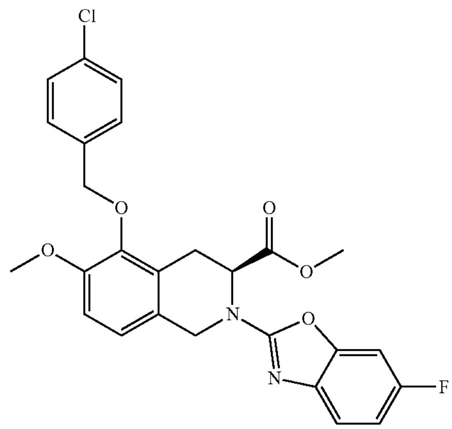 [SMILES: COC(=O)[C@@H]1Cc2c(ccc(OC)c2OCc2ccc(Cl)cc2)CN1c1nc2ccc(F)cc2o1] | methyl (S)-5-((4-chlorobenzyl)oxy)-2-(6-fluorobenzo[d]oxazol-2-yl)-6-methoxy-1,2,3,4-tetrahydroisoquinoline-3-carboxylate |
| 32b | 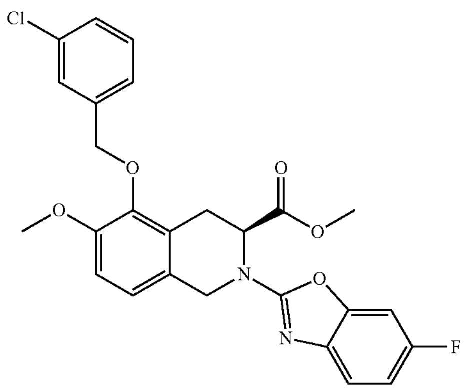 [SMILES: COC(=O)[C@@H]1Cc2c(ccc(OC)c2OCc2cccc(Cl)c2)CN1c1nc2ccc(F)cc2o1] | methyl (S)-5-((3-chlorobenzyl)oxy)-2-(6-fluorobenzo[d]oxazol-2-yl)-6-methoxy-1,2,3,4-tetrahydroisoquinoline-3-carboxylate |
| 33b | 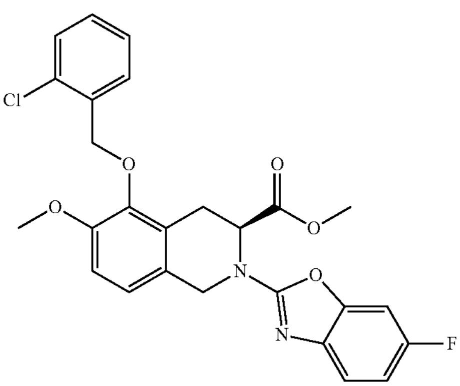 [SMILES: COC(=O)[C@@H]1Cc2c(ccc(OC)c2OCc2ccccc2Cl)CN1c1nc2ccc(F)cc2o1] | methyl (S)-5-((2-chlorobenzyl)oxy)-2-(6-fluorobenzo[d]oxazol-2-yl)-6-methoxy-1,2,3,4-tetrahydroisoquinoline-3-carboxylate |
| 34b | 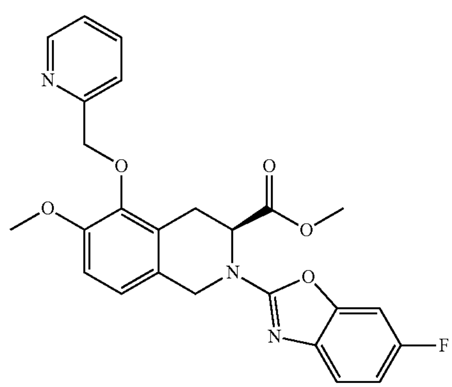 [SMILES: COC(=O)[C@@H]1Cc2c(ccc(OC)c2OCc2ccccn2)CN1c1nc2ccc(F)cc2o1] | methyl (S)-2-(6-fluorobenzo[d]oxazol-2-yl)-6-methoxy-5-(pyridin-2-ylmethoxy)-1,2,3,4-tetrahydroisoquinoline-3-carboxylate |

| Example No. | Structure | Name |
|---|---|---|
| 35b | 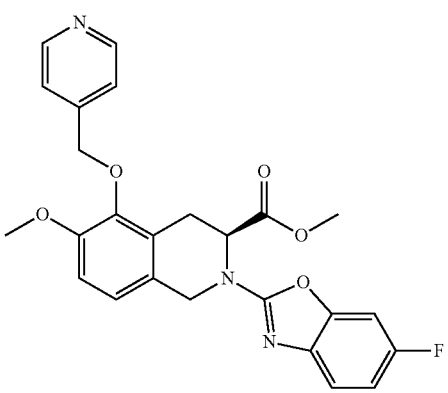 [SMILES: COC(=O)[C@@H]1Cc2c(ccc(OC)c2OCc2ccncc2)CN1c1nc2ccc(F)cc2o1] | methyl (S)-2-(6-fluorobenzo[d]oxazol-2-yl)-6-methoxy-5-(pyridin-4-ylmethoxy)-1,2,3,4-tetrahydroisoquinoline-3-carboxylate |
| 36b | 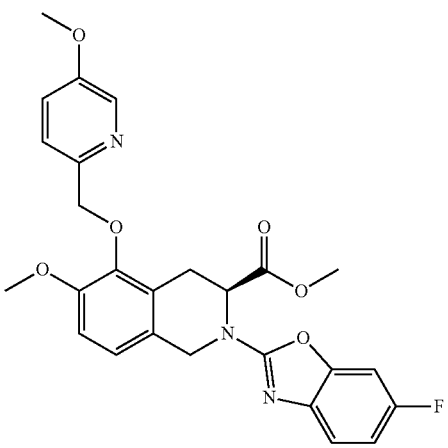 [SMILES: COC(=O)[C@@H]1Cc2c(ccc(OC)c2OCc2ccc(OC)cn2)CN1c1nc2ccc(F)cc2o1] | methyl (S)-2-(6-fluorobenzo[d]oxazol-2-yl)-6-methoxy-5-((5-methoxypyridin-2-yl)methoxy)-1,2,3,4-tetrahydroisoquinoline-3-carboxylate |
| 37b | 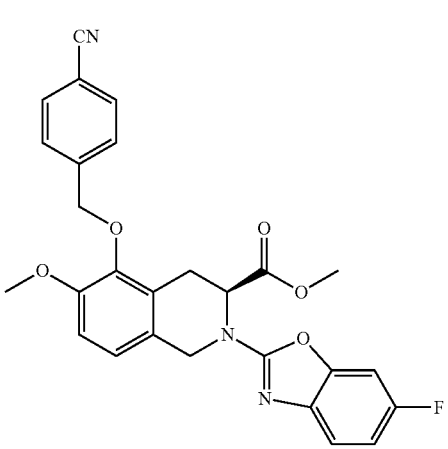 [SMILES: COC(=O)[C@@H]1Cc2c(ccc(OC)c2OCc2ccc(C#N)cc2)CN1c1nc2ccc(F)cc2o1] | methyl (S)-5-((4-cyanobenzyl)oxy)-2-(6-fluoro-benzo[d]oxazol-2-yl)-6-methoxy-1,2,3,4-tetrahydroisoquinoline-3-carboxylate |

| Example No. | Structure | Name |
| --- | --- | --- |
| 38b | 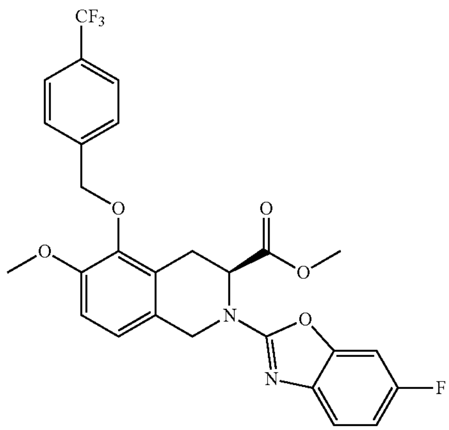 [SMILES: COC(=O)[C@@H]1Cc2c(ccc(OC)c2OCc2ccc(C(F)(F)F)cc2)CN1c1nc2ccc(F)cc2o1] | methyl (S)-2-(6-fluorobenzo[d]oxazol-2-yl)-6-methoxy-5-((4-(trifluoromethyl)benzyl)oxy)-1,2,3,4-tetrahydroisoquinoline-3-carboxylate |
| 39b | 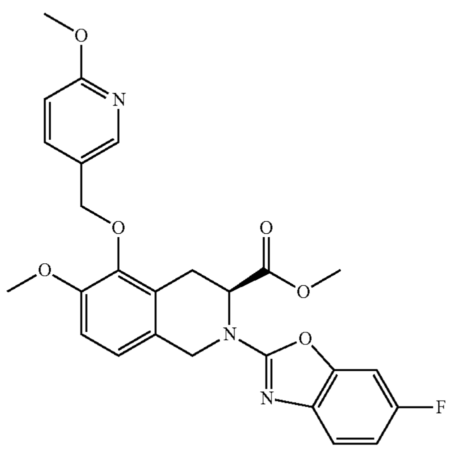 [SMILES: COC(=O)[C@@H]1Cc2c(ccc(OC)c2OCc2ccc(OC)nc2)CN1c1nc2ccc(F)cc2o1] | methyl (S)-2-(6-fluorobenzo[d]oxazol-2-yl)-6-methoxy-5-((6-methoxypyridin-3-yl)methoxy)-1,2,3,4-tetrahydroisoquinoline-3-carboxylate |
| 40b | 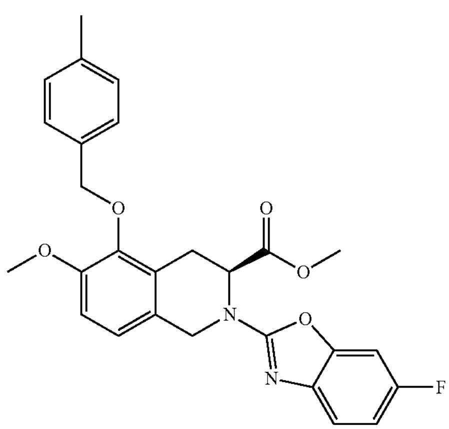 [SMILES: COC(=O)[C@@H]1Cc2c(ccc(OC)c2OCc2ccc(C)cc2)CN1c1nc2ccc(F)cc2o1] | methyl (S)-2-(6-fluorobenzo[d]oxazol-2-yl)-6-methoxy-5-((4-methylbenzyl)oxy)-1,2,3,4-tetrahydroisoquinoline-3-carboxylate |

| Example No. | Structure | Name |
|---|---|---|
| 41b | 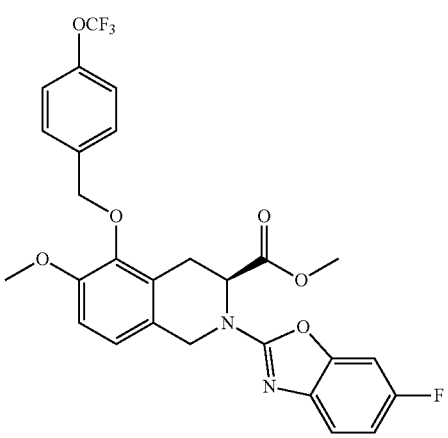 [SMILES: COC(=O)[C@@H]1Cc2c(ccc(OC)c2OCc2ccc(OC(F)(F)F)cc2)CN1c1nc2ccc(F)cc2o1] | methyl (S)-2-(6-fluorobenzo[d]oxazol-2-yl)-6-methoxy-5-((4-trifluoromethoxy)benzyl)oxy)-1,2,3,4-tetrahydroisoquinoline-3-carboxylate |
| 42g | 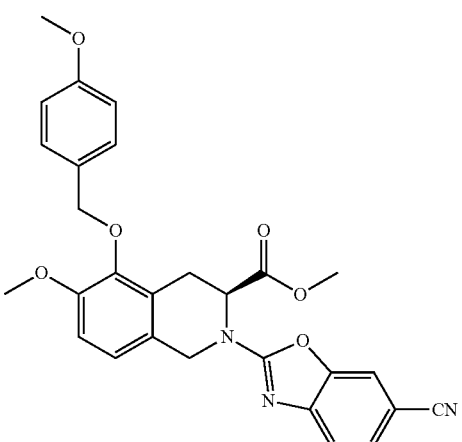 | methyl (S)-2-(6-cyanobenzo[d]oxazol-2-yl)-6-methoxy-5-((4-methoxybenzyl)oxy)-1,2,3,4-tetrahydroisoquinoline-3-carboxylate |
| 43a | 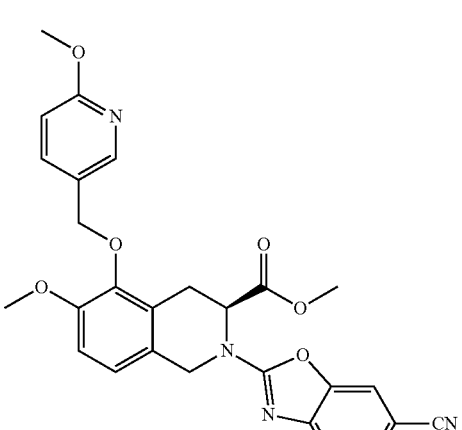 | methyl (S)-2-(6-cyanobenzo[d]oxazol-2-yl)-6-methoxy-5-((6-methoxypyridin-3-yl)methoxy)-1,2,3,4-tetrahydroisoquinoline-3-carboxylate |

| Example No. | Structure | Name |
|---|---|---|
| 44a | 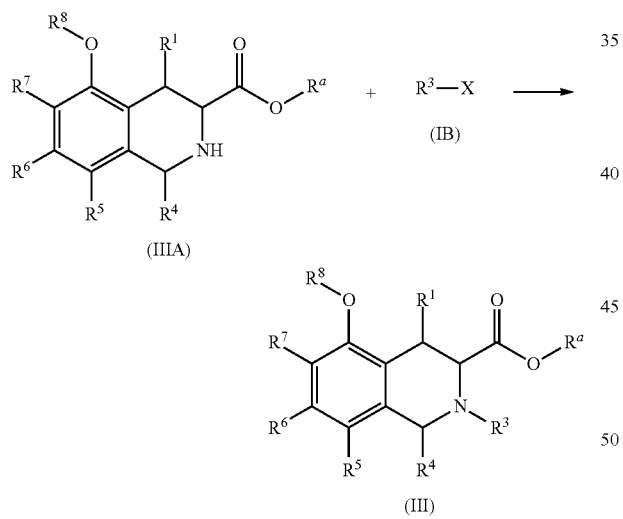 | methyl (S)-2-(6-cyanobenzo[d]oxazol-2-yl)-6-methoxy-5-((5-methoxypyridin-2-yl)methoxy)-1,2,3,4-tetrahydroisoquinoline-3-carboxylate | or a stereoisomer, a tautomer, or a pharmaceutically acceptable salt thereof.

Note: If there is a difference between the drawn structure and the given name of the structure, the drawn structure will be given more weight.

The present disclosure provides a method of preparing the compound of general formula (III) or a stereoisomer, a tautomer, or a pharmaceutically acceptable salt thereof, comprising the following steps

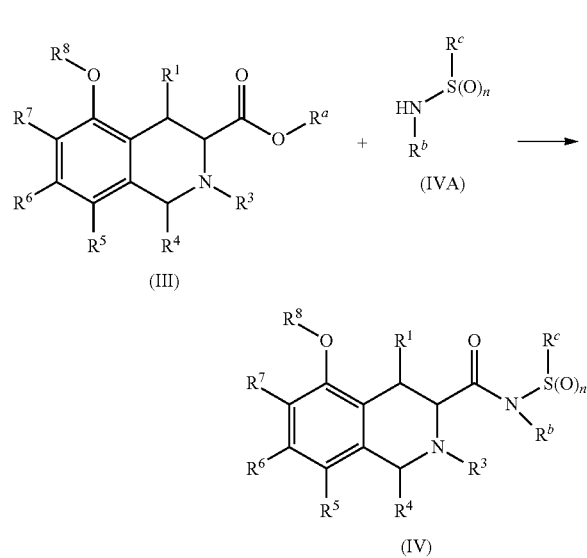

when $R^a$ is an alkyl, reacting a compound of general formula (IIIA) or a salt thereof with a compound of general formula (IB), and optionally further removing the protective group, to obtain a compound of general formula (III) in which $R^a$ is an alkyl;

optionally further performing a hydrolysis reaction of the compound of general formula (III) in which $R^a$ is an alkyl to obtain a compound of general formula (III) in which $R^a$ is hydrogen;

wherein:

X is selected from hydrogen and a leaving group, wherein the leaving group is preferably halogen, more preferably chlorine or bromine; and $R^1$ and $R^3$ to $R^8$ are as defined in general formula (III).

The present disclosure provides a method of preparing the compound of general formula (IV) or a stereoisomer, a tautomer, or a pharmaceutically acceptable salt thereof, comprising the following steps reacting a compound of general formula (III) with a compound of general formula (IVA) to obtain a compound of general formula (IV);

wherein:

$R^a$ is hydrogen;

$R^1$, $R^3$ to $R^8$, $R^b$, $R^c$ and n are as defined in general formula (IV).

The present disclosure provides a method of preparing the compound of general formula (V) or a stereoisomer, a tautomer, or a pharmaceutically acceptable salt thereof, comprising the following steps

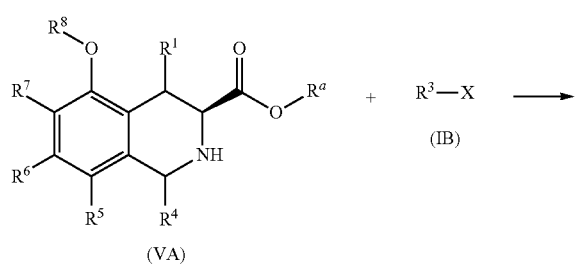

(VA)

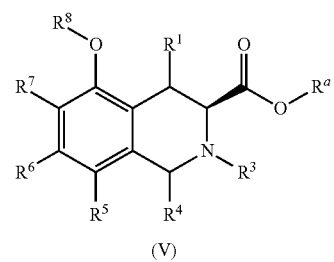

(V)

when $R^a$ is an alkyl, reacting a compound of general formula (VA) or a salt thereof with a compound of general formula (IB), and optionally further removing the protective group, to obtain a compound of general formula (V) in which $R^a$ is an alkyl;

optionally further performing a hydrolysis reaction of the compound of general formula (V) in which $R^a$ is an alkyl to obtain a compound of general formula (V) in which $R^a$ is hydrogen;

wherein:

X is selected from hydrogen and a leaving group, wherein the leaving group is preferably halogen, more preferably chlorine or bromine; and $R^1$ and $R^3$ to $R^8$ are as defined in general formula (V).

The present disclosure provides a method of preparing the compound of general formula (VI) or a stereoisomer, a tautomer, or a pharmaceutically acceptable salt thereof, comprising the following steps

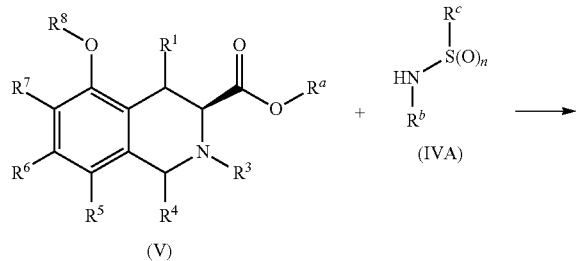

(V)

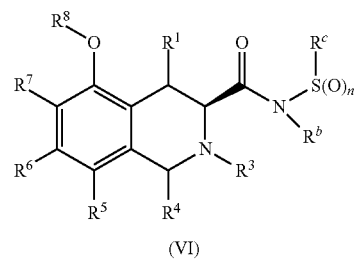

(VI)

reacting a compound of general formula (V) with a compound of general formula (IVA) to obtain a compound of general formula (VI);

wherein:

$R^a$ is hydrogen;

$R^1$, $R^3$ to $R^8$, $R^b$, $R^c$ and n are as defined in general formula (VI).

The present disclosure provides a method of preparing the compound of general formula (III) or a stereoisomer, a tautomer, or a pharmaceutically acceptable salt thereof, comprising the following steps

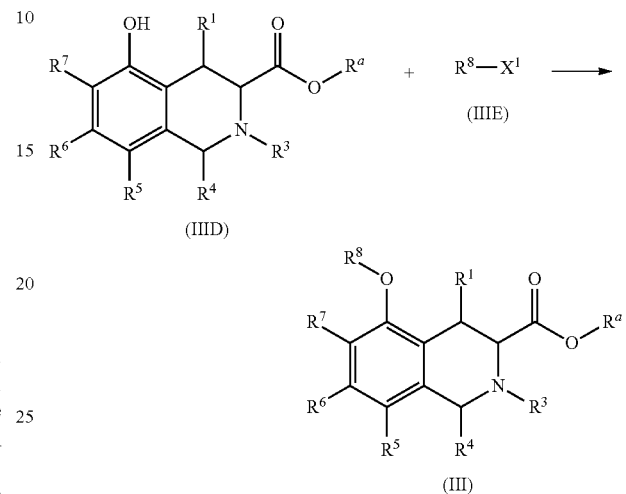

when $R^a$ is an alkyl, reacting a compound of general formula (IIID) with a compound of general formula (IIIE), to obtain a compound of general formula (III) in which $R^a$ is an alkyl;

optionally further performing a hydrolysis reaction of the compound of general formula (III) in which $R^a$ is an alkyl to obtain a compound of general formula (III) in which $R^a$ is hydrogen;

wherein:

$X^1$ is a leaving group, preferably chlorine or hydroxy; and $R^1$ and $R^3$ to $R^8$ are as defined in general formula (III).

The present disclosure provides a method of preparing the compound of general formula (V) or a stereoisomer, a tautomer, or a pharmaceutically acceptable salt thereof, comprising the following steps

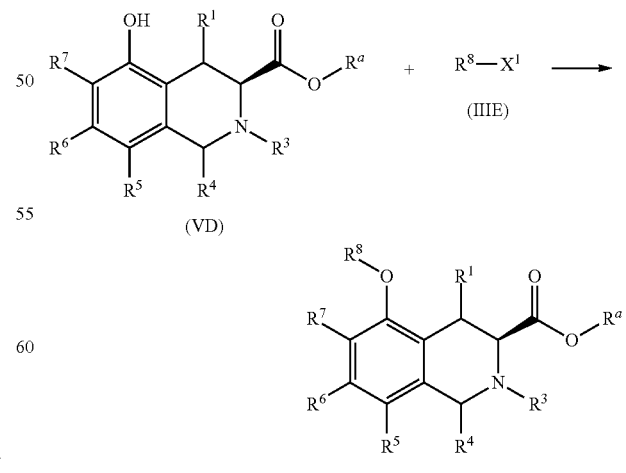

when $R^a$ is an alkyl, reacting a compound of general formula (VD) with a compound of general formula (IIIE), to obtain a compound of general formula (V) in which $R^a$ is an alkyl;

optionally further performing a hydrolysis reaction of the compound of general formula (V) in which $R^a$ is an alkyl to obtain a compound of general formula (V) in which $R^a$ is hydrogen;

wherein:

$X^1$ is a leaving group, preferably chlorine or hydroxy; and $R^1$ and $R^3$ to $R^8$ are as defined in general formula (V).

Furthermore, the present disclosure provides a pharmaceutical composition comprising an effective amount of the compound of general formula (I), (II), (III), (IV), (V) or (VI), or a stereoisomer, a tautomer or a pharmaceutically acceptable salt thereof, and pharmaceutically acceptable carriers, excipients, or combinations thereof.

The present disclosure provides a method of antagonizing $AT_2R$, comprising contacting the $AT_2R$ receptor with the compound of general formula (I), (II), (III), (IV), (V) or (VI), or a stereoisomer, a tautomer or a pharmaceutically acceptable salt thereof, or the pharmaceutical composition thereof.

The present disclosure provides use of the compound of general formula (I), (II), (III), (IV), (V) or (VI), or a stereoisomer, a tautomer or a pharmaceutically acceptable salt thereof, or the pharmaceutical composition thereof in the manufacture of a medicament for treating or preventing diseases or disorders mediated by $AT_2R$, wherein the diseases or disorders mediated by $AT_2R$ are preferably neuropathy or neuropathic pain, wherein the neuropathy or neuropathic pain is preferably primary neuropathy, secondary neuropathy, peripheral neuropathy, neuropathy caused by mechanical nerve injury or biochemical nerve injury, postherpetic neuralgia, diabetic neuralgia or related neurological diseases.

The present disclosure provides use of the compound of general formula (I), (II), (III), (IV), (V) or (VI), or a stereoisomer, a tautomer or a pharmaceutically acceptable salt thereof, or the pharmaceutical composition thereof in the manufacture of an $AT_2R$ antagonist.

The present disclosure provides use of the compound of general formula (I), (II), (III), (IV), (V) or (VI), or a stereoisomer, a tautomer or a pharmaceutically acceptable salt thereof, or the pharmaceutical composition thereof in the manufacture of a medicament for treating or preventing neuropathy or neuropathic pain, wherein the neuropathy or neuropathic pain is preferably primary neuropathy, secondary neuropathy, peripheral neuropathy, neuropathy caused by mechanical nerve injury or biochemical nerve injury, postherpetic neuralgia, diabetic neuralgia or related neurological diseases.

The present disclosure provides a method of regulating the activity of angiotensin II type 2 receptor, comprising administering to a patient in need thereof a therapeutically effective amount of the compound of general formula (I), (II), (III), (IV), (V) or (VI), or a stereoisomer, a tautomer or a pharmaceutically acceptable salt thereof, or the pharmaceutical composition thereof.

The present disclosure provides a method of treating or preventing diseases or disorders mediated by angiotensin II type 2 receptor, comprising administering to a patient in need thereof a therapeutically effective amount of the compound of general formula (I), (II), (III), (IV), (V) or (VI), or a stereoisomer, a tautomer or a pharmaceutically acceptable salt thereof, or the pharmaceutical composition thereof, wherein the diseases or disorders mediated by angiotensin II type 2 receptor are preferably neuropathy or neuropathic pain, wherein the neuropathy or neuropathic pain is preferably primary neuropathy, secondary neuropathy, peripheral neuropathy, neuropathy caused by mechanical nerve injury or biochemical nerve injury, postherpetic neuralgia, diabetic neuralgia or related neurological diseases.

DETAILED DESCRIPTION OF THE PRESENT DISCLOSURE

Unless described to the contrary, some terms used in the specification and claims of the present disclosure are defined as follows:

"Alkyl", when regarded as a group or a part of a group, refers to a $C_1$-$C_{20}$ straight chain or branched aliphatic hydrocarbon group. It is preferably $C_1$-$C_{10}$ alkyl, more preferably $C_1$-$C_6$ alkyl or $C_1$-$C_4$ alkyl. Examples of alkyl include, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, etc. Alkyl can be substituted or unsubstituted.

"Alkenyl" refers to alkyl as defined above composed of at least two carbon atoms and at least one carbon-carbon double bond. Representative examples include, but are not limited to, vinyl, 1-propenyl, 2-propenyl, 1-, 2- or 3-butenyl, etc. Alkenyl can be optionally substituted or unsubstituted.

"Alkynyl" refers to an aliphatic hydrocarbon group containing one carbon-carbon triple bond, which can be straight or branched. It is preferably $C_2$-$C_{10}$ alkynyl, more preferably $C_2$-$C_6$ alkynyl, and most preferably $C_2$-$C_4$ alkynyl. Examples of alkynyl include, but are not limited to, ethynyl, 1-propynyl, 2-propynyl, 1-, 2-, or 3-butynyl, etc. Alkynyl can be substituted or unsubstituted.

"Cycloalkyl" refers to a saturated or partially saturated carbocyclic ring in the form of monocyclic ring, fused ring, bridged ring and spiro ring. It is preferably $C_3$-$C_{12}$ cycloalkyl, more preferably $C_3$-$C_8$ cycloalkyl, and most preferably $C_3$-$C_6$ cycloalkyl. Examples of monocyclic cycloalkyl include, but are not limited to, cyclopropyl, cyclobutyl, cyclopentyl, cyclopentenyl, cyclohexyl, cyclohexenyl, cyclohexadienyl, cycloheptyl, cycloheptatrienyl, cyclooctyl, etc., preferably cyclopropyl and cyclohexenyl.

"Spiro cycloalkyl" refers to a polycyclic group with 5 to 18 members, two or more cyclic structures in which the single rings share one carbon atom (called spiro atom) with each other. The ring contains one or more double bonds, but none of the rings has a fully conjugated π-electron aromatic system. It is preferably 6 to 14-membered, more preferably 7 to 10-membered. According to the number of shared spiro atoms between one ring and another ring, the spiro cycloalkyl is classified into mono-spiro, di-spiro or multi-spiro cycloalkyl, preferably mono-spiro and di-spiro cycloalkyl, preferably 4-membered/5-membered, 4-membered/6-membered, 5-membered/5-membered or 5-membered/6-membered. Non-limiting examples of "spiro cycloalkyl" include, but are not limited to: spiro[4.5]decyl, spiro[4.4]nonyl, spiro[3.5]nonyl, spiro[2.4]heptyl.

"Fused cycloalkyl" refers to a 5 to 18-membered, all-carbon polycyclic group containing two or more cyclic structures which share a pair of carbon atoms with each other. One or more rings may contain one or more double bonds, but none of the rings has a fully conjugated π-electron aromatic system, preferably 6 to 12-membered, more preferably 7 to 10-membered. According to the number of the formed rings, it can be classified into bicyclic, tricyclic, pyridone or polycyclic fused cycloalkyl, preferably bicyclic or tricyclic, more preferably 5-membered/5-membered or 5-membered/6-membered bicyclic alkyl. Non-limiting examples of "fused cycloalkyl" include, but are not limited to: bicyclo[3.1.0]hexyl, bicyclo[3.2.0]hept-1-enyl, bicyclo[3.2.0]heptyl, decahydronaphthyl or tetradecahydrophenanthryl.

"Bridged cycloalkyl" refers to a 5 to 18-membered all-carbon polycyclic group containing two or more cyclic structures that share two carbon atoms that are not directly connected to each other. One or more rings may contain one or more double bonds, but none of the rings has a fully conjugated π-electron aromatic system. It is preferably 6 to 12-membered, and more preferably 7 to 10-membered. It is preferably 6 to 14-membered, more preferably 7 to 10-membered. According to the number of the formed rings, it can be classified into bicyclic, tricyclic, pyridone or polycyclic bridged cycloalkyl, preferably bicyclic, tricyclic or pyridone, more preferably bicyclic or tricyclic. Non-limiting examples of "bridged cycloalkyl" include, but are not limited to: (1s,4s)-bicyclo[2.2.1]heptyl, bicyclo[3.2.1]octyl, (1s,5s)-bicyclo [3.3.1]nonyl, bicyclo[2.2.2]octyl, (1r,5r)-bicyclo[3.3.2]decyl.

The cycloalkyl ring may be fused to an aryl, heteroaryl or heterocyclyl ring, wherein the ring connected to the parent structure is cycloalkyl, and the non-limiting examples include indanyl, tetrahydronaphthyl, benzocycloheptyl, etc. Cycloalkyl can be optionally substituted or unsubstituted.

"Heterocyclyl", "heterocyclic ring" or "heterocyclic" are used interchangeably in this application and all refer to non-aromatic heterocyclic groups, in which one or more ring-forming atoms are heteroatoms, such as oxygen, nitrogen, sulfur, etc., including monocyclic rings, fused rings, bridged rings and spiro rings. It preferably has a 5 to 7-membered monocyclic ring or a 7 to 10-membered bi- or tricyclic ring, which may contain 1, 2 or 3 atoms selected from nitrogen, oxygen and/or sulfur. Examples of "heterocyclyl" include, but are not limited to, morpholinyl, oxetanyl, thiomorpholinyl, tetrahydropyranyl, 1,1-dioxo-thiomorpholinyl, piperidinyl, 2-oxo-piperidinyl, pyrrolidinyl, 2-oxo-pyrrolidinyl, piperazin-2-one, 8-oxa-3-aza-bicyclo[3.2.1]octyl and piperazinyl. The heterocyclyl may be substituted or unsubstituted.

"Spiro heterocyclyl" refers to a polycyclic group with 5 to 18 members, two or more cyclic structures in which the single rings share one carbon atom with each other. The ring contains one or more double bonds, but none of the rings has a fully conjugated π-electron aromatic system, wherein one or more ring atoms are selected from heteroatoms of nitrogen, oxygen and S(O)$_n$ (where n is selected from 0, 1 and 2), and the rest of the ring atoms are carbon. It is preferably 6 to 14-membered, more preferably 7 to 10-membered. According to the number of spiro atoms shared between one ring and another ring, the spirocycloalkyl is classified into single spiro heterocyclyl, dispiro heterocyclyl or polyspiro heterocyclyl, preferably single spiro heterocyclyl and dispiro heterocyclyl. More preferably, it is 4-membered/4-membered, 4-membered/5-membered, 4-membered/6-membered, 5-membered/5-membered, or 5-membered/6-membered monospiro heterocyclyl. Non-limiting examples of "spiro heterocyclyl" include, but are not limited to: 1,7-dioxaspiro[4.5]decyl, 2-oxa-7-azaspiro[4.4]nonyl, 7-oxaspiro[3.5]nonyl and 5-oxaspiro[2.4]heptyl.

"Fused heterocyclyl" refers to an all-carbon polycyclic group containing two or more cyclic structures which share a pair of carbon atoms with each other. One or more rings may contain one or more double bonds, but none of the rings has a fully conjugated π-electron aromatic system, wherein one or more ring atoms are selected from heteroatoms of nitrogen, oxygen and S(O)$_n$ (where n is selected from 0, 1 and 2), and the rest of the ring atoms are carbon. It is preferably 6 to 14-membered, more preferably 7 to 10-membered. According to the number of the formed rings, it can be classified into bicyclic, tricyclic, pyridone or polycyclic fused heterocyclyl, preferably bicyclic or tricyclic, more preferably 5-membered/5-membered or 5-membered/6-membered bicyclic fused heterocyclyl. Non-limiting examples of "fused heterocyclyl" include, but are not limited to octahydropyrrolo[3,4-c]pyrrolyl, octahydro-1H-isoindolyl, 3-azabicyclo[3.1.0]hexyl, octahydrobenzo[b][1,4]dioxine.

"Bridged heterocyclyl" refers to a 5 to 14-membered, 5 to 18-membered polycyclic group containing two or more cyclic structures which share two atoms that are not directly connected to each other. One or more rings may contain one or more double bonds, but none of the rings has a fully conjugated π-electron aromatic system, wherein one or more ring atoms are selected from heteroatoms of nitrogen, oxygen and S(O)$_n$ (where n is selected from 0, 1 and 2), and the rest of the ring atoms are carbon. It is preferably 6 to 14-membered, more preferably 7 to 10-membered. According to the number of the formed rings, it can be classified into bicyclic, tricyclic, pyridone or polycyclic bridged heterocyclyl, preferably bicyclic, tricyclic, or pyridone, more preferably bicyclic or tricyclic.

Non-limiting examples of "fused heterocyclyl" include, but are not limited to 2-azabicyclo[2.2.1]heptyl, 2-azabicyclo[2.2.2]octyl and 2-azabicyclo[3.3.2]decyl.

The heterocyclyl ring may be fused to an aryl, heteroaryl or cycloalkyl ring, wherein the ring connected to the parent structure is heterocyclyl. The heterocyclyl may be optionally substituted or unsubstituted.

"Aryl" refers to a carbocyclic aromatic system containing one or two rings, wherein the rings can be joined together in a fused manner. The term "aryl" includes aromatic groups such as phenyl, naphthyl, and tetrahydronaphthyl. Preferably the aryl is $C_6$-$C_{10}$ aryl, more preferably the aryl is phenyl and naphthyl, and most preferably phenyl. Aryl can be substituted or unsubstituted. The "aryl" can be fused with heteroaryl, heterocyclyl or cycloalkyl, wherein the ring connected to the parent structure is an aryl ring. Non-limiting examples include but are not limited to:

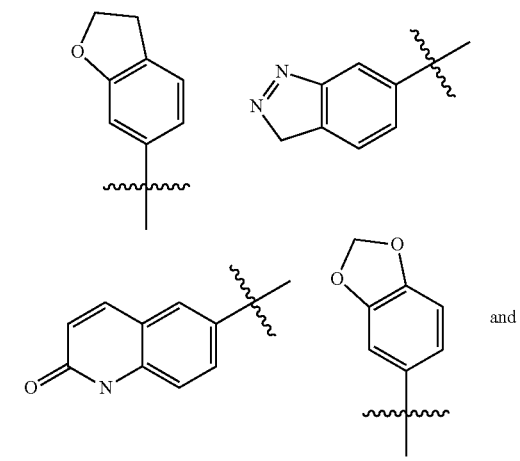

and

-continued

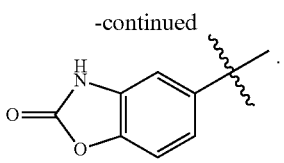

"Heteroaryl" refers to an aromatic 5 to 6-membered monocyclic ring or 8 to 10-membered bicyclic ring, which may contain 1 to 4 atoms selected from nitrogen, oxygen and/or sulfur. Examples of "heteroaryl" include but are not limited to furyl, pyridyl, 2-oxo-1,2-dihydropyridyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzodioxole group, benzothienyl, benzimidazolyl, indolyl, isoindolyl, 1,3-dioxo-isoindolyl, quinolinyl, indazolyl, benzoisothiazolyl, benzoxazolyl and benzisoxazolyl. Heteroaryl can be substituted or unsubstituted. The heteroaryl ring may be fused to an aryl, heterocyclyl or cycloalkyl ring, wherein the ring connected to the parent structure is a heteroaryl ring. Non-limiting examples include but are not limited to:

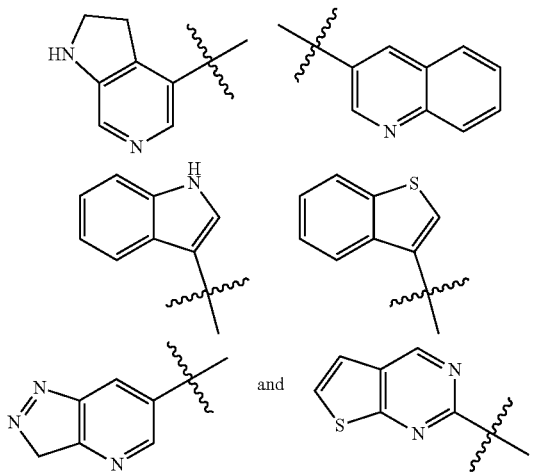

"Alkoxy" refers to a group of (alkyl-O—), wherein alkyl is as defined herein. $C_1$-$C_6$ or $C_1$-$C_4$ alkoxy is preferred. Examples thereof include, but are not limited to: methoxy, ethoxy, n-propoxy, isopropoxy, n-butoxy, isobutoxy, tert-butoxy, etc.

"Aryloxy" refers to a group of (aryl-O—), wherein aryl is as defined herein. $C_6$-$C_{10}$ aryloxy is preferred. Examples thereof include, but are not limited to: phenoxy, naphthoxy, etc; most preferably, phenoxy.

"Hydroxy" refers to —OH.

"Halogen" refers to fluorine, chlorine, bromine or iodine.

"Amino" refers to —$NH_2$.

"Cyano" refers to —CN.

"Nitro" refers to —$NO_2$.

"Benzyl" refers to —$CH_2$-phenyl or "Bn".

"Carboxy" refers to —C(O)OH.

"Carboxylate ester group" refers to —C(O)O-alkyl or —C(O)O-cycloalkyl, wherein the definitions of alkyl and cycloalkyl are as described above.

"DMSO" refers to dimethyl sulfoxide.

"BOC" means tert-butoxycarbonyl.

"Substituted" means one or more hydrogen atoms, preferably up to 5, and more preferably 1 to 3 hydrogen atoms in the group are independently substituted by a corresponding number of substituents. It goes without saying that the substituents are only in their possible chemical positions, and those skilled in the art can determine (by experiment or theory) possible or impossible substitutions without too much effort. For example, amino or hydroxyl with free hydrogen may be unstable when combined with a carbon atom with an unsaturated (eg, olefinic) bond.

"Substitution" or "substituted" mentioned in this specification, unless otherwise specified, means that the group can be substituted by one or more groups selected from alkyl, alkenyl, alkynyl, alkoxy, alkylthio, alkylamino, halogen, mercapto, hydroxyl, nitro, cyano, cycloalkyl, heterocyclyl, aryl, heteroaryl, cycloalkoxy, heterocycloalkoxy, cycloalkylthio, heterocycloalkylthio, amino, haloalkyl, hydroxyalkyl, carboxyl, carboxylate group, =O, —C(O)$R^6$, —C(O)O$R^6$, —OC(O)$R^6$, —N$R^7R^8$, —C(O)N$R^7R^8$, —S(O)$_n$N$R^7R^8$ and —N$R^7$C(O)$R^8$;

$R^6$, $R^7$ and $R^8$ are each independently selected from hydrogen, hydroxyl, halogen, nitro, cyano, alkyl, alkoxy, cycloalkyl, heterocyclyl, aryl and heteroaryl, wherein the alkyl, alkoxy, cycloalkyl, heterocyclyl, aryl or heteroaryl is optionally further substituted by one or more groups selected from hydroxyl, halogen, nitro, cyano, alkyl, alkoxy, cycloalkyl, heterocyclyl, aryl, heteroaryl, —C(O)$R^9$, —C(O)O$R^9$, —OC(O)$R^9$, —N$R^{10}R^{11}$, —C(O)N$R^{10}R^{11}$, —S(O)$_n$N$R^{10}R^{11}$ and —N$R^{10}$C(O)$R''$;

Alternatively, $R^7$ and $R^8$ together with the N to which they are connected form a 4 to 8-membered heterocyclyl, wherein the 4 to 8-membered heterocyclyl contains one or more N, O or S(O)$_n$, and the 4 to 8-membered heterocyclyl is optionally further substituted by one or more groups selected from hydroxyl, halogen, nitro, cyano, alkyl, alkoxy, cycloalkyl, heterocyclyl, aryl, heteroaryl, =O, —C(O)$R^9$, —C(O)O$R^9$, —OC(O)$R^9$, —N$R^{10}R^{11}$, —C(O)N$R^{10}R^{11}$, —S(O)$_n$N$R^{10}R^{11}$ and —N$R^{10}$C(O)$R''$;

$R^9$, $R^{10}$ and $R^{11}$ are each independently selected from hydrogen, alkyl, cycloalkyl, heterocyclyl, aryl and heteroaryl, wherein the alkyl, cycloalkyl, heterocyclyl, aryl or heteroaryl is optionally further substituted by one or more groups selected from hydroxyl, halogen, nitro, cyano, alkyl, alkoxy, cycloalkyl, heterocyclyl, aryl, heteroaryl, carboxyl or carboxylate group;

n is selected from 0, 1 and 2.

"Pharmaceutically acceptable salts" refer to certain salts of the above compounds that can maintain the original biological activity and are suitable for medical use. The pharmaceutically acceptable salt of the compound represented by formula (I) may be a metal salt or an amine salt formed with a suitable acid.

"Pharmaceutical composition" means a mixture containing one or more of the compounds described herein or their physiologically pharmaceutically acceptable salts or prodrugs and other chemical components, and other components such as physiologically pharmaceutically acceptable carriers and excipients. The purpose of the pharmaceutical composition is to promote the administration to an organism, facilitate the absorption of the active ingredients and then exert the biological activity.

Synthetic Method of the Compound of the Present Disclosure

In order to accomplish the purpose of the present disclosure, the following technical solutions are adopted:

The prevention provides a preparation method of the compound of general formula (III) or a stereoisomer, a tautomer, or a pharmaceutically acceptable salt thereof, comprising the following steps:

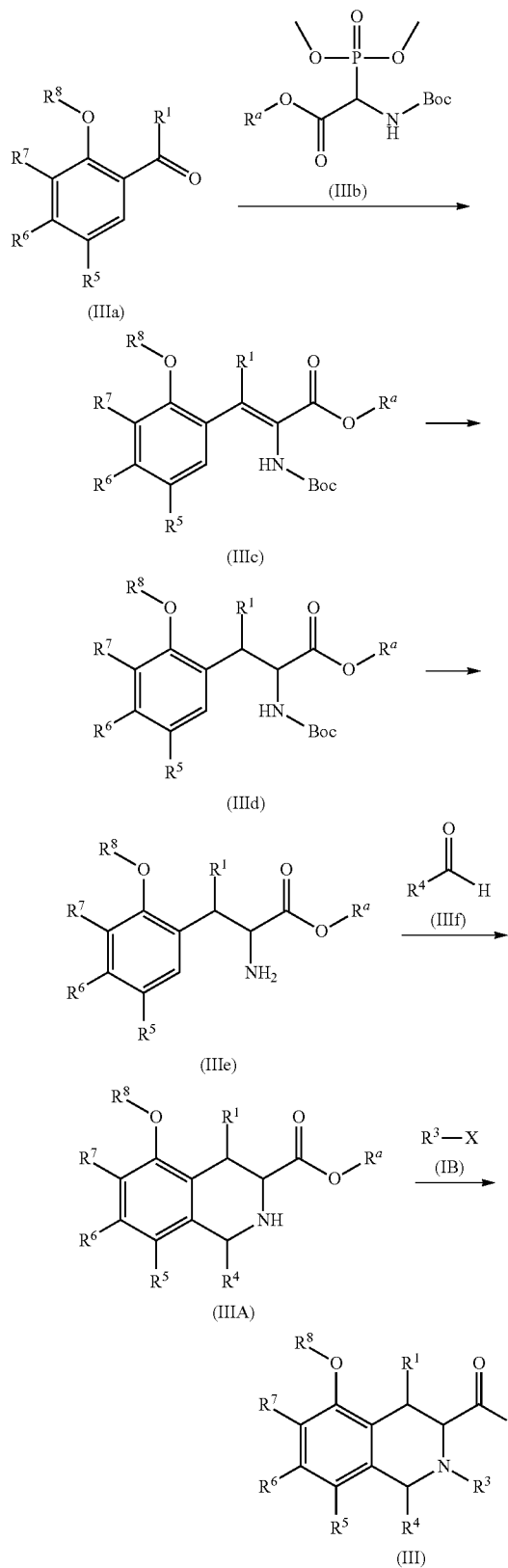

reacting a compound of general formula (IIIa) with a compound of general formula (IIIb) to obtain a compound of general formula (IIIc); reducing the double bond of the compound of general formula (IIIc) to obtain a compound of general formula (IIId); removing the amino protective group of the compound of general formula (IIId) to obtain a compound of general formula (IIIe); reacting the compound of general formula (IIIe) with a compound of general formula (IIIf) to obtain a compound of general formula (IIIA);

when $R^a$ is an alkyl, reacting a compound of general formula (IIIA) or a salt thereof with a compound of general formula (IB), and optionally further removing the protective group, to obtain a compound of general formula (III) in which $R^a$ is an alkyl;

optionally further performing a hydrolysis reaction of the compound of general formula (III) in which $R^a$ is an alkyl to obtain a compound of general formula (III) in which $R^a$ is hydrogen;

wherein:

X is selected from hydrogen and a leaving group, wherein the leaving group is preferably halogen, more preferably chlorine or bromine; and $R^1$ and $R^3$ to $R^8$ are as defined in the general formula (III).

The prevention provides a preparation method of the compound of general formula (III) or a stereoisomer, a tautomer, or a pharmaceutically acceptable salt thereof, comprising the following steps:

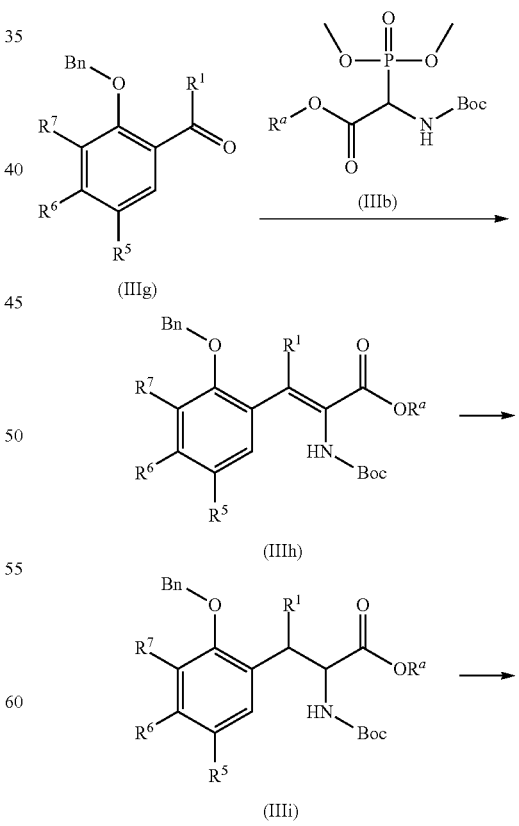

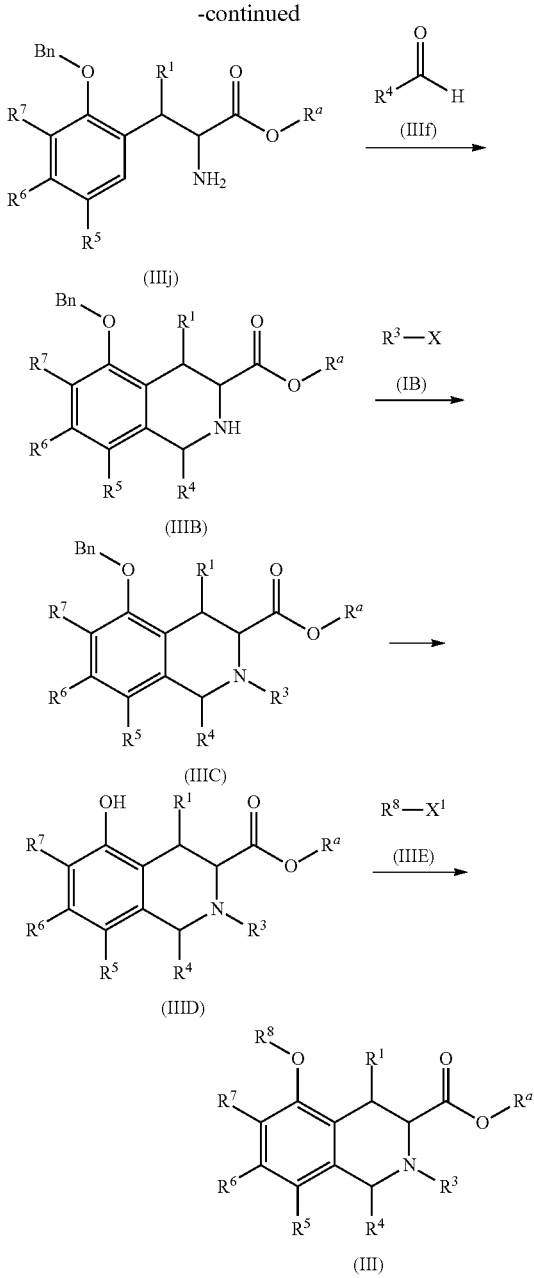

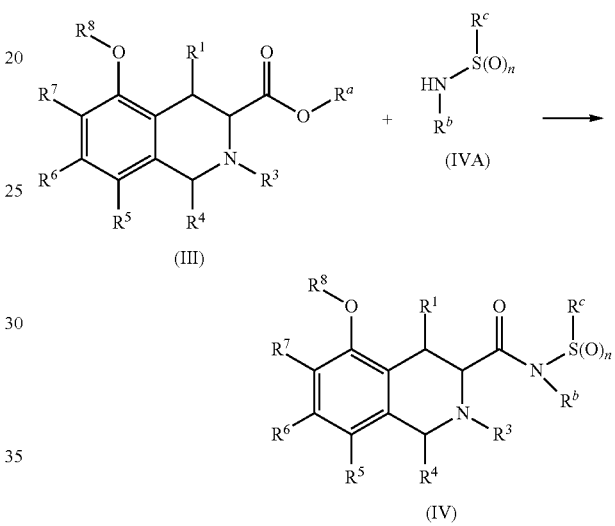

reacting a compound of general formula (IIIg) with a compound of general formula (IIIb) to obtain a compound of general formula (IIIh); reducing the double bond of the compound of general formula (IIIh) to obtain a compound of general formula (IIIi); removing the amino protective group of the compound of general formula (IIIi) to obtain a compound of general formula (IIIj); reacting the compound of general formula (IIIj) with a compound of general formula (IIIf) to obtain a compound of general formula (IIIB); reacting the compound of general formula (IIIB) or a salt thereof with a compound of general formula (IB) to obtain a compound of general formula (IIIC); removing the amino protective group of the compound of general formula (IIIC) to obtain a compound of general formula (IIID).

when $R^a$ is an alkyl, reacting a compound of general formula (IIID) with a compound of general formula (IIIE), to obtain a compound of general formula (III) in which $R^a$ is an alkyl;

optionally further performing a hydrolysis reaction of the compound of general formula (III) in which $R^a$ is an alkyl to obtain a compound of general formula (III) in which $R^a$ is hydrogen;

wherein:

X is selected from hydrogen and a leaving group, wherein the leaving group is preferably halogen, more preferably chlorine or bromine; $X^1$ is a leaving group, preferably chlorine or hydroxy; and $R^1$ and $R^3$ to $R^8$ are as defined in the general formula (III).

The prevention provides a preparation method of the compound of general formula (IV) or a stereoisomer, a tautomer, or a pharmaceutically acceptable salt thereof, comprising the following steps:

reacting a compound of general formula (III) with a compound of general formula (IVA) to obtain a compound of general formula (IV);

wherein:

$R^a$ is hydrogen;

$R^1$, $R^3$ to $R^8$, $R^b$, $R^c$ and n are as defined in the general formula (IV).

The prevention provides a preparation method of the compound of general formula (V) or a stereoisomer, a tautomer, or a pharmaceutically acceptable salt thereof, comprising the following steps:

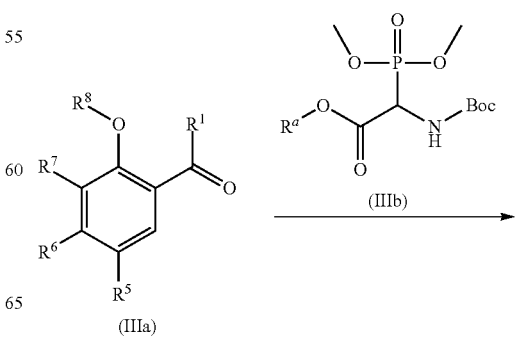

71

-continued

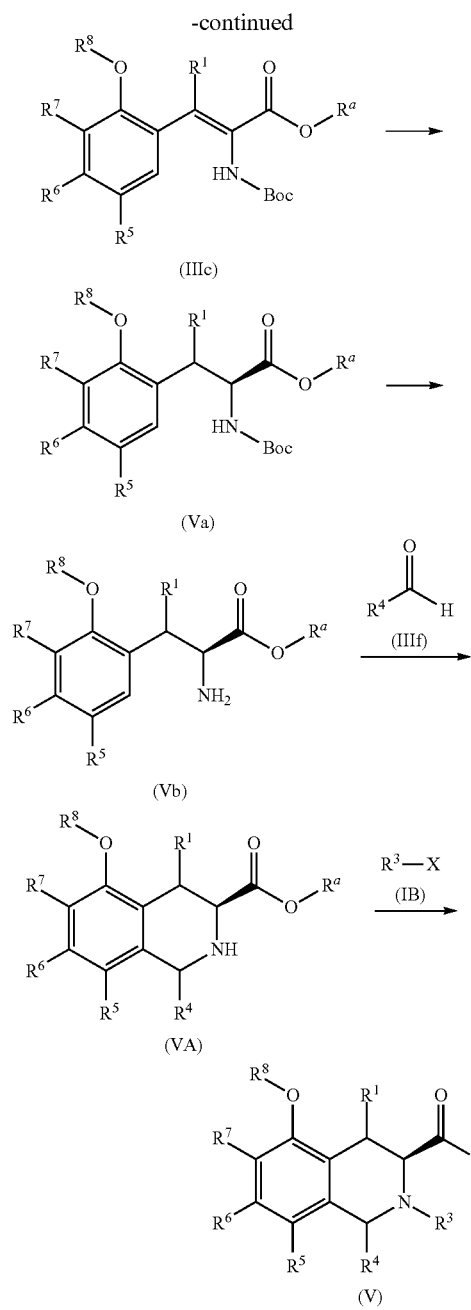

(IIIc)

(Va)

(Vb)

(VA)

(V)

reacting a compound of general formula (IIIa) with a compound of general formula (IIIb) to obtain a compound of general formula (IIIc); performing a chiral reduction of the double bond of the compound of general formula (IIIc) to obtain a compound of general formula (Va); removing the amino protective group of the compound of general formula (Va) to obtain a compound of general formula (Vb); reacting the compound of general formula (Vb) with a compound of general formula (IIIf) to obtain a compound of general formula (VA);

when $R^a$ is an alkyl, reacting a compound of general formula (VA) or a salt thereof with a compound of general formula (IB), and optionally further removing the protective group, to obtain a compound of general formula (V) in which $R^a$ is an alkyl;

72 optionally further performing a hydrolysis reaction of the compound of general formula (V) in which $R^a$ is an alkyl to obtain a compound of general formula (V) in which $R^a$ is hydrogen;

wherein:

X is selected from hydrogen and a leaving group, wherein the leaving group is preferably halogen, more preferably chlorine or bromine; and $R^1$ and $R^3$ to $R^8$ are as defined in the general formula (V).

The prevention provides a preparation method of the compound of general formula (V) or a stereoisomer, a tautomer, or a pharmaceutically acceptable salt thereof, comprising the following steps:

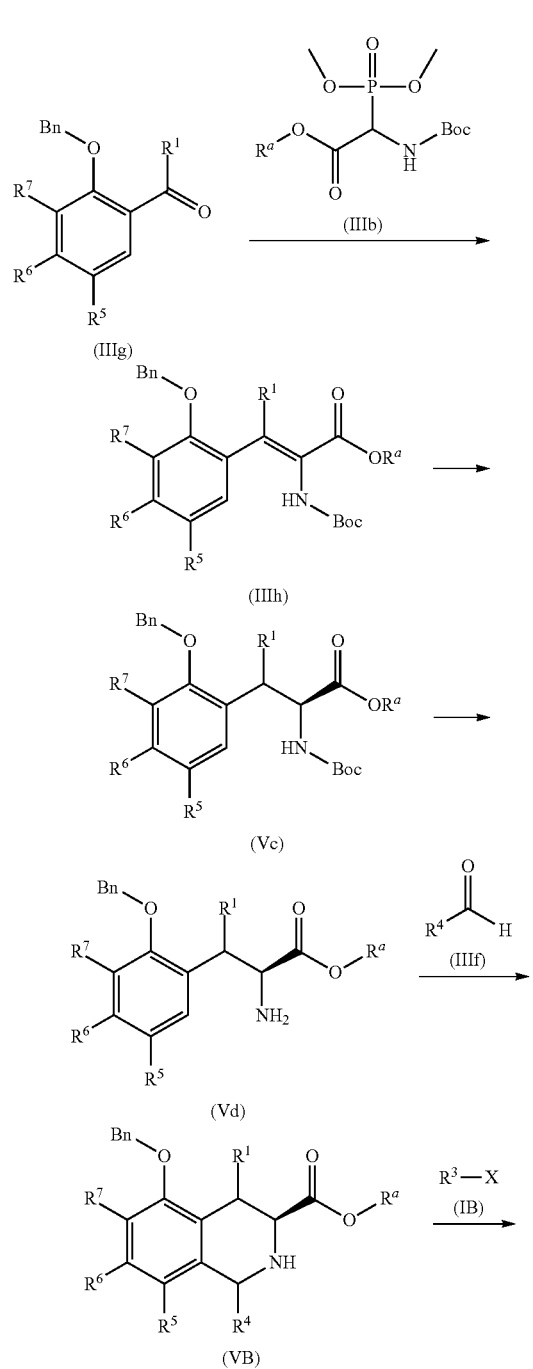

(IIIg)

(IIIh)

(Vc)

(Vd)

(VB)

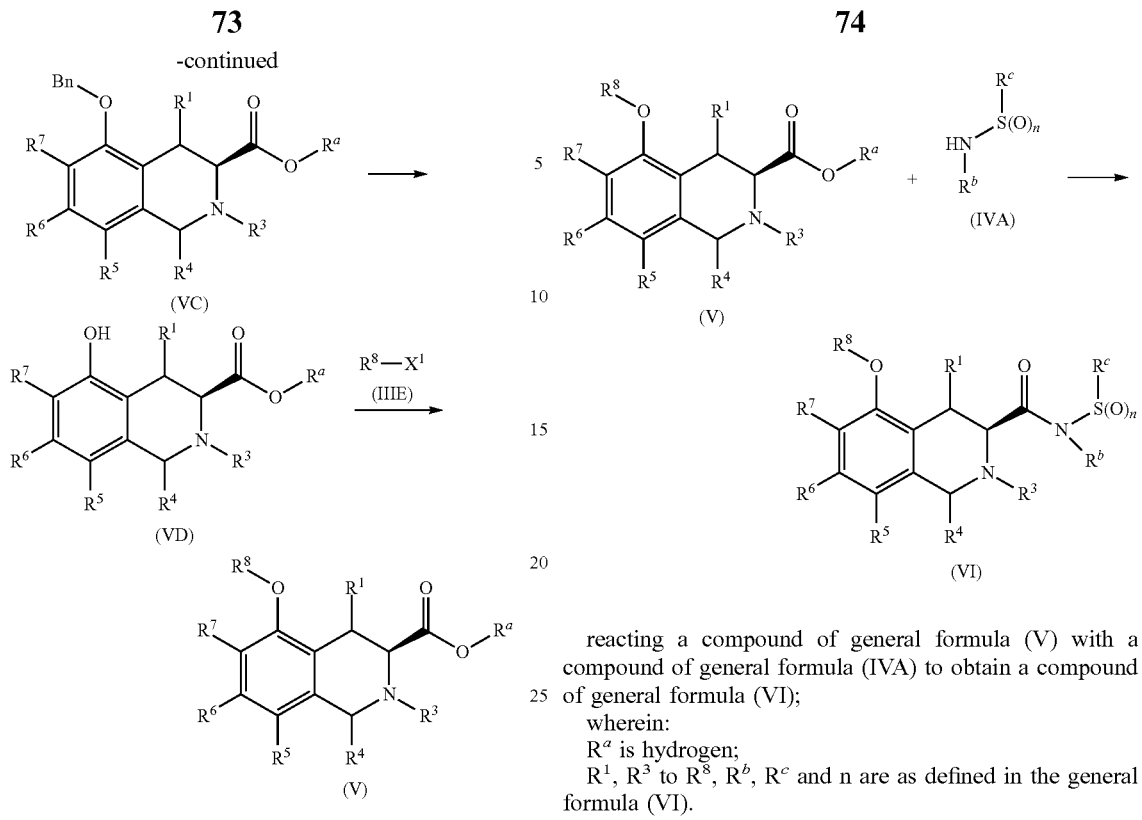

(VC)

(VD)

(V)

(IVA)

(V)

(VI)

reacting a compound of general formula (IIIg) with a compound of general formula (IIIb) to obtain a compound of general formula (IIIh); performing a chiral reduction of the double bond of the compound of general formula (IIIh) to obtain a compound of general formula (Vc); removing the amino protective group of the compound of general formula (Vc) to obtain a compound of general formula (Vd); reacting the compound of general formula (Vd) with a compound of general formula (IIIf) to obtain a compound of general formula (VB); reacting the compound of general formula (VB) or a salt thereof with a compound of general formula (IB) to obtain a compound of general formula (VC); removing the benzyl protective group of the compound of general formula (VC) to obtain a compound of general formula (VD);

when $R^a$ is an alkyl, reacting a compound of general formula (VD) with a compound of general formula (IIIE), to obtain a compound of general formula (V) in which $R^a$ is an alkyl;

optionally further performing a hydrolysis reaction of the compound of general formula (V) in which $R^a$ is an alkyl to obtain a compound of general formula (V) in which $R^a$ is hydrogen;

wherein:

X is selected from hydrogen and a leaving group, wherein the leaving group is preferably halogen, more preferably chlorine or bromine; $X^1$ is a leaving group and preferably chlorine or bromine; and $R^1$ and $R^3$ to $R^8$ are as defined in the general formula (V).

The prevention provides a preparation method of the compound of general formula (VI) or a stereoisomer, a tautomer, or a pharmaceutically acceptable salt thereof, comprising the following steps:

reacting a compound of general formula (V) with a compound of general formula (IVA) to obtain a compound of general formula (VI);

wherein:

$R^a$ is hydrogen;

$R^1$, $R^3$ to $R^8$, $R^b$, $R^c$ and n are as defined in the general formula (VI).

DETAILED DESCRIPTION

The present disclosure will be further described in detail in conjunction with examples, but these examples do not limit the scope of the present disclosure.

The examples provide the preparation of representative compounds represented by formula (I) and related structural identification data. It should be noted that the following examples are intended to illustrate the disclosure and not to limit the disclosure. The $^1$H NMR spectrum was measured with a Bruker instrument (400 MHz) and the chemical shift was expressed in ppm. The internal standard of tetramethylsilane (0.00 ppm) was used. $^1$H NMR representation: s=singlet, d=doublet, t=triplet, q=quartet, m=multiplet, br=broadened, dd=doublet of the doublet, dt=doublet of the triplet. If a coupling constant is provided, its unit is Hz.

Mass spectrum was tested by LC/MS equipment. The method of ionization may be ESI or APCI.

The thin layer chromatography silica gel plates were Yantai Yellow Sea HSGF254 or Qingdao GF254 silica gel plate. The silica gel plate used for thin layer chromatography (TLC) is 0.15 mm-0.2 mm, and the thin layer chromatography separation and purification product used is 0.4 mm-0.5 mm.

Column chromatography generally uses 200-300 meshes Yantai Huanghai silica gel as the carrier.

In the following examples, unless otherwise indicated, all temperatures are degrees Celsius. Unless otherwise indicated, the various starting materials and reagents are either commercially available or synthesized according to known methods, and commercially available starting materials and reagents are used without further purification. Unless otherwise indicated, commercial manufacturers include, but are not limited to, Aldrich Chemical Company, ABCR GmbH & Co. KG, Acros Organics, Guangzan Chemical Technology Co., Ltd. and Jingyan Chemical Technology Co., Ltd., etc.

$CD_3OD$: deuterated methanol.

CDCl₃: deuterated chloroform.

DMSO-d6: deuterated dimethyl sulfoxide.

Argon atmosphere indicates that the reaction flask is connected to an argon balloon with a volume of about 1 L.

In the examples, unless otherwise indicated, the solution in the reaction is aqueous solution.

The compounds are purified by silica gel column chromatography and thin layer chromatography, wherein the eluent or developing solvents are selected from A: petroleum ether and ethyl acetate system; B: dichloromethane and methanol system; and C: dichloromethane and ethyl acetate system; D: acetonitrile, water and trifluoroacetic acid system; and wherein the volume ratio of solvent depends on the polarity of compound, and may be adjusted by adding a small amount of acid or basic reagents such as acetic acid or triethylamine.

Example 1

2-(benzo[d]oxazol-2-yl)-5-(benzyloxy)-6-methoxy-1,2,3,4-tetrahydroisoquinoline-3-carboxylic acid

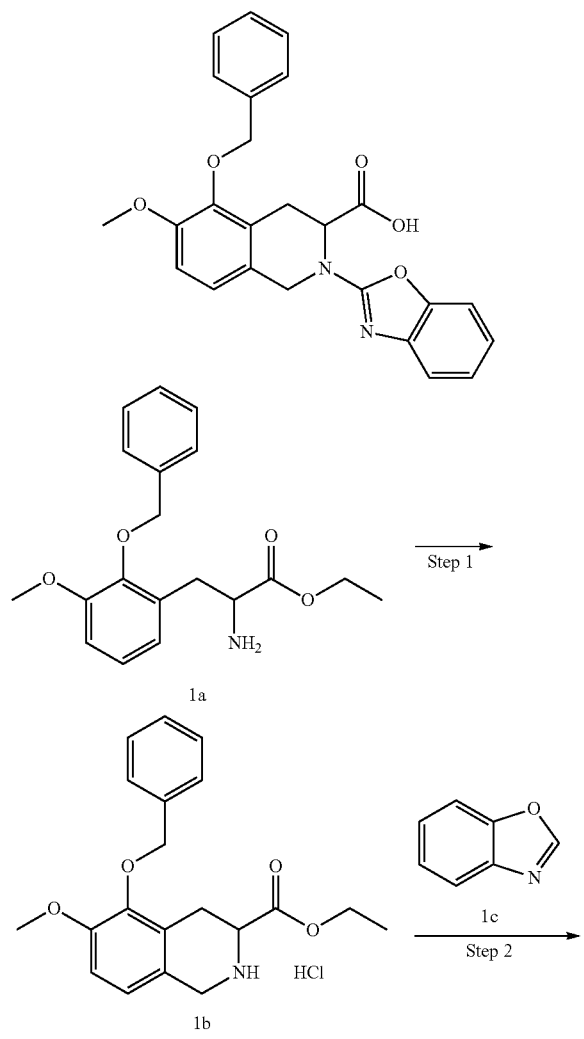

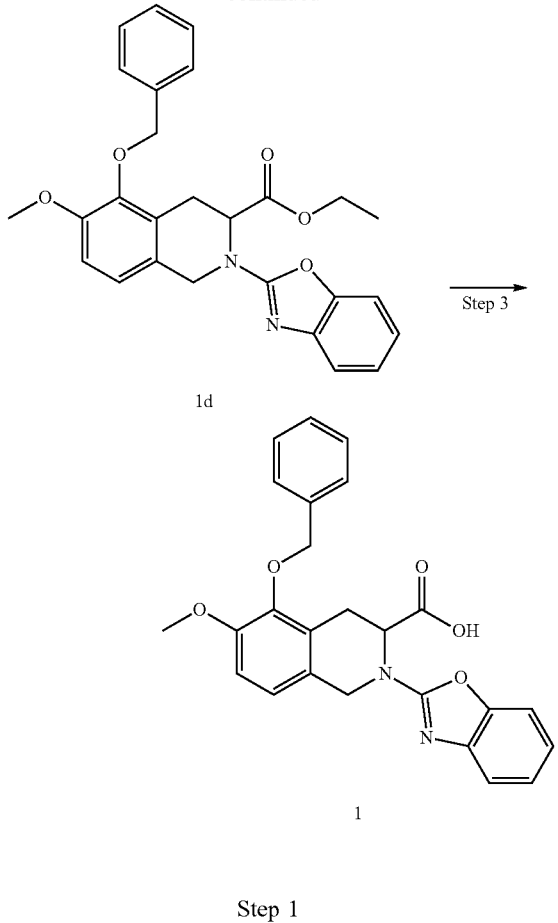

Step 1

Ethyl 5-(benzyloxy)-6-methoxy-1,2,3,4-tetrahydroisoquinoline-3-carboxylate hydrochloride Ethyl 2-amino-3-(2-(benzyloxy)-3-methoxyphenyl)propionate 1a (20.5 g, 62.2 mmol, prepared according to patent publication WO 2017036318) was dissolved in 2N dilute hydrochloric acid (250 mL), and the resultant mixture was bubbled with argon gas for three times. After stirring at room temperature for 30 minutes, aqueous formaldehyde solution (50 mL, 622 mmol, 37 wt. %) and tetrahydrofuran (5 mL) were added in sequence, and the mixture was bubbled with argon gas for 3 times again, and reacted overnight at room temperature. After the reaction was completed, acetonitrile was added to the reaction solution, and the mixture was concentrated under reduced pressure for several times, to obtain ethyl 5-(benzyloxy)-6-methoxy-1,2,3,4-tetrahydroisoquinoline-3-carboxylate hydrochloride 1b (21 g, white solid), yield: 91%.

MS m/z(ESI): 342.0 [M+1]

Step 2

Ethyl 2-(benzo[d]oxazol-2-yl)-5-(benzyloxy)-6-methoxy-1,2,3,4-tetrahydroisoquinoline-3-carboxylate Under protection of argon gas, ethyl 5-(benzyloxy)-6-methoxy-1,2,3,4-tetrahydroisoquinoline-3-carboxylate hydrochloride 1b (754 mg, 2.0 mmol), benzoxazole 1c (285 mg, 2.4 mmol), silver carbonate (660 mg, 2.4 mmol) and benzoic acid (448 mg, 4.0 mmol) were dissolved in 10 mL of acetonitrile and the mixture was reacted at 60° C. for 8 hours. After the reaction was completed, the reaction solution was filtered with celite, the filter cake was washed with ethyl acetate (5 mL), and the filtrate was concentrated under reduced pressure. The residue obtained was purified by silica gel column chromatography (eluent: system A) to obtain ethyl 2-(benzo[d]oxazol-2-yl)-5-(benzyloxy)-6-methoxy-1, 2,3,4-tetrahydroisoquinoline-3-carboxylate 1d (120 mg), yield: 13%.

MS m/z(ESI): 458.9 [M+1]

$^1$H NMR (400 MHz, CDCl$_3$) δ 7.50-7.29 (m, 7H), 7.19 (t, J=7.6 Hz, 1H), 7.05 (t, J=7.8 Hz, 1H), 6.94 (d, J=8.4 Hz, 1H), 6.86 (d, J=8.0 Hz, 1H), 5.20 (d, J=3.2 Hz, 1H), 5.05 (d, J=10.4 Hz, 1H), 4.96-4.91 (m, 2H), 4.80 (d, J=15.6 Hz, 1H), 4.13-4.00 (m, 2H), 3.87 (s, 3H), 3.65 (d, J=16.4 Hz, 1H), 2.94 (dd, J=16.4, 6.0 Hz, 1H), 1.10 (t, J=7.0 Hz, 3H).

Step 3

2-(Benzo[d]oxazol-2-yl)-5-(benzyloxy)-6-methoxy-1,2,3,4-tetrahydroisoquinoline-3-carboxylic acid Ethyl 2-(benzo[d]oxazol-2-yl)-5-(benzyloxy)-6-methoxy-1,2,3,4-tetrahydroisoquinoline-3-carboxylate 1d (120 mg, 0.26 mmol) was dissolved in 5 mL of a mixed solvent of tetrahydrofuran and methanol (V:V=3:2), and 1N sodium hydroxide solution (1.5 mL) was added dropwise, and the mixture was reacted at room temperature for 2 hours. After the reaction was completed, the reaction solution was concentrated under reduced pressure, 6 mL of water was added to the residue, the pH of the solution was adjusted to pH=7 with 1N dilute hydrochloric acid, the solid was precipitated, the solution was filtered, and the filter cake was washed with water (3 mL), and dried, to obtain 2-(benzo[d]oxazol-2-yl)-5-(benzyloxy)-6-methoxy-1,2,3,4-tetrahydroisoquinoline-3-carboxylic acid 1 (90 mg), yield: 81%.

MS m/z(ESI): 430.9 [M+1]

$^1$H NMR (400 MHz, DMSO-d$_6$) δ 13.05 (s, 1H), 7.49-7.34 (m, 7H), 7.19 (t, J=7.6 Hz, 1H), 7.08-7.00 (m, 3H), 5.11 (d, J=3.6 Hz, 1H), 4.98 (d, J=10.8 Hz, 1H), 4.86 (d, J=10.8 Hz, 1H), 4.80 (d, J=15.6 Hz, 1H), 4.68 (d, J=15.6 Hz, 1H), 3.84 (s, 3H), 3.52 (d, J=16.4 Hz, 1H), 2.99 (dd, J=16.4, 5.8 Hz, 1H).

Example 2

2-(1H-Benzo[d]imidazol-2-yl)-5-(benzyloxy)-6-methoxy-1,2,3,4-tetrahydroisoquinoline-3-carboxylic acid

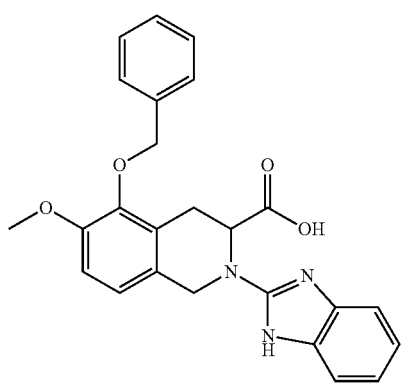

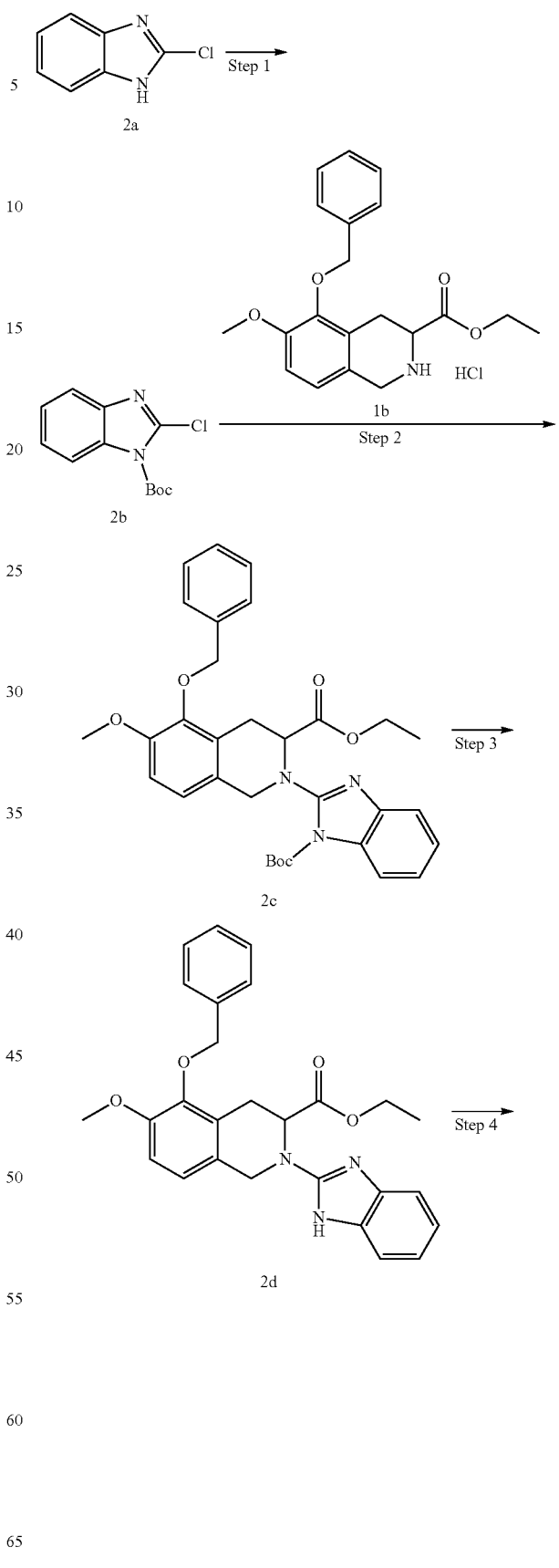

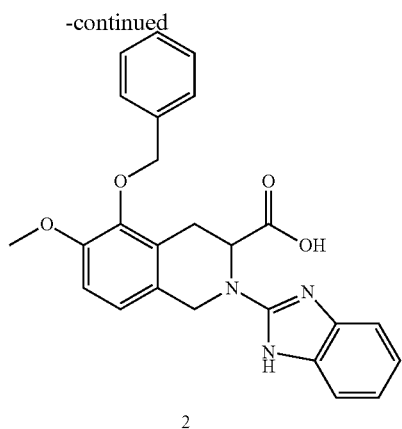

2

Step 1

Tert-butyl 2-chloro-1H-benzo[d]imidazole-1-carboxylate

2-Chloro-1H-benzo[d]imidazole 2a (1.52 g, 10 mmol) was dissolved in 45 mL of acetonitrile, and the mixture was cooled to 0° C. Di-tert-butyl dicarbonate (2.4 g, 11 mmol) 4-dimethylaminopyridine (122 mg, 1.0 mmol) were added in sequence, the reaction solution was naturally warmed to room temperature, and the reaction was continued at room temperature for 3 hours. After the reaction was completed, 50 mL of water was added, the mixture was concentrated under reduced pressure to remove acetonitrile. A solid was precipitated, the solution was filtered, and the filter cake was washed with water (10 mL). The filter cake was dissolved in ethyl acetate (120 mL), and washed with water (50 mL) and saturated brine (50 mL), dried over anhydrous sodium sulfate, filtered, and concentrated under reduced pressure to obtain tert-butyl 2-chloro-1H-benzo[d]imidazole-1-carboxylate 2b (2.5 g, colourless solid), yield: 99%.

MS m/z(ESI): 196.9 [M−55]

Step 2

Ethyl 5-(benzyloxy)-2-(1-(tert-butyloxycarbonyl)-1H-benzo[d]imidazol-2-yl)-6-methoxy-1,2,3,4-tetrahydroisoquinoline-3-carboxylate Ethyl 5-(benzyloxy)-6-methoxy-1,2,3,4-tetrahydroisoquinoline-3-carboxylate hydrochloride 1b (863 mg, 2.29 mmol) was added to 22 mL acetonitrile. Tert-butyl 2-chloro-1H-benzo[d]imidazole-1-carboxylate 2b (686 mg, 2.7 mmol) and N,N-diisopropylethylamine (1.12 mL, 6.8 mmol) were added, and the mixture was reacted under reflux for 8 hours. The reaction solution was cooled to room temperature, concentrated under reduced pressure, and the obtained residue was purified by silica gel column chromatography (eluent: system A) to obtain ethyl 5-(benzyloxy)-2-(1-(tert-butyloxycarbonyl)-1H-benzo[d]imidazol-2-yl)-6-methoxy-1,2,3,4-tetrahydroisoquinoline-3-carboxylate 2c (470 mg, foamy solid), yield: 37%.

MS m/z(ESI): 557.9 [M+1]

Step 3

Ethyl 2-(1H-benzo[d]imidazol-2-yl)-5-(benzyloxy)-6-methoxy-1,2,3,4-tetrahydroisoquinoline-3-carboxylate 1 mL of trifluoroacetic acid was dissolved in 2 mL of dichloromethane, and the mixture was cooled to 0° C. Ethyl 5-(benzyloxy)-2-(1-(tert-butyloxycarbonyl)-1H-benzo[d] imidazol-2-yl)-6-methoxy-1,2,3,4-tetrahydroisoquinoline-3-carboxylate 2c (470 mg, 0.84 mmol) was added, and the mixture was reacted at room temperature for 3 hours. After the reaction was completed, the reaction solution was concentrated under reduced pressure, and 30 mL of dichloromethane was added. The resulting mixture was washed with saturated sodium bicarbonate solution (20 mL) and saturated brine (20 mL) in sequence, dried with anhydrous sodium sulfate, filtered, and concentrated under reduced pressure. The obtained residue was purified by thin layer chromatography (developing solvent: System A) to obtain ethyl 2-(1H-benzo[d]imidazol-2-yl)-5-(benzyloxy)-6-methoxy-1,2,3,4-tetrahydroisoquinoline-3-carboxylate 2d (350 mg), yield: 91%.

MS m/z(ESI): 457.9 [M+1]

Step 4

2-(1H-Benzo[d]imidazol-2-yl)-5-(benzyloxy)-6-methoxy-1,2,3,4-tetrahydroisoquinoline-3-carboxylic acid Ethyl 2-(1H-benzo[d]imidazol-2-yl)-5-(benzyloxy)-6-methoxy-1,2,3,4-tetrahydroisoquinoline-3-carboxylate 2d (60 mg, 0.13 mmol) was dissolved in 1.5 mL of tetrahydrofuran, and 1N sodium hydroxide solution (0.8 mL) was added dropwise, and the resulting mixture was reacted at room temperature for 2.5 hours. After the reaction was completed, the reaction solution was concentrated under reduced pressure, 6 mL of water was added to the residue, the pH of the solution was adjusted to pH=7 with 1N dilute hydrochloric acid, the solid was precipitated, the solution was filtered, and the filter cake was washed with water (2 mL), and dried, to obtain 2-(1H-benzo[d]imidazol-2-yl)-5-(benzyloxy)-6-methoxy-1,2,3,4-tetrahydroisoquinoline-3-carboxylic acid 2 (20 mg), yield: 36%.

MS m/z(ESI): 429.9 [M+1]

Example 3

5-(Benzyloxy)-6-methoxy-2-(4-methylbenzo[d]oxazol-2-yl)-1,2,3,4-tetrahydroisoquinoline-3-carboxylic acid

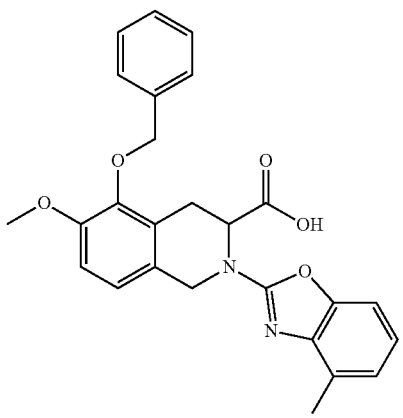

-continued

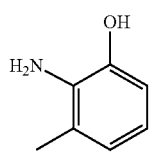

3a

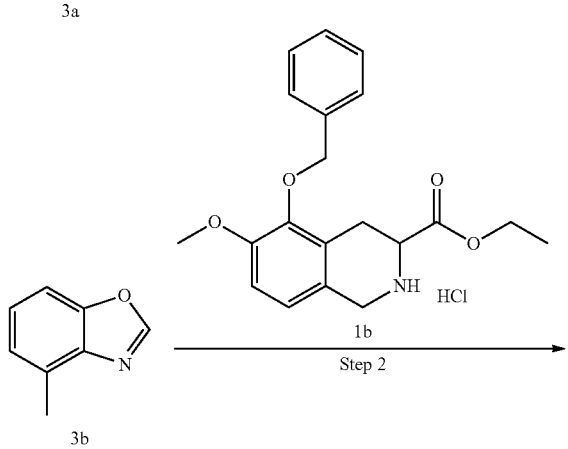

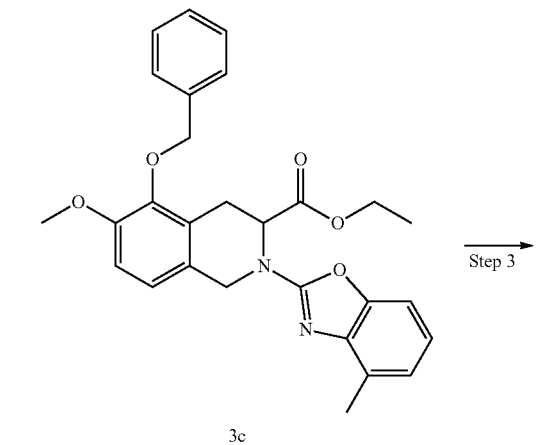

Step 1

4-Methylbenzo[d]oxazole

2-Amino-3-methylphenol 3a (615 mg, 5.0 mmol) was dissolved in 9 mL of triethyl orthocarboxylate and the mixture was reacted under reflux for 4 hours. After the reaction was completed, it was cooled to room temperature and concentrated under reduced pressure. The obtained residue was purified by silica gel column chromatography (eluent: system A) to obtain 4-methylbenzo[d]oxazole 3b (500 mg, red oily), yield: 75%.

Step 2

Ethyl 5-(benzyloxy)-6-methoxy-2-(4-methylbenzo[d]oxazol-2-yl)-1,2,3,4-tetrahydroisoquinoline-3-carboxylate Under protection of argon gas, ethyl 5-(benzyloxy)-6-methoxy-1,2,3,4-tetrahydroisoquinoline-3-carboxylate hydrochloride 1b (377 mg, 1.0 mmol), 4-methylbenzo[d]oxazole 3b (160 mg, 1.2 mmol), silver carbonate (330 mg, 1.2 mmol) and benzoic acid (224 mg, 2.0 mmol) were dissolved in 5 mL acetonitrile, and the mixture was reacted at 60° C. for 8 hours. After the reaction was completed, the reaction solution was filtered with celite, the filter cake was washed with ethyl acetate (5 mL), and the filtrate was concentrated under reduced pressure. The obtained residue was purified by silica gel column chromatography (eluent: system A) to obtain ethyl 5-(benzyloxy)-6-methoxy-2-(4-methylbenzo[d]oxazol-2-yl)-1,2,3,4-tetrahydroisoquinoline-3-carboxylate 3c (180 mg), yield: 38%.

MS m/z(ESI): 473.0 [M+1]

Step 3

5-(Benzyloxy)-6-methoxy-2-(4-methylbenzo[d]oxazol-2-yl)-1,2,3,4-tetrahydroisoquinoline-3-carboxylic acid Ethyl 5-(benzyloxy)-6-methoxy-2-(4-methylbenzo[d]oxazol-2-yl)-1,2,3,4-tetrahydroisoquinoline-3-carboxylate 3c (180 mg, 0.38 mmol) was dissolved in 4.5 mL of a mixed solvent of tetrahydrofuran and methanol (V:V=2:1), and 1N sodium hydroxide solution (1.5 mL) was added dropwise, and the resulting mixture was reacted at room temperature for 2 hours. After the reaction was completed, the reaction solution was concentrated under reduced pressure, 6 mL of water was added to the residue, the pH of the solution was adjusted to pH=7 with 1N dilute hydrochloric acid, the solid was precipitated, the solution was filtered, and the filter cake was washed with water (5 mL), and dried, to obtain 5-(benzyloxy)-6-methoxy-2-(4-methylbenzo[d]oxazol-2-yl)-1,2,3,4-tetrahydroisoquinoline-3-carboxylic acid 3 (27 mg), yield: 16%.

MS m/z(ESI): 444.9 [M+1]

$^1$H NMR (400 MHz, DMSO-$d_6$) δ 13.05 (s, 1H), 7.49-7.32 (m, 5H), 7.27 (d, J=8.4 Hz, 1H), 7.09 (d, J=8.4 Hz, 1H), 7.01 (d, J=7.6 Hz, 2H), 6.95 (t, J=8.0 Hz, 1H), 5.13 (d, J=4.0 Hz, 1H), 4.98 (d, J=10.8 Hz, 1H), 4.86 (d, J=10.8 Hz, 1H), 4.80 (d, J=16.0 Hz, 1H), 4.67 (d, J=15.2 Hz, 1H), 3.84 (s, 3H), 3.54 (d, J=16.8 Hz, 1H), 2.98 (dd, J=11.4, 6.4 Hz, 1H), 2.41 (s, 3H).

Example 4

5-(Benzyloxy)-6-methoxy-2-(5-methylbenzo[d]oxazol-2-yl)-1,2,3,4-tetrahydroisoquinoline-3-carboxylic acid

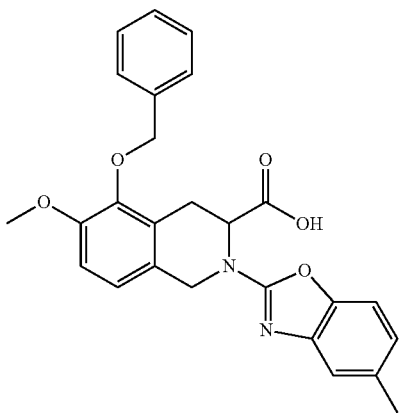

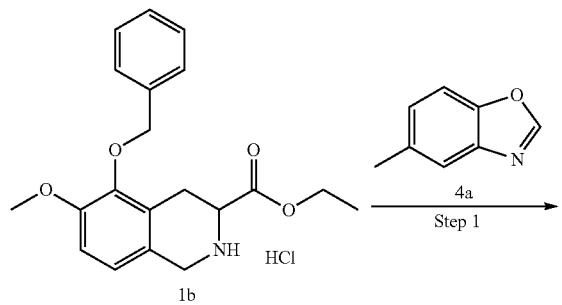

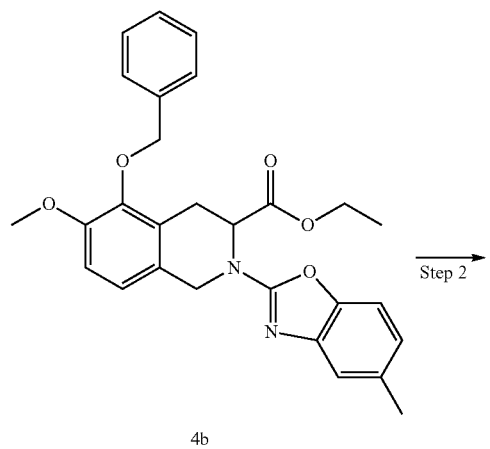

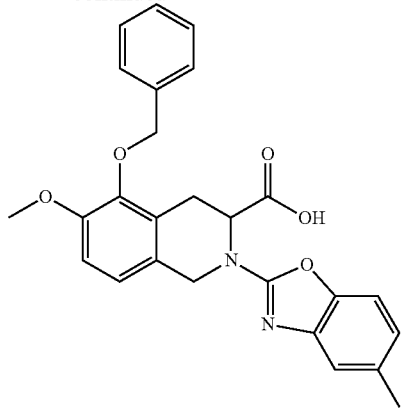

4

Step 1

Ethyl 5-(benzyloxy)-6-methoxy-2-(5-methylbenzo[d]oxazol-2-yl)-1,2,3,4-tetrahydroisoquinoline-3-carboxylate Under protection of argon gas, ethyl 5-(benzyloxy)-6-methoxy-1,2,3,4-tetrahydroisoquinoline-3-carboxylate hydrochloride 1b (377 mg, 1.0 mmol), 5-methylbenzo[d]oxazole 4a (160 mg, 1.2 mmol), silver carbonate (330 mg, 1.2 mmol) and benzoic acid (224 mg, 2.0 mmol) were dissolved in 5 mL acetonitrile, and the mixture was reacted at 60° C. for 8 hours. After the reaction was completed, the reaction solution was filtered with celite, the filter cake was washed with ethyl acetate (5 mL), and the filtrate was concentrated under reduced pressure. The obtained residue was purified by silica gel column chromatography (eluent: system A) to obtain ethyl 5-(benzyloxy)-6-methoxy-2-(5-methylbenzo[d]oxazol-2-yl)-1,2,3,4-tetrahydroisoquinoline-3-carboxylate 4b (230 mg), yield: 49%.

MS m/z(ESI): 473.0 [M+1]

Step 2

5-(Benzyloxy)-6-methoxy-2-(5-methylbenzo[d]oxazol-2-yl)-1,2,3,4-tetrahydroisoquinoline-3-carboxylic acid Ethyl 5-(benzyloxy)-6-methoxy-2-(5-methylbenzo[d]oxazol-2-yl)-1,2,3,4-tetrahydroisoquinoline-3-carboxylate 4b (230 mg, 0.48 mmol) was dissolved in 6 mL of a mixed solvent of tetrahydrofuran and methanol (V:V=2:1), and 1N sodium hydroxide solution (2.4 mL) was added dropwise, and the resulting mixture was reacted at room temperature for 2 hours. After the reaction was completed, the reaction solution was concentrated under reduced pressure, 10 mL of water was added to the residue, the pH of the solution was adjusted to pH=7 with 1N dilute hydrochloric acid, the solid was precipitated, the solution was filtered, and the filter cake was washed with water (5 mL), and dried, to obtain 5-(benzyloxy)-6-methoxy-2-(5-methylbenzo[d]oxazol-2-yl)-1,2,3,4-tetrahydroisoquinoline-3-carboxylic acid 4 (160 mg), yield: 36%.

MS m/z(ESI): 445.0 [M+1]

$^1$H NMR (400 MHz, DMSO-$d_6$) δ 12.99 (s, 1H), 7.48-7.31 (m, 6H), 7.15 (s, 1H), 7.06 (d, J=8.8 Hz, 1H), 7.01 (d,

J=8.4 Hz, 1H), 6.86 (d, J=8.0 Hz, 1H), 5.09 (d, J=4.4 Hz, 1H), 4.98 (d, J=11.2 Hz, 1H), 4.86 (d, J=11.2 Hz, 1H), 4.78 (d, J=16.0 Hz, 1H), 4.66 (d, J=16.0 Hz, 1H), 3.84 (s, 3H), 3.51 (d, J=16.4 Hz, 1H), 2.99 (dd, J=16.0, 6.4 Hz, 1H), 2.35 (s, 3H).

Example 5

5-(Benzyloxy)-6-methoxy-2-(6-methylbenzo[d]oxazol-2-yl)-1,2,3,4-tetrahydroisoquinoline-3-carboxylic acid

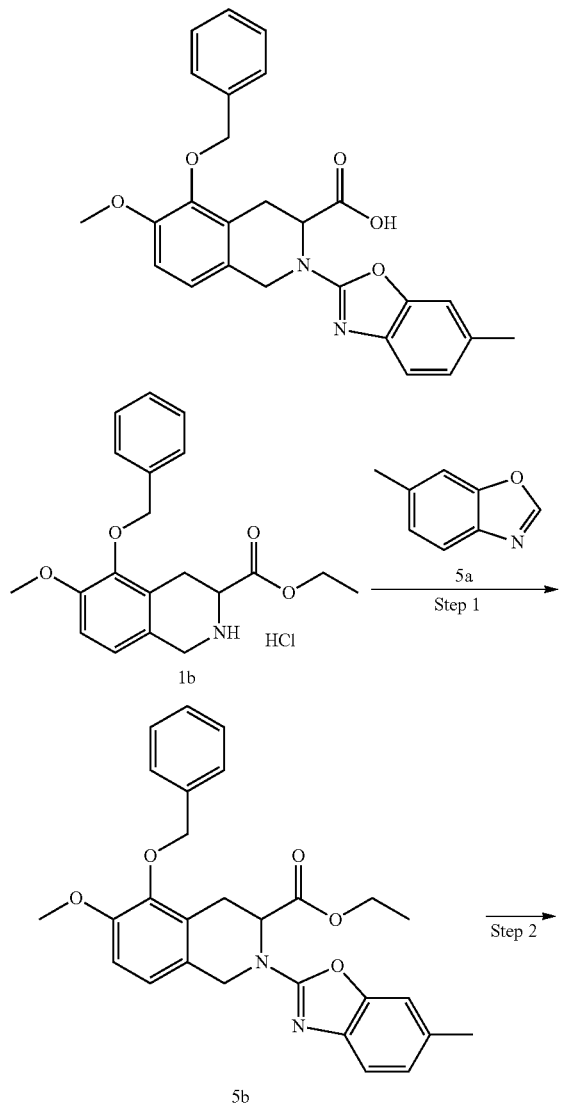

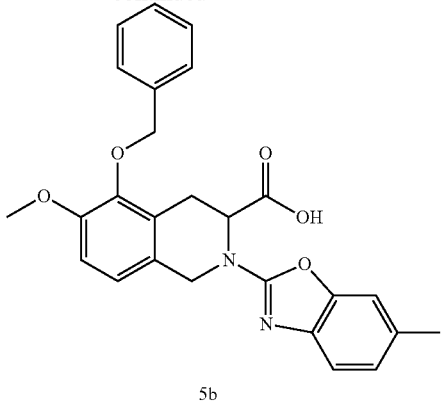

5b

Step 1

Ethyl 5-(benzyloxy)-6-methoxy-2-(6-methylbenzo[d]oxazol-2-yl)-1,2,3,4-tetrahydroisoquinoline-3-carboxylate Under protection of argon gas, ethyl 5-(benzyloxy)-6-methoxy-1,2,3,4-tetrahydroisoquinoline-3-carboxylate hydrochloride 1b (377 mg, 1.0 mmol), 6-methylbenzo[d]oxazole 5a (160 mg, 1.2 mmol), silver carbonate (330 mg, 1.2 mmol) and benzoic acid (224 mg, 2.0 mmol) were dissolved in 5 mL acetonitrile, and the mixture was reacted at 60° C. for 8 hours. After the reaction was completed, the reaction solution was filtered with celite, the filter cake was washed with ethyl acetate (5 mL), and the filtrate was concentrated under reduced pressure. The obtained residue was purified by silica gel column chromatography (eluent: system A) to obtain ethyl 5-(benzyloxy)-6-methoxy-2-(6-methylbenzo[d]oxazol-2-yl)-1,2,3,4-tetrahydroisoquinoline-3-carboxylate 5b (100 mg), yield: 21%.

MS m/z(ESI): 473.0 [M+1]

$^1$H NMR (400 MHz, CDCl$_3$) δ 7.48 (d, J=7.2 Hz, 2H), 7.41-7.31 (m, 4H), 7.12 (s, 1H), 7.02 (d, J=8.0 Hz, 1H), 6.95 (d, J=8.4 Hz, 1H), 6.87 (d, J=8.4 Hz, 1H), 5.18 (d, J=3.2 Hz, 1H), 5.05 (d, J=10.8 Hz, 1H), 4.96-4.90 (m, 2H), 4.79 (d, J=15.6 Hz, 1H), 4.13-4.01 (m, 2H), 3.88 (s, 3H), 3.64 (dd, J=16.2, 2.2 Hz, 1H), 2.94 (dd, J=16.4, 6.0 Hz, 1H), 2.41 (s, 3H), 1.11 (t, J=7.2 Hz, 3H).

Step 2

5-(Benzyloxy)-6-methoxy-2-(6-methylbenzo[d]oxazol-2-yl)-1,2,3,4-tetrahydroisoquinoline-3-carboxylic acid Ethyl 5-(benzyloxy)-6-methoxy-2-(6-methylbenzo[d]oxazol-2-yl)-1,2,3,4-tetrahydroisoquinoline-3-carboxylate 5b (100 mg, 0.21 mmol) was dissolved in 3 mL of a mixed solvent of tetrahydrofuran and methanol (V:V=2:1), and 1N sodium hydroxide solution (1 mL) was added dropwise, and the resulting mixture was reacted at room temperature for 3 hours. After the reaction was completed, the reaction solution was concentrated under reduced pressure, 5 mL of water was added to the residue, the pH of the solution was adjusted to pH=7 with 1N dilute hydrochloric acid, the solid was precipitated, the solution was filtered, and the filter cake was washed with water (3 mL), and dried, to obtain 5-(benzyloxy)-6-methoxy-2-(6-methylbenzo[d]oxazol-2-yl)-1,2,3,4-tetrahydroisoquinoline-3-carboxylic acid 5 (50 mg), yield: 54%.

MS m/z(ESI): 445.0 [M+1]

$^1$H NMR (400 MHz, DMSO-d$_6$) δ 13.00 (s, 1H), 7.49-7.36 (m, 5H), 7.28 (s, 1H), 7.22 (d, J=7.6 Hz, 1H), 7.07-7.00 (m, 3H), 5.08 (d, J=4.8 Hz, 1H), 4.98 (d, J=11.2 Hz, 1H), 4.86 (d, J=11.2 Hz, 1H), 4.78 (d, J=15.2 Hz, 1H), 4.65 (d, J=15.2 Hz, 1H), 3.84 (s, 3H), 3.51 (d, J=16.0 Hz, 1H), 2.98 (dd, J=16.8, 6.8 Hz, 1H), 2.36 (s, 3H).

Example 6

5-(Benzyloxy)-6-methoxy-2-(7-methylbenzo[d]oxazol-2-yl)-1,2,3,4-tetrahydroisoquinoline-3-carboxylic acid

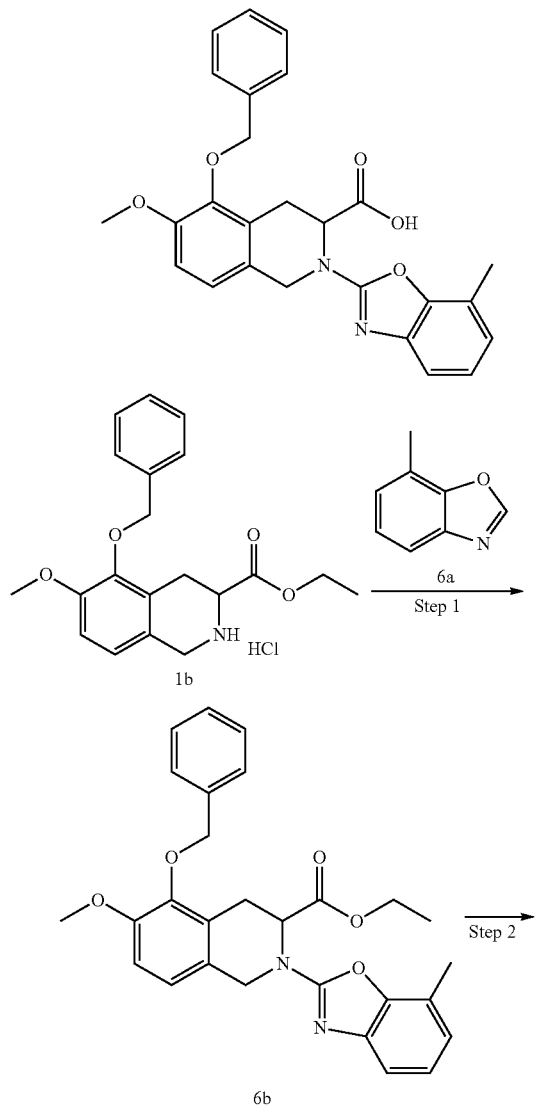

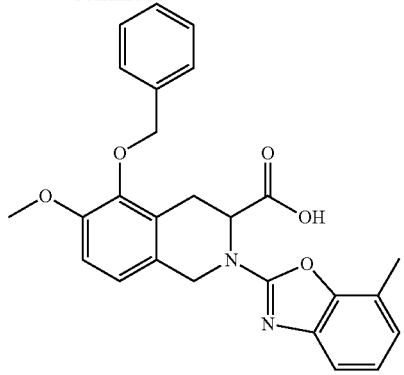

Step 1

Ethyl 5-(benzyloxy)-6-methoxy-2-(7-methylbenzo[d]oxazol-2-yl)-1,2,3,4-tetrahydroisoquinoline-3-carboxylate Under protection of argon gas, ethyl 5-(benzyloxy)-6-methoxy-1,2,3,4-tetrahydroisoquinoline-3-carboxylate hydrochloride 1b (377 mg, 1.0 mmol), 7-methylbenzo[d]oxazole 6a (160 mg, 1.2 mmol), silver carbonate (330 mg, 1.2 mmol) and benzoic acid (224 mg, 2.0 mmol) were dissolved in 5 mL acetonitrile, and the mixture was reacted at 60° C. for 8 hours. After the reaction was completed, the reaction solution was filtered with celite, the filter cake was washed with ethyl acetate (5 mL), and the filtrate was concentrated under reduced pressure. The obtained residue was purified by silica gel column chromatography (eluent: system A) to obtain ethyl 5-(benzyloxy)-6-methoxy-2-(7-methylbenzo[d]oxazol-2-yl)-1,2,3,4-tetrahydroisoquinoline-3-carboxylate 6b (140 mg), yield: 30%.

MS m/z(ESI): 473.0 [M+1]

Step 2

5-(Benzyloxy)-6-methoxy-2-(7-methylbenzo[d]oxazol-2-yl)-1,2,3,4-tetrahydroisoquinoline-3-carboxylic acid Ethyl 5-(benzyloxy)-6-methoxy-2-(7-methylbenzo[d]oxazol-2-yl)-1,2,3,4-tetrahydroisoquinoline-3-carboxylate 6b (140 mg, 0.30 mmol) was dissolved in 3.5 mL of a mixed solvent of tetrahydrofuran and methanol (V:V=2.5:1), and 1N sodium hydroxide solution (1.5 mL) was added dropwise, and the resulting mixture was reacted at room temperature for 3 hours. After the reaction was completed, the reaction solution was concentrated under reduced pressure, 5 mL of water was added to the residue, the pH of the solution was adjusted to pH=7 with 1N dilute hydrochloric acid, the solid was precipitated, the solution was filtered, and the filter cake was washed with water (3 mL), and dried, to obtain 5-(benzyloxy)-6-methoxy-2-(7-methylbenzo[d]oxazol-2-yl)-1,2,3,4-tetrahydroisoquinoline-3-carboxylic acid 6 (110 mg), yield: 83%.

MS m/z(ESI): 445.0 [M+1]

$^1$H NMR (400 MHz, DMSO-d$_6$) δ 13.04 (s, 1H), 7.52-7.36 (m, 5H), 7.15 (d, J=7.6 Hz, 1H), 7.09-7.00 (m, 3H), 6.88 (d, J=7.2 Hz, 1H), 5.13 (d, J=4.4 Hz, 1H), 4.98 (d, J=10.8 Hz, 1H), 4.86 (d, J=10.4 Hz, 1H), 4.81 (d, J=16.0 Hz,

1H), 4.68 (d, J=15.6 Hz, 1H), 3.84 (s, 3H), 3.53 (d, J=16.4 Hz, 1H), 2.98 (dd, J=16.4, 6.4 Hz, 1H), 2.41 (s, 3H).

Example 7

5-(Benzyloxy)-2-(4-chlorobenzo[d]oxazol-2-yl)-6-methoxy-1,2,3,4-tetrahydroisoquinoline-3-carboxylic acid

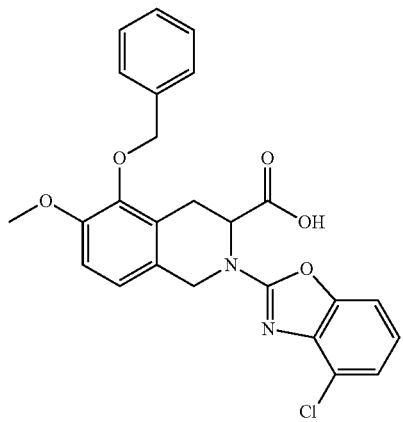

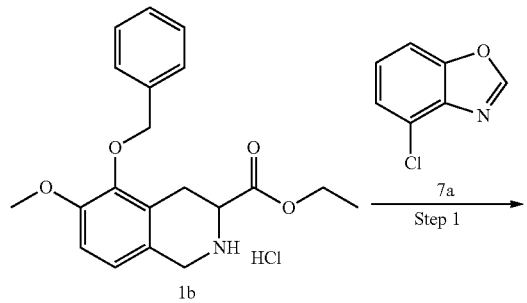

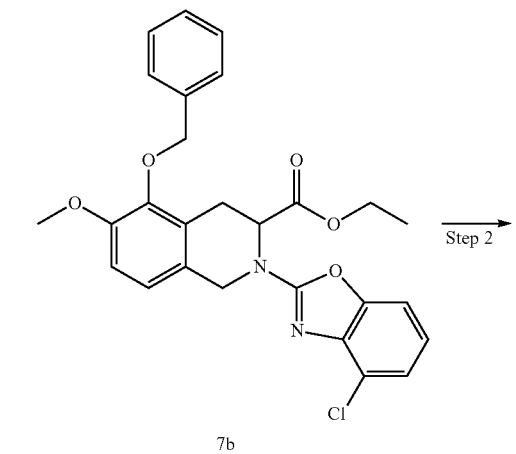

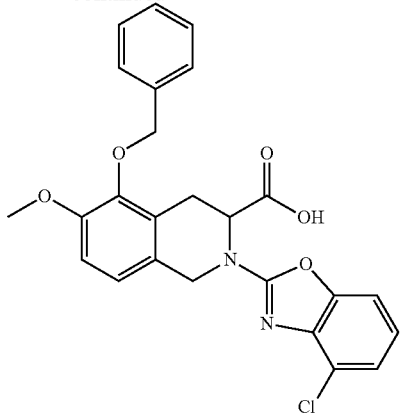

7

Step 1

Ethyl 5-(benzyloxy)-2-(4-chlorobenzo[d]oxazol-2-yl)-6-methoxy-1,2,3,4-tetrahydroisoquinoline-3-carboxylate Under protection of argon gas, ethyl 5-(benzyloxy)-6-methoxy-1,2,3,4-tetrahydroisoquinoline-3-carboxylate hydrochloride 1b (377 mg, 1.0 mmol), 4-chlorobenzo[d]oxazole 7a (184 mg, 1.2 mmol), silver carbonate (330 mg, 1.2 mmol) and benzoic acid (224 mg, 2.0 mmol) were dissolved in 5 mL acetonitrile, and the mixture was reacted at 60° C. for 8 hours. After the reaction was completed, the reaction solution was filtered with celite, the filter cake was washed with ethyl acetate (5 mL), and the filtrate was concentrated under reduced pressure. The obtained residue was purified by silica gel column chromatography (eluent: system A) to obtain ethyl 5-(benzyloxy)-2-(4-chlorobenzo[d]oxazol-2-yl)-6-methoxy-1,2,3,4-tetrahydroisoquinoline-3-carboxylate 7b (30 mg), yield: 30%.

MS m/z(ESI): 493.0 [M+1]

Step 2

5-(Benzyloxy)-2-(4-chlorobenzo[d]oxazol-2-yl)-6-methoxy-1,2,3,4-tetrahydroisoquinoline-3-carboxylic acid Ethyl 5-(benzyloxy)-2-(4-chlorobenzo[d]oxazol-2-yl)-6-methoxy-1,2,3,4-tetrahydroisoquinoline-3-carboxylate 7b (30 mg, 0.06 mmol) was dissolved in 1.5 mL of a mixed solvent of tetrahydrofuran and methanol (V:V=2:1), and 1N sodium hydroxide solution (0.5 mL) was added dropwise, and the resulting mixture was reacted at room temperature for 2 hours. After the reaction was completed, the reaction solution was concentrated under reduced pressure, 3 mL of water was added to the residue, the pH of the solution was adjusted to pH=7 with 1N dilute hydrochloric acid, the solid was precipitated, the solution was filtered, and the filter cake was washed with water (2 mL), and dried, to obtain 5-(benzyloxy)-2-(4-chlorobenzo[d]oxazol-2-yl)-6-methoxy-1,2,3,4-tetrahydroisoquinoline-3-carb oxylic acid 7 (8 mg), yield: 29%.

MS m/z(ESI): 464.9 [M+1]

Example 8

5-(Benzyloxy)-2-(5-chlorobenzo[d]oxazol-2-yl)-6-methoxy-1,2,3,4-tetrahydroisoquinoline-3-carboxylic acid

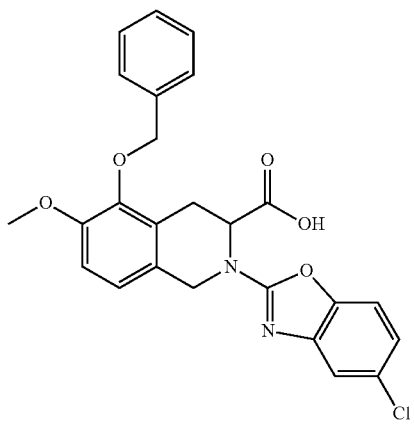

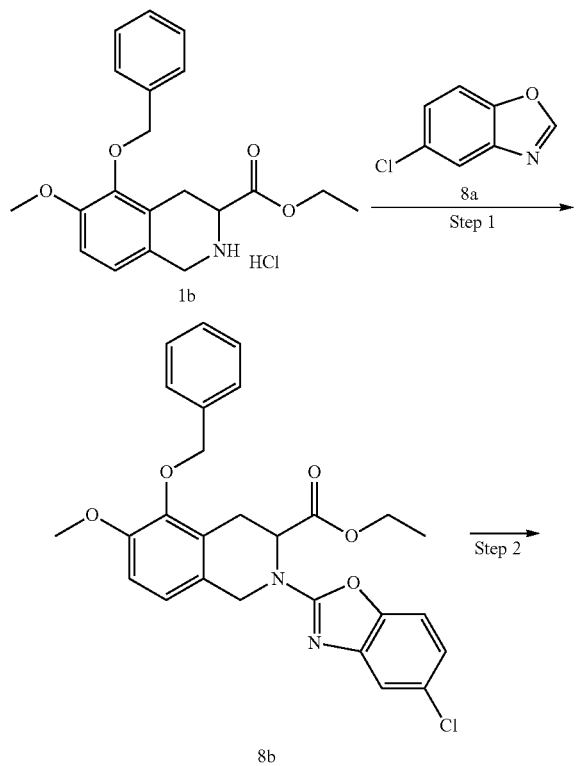

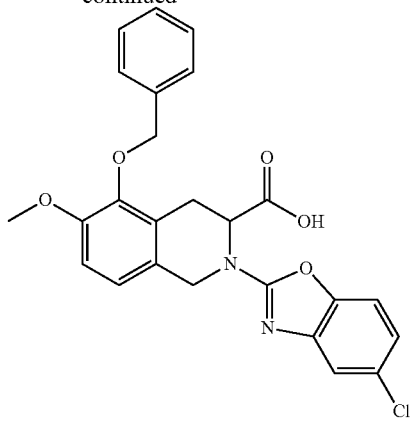

8

Step 1

Ethyl 5-(benzyloxy)-2-(5-chlorobenzo[d]oxazol-2-yl)-6-methoxy-1,2,3,4-tetrahydroisoquinoline-3-carboxylate Under protection of argon gas, ethyl 5-(benzyloxy)-6-methoxy-1,2,3,4-tetrahydroisoquinoline-3-carboxylate hydrochloride 1b (377 mg, 1.0 mmol), 5-chlorobenzo[d]oxazole 8a (184 mg, 1.2 mmol), silver carbonate (330 mg, 1.2 mmol) and benzoic acid (224 mg, 2.0 mmol) were dissolved in 5 mL acetonitrile, and the mixture was reacted at 60° C. for 8 hours. After the reaction was completed, the reaction solution was filtered with celite, the filter cake was washed with ethyl acetate (5 mL), and the filtrate was concentrated under reduced pressure. The obtained residue was purified by silica gel column chromatography (eluent: system A) to obtain ethyl 5-(benzyloxy)-2-(5-chlorobenzo[d]oxazol-2-yl)-6-methoxy-1,2,3,4-tetrahydroisoquinoline-3-carboxylate 8b (80 mg), yield: 16%.

MS m/z(ESI): 492.9 [M+1]

Step 2

5-(Benzyloxy)-2-(5-chlorobenzo[d]oxazol-2-yl)-6-methoxy-1,2,3,4-tetrahydroisoquinoline-3-carboxylic acid Ethyl 5-(benzyloxy)-2-(5-chlorobenzo[d]oxazol-2-yl)-6-methoxy-1,2,3,4-tetrahydroisoquinoline-3-carboxylate 8b (80 mg, 0.16 mmol) was dissolved in 5 mL of a mixed solvent of tetrahydrofuran and methanol (V:V=3:2), and 1N sodium hydroxide solution (1.5 mL) was added dropwise, and the resulting mixture was reacted at room temperature for 2 hours. After the reaction was completed, the reaction solution was concentrated under reduced pressure, 6 mL of water was added to the residue, the pH of the solution was adjusted to pH=7 with 1N dilute hydrochloric acid, the solid was precipitated, the solution was filtered, and the filter cake was washed with water (5 mL), and dried, to obtain 5-(benzyloxy)-2-(5-chlorobenzo[d]oxazol-2-yl)-6-methoxy-1,2,3,4-tetrahydroisoquinoline-3-carboxylic acid 8 (60 mg), yield: 81%.

MS m/z(ESI): 464.9 [M+1]

$^1$H NMR (400 MHz, DMSO-$d_6$) δ 13.11 (s, 1H), 7.50-7.34 (m, 7H), 7.10-7.00 (m, 3H), 5.09 (d, J=4.0 Hz, 1H), 4.98 (d, J=10.8 Hz, 1H), 4.85 (d, J=11.2 Hz, 1H), 4.79 (d, J=16.0 Hz, 1H), 4.68 (d, J=16.0 Hz, 1H), 3.84 (s, 3H), 3.53 (d, J=16.0 Hz, 1H), 2.99 (dd, J=15.6, 6.4 Hz, 1H).

Example 9

2-(Benzo[d]oxazol-2-yl)-5-(benzyloxy)-N—(N,N-dimethylsulfonyl)-6-methoxy-1,2,3,4-tetrahydroisoquinoline-3-carboxamide

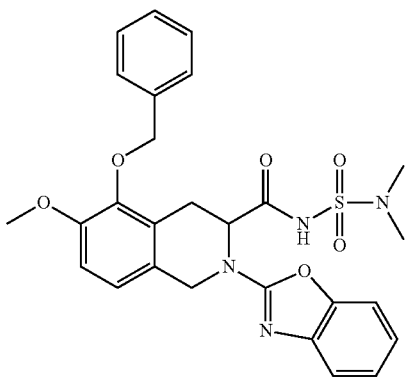

0.23 mmol) was dissolved in 2 mL of dichloromethane, and N,N-dimethylsulfonamide 9a (35 mg, 0.28), N,N'-dicyclohexylcarbimide (60 mg, 0.28 mmol) and 4-dimethylaminopyridine (9 mg, 0.07 mmol) were added, and the resulting mixture was reacted overnight at room temperature. After the reaction was completed, the resulting mixture was washed with 1N diluted hydrochloric acid (20 mL), extracted with dichloromethane (10 mL×2). The organic phases were combined, washed with saturated brine (20 mL), dried with anhydrous sodium sulfate, filtered and concentrated under reduced pressure. The obtained residue was purified by thin layer chromatography (developing solvent: System A) to obtain 2-(benzo[d]oxazol-2-yl)-5-(benzyloxy)-N—(N,N-dimethylsulfonyl)-6-methoxy-1,2,3,4-tetrahydroisoquinoline-3-carboxamide 9 (7 mg), yield: 5%.

MS m/z(ESI): 536.9 [M+1]

$^1$H NMR (400 MHz, d$_6$-DMSO) δ 11.88 (s, 1H), 7.51-7.33 (m, 7H), 7.19 (t, J=7.4 Hz, 1H), 7.11-7.00 (m, 4H), 4.98 (d, J=10.8 Hz, 1H), 4.94 (dd, J=6.4, 4.0 Hz, 1H), 4.86 (d, J=10.4 Hz, 1H), 4.82 (d, J=15.2 Hz, 1H), 4.73 (d, J=14.8 Hz, 1H), 3.84 (s, 3H), 3.45 (dd, J=16.2, 3.4 Hz, 1H), 3.12 (dd, J=16.0, 6.4 Hz, 1H), 2.64 (s, 6H).

Example 10

2-(Benzo[d]oxazol-2-yl)-5-(benzyloxy)-N-(ethylsulfonyl)-6-methoxy-1,2,3,4-tetrahydroisoquinoline-3-carboxamide

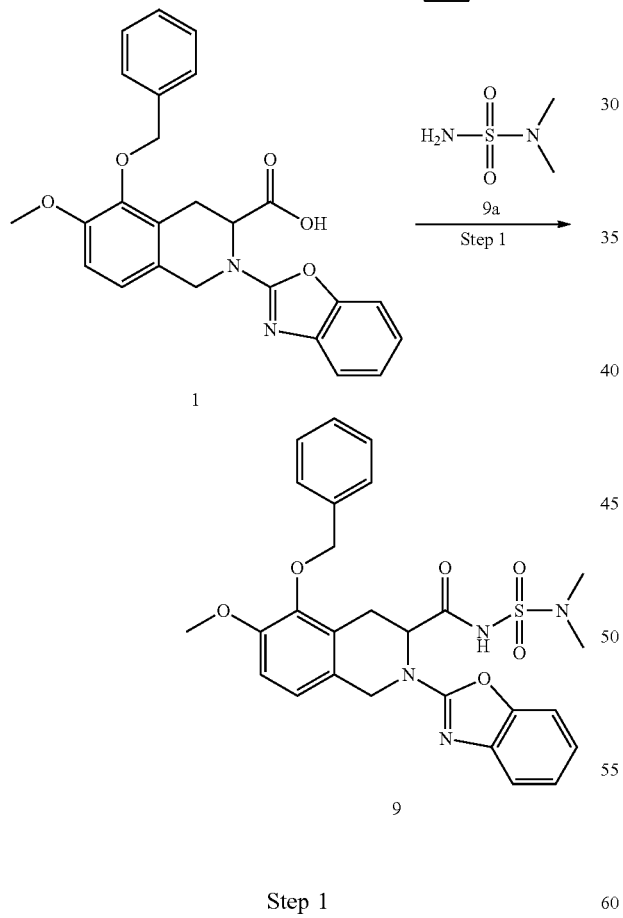

Step 1

2-(Benzo[d]oxazol-2-yl)-5-(benzyloxy)-N—(N,N-dimethylsulfonyl)-6-methoxy-1,2,3,4-tetrahydroisoquinoline-3-carboxamide 2-(Benzo[d]oxazol-2-yl)-5-(benzyloxy)-6-methoxy-1,2,3,4-tetrahydroisoquinoline-3-carboxylic acid 1 (100 mg,

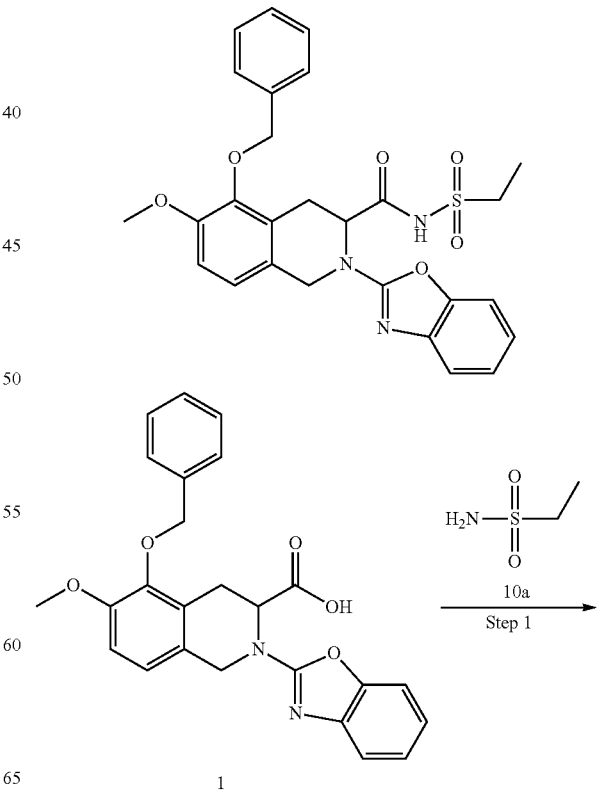

Example 11

2-(Benzo[d]oxazol-2-yl)-5-(benzyloxy)-N-(cyclo-propylsulfonyl)-6-methoxy-1,2,3,4-tetrahydroisoquinoline-3-carboxamide

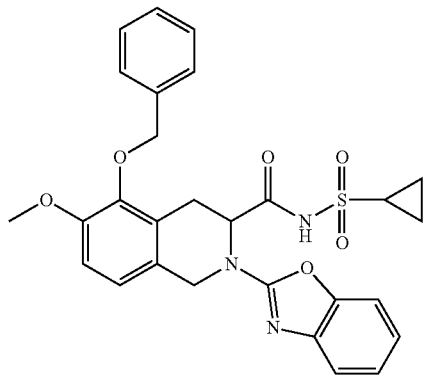

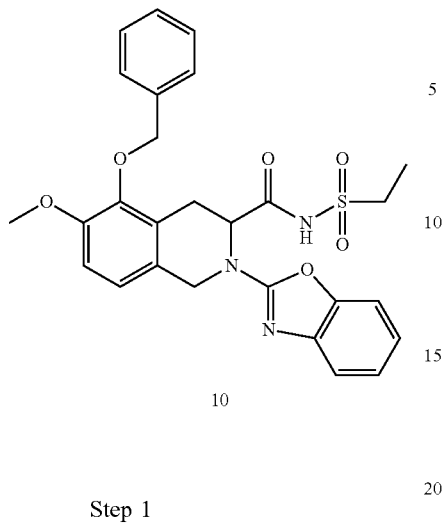

10

Step 1

2-(Benzo[d]oxazol-2-yl)-5-(benzyloxy)-N-(ethylsulfonyl)-6-methoxy-1,2,3,4-tetrahydroisoquinoline-3-carboxamide 2-(Benzo[d]oxazol-2-yl)-5-(benzyloxy)-6-methoxy-1,2,3,4-tetrahydroisoquinoline-3-carboxylic acid 1 (43 mg, 0.1 mmol) was dissolved in 1 mL of tetrahydrofuran, and N,N'-carbonyldiimidazole (32 mg, 0.2 mmol) was added. The mixture was heated to 30° C. and stirred for 4 hours. Ethanesulfonamide 10a (22 mg, 0.2 mmol) and 1,8-diazabicycloundec-7-ene (30 mg, 0.2 mmol) were added and the resulting mixture was reacted overnight at 30° C. After the reaction was completed, ethyl acetate (5 mL) was added to dilute the reaction solution, and the resulting mixture was washed with 1N diluted hydrochloric acid (10 mL), extracted with ethyl acetate (10 mL×2). The organic phases were combined, washed with water (10 mL) and saturated brine (10 mL) in sequence, dried with anhydrous sodium sulfate, filtered and concentrated under reduced pressure. The obtained residue was purified by thin layer chromatography (developing solvent: System A) to obtain 2-(benzo[d]oxazol-2-yl)-5-(benzyloxy)-N-(ethylsulfonyl)-6-methoxy-1,2,3,4-tetrahydroisoquinoline-3-carboxamide 10 (25 mg), yield: 48%.

MS m/z(ESI): 521.9 [M+1]

$^1$H NMR (400 MHz, d$_6$-DMSO) δ 12.11 (s, 1H), 7.52-7.32 (m, 7H), 7.19 (td, J=7.6, 1.2 Hz, 1H), 7.10 (d, J=8.4 Hz, 1H), 7.06 (td, J=7.6, 1.2 Hz, 1H), 7.01 (d, J=8.4 Hz, 1H), 5.00-4.96 (m, 2H), 4.84 (d, J=10.4 Hz, 1H), 4.81 (d, J=15.6 Hz, 1H), 4.75 (d, J=14.8 Hz, 1H), 3.84 (s, 3H), 3.43 (dd, J=15.8, 3.8 Hz, 1H), 3.28-3.20 (m, 2H), 3.14 (dd, J=16.2, 6.2 Hz, 1H), 1.13 (t, J=7.4 Hz, 3H).

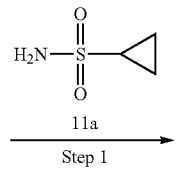

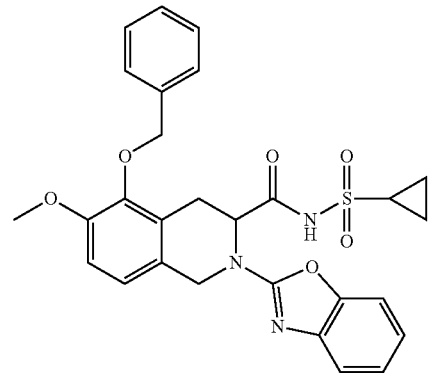

Step 1

2-(Benzo[d]oxazol-2-yl)-5-(benzyloxy)-N-(cyclo-propylsulfonyl)-6-methoxy-1,2,3,4-tetrahydroisoquinoline-3-carboxamide 2-(Benzo[d]oxazol-2-yl)-5-(benzyloxy)-6-methoxy-1,2,3,4-tetrahydroisoquinoline-3-carboxylic acid 1 (43 mg, 0.1 mmol) was dissolved in 1 mL of tetrahydrofuran, and N,N'-carbonyldiimidazole (24 mg, 0.15 mmol) was added. The mixture was stirred at room temperature for 4 ours. Cyclopropanesulfonamide 11a (18 mg, 0.15 mmol) and 1,8-diazabicycloundec-7-ene (30 mg, 0.2 mmol) were added and the resulting mixture was reacted overnight at room temperature. After the reaction was completed, ethyl acetate (5 mL) was added to dilute the reaction solution, and the resulting mixture was washed with 1N diluted hydrochloric acid (10 mL), extracted with ethyl acetate (10 mL×2). The organic phases were combined, washed with water (10 mL) and saturated brine (10 mL) in sequence, dried with anhydrous sodium sulfate, filtered and concentrated under reduced pressure. The obtained residue was purified by thin layer chromatography (developing solvent: System A) to obtain 2-(benzo[d]oxazol-2-yl)-5-(benzyloxy)-N-(cyclopropylsulfonyl)-6-methoxy-1,2,3,4-tetrahydroisoquinoline-3-carboxamide 11 (11 mg), yield: 21%.

MS m/z(ESI): 534.0 [M+1]

$^1$H NMR (400 MHz, DMSO-d$_6$) δ 12.15 (s, 1H), 7.52-7.35 (m, 7H), 7.19 (t, J=7.4 Hz, 1H), 7.11-7.00 (m, 3H), 5.00-4.97 (m, 2H), 4.86-4.78 (m, 3H), 3.84 (s, 3H), 3.45-3.44 (m, 1H), 3.12 (dd, J=16.4, 6.4 Hz, 1H), 2.81-2.78 (m, 1H), 1.08-0.91 (m, 4H).

Example 12

5-(Benzyloxy)-6-methoxy-2-(quinazolin-2-yl)-1,2,3,4-tetrahydroisoquinoline-3-carboxylic acid

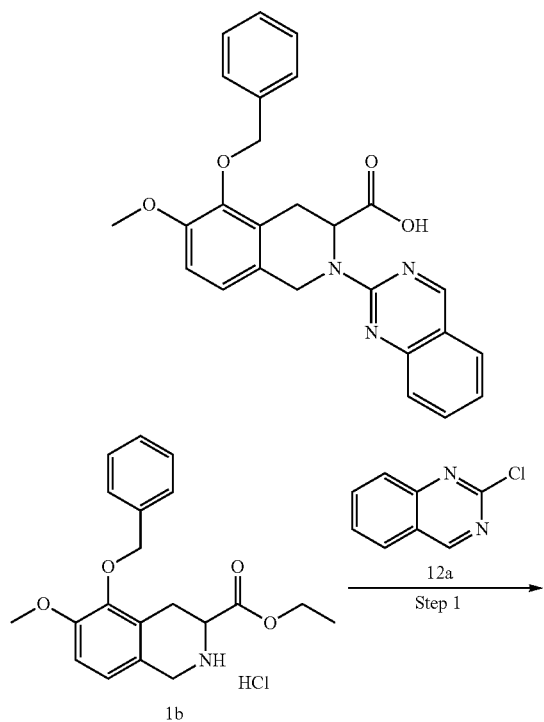

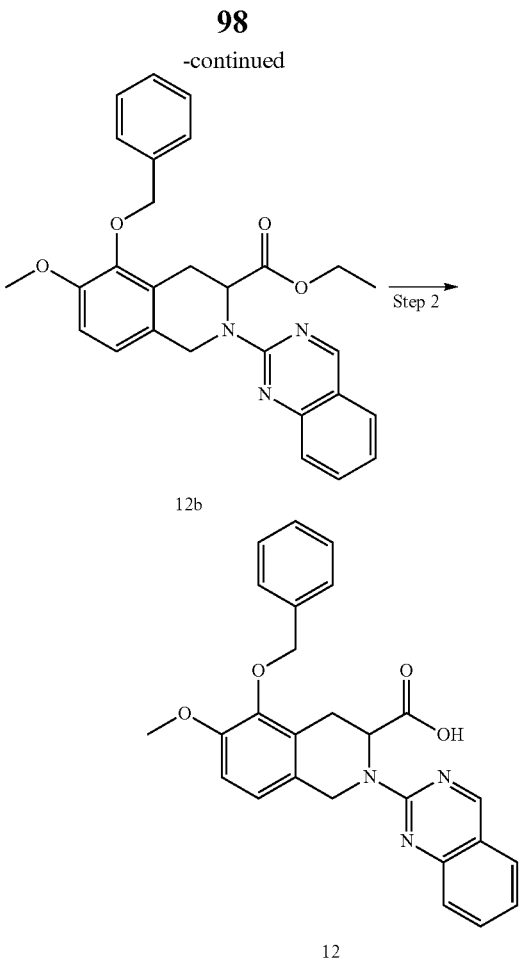

Step 1

Ethyl 5-(benzyloxy)-6-methoxy-2-(quinazolin-2-yl)-1,2,3,4-tetrahydroisoquinoline-3-carboxylate Ethyl 5-(benzyloxy)-6-methoxy-1,2,3,4-tetrahydroisoquinoline-3-carboxylate hydrochloride 1b (377 mg, 1.0 mmol), 2-chloroquinazoline 12a (181 mg, 1.1 mmol) and N,N-diisopropylethylamine (0.55 mL, 3.0 mmol) were dissolved in 7 mL of N-methylpyrrolidone. The mixture was stirred at 100-110° C. for 7 hours. After the reaction was completed, ethyl acetate (10 mL) was added to dilute the reaction solution, and the resulting mixture was washed with water (15 mL) and saturated brine (15 mL) in sequence, dried with anhydrous sodium sulfate, filtered and concentrated under reduced pressure. The obtained residue was purified by thin layer chromatography (developing solvent: System A) to obtain ethyl 5-(benzyloxy)-6-methoxy-2-(quinazolin-2-yl)-1,2,3,4-tetrahydroisoquinoline-3-carboxylate 12b (46 mg), yield: 10%.

Step 2

5-(Benzyloxy)-6-methoxy-2-(quinazolin-2-yl)-1,2,3,4-tetrahydroisoquinoline-3-carboxylic acid Ethyl 5-(benzyloxy)-6-methoxy-2-(quinazolin-2-yl)-1,2,3,4-tetrahydroisoquinoline-3-carboxylate 12b (46 mg, 0.098 mmol) was dissolved in 1.5 mL of tetrahydrofuran, and 1N sodium hydroxide solution (0.5 mL) was added, and the resulting mixture was reacted at room temperature for 3 hours. After the reaction was completed, the reaction solution was concentrated under reduced pressure, 2 mL of water was added to the residue, the pH of the solution was adjusted to pH=7 with 1N dilute hydrochloric acid, the solid was precipitated, filtered, and dried, to obtain 5-(benzyloxy)-6-methoxy-2-(quinazolin-2-yl)-1,2,3,4-tetrahydroisoquinoline-3-carboxylic acid 12 (25 mg), yield: 58%.

MS m/z(ESI): 442.0 [M+1]

¹H NMR (400 MHz, d₆-DMSO) δ 9.18 (s, 0.4H), 9.13 (s, 0.6H), 7.79 (d, J=7.2 Hz, 1H), 7.69 (t, J=7.2 Hz, 1H), 7.53-7.32 (m, 7H), 7.21 (t, J=6.2 Hz, 1H), 6.98-6.89 (m, 2H), 5.51 (d, J=5.2 Hz, 1H), 5.26 (d, J=16.4 Hz, 0.4H), 5.07 (d, J=16.8 Hz, 0.6H), 4.90 (s, 2H), 4.66 (t, J=18.0 Hz, 1H), 3.80 (s, 3H), 3.75 (d, J=16.0 Hz, 1H), 2.67 (dd, J=16.2, 6.6 Hz, 1H).

Example 13

5-(Benzyloxy)-6-methoxy-2-(quinazolin-4-yl)-1,2,3,4-tetrahydroisoquinoline-3-carboxylic acid hydrochloride

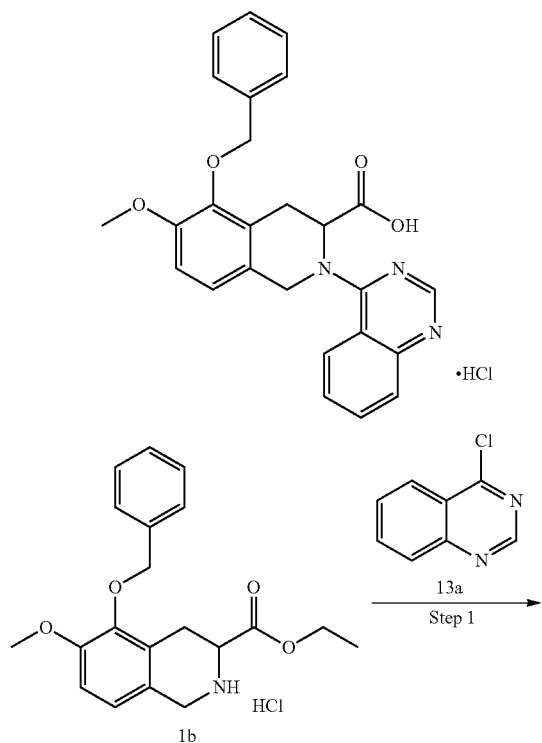

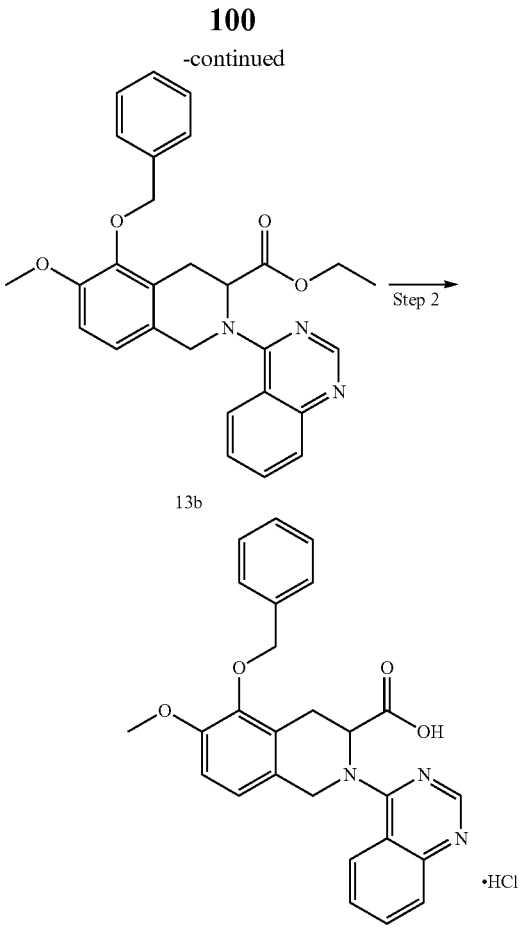

Step 1

Ethyl 5-(benzyloxy)-6-methoxy-2-(quinazolin-4-yl)-1,2,3,4-tetrahydroisoquinoline-3-carboxylate Ethyl 5-(benzyloxy)-6-methoxy-1,2,3,4-tetrahydroisoquinoline-3-carboxylate hydrochloride 1b (377 mg, 1.0 mmol), 4-chloroquinazoline 13a (181 mg, 1.1 mmol) and N,N-diisopropylethylamine (0.55 mL, 3.0 mmol) were dissolved in 7 mL of N-methylpyrrolidone. The mixture was stirred at 80° C. for 3 hours. After the reaction was completed, 10 mL of ethyl acetate was added to dilute the reaction solution, and the resulting mixture was washed with water (15 mL) and saturated brine (15 mL) in sequence, dried with anhydrous sodium sulfate, filtered and concentrated under reduced pressure. The obtained residue was purified by thin layer chromatography (developing solvent: System A) to obtain ethyl 5-(benzyloxy)-6-methoxy-2-(quinazolin-4-yl)-1,2,3,4-tetrahydroisoquinoline-3-carboxylate 13b (140 mg), yield: 30%.

MS m/z(ESI): 470.0 [M+1]

Step 2

5-(Benzyloxy)-6-methoxy-2-(quinazolin-4-yl)-1,2,3,4-tetrahydroisoquinoline-3-carboxylic acid hydrochloride Ethyl 5-(benzyloxy)-6-methoxy-2-(quinazolin-4-yl)-1,2,3,4-tetrahydroisoquinoline-3-carboxylate 13b (140 mg, 0.30 mmol) was dissolved in 6 mL of a mixed solvent of tetrahydrofuran and methanol (V:V=2:1), and 1N sodium hydroxide solution (1.5 mL) was added, and the resulting mixture was reacted at room temperature for 4 hours. After the reaction was completed, the reaction solution was concentrated under reduced pressure, 8 mL of water was added to the residue, the pH of the solution was adjusted to pH=7 with 1N dilute hydrochloric acid, the solid was precipitated, filtered, and dried, to obtain 5-(benzyloxy)-6-methoxy-2-(quinazolin-4-yl)-1,2,3,4-tetrahydroisoquinoline-3-carboxylic acid hydrochloride 13 (100 mg), yield: 76%.

MS m/z(ESI): 442.0 [M+1]

$^1$H NMR (400 MHz, DMSO-d$_6$) δ 12.77 (s, 1H), 8.59 (s, 1H), 8.23 (d, J=8.0 Hz, 1H), 7.87-7.81 (m, 2H), 7.59 (t, J=7.6 Hz, 1H), 7.51-7.35 (m, 5H), 7.01 (d, J=8.4 Hz, 1H), 6.96 (d, J=8.0 Hz, 1H), 5.29 (t, J=4.8 Hz, 1H), 5.07-4.89 (m, 4H), 3.83 (s, 3H), 3.42 (dd, J=16.0, 4.4 Hz, 1H), 3.20 (dd, J=16.4, 5.2 Hz, 1H).

Example 14

(S)-5-(Benzyloxy)-2-(6-fluorobenzo[d]oxazol-2-yl)-6-methoxy-1,2,3,4-tetrahydroisoquinoline-3-carboxylic acid

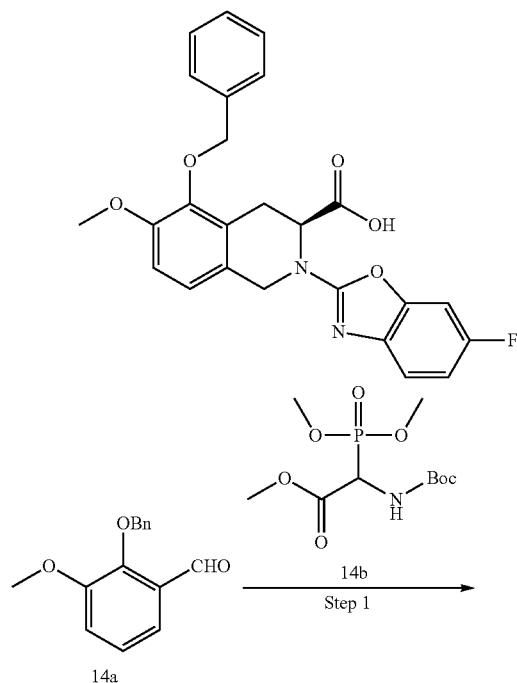

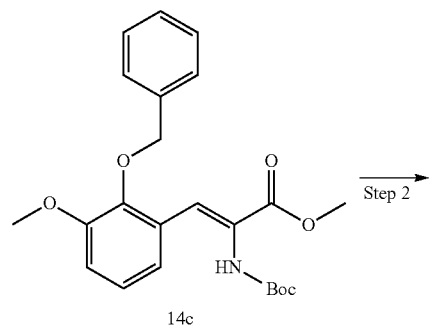

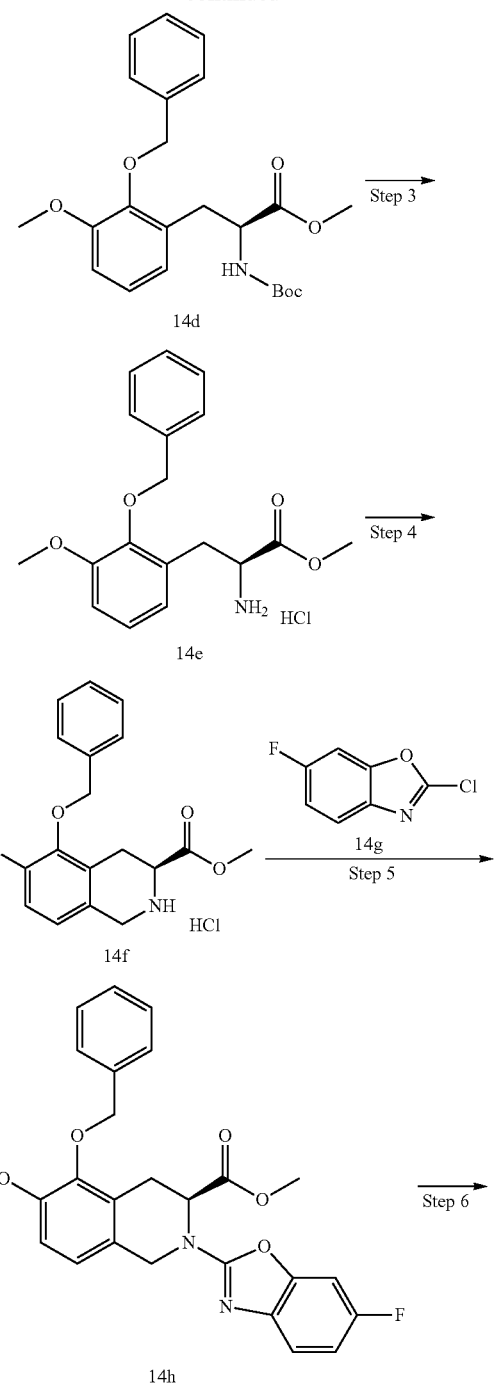

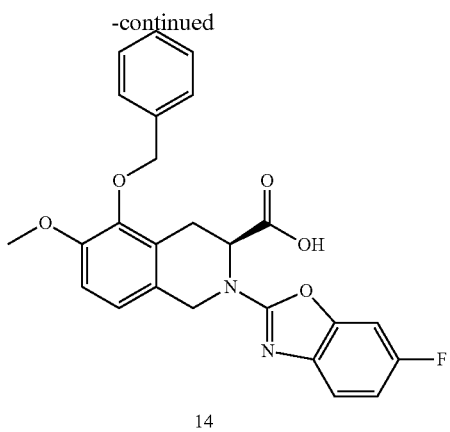

14

Step 1

Methyl (Z)-3-(2-(Benzyloxy)-3-methoxyphenyl)-2-((tert-butoxycarbonyl)amino)acrylate (±)-BOC-A-phosphonoglycine trimethyl ester 14b (9.8 g, 33 mmol) and tetramethylguanidine (4.0 g, 34.4 mmol) were dissolved in 100 mL tetrahydrofuran, and the mixture was cooled to 0° C. A solution of 2-(benzyloxy)-3-methoxybenzaldehyde 14a (7.0 g, 28.7 mmol) in tetrahydrofuran (5 mL) was added, and the resulting mixture was reacted overnight at room temperature. After the reaction was completed, the resulting solution was concentrated under reduced pressure, and ethyl acetate (40 mL) was added to dissolve the residue. The resulting mixture was washed with 10% citric acid solution (30 mL) and saturated brine (30 mL) in sequence, dried with anhydrous sodium sulfate, filtered and concentrated under reduced pressure. The obtained residue was purified by silica gel column chromatography (eluent: system A) to obtain methyl (Z)-3-(2-(benzyloxy)-3-methoxyphenyl)-2-((tert-butoxycarbonyl) amino)acrylate 14c (9.5 g, white solid), yield: 80%.

MS m/z(ESI): 314.0 [M−100]

Step 2

Methyl (S)-3-(2-(Benzyloxy)-3-methoxyphenyl)-2-((tert-butoxycarbonyl)amino)propionate Methyl (Z)-3-(2-(Benzyloxy)-3-methoxyphenyl)-2-((tert-butoxycarbonyl)amino) acrylate 14c (5.0 g, 12.0 mmol) and (R)—N-diphenylphosphine-N-methyl-(S)-2-(diphenylphosphine)ferrocenylethylamine (90 mg, 0.06 mmol) and bis(1,5-cyclooctadiene) Rhodium(I) tetrafluoroborate (100 mg, 0.024 mmol) were dissolved in 50 mL of methanol. The mixture was bubbled with hydrogen for three times, and a hydrogen balloon was inserted. The resulting mixture was reacted overnight at room temperature. After the reaction was completed, the resulting solution was filtered and the filter liquor was concentrated under reduced pressure. The obtained residue was purified by silica gel column chromatography (eluent: system A) to obtain methyl (S)-3-(2-(Benzyloxy)-3-methoxyphenyl)-2-((tert-butoxycarbonyl) amino) propionate 14d (3.2 g, colorless oil), yield: 64%.

MS m/z(ESI): 316.0 [M−100]

$^1$H NMR (400 MHz, DMSO-$d_6$) δ 7.48-7.32 (m, 5H), 7.23 (d, J=8.0 Hz, 1H), 6.98-6.96 (m, 2H), 6.78 (dd, J=6.4, 2.0 Hz, 1H), 4.96 (q, J=10.4 Hz, 2H), 4.20 (td, J=8.8, 5.2 Hz, 1H), 3.82 (s, 3H), 3.55 (s, 3H), 3.05 (dd, J=13.4, 5.0 Hz, 1H), 2.71 (dd, J=13.2, 10.0 Hz, 1H), 1.30 (s, 9H).

Step 3

Methyl (S)-2-amino-3-(2-(benzyloxy)-3-methoxyphenyl)propionate hydrochloride

Methyl (S)-3-(2-(benzyloxy)-3-methoxyphenyl)-2-((tert-butoxycarbonyl)amino) propionate 14d (3.2 g, 7.7 mmol) was dissolved to 10 mL of 1,4-dioxane, and a solution of hydrogen chloride in 1,4-dioxane (9.6 mL, 38.5 mmol, 4M), and the mixture was reacted at room temperature for 2 hours. After the reaction was completed, the resulting solution was concentrated under reduced pressure to obtain methyl (S)-2-amino-3-(2-(benzyloxy)-3-methoxyphenyl)propionate hydrochloride 14e (2.7 g, white solid), yield: 100%.

MS m/z(ESI): 316.0 [M+1]

1H NMR (400 MHz, DMSO-$d_6$) δ 8.62 (s, 3H), 7.47-7.32 (m, 5H), 7.03-7.02 (m, 2H), 6.81-6.78 (m, 1H), 4.94 (q, J=11.2 Hz, 2H), 4.04 (t, J=7.2 Hz, 1H), 3.83 (s, 3H), 3.50 (s, 2H), 3.05 (d, J=7.2 Hz, 2H).

Step 4

Methyl (S)-5-(benzyloxy)-6-methoxy-1,2,3,4-tetrahydroisoquinoline-3-carboxylate hydrochloride Methyl (S)-2-amino-3-(2-(benzyloxy)-3-methoxyphenyl) propionate hydrochloride 14e (1.3 g, 3.7 mmol) was dissolved in 2N dilute hydrochloric acid (26 mL). The mixture was bubbled with argon gas for three times, and stirred at room temperature for 30 minutes. Aqueous formaldehyde solution (2.8 mL, 37 mmol, 37 wt. %) and tetrahydrofuran (5 mL) were added in sequence, and the mixture was bubbled with argon gas for three times again, and reacted overnight at room temperature. After the reaction was completed, acetonitrile was added to the reaction solution, and the resulting solution was concentrated under reduced pressure for several times to obtain methyl (S)-5-(benzyloxy)-6-methoxy-1,2,3,4-tetrahydroisoquinoline-3-carboxylate hydrochloride14f (400 mg, white solid), yield: 30%.

MS m/z(ESI): 328.0 [M+1]

$^1$H NMR (400 MHz, DMSO-$d_6$) δ 10.12 (s, 2H), 7.45-7.33 (m, 5H), 7.05 (d, J=8.8 Hz, 1H), 7.00 (d, J=8.4 Hz, 1H), 4.96 (d, J=2.0 Hz, 2H), 4.41 (dd, J=10.8, 5.2 Hz, 1H), 4.22 (q, J=15.6 Hz, 2H), 3.82 (s, 3H), 3.77 (s, 3H), 3.21 (dd, J=17.2, 5.2 Hz, 1H), 2.92 (dd, J=17.6, 11.2 Hz, 1H).

Step 5

Methyl (S)-5-(benzyloxy)-2-(6-fluorobenzo[d]oxazol-2-yl)-6-methoxy-1,2,3,4-tetrahydroisoquinoline-3-carboxylate Methyl (S)-5-(benzyloxy)-6-methoxy-1,2,3,4-tetrahydroisoquinoline-3-carboxylate hydrochloride14f (80 mg, 0.22 mmol), 2-chloro-6-fluorobenzo[d]oxazole 14g (37 mg, 0.22 mmol) and triethylamine (91 μL, 0.66 mmol) were dissolved in 2 mL of tetrahydrofuran, and the mixture was reacted at 50-60° C. for 5 hours. After the reaction was completed, the resulting solution was cooled to room temperature and concentrated under reduced pressure. The residue obtained was purified by thin layer chromatography (developer: system A) to obtain methyl (S)-5-(benzyloxy)-2-(6-fluorobenzo[d]oxazol-2-yl)-6-methoxy-1,2,3,4-tetrahydroisoquinoline-3-carboxylate 14h (60 mg), yield: 59%.

MS m/z(ESI): 462.9 [M+1]

1H NMR (400 MHz, CDCl3) δ 7.49-7.29 (m, 6H), 7.06 (dd, J=7.8, 2.2 Hz, 1H), 6.96-6.86 (m, 3H), 5.19 (dd, J=6.4, 2.4 Hz, 1H), 5.05 (d, J=10.8 Hz, 1H), 4.95 (d, J=11.2 Hz, 1H), 4.90 (d, J=15.6 Hz, 1H), 4.76 (d, J=15.2 Hz, 1H), 3.89 (s, 3H), 3.66-3.61 (m, 4H), 2.94 (dd, J=16.4, 6.4 Hz, 1H).

Step 6

(S)-5-(Benzyloxy)-2-(6-fluorobenzo[d]oxazol-2-yl)-6-methoxy-1,2,3,4-tetrahydroisoquinoline-3-carboxylic acid Methyl (S)-5-(benzyloxy)-2-(6-fluorobenzo[d]oxazol-2-yl)-6-methoxy-1,2,3,4-tetrahydroisoquinoline-3-carboxylate 14h (60 mg, 0.13 mmol) was dissolved in 2 mL of tetrahydrofuran; lithium hydroxide monohydrate (17 mg, 0.39 mmol) was dissolved in 0.2 mL of water, and the mixture was added dropwise to the above solution. The resulting solution was reacted overnight at room temperature. After the reaction was completed, 2N dilute hydrochloric acid was added dropwise so that the reaction solution was adjusted to pH=5. The resulting solution was extracted with ethyl acetate (10 mL×2). The organic phases were combined, dried with anhydrous sodium sulfate, filtered, and concentrated under reduced pressure. The obtained residue was separated and purified by a preparative column to obtain (S)-5-(benzyloxy)-2-(6-fluorobenzo[d]oxazol-2-yl)-6-methoxy-1,2,3,4-tetrahydroisoquinoline-3-carboxylic acid 14 (30 mg), yield: 52%.

MS m/z(ESI): 448.9 [M+1]

1H NMR (400 MHz, DMSO-d6) δ 7.51-7.33 (m, 7H), 7.09-7.01 (m, 3H), 5.09 (dd, J=6.2, 2.6 Hz, 1H), 4.99 (d, J=10.8 Hz, 1H), 4.87 (d, J=11.2 Hz, 1H), 4.78 (d, J=16.0 Hz, 1H), 4.67 (d, J=16.0 Hz, 1H), 3.85 (s, 3H), 3.53 (dd, J=16.2, 2.2 Hz, 1H), 3.00 (dd, J=16.4, 6.4 Hz, 1H).

Example 15

(S)-5-(Benzyloxy)-2-(6-cyanobenzo[d]oxazol-2-yl)-6-methoxy-1,2,3,4-tetrahydroisoquinoline-3-carboxylic acid

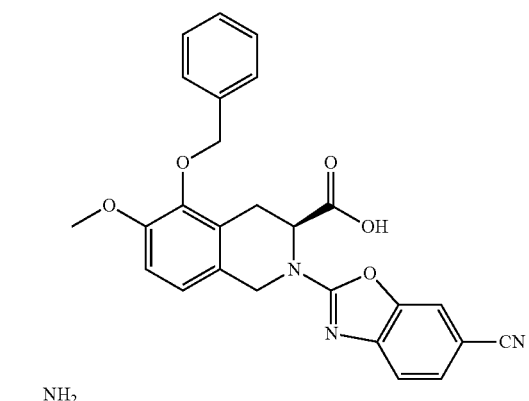

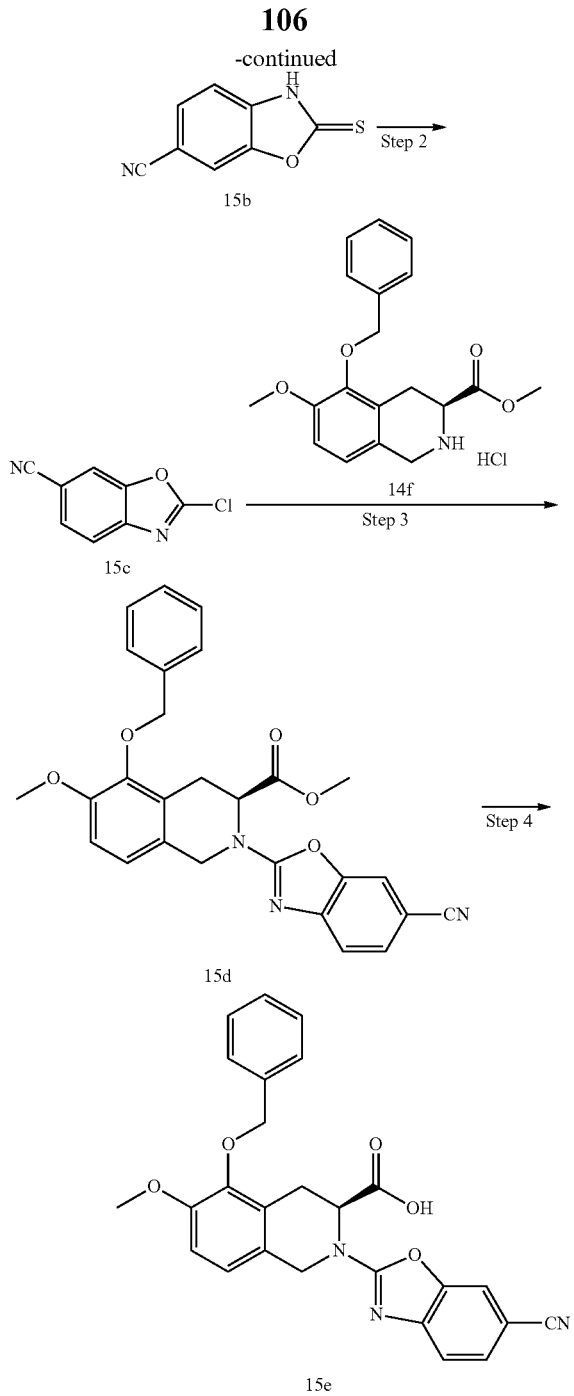

Step 1

2-Thio-2,3-dihydrobenzo[d]oxazole-6-formonitrile

4-Amino-3-hydroxybenzonitrile 15a (631 g, 4.7 mol, prepared according to the published patent WO 2000072845) and potassium ethylxanthogenate (1.2 kg, 7.1 mol) were dissolved in 630 mL ethanol, and the mixture was reacted under reflux for 10 hours. After the reaction was completed, the reaction solution was cooled to room temperature, and poured into 1000 mL of iced water, solid was precipitated, filtered, and dried to obtain 2-thio-2,3-dihydrobenzo[d]oxazole-6-formonitrile 15b (827 g, brown solid), yield: 100%.

Step 2

2-Chlorobenzo[d]oxazole-6-formonitrile

2-Thio-2,3-dihydrobenzo[d]oxazole-6-formonitrile 15b (150 g, 0.85 mol) was dissolved in 750 mL thionyl chloride, and 7.5 mL dimethyl sulfoxide was added dropwise. The mixture was reacted under reflux for 7 hours. After the reaction was completed, the resulting solution was concentrated under reduced pressure. Petroleum ether (500 mL) was added to the obtained residue. The mixture was stirred at room temperature for 30 minutes. A solid was precipitated out and filtered to obtain 2-chlorobenzo[d]oxazole-6-formonitrile 15c (110 g, brown solid), yield: 73%.

MS m/z(ESI): 178.7 [M+1]

Step 3

Methyl (S)-5-(benzyloxy)-2-(6-cyanobenzo[d]oxazol-2-yl)-6-methoxy-1,2,3,4-tetrahydroisoquinoline-3-carboxylate Methyl (S)-5-(benzyloxy)-6-methoxy-1,2,3,4-tetrahydroisoquinoline-3-carboxylate hydrochloride 14f (200 mg, 0.55 mmol), 2-chlorobenzo[d]oxazole-6-formonitrile 15c (98 mg, 0.55 mmol) and triethylamine (0.23 mL, 1.65 mmol) were dissolved in 2 mL of tetrahydrofuran, and the mixture was reacted at 50-60° C. for 6 hours. After the reaction was completed, the resulting solution was cooled to room temperature and concentrated under reduced pressure. The residue obtained was purified by thin layer chromatography (developer: system C) to obtain methyl (S)-5-(benzyloxy)-2-(6-cyanobenzo[d]oxazol-2-yl)-6-methoxy-1,2,3,4-tetrahydroisoquinoline-3-carboxylate 15d (80 mg), yield: 31%.

MS m/z(ESI): 470.0 [M+1]

1H NMR (400 MHz, CDCl3) δ 7.56 (d, J=1.2 Hz, 1H), 7.52-7.46 (m, 3H), 7.42-7.35 (m, 4H), 6.94 (d, J=8.8 Hz, 1H), 6.88 (d, J=8.4 Hz, 1H), 5.20 (br, 1H), 5.06 (d, J=11.2 Hz, 1H), 4.97-4.91 (m, 2H), 4.80 (d, J=15.6 Hz, 1H), 3.89 (s, 3H), 3.64 (s, 3H), 3.64 (dd, J=16.2, 3.0 Hz, 1H), 2.95 (dd, J=16.4, 6.4 Hz, 1H).

Step 4

(S)-5-(Benzyloxy)-2-(6-cyanobenzo[d]oxazol-2-yl)-6-methoxy-1,2,3,4-tetrahydroisoquinoline-3-carboxylic acid Methyl (S)-5-(benzyloxy)-2-(6-cyanobenzo[d]oxazol-2-yl)-6-methoxy-1,2,3,4-tetrahydroisoquinoline-3-carboxylate 15d (80 mg, 0.17 mmol) was dissolved in 2 mL of tetrahydrofuran; lithium hydroxide monohydrate (14 mg, 0.34 mmol) was dissolved in 0.2 mL of water, and the mixture was added dropwise to the above solution. The resulting solution was reacted overnight at room temperature. After the reaction was completed, 10% citric acid solution was added dropwise so that the reaction solution was adjusted to pH=5. The resulting solution was extracted with ethyl acetate (10 mL×2). The organic phases were combined, dried with anhydrous sodium sulfate, filtered, and concentrated under reduced pressure. The obtained residue was purified by thin layer chromatography (developer: system B) to obtain (S)-5-(benzyloxy)-2-(6-cyanobenzo[d]oxazol-2-yl)-6-methoxy-1,2,3,4-tetrahydroisoquinoline-3-carboxylic acid 15 (20 mg), yield: 26%.

MS m/z(ESI): 455.9 [M+1]

1H NMR (400 MHz, DMSO-d6) δ 13.14 (s, 1H), 8.05 (s, 1H), 7.67 (dd, J=8.4, 1.2 Hz, 1H), 7.49-7.34 (m, 6H), 7.09 (d, J=8.4 Hz, 1H), 7.02 (d, J=8.4 Hz, 1H), 5.14 (dd, J=6.0, 2.8 Hz, 1H), 4.98 (d, J=10.8 Hz, 1H), 4.85 (d, J=10.8 Hz, 1H), 4.82 (d, J=15.2 Hz, 1H), 4.73 (d, J=15.2 Hz, 1H), 3.84 (s, 3H), 3.54 (dd, J=16.2, 2.6 Hz, 1H), 3.01 (dd, J=16.4, 5.6 Hz, 1H).

Example 16

(S)-5-(benzyloxy)-2-(6-chlorobenzo[d]oxazol-2-yl)-6-methoxy-1,2,3,4-tetrahydroisoquinoline-3-carboxylic acid

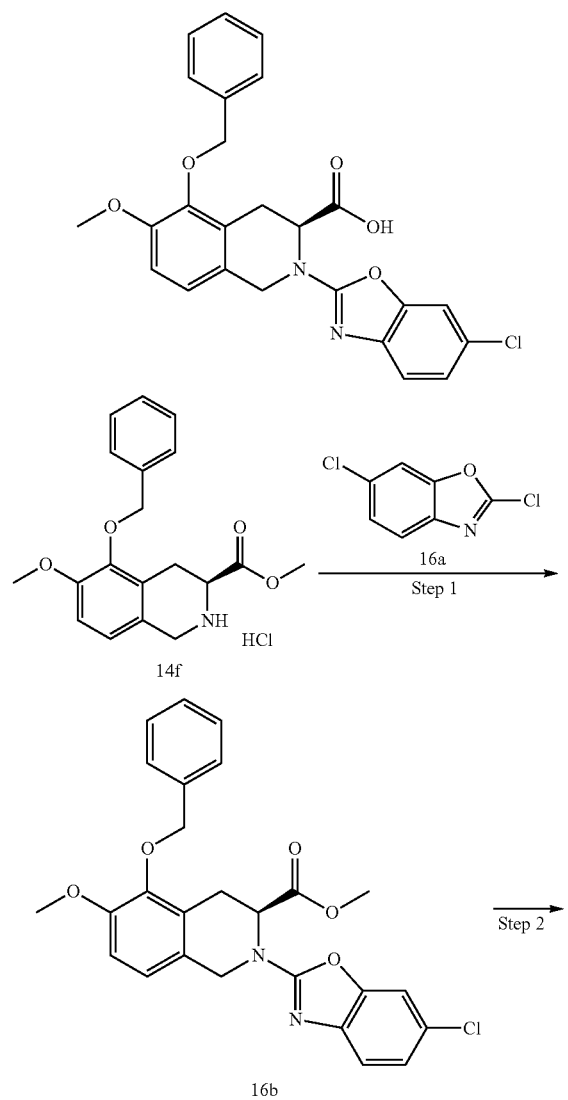

-continued

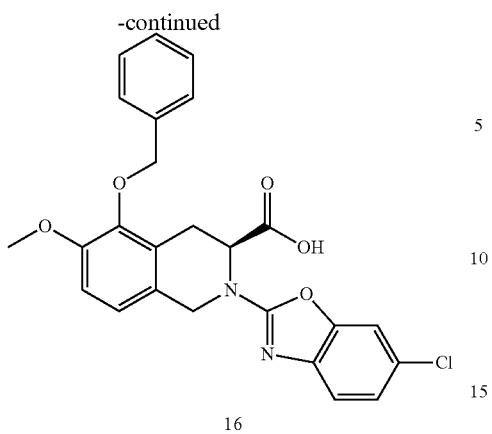

16

Step 1

Methyl (S)-5-(benzyloxy)-2-(6-chlorobenzo[d]oxazol-2-yl)-6-methoxy-1,2,3,4-tetrahydroisoquinoline-3-carboxylate Methyl (S)-5-(benzyloxy)-6-methoxy-1,2,3,4-tetrahydroisoquinoline-3-carboxylate hydrochloride14f (80 mg, 0.22 mmol), 2,6-dichlorobenzo[d]oxazole 16a (41 mg, 0.22 mmol) and triethylamine (91 μL, 0.66 mmol) were dissolved in 2 mL of tetrahydrofuran, and the mixture was reacted at 50-60° C. for 5 hours. After the reaction was completed, the resulting solution was cooled to room temperature and concentrated under reduced pressure. The residue obtained was purified by thin layer chromatography (developer: system A) to obtain methyl (S)-5-(benzyloxy)-2-(6-chlorobenzo[d]oxazol-2-yl)-6-methoxy-1,2,3,4-tetrahydroisoquinoline-3-carboxylate 16b (60 mg), yield: 57%.

MS m/z(ESI): 478.9 [M+1]

1H NMR (400 MHz, DMSO-d$_6$) δ 7.65 (d, J=1.6 Hz, 1H), 7.48-7.35 (m, 6H), 7.25 (dd, J=8.4, 2.0 Hz, 1H), 7.07 (d, J=8.4 Hz, 1H), 7.01 (d, J=8.4 Hz, 1H), 5.22 (dd, J=6.0, 2.4 Hz, 1H), 5.00 (d, J=10.8 Hz, 1H), 4.85-4.79 (m, 2H), 4.67 (d, J=16.0 Hz, 1H), 3.84 (s, 3H), 3.57 (s, 3H), 3.49 (dd, J=16.2, 2.6 Hz, 1H), 3.04 (dd, J=16.2, 6.2 Hz, 1H).

Step 2

(S)-5-(Benzyloxy)-2-(6-chlorobenzo[d]oxazol-2-yl)-6-methoxy-1,2,3,4-tetrahydroisoquinoline-3-carboxylic acid Methyl (S)-5-(benzyloxy)-2-(6-chlorobenzo[d]oxazol-2-yl)-6-methoxy-1,2,3,4-tetrahydroisoquinoline-3-carboxylate 16b (60 mg, 0.125 mmol) was dissolved in 2 mL of tetrahydrofuran; lithium hydroxide monohydrate (16 mg, 0.375 mmol) was dissolved in 0.2 mL of water, and the mixture was added dropwise to the above solution. The resulting solution was reacted overnight at room temperature. After the reaction was completed, 2N dilute hydrochloric acid was added dropwise so that the reaction solution was adjusted to pH=5. The resulting solution was extracted with ethyl acetate (10 mL×2). The organic phases were combined, dried with anhydrous sodium sulfate, filtered, and concentrated under reduced pressure. The obtained residue was separated and purified by preparative column chromatography (developer: system B) to obtain (S)-5-(benzyloxy)-2-(6-chlorobenzo[d]oxazol-2-yl)-6-methoxy-1,2,3,4-tetrahydroisoquinoline-3-carboxylic acid 16 (30 mg), yield: 52%.

MS m/z(ESI): 464.9 [M+1]

1H NMR (400 MHz, DMSO-d$_6$) δ7.64 (d, J=2.0 Hz, 1H), 7.49-7.34 (m, 6H), 7.24 (dd, J=8.4, 1.6 Hz, 1H), 7.07 (d, J=8.4 Hz, 1H), 7.01 (d, J=8.4 Hz, 1H), 5.10 (dd, J=6.2, 2.2 Hz, 1H), 4.99 (d, J=11.2 Hz, 1H), 4.87 (d, J=11.2 Hz, 1H), 4.79 (d, J=15.6 Hz, 1H), 4.68 (d, J=15.6 Hz, 1H), 3.84 (s, 3H), 3.54 (dd, J=16.2, 1.8 Hz, 1H), 3.00 (dd, J=16.4, 6.4 Hz, 1H).

Example 17

(S)-5-(Benzyloxy)-6-methoxy-2-(quinazolin-4-yl)-1,2,3,4-tetrahydroisoquinoline-3-carboxylic acid

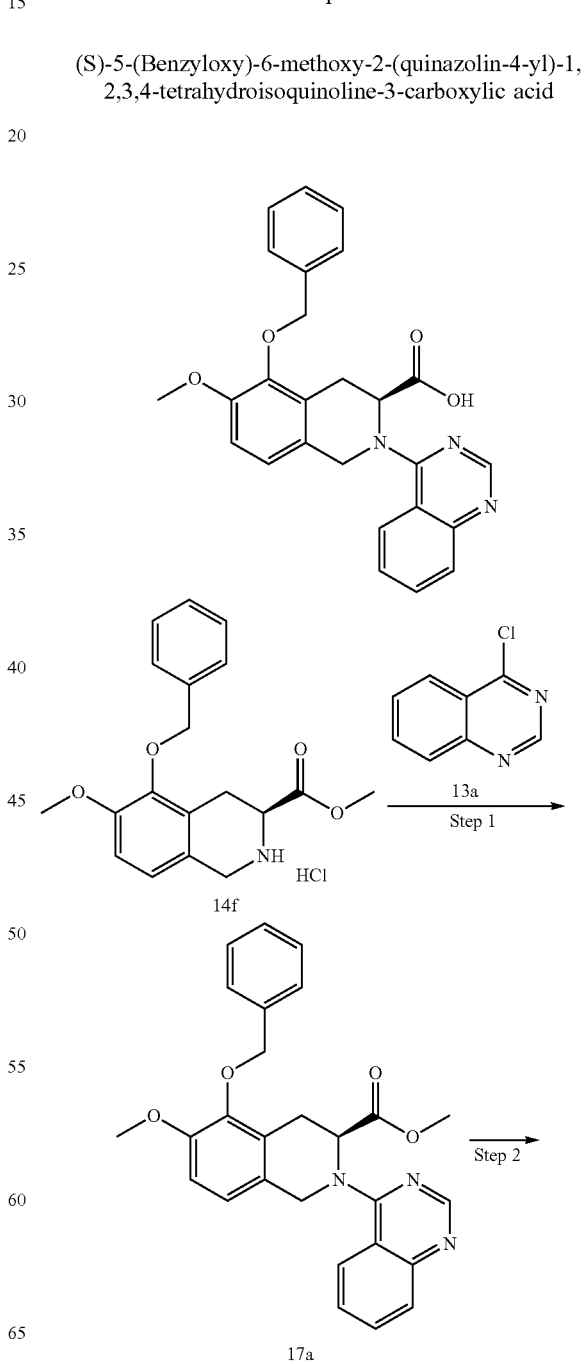

-continued

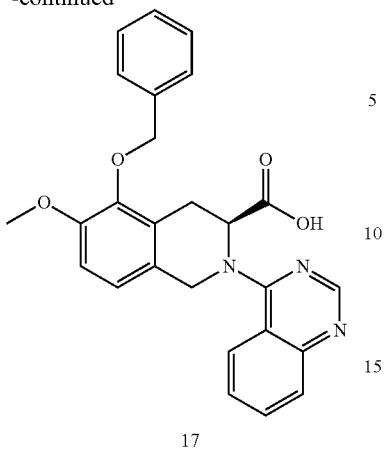

17

Step 1

Methyl (S)-5-(benzyloxy)-6-methoxy-2-(quinazolin-4-yl)-1,2,3,4-tetrahydroisoquinoline-3-carboxylate Methyl (S)-5-(benzyloxy)-6-methoxy-1,2,3,4-tetrahydroisoquinoline-3-carboxylate hydrochloride14f (70 mg, 0.19 mmol), 4-chloroquinazoline 13a (38 mg, 0.23 mmol) and N,N-diisopropylethylamine (75 mg, 0.57 mmol) were dissolved in 2 mL of acetonitrile, and the mixture was reacted at 75° C. for 10 hours. After the reaction was completed, the resulting solution was cooled to room temperature and concentrated under reduced pressure. The residue obtained was purified by thin layer chromatography (developer: system A) to obtain methyl (S)-5-(benzyloxy)-6-methoxy-2-(quinazolin-4-yl)-1,2,3,4-tetrahydroisoquinoline-3-carboxylate 17a (60 mg) yield: 70%.

MS m/z(ESI): 455.9 [M+1]

Step 2

(S)-5-(Benzyloxy)-6-methoxy-2-(quinazolin-4-yl)-1,2,3,4-tetrahydroisoquinoline-3-carboxylic acid Methyl (S)-5-(benzyloxy)-6-methoxy-2-(quinazolin-4-yl)-1,2,3,4-tetrahydroisoquinoline-3-carboxylate 17a (60 mg, 0.13 mmol) was dissolved in 2 mL of tetrahydrofuran; lithium hydroxide monohydrate (11 mg, 0.26 mmol) was dissolved in 0.2 mL of water, and the mixture was added dropwise to the above solution. The resulting solution was reacted overnight at room temperature. After the reaction was completed, saturated citric acid solution was added dropwise so that the reaction solution was adjusted to pH=5. The resulting solution was extracted with ethyl acetate (10 mL×2). The organic phases were combined, dried with anhydrous sodium sulfate, filtered, and concentrated under reduced pressure. The obtained residue was purified by a preparative column to obtain (S)-5-(benzyloxy)-6-methoxy-2-(quinazolin-4-yl)-1,2,3,4-tetrahydroisoquinoline-3-carboxylic acid 17 (41.2 mg), yield: 72%.

MS m/z(ESI): 441.9 [M+1]

1H NMR (400 MHz, DMSO-$d_6$) δ 8.84 (s, 1H), 8.46 (d, J=8.0 Hz, 1H), 8.04 (t, J=7.6 Hz, 1H), 7.87 (d, J=7.6 Hz, 1H), 7.76 (t, J=8.0 Hz, 1H), 7.50-7.40 (m, 5H), 7.06 (d, J=8.4 Hz, 1H), 6.99 (d, J=8.8 Hz, 1H), 5.50 (t, J=4.8 Hz, 1H), 5.27 (d, J=15.2 Hz, 1H), 5.17 (d, J=15.2 Hz, 1H), 5.02 (d, J=11.2 Hz, 1H), 4.88 (d, J=10.8 Hz, 1H), 3.84 (s, 3H), 3.49 (dd, J=15.8, 4.6 Hz, 1H), 3.17 (dd, J=16.0, 5.2 Hz, 1H).

Example 18

(S)-5-(Benzyloxy)-6-methoxy-2-(6-(trifluoromethyl)benzo[d]oxazol-2-yl)-1,2,3,4-tetrahydroisoquinoline-3-carboxylic acid

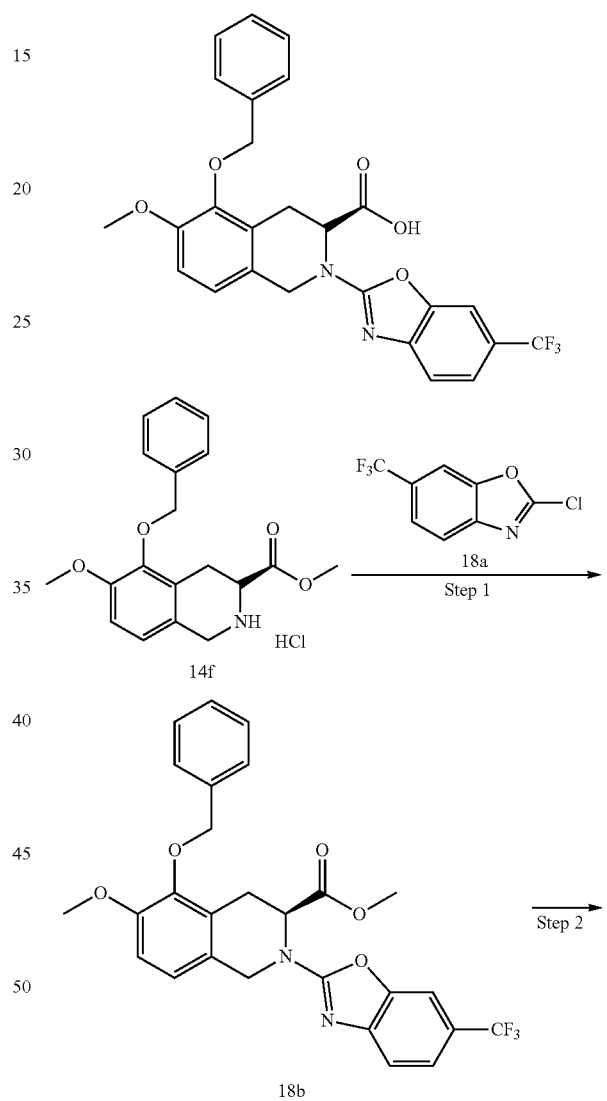

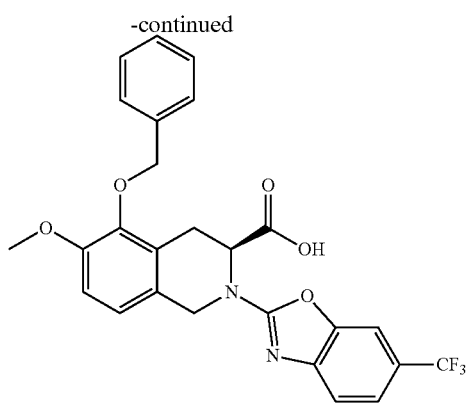

Step 1

Methyl (S)-5-(Benzyloxy)-6-methoxy-2-(6-(trifluoromethyl)benzo[d]oxazol-2-yl)-1,2,3,4-tetrahydroisoquinoline-3-carboxylate Methyl (S)-5-(benzyloxy)-6-methoxy-1,2,3,4-tetrahydroisoquinoline-3-carboxylate hydrochloride 14f (55 mg, 0.15 mmol), 2-chloro-6-(trifluoromethyl)benzo[d]oxazole 18a (34 mg, 0.15 mmol, prepared according to the published patent WO 2010118670) and triethylamine (46 mg, 0.45 mmol) were dissolved in 2 mL of tetrahydrofuran, and the mixture was reacted at 50-60° C. for 4 hours. After the reaction was completed, the resulting solution was cooled to room temperature and concentrated under reduced pressure. The residue obtained was purified by thin layer chromatography (developer: system A) to obtain methyl (S)-5-(Benzyloxy)-6-methoxy-2-(6-(trifluoromethyl)benzo[d]oxazol-2-yl)-1,2,3,4-tetrahydroisoquinoline-3-carboxylate 18b (80 mg), yield: 100%.

MS m/z(ESI): 512.8 [M+1]

Step 2

(S)-5-(Benzyloxy)-6-methoxy-2-(6-(trifluoromethyl)benzo[d]oxazol-2-yl)-1,2,3,4-tetrahydroisoquinoline-3-carboxylic acid Methyl (S)-5-(Benzyloxy)-6-methoxy-2-(6-(trifluoromethyl)benzo[d]oxazol-2-yl)-1,2,3,4-tetrahydroisoquinoline-3-carboxylate 18b (80 mg, 0.156 mmol) was dissolved in 3 mL of tetrahydrofuran; lithium hydroxide monohydrate (39 mg, 0.93 mmol) was dissolved in 0.3 mL of water, and the mixture was added dropwise to the above solution. The resulting solution was reacted overnight at room temperature. After the reaction was completed, 2N dilute hydrochloric acid was added dropwise so that the reaction solution was adjusted to pH=1. The resulting solution was extracted with ethyl acetate (10 mL×2). The organic phases were combined, dried with anhydrous sodium sulfate, filtered, and concentrated under reduced pressure. The obtained residue was separated and purified by a preparative column to obtain (S)-5-(benzyloxy)-6-methoxy-2-(6-(trifluoromethyl)benzo[d]oxazol-2-yl)-1,2,3,4-tetrahydroisoquinoline-3-carboxylic acid 18 (44 mg), yield: 57%.

MS m/z(ESI): 498.9 [M+1]

1H NMR (400 MHz, DMSO-d$_6$) δ 7.89 (s, 1H), 7.56-7.40 (m, 7H), 7.09 (d, J=8.8 Hz, 1H), 7.02 (d, J=8.4 Hz, 1H), 5.14 (dd, J=6.2, 2.6 Hz, 1H), 4.99 (d, J=10.8 Hz, 1H), 4.88-4.80 (m, 2H), 4.72 (d, J=15.6 Hz, 1H), 3.84 (s, 3H), 3.55 (dd, J=16.2, 2.6 Hz, 1H), 3.02 (dd, J=16.4, 6.4 Hz, 1H).

Example 19

(S)—N-(ethylsulfonyl)-2-(6-fluorobenzo[d]oxazol-2-yl)-6-methoxy-5-(phenoxymethyl)-1,2,3,4-tetrahydroisoquinoline-3-carboxamide

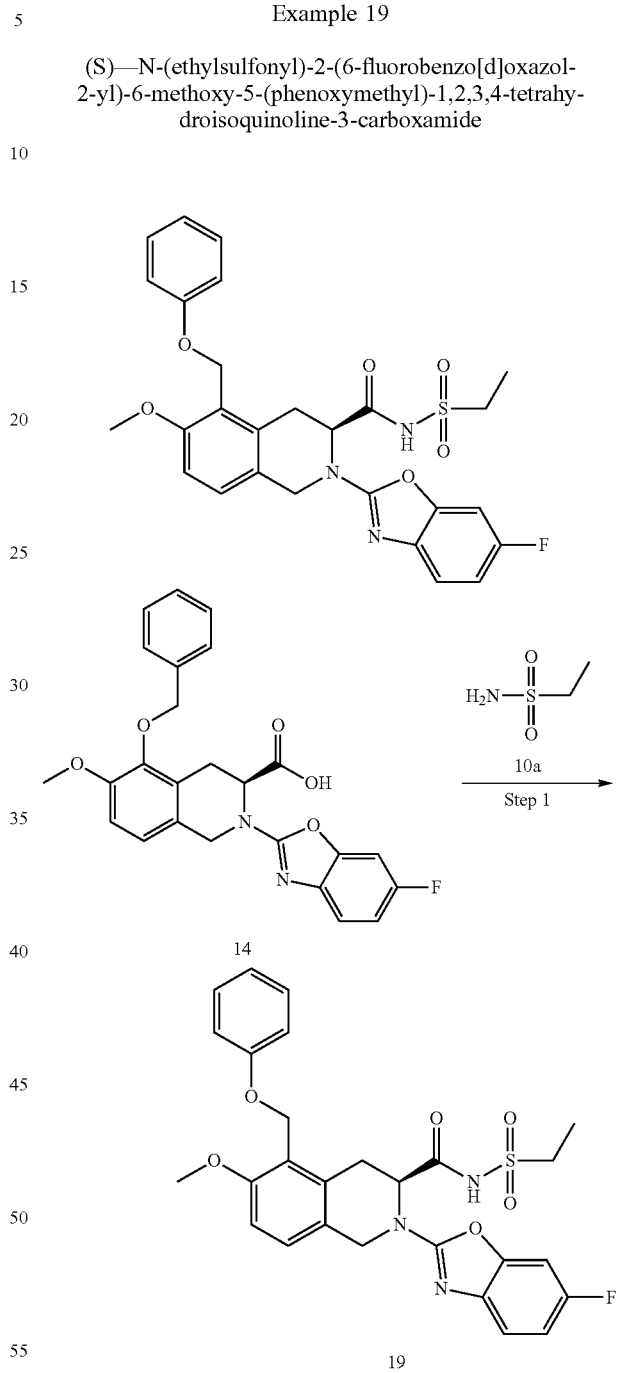

Step 1

(S)—N-(ethylsulfonyl)-2-(6-fluorobenzo[d]oxazol-2-yl)-6-methoxy-5-(phenoxymethyl)-1,2,3,4-tetrahydroisoquinoline-3-carboxamide (S)-5-(Benzyloxy)-2-(6-fluorobenzo(d)oxazol-2-yl)-6-methoxy-1,2,3,4-tetrahydroisoquinoline-3-carboxylic acid 14 (50 mg, 0.11 mmol), ethanesulfonamide 10a (24.3 mg, 0.22 mmol), 2-(7-benzotriazole oxide)-N,N,N',N'-tetramethylurea hexafluorophosphate (102 mg, 0.27 mmol) and 1-hydroxybenzotriazole (36 mg, 0.27 mmol) were added to 5 mL of dichloromethane, and N,N-diisopropylethylamine (0.14 mL, 0.84 mmol) was added dropwise under ice bath. The mixture was continued to stir at low temperature for 1 hour, and then transferred to room temperature, and reacted overnight. After the reaction was completed, 5 mL of water was added. The resulting solution was extracted with dichloromethane (10 mL×2), and concentrated under reduced pressure. The residue obtained was separated to obtain (S)—N-(ethylsulfonyl)-2-(6-fluorobenzo[d]oxazol-2-yl)-6-methoxy-5-(phenoxymethyl)-1,2,3,4-tetrahydroisoquinoline-3-carboxamide 19 (21 mg, white solid), yield: 35%.

MS m/z(ESI): 540.2 [M+1]

1H NMR (400 MHz, CDCl₃) δ 7.47-7.45 (m, 2H), 7.40-7.36 (m, 4H), 7.14 (dd, J=7.6, 2.4 Hz, 1H), 7.02-6.97 (m, 2H), 6.87 (d, J=8.0 Hz, 1H), 5.10 (d, J=11.2 Hz, 1H), 5.00 (d, J=11.2 Hz, 1H), 4.82-4.79 (m, 2H), 4.70 (d, J=14.8 Hz, 1H), 3.90 (s, 3H), 3.48 (d, J=16.0 Hz, 1H), 3.33 (q, J=7.2 Hz, 2H), 2.99 (dd, J=15.8, 5.0 Hz, 1H), 1.22 (t, J=7.4 Hz, 3H).

Example 20

(S)—N—(N,N-dimethylaminosulfonyl)-2-(6-fluorobenzo[d]oxazol-2-yl)-6-methoxy-5-(phenoxymethyl)-1,2,3,4-tetrahydroisoquinoline-3-carboxamide

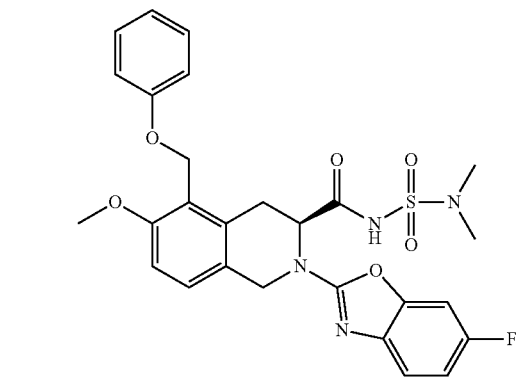

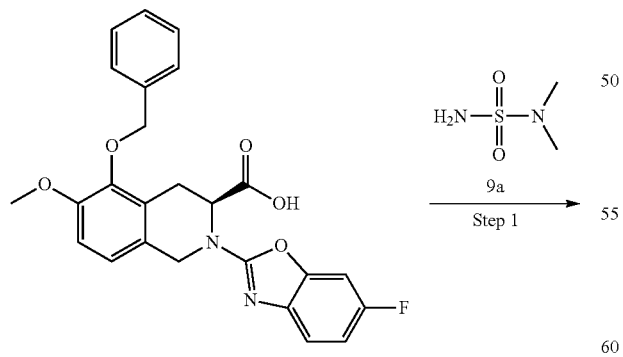

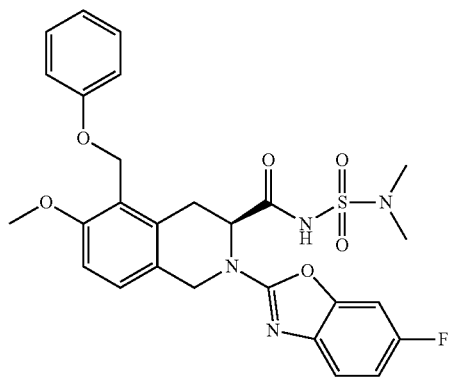

Step 1

(S)—N—(N,N-dimethylaminosulfonyl)-2-(6-fluorobenzo[d]oxazol-2-yl)-6-methoxy-5-(phenoxymethyl)-1,2,3,4-tetrahydroisoquinoline-3-carboxamide (S)-5-(Benzyloxy)-2-(6-fluorobenzo(d)oxazol-2-yl)-6-methoxy-1,2,3,4-tetrahydroisoquinoline-3-carboxylic acid 14 (80 mg, 0.18 mmol) was dissolved in 5 mL of tetrahydrofuran, and N,N'-carbonyldiimidazole (50.3 mg, 0.36 mmol) was added. The mixture was heated to 30° C., and reacted at 30° C. for 2 hours. N,N-dimethylsulfonamide 9a (46.5 mg, 0.37 mmol) and 1,8-diazabicycloundec-7-ene (89.5 mg, 0.36 mmol) were added, and the resulting mixture was continued to react at 30° C. for 15 hours. After the reaction was completed, the resulting solution was concentrated under reduced pressure. The obtained residue was purified by thin layer chromatography (developer: system B) to obtain (S)—N—(N,N-dimethylaminosulfonyl)-2-(6-fluorobenzo[d]oxazol-2-yl)-6-methoxy-5-(phenoxymethyl)-1,2,3,4-tetrahydroisoquinoline-3-carboxamide 20 (21 mg), yield: 21%.

MS m/z(ESI): 554.9 [M+1]

1H NMR (400 MHz, CDCl3) δ 7.46-7.45 (m, 2H), 7.38-7.31 (m, 4H), 7.10 (d, J=6.4 Hz, 1H), 6.99-6.95 (m, 2H), 6.86 (d, J=8.4 Hz, 1H), 5.07 (d, J=10.8 Hz, 1H), 4.99 (d, J=10.8 Hz, 1H), 4.77-4.64 (m, 3H), 3.89 (s, 3H), 3.47 (d, J=12.4 Hz, 1H), 2.92 (dd, J=15.6, 5.2 Hz, 1H), 2.75 (s, 6H).

Example 21

(S)—N-(cyclopropylsulfonyl)-2-(6-fluorobenzo[d]oxazol-2-yl)-6-methoxy-5-(phenoxymethyl)-1,2,3,4-tetrahydroisoquinoline-3-carboxamide

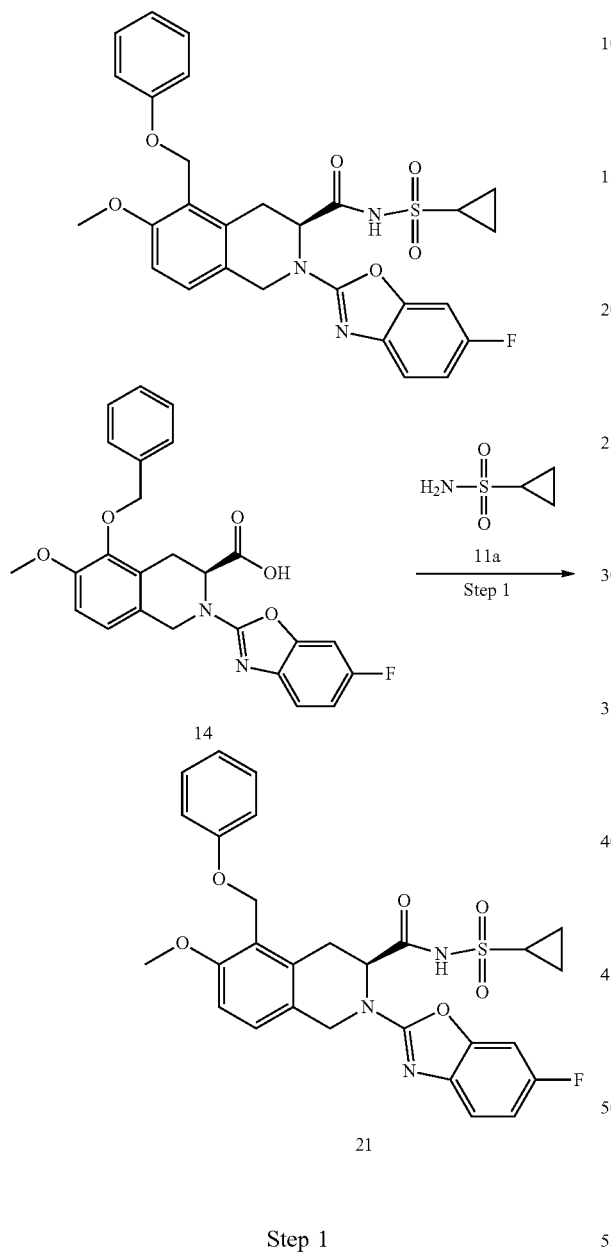

Step 1

(S)—N-(cyclopropylsulfonyl)-2-(6-fluorobenzo[d]oxazol-2-yl)-6-methoxy-5-(phenoxymethyl)-1,2,3,4-tetrahydroisoquinoline-3-carboxamide (S)-5-(Benzyloxy)-2-(6-fluorobenzo[d]oxazol-2-yl)-6-methoxy-1,2,3,4-tetrahydroisoquinoline-3-carboxylic acid 14 (80 mg, 0.18 mmol) was dissolved in 5 mL of tetrahydrofuran, and N,N'-carbonyldiimidazole (50.3 mg, 0.36 mmol) was added. The mixture was heated to 30° C., and reacted at 30° C. for 2 hours. Cyclopropanesulfonamide 11a (45.4 mg, 0.37 mmol) and 1,8-diazabicycloundec-7-ene (89.5 mg, 0.36 mmol) were added, and the resulting mixture was continued to react at 30° C. for 5 hours. After the reaction was completed, the resulting solution was concentrated under reduced pressure. The obtained residue was purified by thin layer chromatography (developer: system B) to obtain (S)—N-(cyclopropylsulfonyl)-2-(6-fluorobenzo[d]oxazol-2-yl)-6-methoxy-5-(phenoxymethyl)-1,2,3,4-tetrahydroisoquinoline-3-carboxamide 21 (15 mg), yield: 15%.

MS m/z(ESI): 551.8 [M+1]

1H NMR (400 MHz, CDCl$_3$) δ 7.47-7.44 (m, 2H), 7.39-7.31 (m, 4H), 7.10 (dd, J=7.6, 2.4 Hz, 1H), 7.00-6.95 (m, 2H), 6.86 (d, J=8.4 Hz, 1H), 5.08 (d, J=10.8 Hz, 1H), 5.01 (d, J=10.8 Hz, 1H), 4.78 (d, J=14.8 Hz, 1H), 4.72 (t, J=5.6 Hz, 1H), 4.63 (d, J=14.8 Hz, 1H), 3.89 (s, 3H), 3.48 (dd, J=16.0, 4.8 Hz, 1H), 2.96 (dd, J=16.0, 6.0 Hz, 1H), 2.86-2.79 (m, J=4.8 Hz, 1H), 1.31-1.17 (m, 2H), 1.04-0.92 (m, 2H).

Example 22

(S)-5-(benzyloxy)-6-methoxy-2-(oxazolo[5,4-c]pyridin-2-yl)-1,2,3,4-tetrahydroisoquinoline-3-carboxylic acid

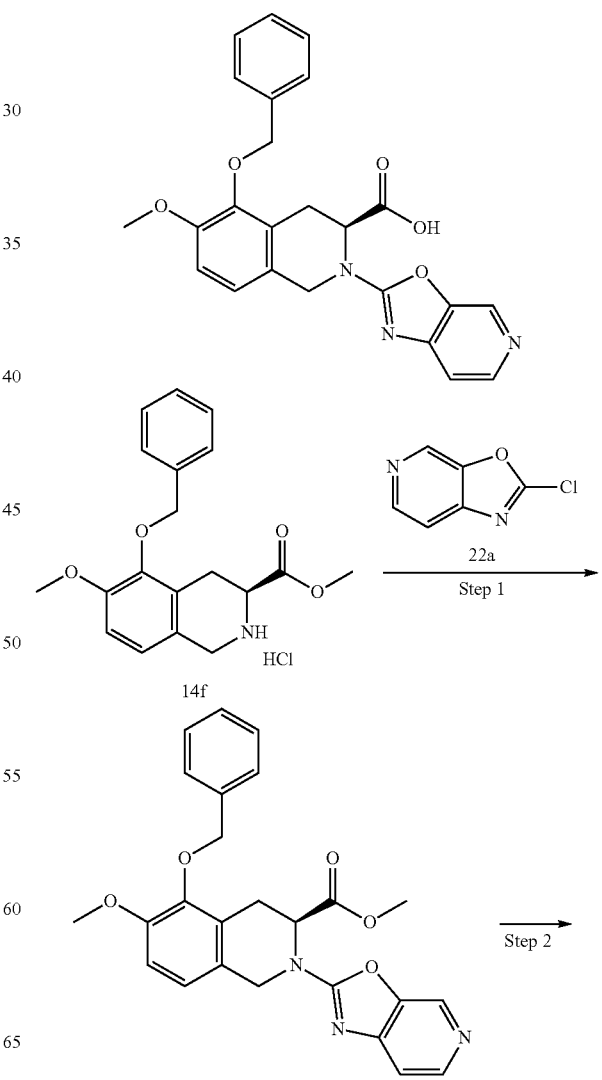

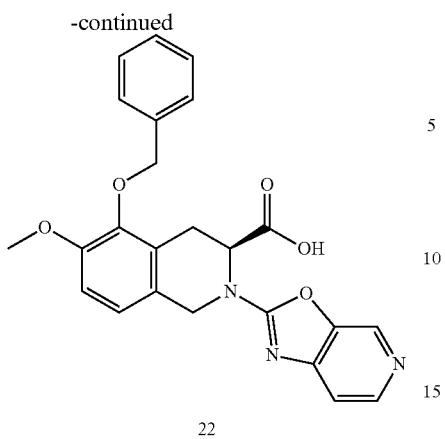

22

Step 1

Methyl (S)-5-(benzyloxy)-6-methoxy-2-(oxazolo[5,4-c]pyridin-2-yl)-1,2,3,4-tetrahydroisoquinoline-3-carboxylate Methyl (S)-5-(benzyloxy)-6-methoxy-1,2,3,4-tetrahydroisoquinoline-3-carboxylate hydrochloride 14f (50 mg, 0.137 mmol), 2-chlorooxazolo[5,4-c]pyridine 22a (26 mg, 0.16 mmol) and triethylamine (42 mg, 0.41 mmol) were dissolved in 2 mL of tetrahydrofuran, and the mixture was reacted at 60-70° C. for 4 hours. After the reaction was completed, the resulting solution was cooled to room temperature and concentrated under reduced pressure. The residue obtained was purified by thin layer chromatography (developer: system B) to obtain methyl (S)-5-(benzyloxy)-6-methoxy-2-(oxazolo[5,4-c]pyridin-2-yl)-1,2,3,4-tetrahydroisoquinoline-3-carboxylate 22b (60 mg, yellow oil), yield: 100%.

MS m/z(ESI): 445.9 [M+1]

$^1$H NMR (400 MHz, DMSO-$d_6$) δ 9.05 (s, 1H), 8.57 (s, 1H), 7.73 (s, 1H), 7.49-7.35 (m, 5H), 7.12 (d, J=8.8 Hz, 1H), 7.04 (d, J=8.0 Hz, 1H), 5.35 (dd, J=5.8, 3.0 Hz, 1H), 5.02 (d, J=11.2 Hz, 1H), 4.93-4.81 (m, 3H), 3.85 (s, 3H), 3.59 (s, 3H), 3.54 (dd, J=16.4, 2.8 Hz, 1H), 3.08 (dd, J=16.0, 6.0 Hz, 1H)

Step 2

(S)-5-(benzyloxy)-6-methoxy-2-(oxazolo[5,4-c]pyridin-2-yl)-1,2,3,4-tetrahydroisoquinoline-3-carboxylic acid Methyl (S)-5-(benzyloxy)-6-methoxy-2-(oxazolo[5,4-c]pyridin-2-yl)-1,2,3,4-tetrahydroisoquinoline-3-carboxylate 22b (60 mg, 0.135 mmol) was dissolved in 2 mL of tetrahydrofuran; lithium hydroxide monohydrate (11 mg, 0.27 mmol) was dissolved in 0.2 mL of water, and the mixture was added dropwise to the above solution. The resulting solution was reacted overnight at room temperature. After the reaction was completed, 2N dilute hydrochloric acid was added dropwise so that the reaction solution was adjusted to pH=1. The resulting solution was extracted with ethyl acetate (10 mL×2). The organic phases were combined, dried with anhydrous sodium sulfate, filtered, and concentrated under reduced pressure. The obtained residue was separated and purified by a preparative column to obtain (S)-5-(benzyloxy)-6-methoxy-2-(oxazolo[5,4-c]pyridin-2-yl)-1,2,3,4-tetrahydroisoquinoline-3-carboxylic acid 22 (7 mg), yield: 12%.

MS m/z(ESI): 431.9 [M+1]

1H NMR (400 MHz, DMSO-$d_6$) δ 9.05 (s, 1H), 8.55 (d, J=6.4 Hz, 1H), 7.74 (d, J=6.0 Hz, 1H), 7.50-7.36 (m, 5H), 7.13 (d, J=8.0 Hz, 1H), 7.05 (d, J=8.0 Hz, 1H), 5.22 (s, 1H), 5.01 (d, J=11.2 Hz, 1H), 4.92-4.82 (m, 3H), 3.86 (s, 3H), 3.59 (dd, J=16.2, 2.2 Hz, 1H), 3.05 (dd, J=16.4, 6.0 Hz, 1H).

Example 23

(S)-5-(benzyloxy)-2-(5-fluorobenzo[d]oxazol-2-yl)-6-methoxy-1,2,3,4-tetrahydroisoquinoline-3-carboxylic acid

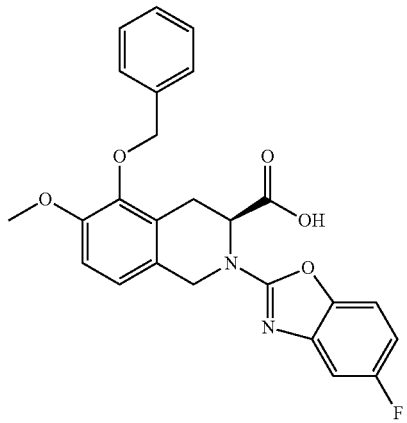

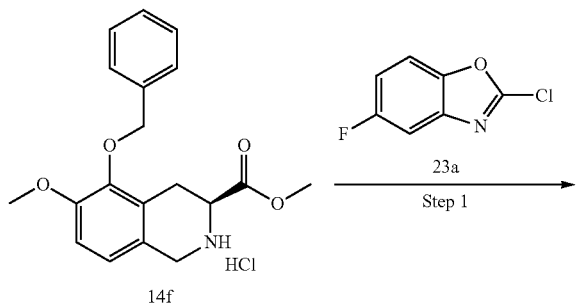

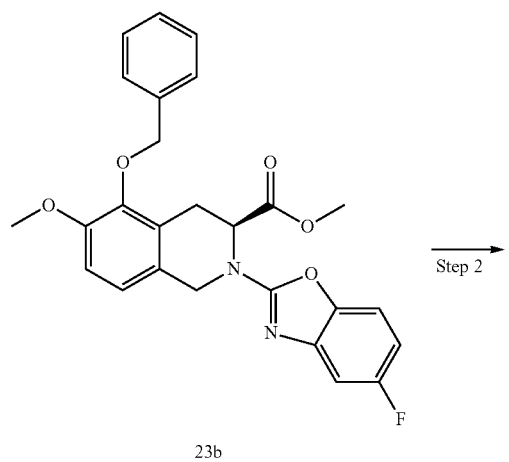

23b

-continued

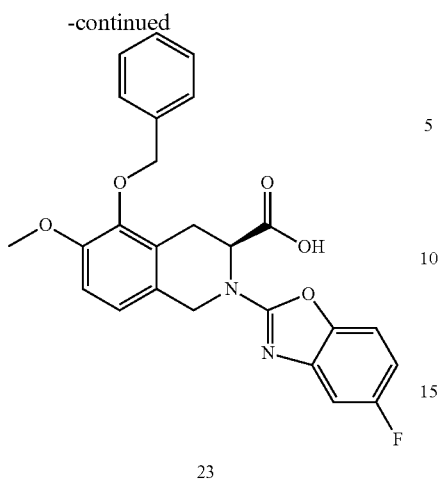

23

Step 1

Methyl (S)-5-(benzyloxy)-2-(5-fluorobenzo[d]oxazol-2-yl)-6-methoxy-1,2,3,4-tetrahydroisoquinoline-3-carboxylate Methyl (S)-5-(benzyloxy)-6-methoxy-1,2,3,4-tetrahydroisoquinoline-3-carboxylate hydrochloride14f (50 mg, 0.137 mmol), 2-chloro-6-fluorobenzo[d]oxazole 23a (23.6 mg, 0.137 mmol) and triethylamine (42 mg, 0.41 mmol) were dissolved in 1 mL of tetrahydrofuran, and the mixture was reacted at 60-70° C. for 5 hours. After the reaction was completed, the resulting solution was cooled to room temperature and concentrated under reduced pressure. The residue obtained was purified by thin layer chromatography (developer: system A) to obtain methyl (S)-5-(benzyloxy)-2-(5-fluorobenzo[d]oxazol-2-yl)-6-methoxy-1,2,3,4-tetrahydroisoquinoline-3-carboxylate 23b (63 mg), yield: 100%.

MS m/z(ESI): 462.9[M+1]

Step 2

(S)-5-(benzyloxy)-2-(5-fluorobenzo[d]oxazol-2-yl)-6-methoxy-1,2,3,4-tetrahydroisoquinoline-3-carboxylic acid Methyl (S)-5-(benzyloxy)-2-(5-fluorobenzo[d]oxazol-2-yl)-6-methoxy-1,2,3,4-tetrahydroisoquinoline-3-carboxylate 23b (63 mg, 0.137 mmol) was dissolved in 2 mL of tetrahydrofuran; lithium hydroxide monohydrate (36 mg, 0.82 mmol) was dissolved in 0.2 mL of water, and the mixture was added dropwise to the above solution. The resulting solution was reacted overnight at room temperature. After the reaction was completed, 2N dilute hydrochloric acid was added dropwise so that the reaction solution was adjusted to pH=1. The resulting solution was extracted with ethyl acetate (10 mL×2). The organic phases were combined, dried with anhydrous sodium sulfate, filtered, and concentrated under reduced pressure. The obtained residue was separated and purified by a preparative column to obtain (S)-5-(benzyloxy)-2-(5-fluorobenzo[d]oxazol-2-yl)-6-methoxy-1,2,3,4-tetrahydroisoquinoline-3-carboxylic acid 23 (20 mg), yield: 33%.

MS m/z(ESI): 448.9 [M+1]

1H NMR (400 MHz, DMSO-$d_6$) δ 7.50-7.35 (m, 6H), 7.21 (dd, J=9.2, 2.8 Hz, 1H), 7.08 (d, J=8.6 Hz, 1H), 7.02 (d, J=8.6 Hz, 1H), 6.88 (td, J=9.2, 2.3 Hz, 1H), 5.11 (dd, J=6.2, 2.6 Hz, 1H), 4.99 (d, J=10.8 Hz, 1H), 4.87 (d, J=10.8 Hz, 1H), 4.80 (d, J=15.6 Hz, 1H), 4.69 (d, J=16.0 Hz, 1H), 3.85 (s, 3H), 3.53 (dd, J=16.4, 2.4 Hz, 1H), 3.01 (dd, J=16.0, 6.4 Hz, 1H).

Example 24

(S)-5-(benzyloxy)-2-(6-isopropylbenzo[d]oxazol-2-yl)-6-methoxy-1,2,3,4-tetrahydroisoquinoline-3-carboxylic acid

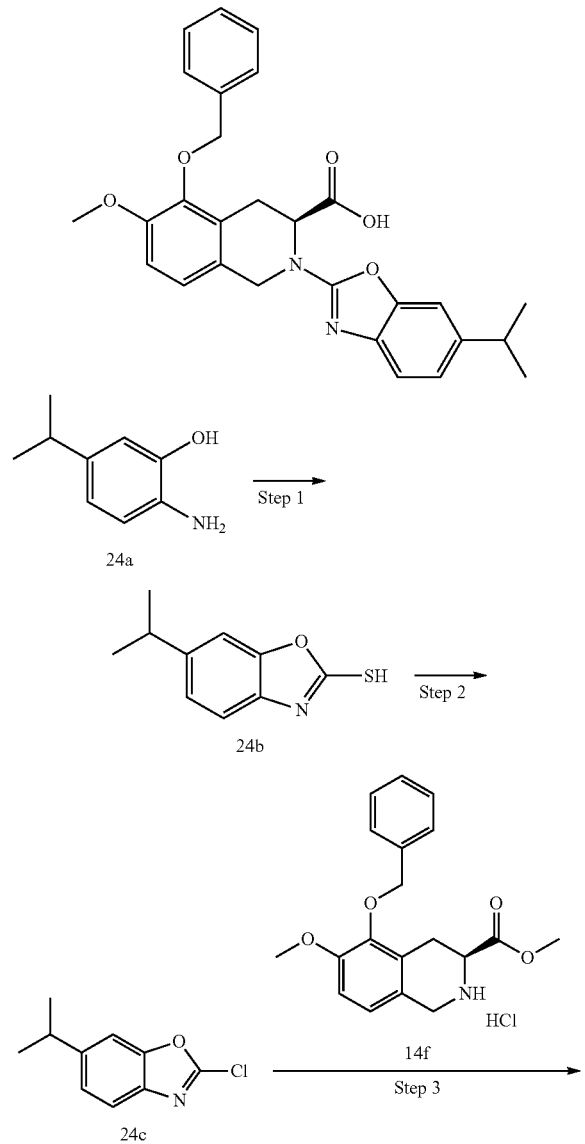

-continued

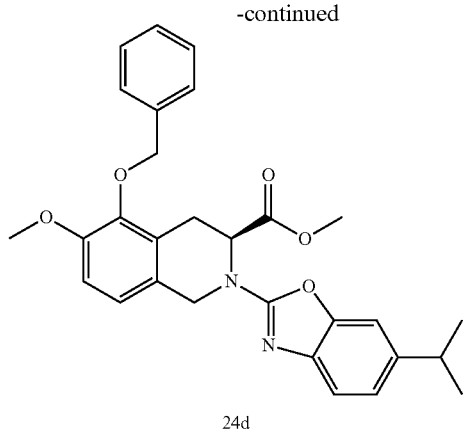

24d

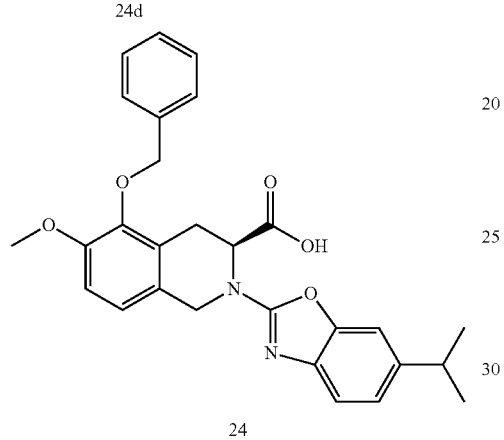

24

Step 1

6-isopropylbenzo[d]oxazole-2-thiol

2-Amino-5-isopropylphenol 24a (220 mg, 1.45 mmol) and potassium ethylxanthate (350 mg, 2.18 mmol) were dissolved in 3 mL N,N-dimethylformamide, and the mixture was reacted at 110-110° C. for 4 hours. After the reaction was completed, the resulting solution was cooled to room temperature. 10 mL of water was added, and 2N dilute hydrochloric acid was added dropwise so that the system was adjusted to pH=3. A solid was precipitated, filtered and dried to obtain 6-isopropylbenzo[d]oxazole-2-thiol 24b (110 mg, pale yellow solid), yield: 39%.

MS m/z(ESI): 193.9 [M+1]

Step 2

2-chloro-6-isopropylbenzo[d]oxazole

6-Isopropylbenzo[d]oxazole-2-thiol 24b (30 mg, 0.155 mmol) was dissolved in 3 mL of thionyl chloride, and the mixture was reacted under reflux for 4 hours. After the reaction was completed, the resulting solution was cooled to room temperature, concentrated under reduced pressure to obtain 2-chloro-6-isopropylbenzo[d]oxazole 24c (30 mg, yellow oil), yield: 100%.

MS m/z(ESI): 195.9 [M+1]

Step 3

Methyl (S)-5-(benzyloxy)-2-(6-isopropylbenzo[d]oxazol-2-yl)-6-methoxy-1,2,3,4-tetrahydroisoquinoline-3-carboxylate Methyl (S)-5-(benzyloxy)-6-methoxy-1,2,3,4-tetrahydroisoquinoline-3-carboxylate hydrochloride14f (50 mg, 0.137 mmol), 2-chloro-6-isopropylbenzo[d]oxazole 24c (27 mg, 0.137 mmol) and triethylamine (42 mg, 0.41 mmol) were dissolved in 1 mL of tetrahydrofuran, and the mixture was reacted at 60-70° C. for 5 hours. After the reaction was completed, the resulting solution was cooled to room temperature and concentrated under reduced pressure. The residue obtained was purified by thin layer chromatography (developer: system A) to obtain methyl (S)-5-(benzyloxy)-2-(6-isopropylbenzo[d]oxazol-2-yl)-6-methoxy-1,2,3,4-tetrahydroisoquinoline-3-carboxylate 24d (50 mg), yield: 75%.

MS m/z(ESI): 486.9 [M+1]

Step 4

(S)-5-(benzyloxy)-2-(6-isopropylbenzo[d]oxazol-2-yl)-6-methoxy-1,2,3,4-tetrahydroisoquinoline-3-carboxylic acid Methyl (S)-5-(benzyloxy)-2-(6-isopropylbenzo[d]oxazol-2-yl)-6-methoxy-1,2,3,4-tetrahydroisoquinoline-3-carboxylate 24d (50 mg, 0.103 mmol) was dissolved in 1 mL of tetrahydrofuran; lithium hydroxide monohydrate (30 mg, 0.715 mmol) was dissolved in 0.1 mL of water, and the mixture was added dropwise to the above solution. The resulting solution was reacted overnight at room temperature. After the reaction was completed, 2N dilute hydrochloric acid was added dropwise so that the reaction solution was adjusted to pH=1. The resulting solution was extracted with ethyl acetate (5 mL×2). The organic phases were combined, dried with anhydrous sodium sulfate, filtered, and concentrated under reduced pressure. The obtained residue was separated and purified by a preparative column to obtain (S)-5-(benzyloxy)-2-(6-isopropylbenzo[d]oxazol-2-yl)-6-methoxy-1,2,3,4-tetrahydroisoquinoline-3-carboxylic acid 24 (20 mg), yield: 41%.

MS m/z(ESI): 473.0[M+1]

1H NMR (400 MHz, DMSO-d6) δ 7.50-7.36 (m, 6H), 7.25 (d, J=8.0 Hz, 1H), 7.09-7.06 (m, 2H), 7.02 (d, J=8.4 Hz, 1H), 5.10 (dd, J=6.4, 2.4 Hz, 1H), 4.99 (d, J=10.8 Hz, 1H), 4.88 (d, J=10.8 Hz, 1H), 4.79 (d, J=16.0 Hz, 1H), 4.66 (d, J=15.6 Hz, 1H), 3.85 (s, 3H), 3.55-3.54 (m, 1H), 3.03-2.93 (m, 2H), 1.23 (d, J=6.8 Hz, 6H).

Example 25

2-(Benzo[d]thiazol-2-yl)-5-(benzyloxy)-6-methoxy-1,2,3,4-tetrahydroisoquinoline-3-carboxylic acid

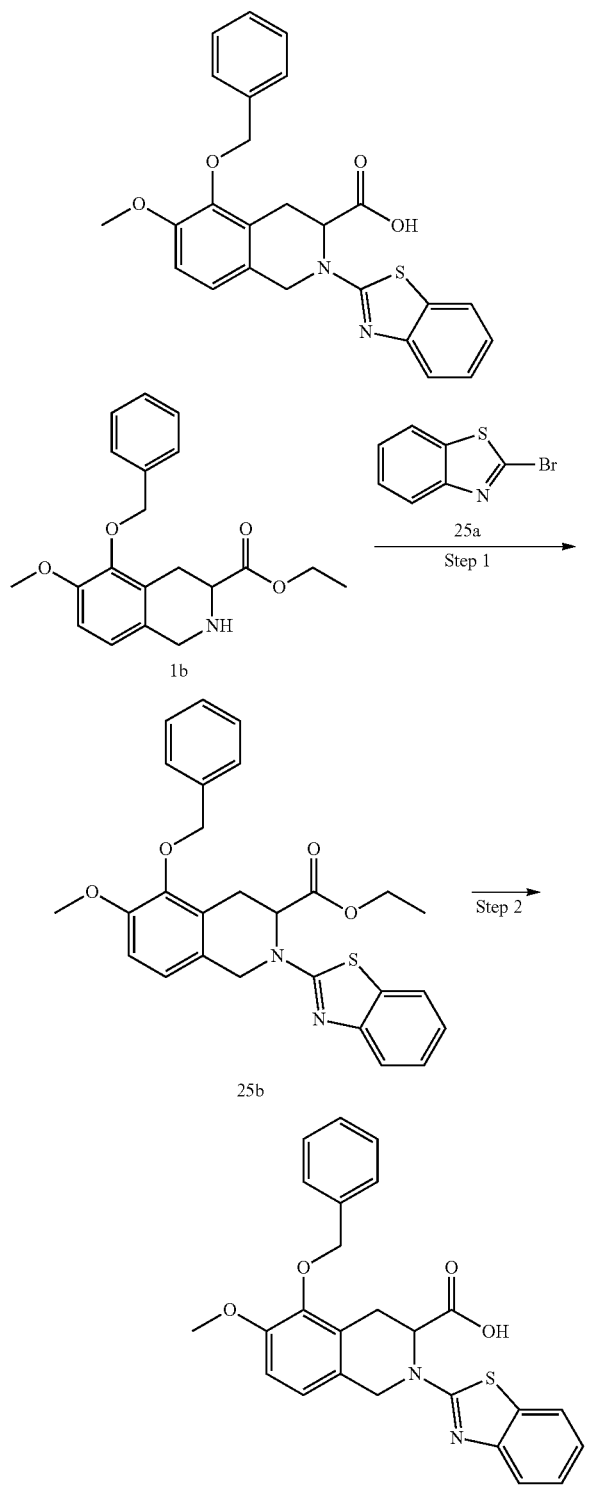

Step 1

Ethyl 2-(benzo[d]thiazol-2-yl)-5-(benzyloxy)-6-methoxy-1,2,3,4-tetrahydroisoquinoline-3-carboxylate Ethyl 5-(benzyloxy)-6-methoxy-1,2,3,4-tetrahydroisoquinoline-3-carboxylate hydrochloride 1b (50 mg, 0.13 mmol), 2-bromobenzo[d]thiazole 25a (28 mg, 0.13 mmol) and potassium carbonate (37 mg, 0.26 mmol) were dissolved in 1 mL of N,N-dimethylformamide, and the mixture was reacted overnight at room temperature. After the reaction was completed, 10 mL of water was added, and the resulting solution was extracted with ethyl acetate (5 mL×3). The organic phases were combined, washed with saturated sodium chloride solution (10 mL), dried with anhydrous sodium sulfate, filtered, and concentrated under reduced pressure. The obtained residue was purified by thin layer chromatography (developer: system B) to obtain ethyl 2-(benzo[d]thiazol-2-yl)-5-(benzyloxy)-6-methoxy-1,2,3,4-tetrahydroisoquinoline-3-carboxylate 25b (50 mg), yield: 82%.

MS m/z(ESI): 474.9 [M+1]

Step 2

2-(Benzo[d]thiazol-2-yl)-5-(benzyloxy)-6-methoxy-1,2,3,4-tetrahydroisoquinoline-3-carboxylic acid Ethyl 2-(benzo[d]thiazol-2-yl)-5-(benzyloxy)-6-methoxy-1,2,3,4-tetrahydroisoquinoline-3-carboxylate 25b (50 mg, 0.11 mmol) was dissolved in 2 mL of tetrahydrofuran; lithium hydroxide monohydrate (9 mg, 0.22 mmol) was dissolved in 0.2 mL of water, and the mixture was added dropwise to the above solution. The resulting solution was reacted overnight at room temperature. After the reaction was completed, 2N dilute hydrochloric acid was added dropwise so that the reaction solution was adjusted to pH=1. The resulting solution was extracted with ethyl acetate (10 mL×2). The organic phases were combined, dried with anhydrous sodium sulfate, filtered, and concentrated under reduced pressure. The obtained residue was separated and purified by a preparative column to obtain 2-(benzo[d]thiazol-2-yl)-5-(benzyloxy)-6-methoxy-1,2,3,4-tetrahydroisoquinoline-3-carboxylic acid 25 (15 mg), yield: 30%.

MS m/z(ESI): 446.9 [M+1]

$^1$H NMR (400 MHz, DMSO-$d_6$) δ 7.84 (d, J=7.6 Hz, 1H), 7.46-7.31 (m, 7H), 7.14-7.09 (m, 2H), 7.03 (d, J=8.8 Hz, 1H), 5.19 (s, 1H), 5.00 (d, J=10.8 Hz, 1H), 4.87 (d, J=10.8 Hz, 1H), 4.71 (d, J=15.6 Hz, 1H), 4.64 (d, J=14.8 Hz, 1H), 3.85 (s, 3H), 3.58-3.57 (m, 1H), 3.01 (dd, J=16.6, 6.6 Hz, 1H).

Example 26

(S)-5-(Benzyloxy)-2-(6-fluorobenzo[d]oxazol-2-yl)-6-methoxy-N-(methylsulfonyl)-1,2,3,4-tetrahydroisoquinoline-3-carboxamide

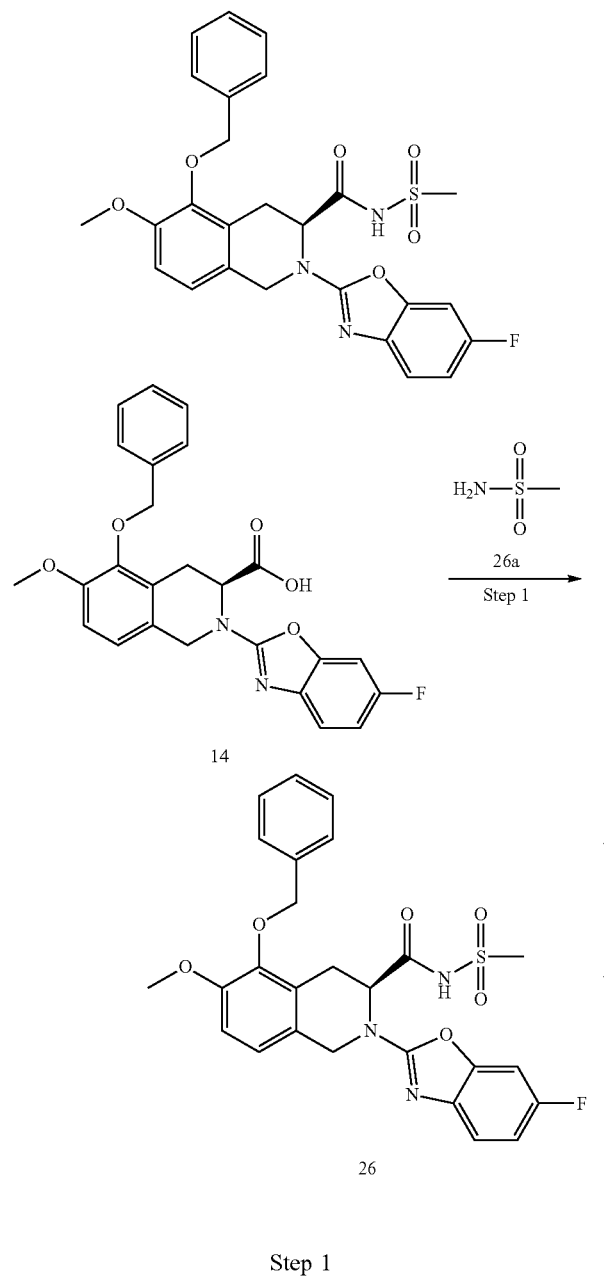

Step 1

(S)-5-(Benzyloxy)-2-(5-fluorobenzo[d]oxazol-2-yl)-6-methoxy-N-(methylsulfonyl)-1,2,3,4-tetrahydroisoquinoline-3-carboxamide (S)-5-(Benzyloxy)-2-(6-fluorobenzo(d)oxazol-2-yl)-6-methoxy-1,2,3,4-tetrahydroisoquinoline-3-carboxylic acid 14 (50 mg, 0.11 mmol), methanesulfonamide 26a (21.2 mg, 0.22 mmol), 2-(7-benzotriazole oxide)-N,N,N',N'-tetramethylurea hexafluorophosphate (102 mg, 0.27 mmol) and 1-hydroxybenzotriazole (36 mg, 0.27 mmol) were added to 5 mL of dichloromethane, and N,N-diisopropylethylamine (0.14 mL, 0.84 mmol) was added dropwise under ice bath. The mixture was continued to stir at low temperature for 1 hour, and then transferred to room temperature, and reacted overnight. After the reaction was completed, 5 mL of water was added. The resulting solution was extracted with dichloromethane (10 mL×2), and concentrated under reduced pressure. The residue obtained was separated to obtain (S)-5-(benzyloxy)-2-(6-fluorobenzo[d]oxazol-2-yl)-6-methoxy-N-(methylsulfonyl)-1,2,3,4-tetrahydroisoquinoline-3-carboxamide 26 (14 mg), yield: 13%.

MS m/z(ESI): 526.2 [M+1]

$^1$H NMR (400 MHz, DMSO-$d_6$) δ 12.27 (s, 1H), 7.52-7.33 (m, 7H), 7.11-7.01 (m, 3H), 5.01-4.98 (m, 2H), 4.84 (d, J=10.8 Hz, 1H), 4.78-4.74 (m, 2H), 3.85 (s, 3H), 3.44 (dd, J=16.2, 2.6 Hz, 1H), 3.14 (s, 3H), 3.12-3.11 (m, 1H).

Example 27

5-(Benzyloxy)-8-bromo-2-(6-fluorobenzo[d]oxazol-2-yl)-6-methoxy-1,2,3,4-tetrahydroisoquinoline-3-carboxylic acid

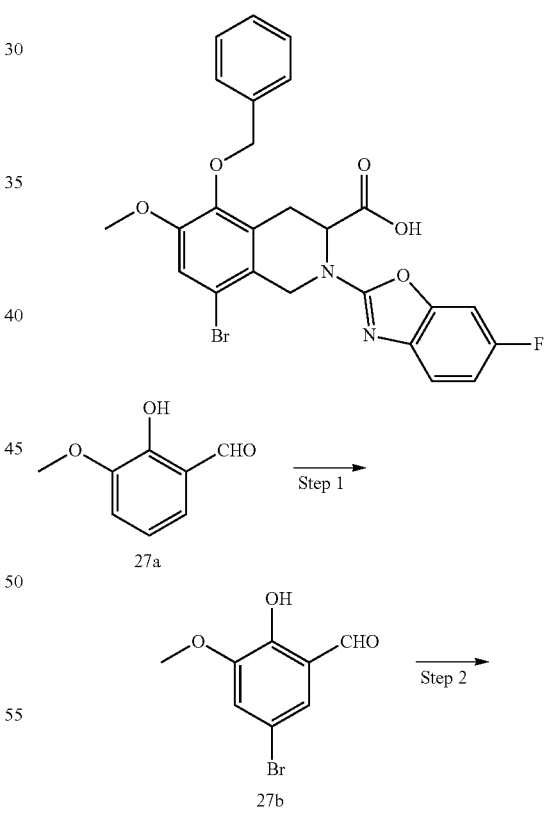

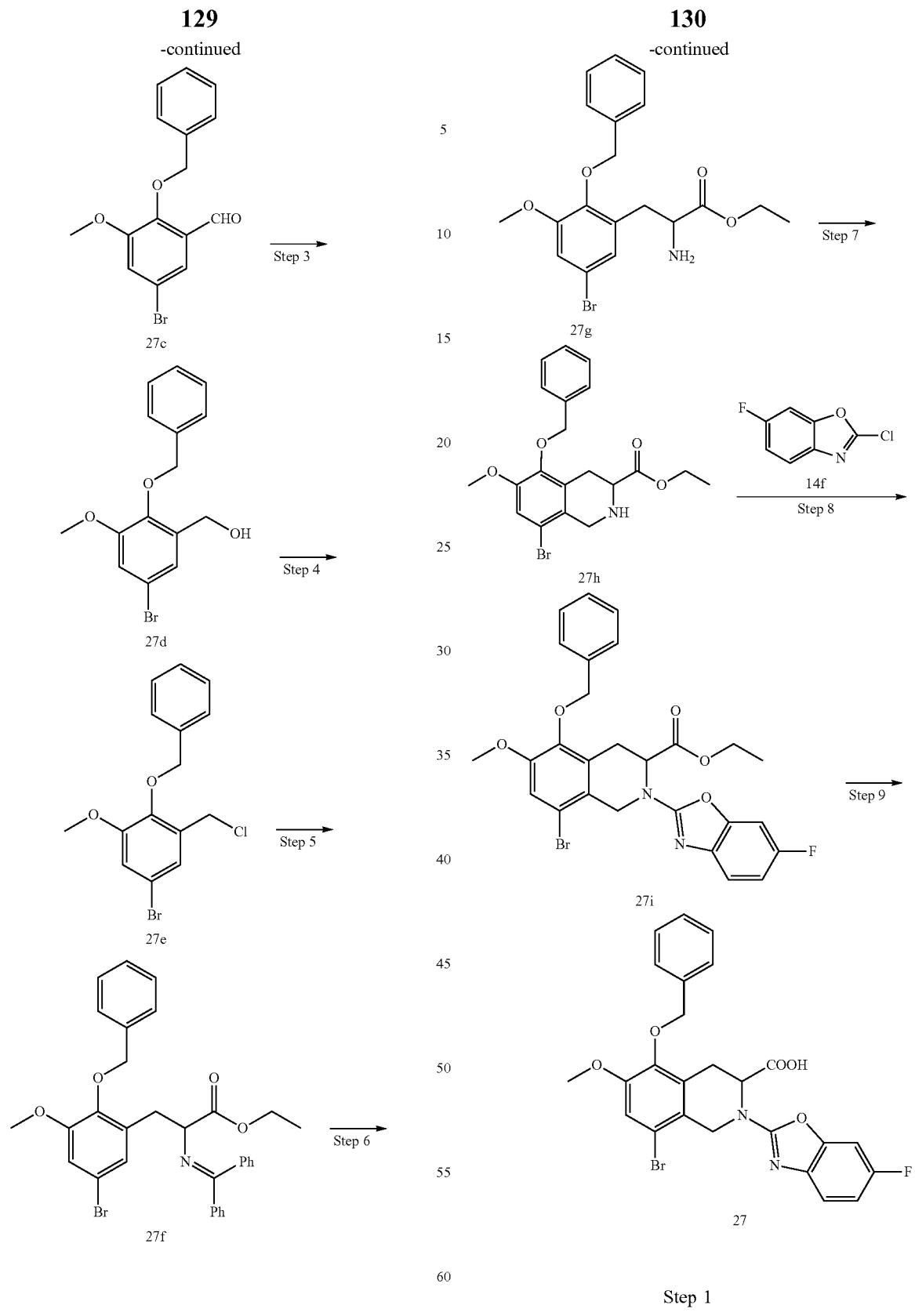
Step 1
5-Bromo-2-hydroxy-3-methoxybenzaldehyde
2-Hydroxy-3-methoxybenzaldehyde 27a (20.0 g, 130 mmol) was dissolved in 130 mL of acetic acid, liquid bromine (21 g, 130 mmol) was added. The mixture was reacted overnight at room temperature. After the reaction was completed, the reaction solution was poured into 1.3 L of water, and the mixture was slurried and filtered. The filter cake was washed with water (1 L), and dried under vacuum to obtain 5-bromo-2-hydroxy-3-methoxybenzaldehyde 27b (28.3 g, yellow solid), yield: 93%.

MS m/z(ESI): 230.8 [M+1]

Step 2

2-(Benzyloxy)-5-bromo-3-methoxybenzaldehyde

5-Bromo-2-hydroxy-3-methoxybenzaldehyde 27b (16.7 g, 72.3 mmol), benzyl bromide (12.4 g, 72.3 mmol) and potassium carbonate (25.0 g, 181 mmol) were dissolved in 150 mL ethanol, and the mixture was reacted at 90-100° C. for 6 hours. After the reaction was completed, the mixture was cooled, filtered, and the filtrate was concentrated under reduced pressure to obtain a yellow solid. The obtained yellow solid was dissolved in a mixed solvent of 115 mL petroleum ether and ethyl acetate (V:V=1:20), and the resulting solution was heated to reflux, and then naturally cooled to room temperature, crystallized, filtered, and dried to obtain 2-(benzyloxy)-5-bromo-3-methoxybenzaldehyde 27c (14.0 g, yellow solid), yield: 60%.

$^1$H NMR (400 MHz, CDCl$_3$) δ 7.49 (d, J=2.0 Hz, 1H), 7.35 (s, 5H), 7.26 (d, J=2.4 Hz, 1H), 5.16 (s, 2H), 3.95 (s, 3H).

Step 3

(2-(Benzyloxy)-5-bromo-3-methoxyphenyl)methanol

Under ice bath conditions, sodium borohydride (91 mg, 2.39 mmol) and 0.5 N sodium hydroxide solution (0.8 mL) were mixed with stirring, and then a solution of 2-(benzyloxy)-5-bromo-3-methoxybenzaldehyde 27c (2.0 g, 6.25 mmol) in 5 mL tetrahydrofuran was added dropwise. The mixture was reacted at room temperature overnight. After the reaction was completed, 20 mL ethyl acetate and 10 mL water were added to separate the layers. The organic phase was dried over anhydrous sodium sulfate, filtered, and concentrated under reduced pressure to obtain (2-(benzyloxy)-5-bromo-3-methoxyphenyl)methanol 27d (2.01 g, yellow liquid), which was used directly in the next reaction.

MS m/z(ESI): 344.8 [M+23]

Step 4

2-(Benzyloxy)-5-bromo-1-(chloromethyl)-3-methoxybenzene (2-(Benzyloxy)-5-bromo-3-methoxyphenyl)methanol 27d (2.01 g, 6.2 mmol) was dissolved in 5 mL of thionyl chloride, and the mixture was reacted at 70° C. for 6 hours. After the reaction was completed, the resulting solution was concentrated under reduced pressure. 30 mL of dichloromethane and 20 mL of water were added to separate the layers. The organic phase was dried with anhydrous sodium sulfate, filtered, and concentrated under reduced pressure. The obtained residue was purified by silica gel column chromatography (eluent: system B) to obtain 2-(benzyloxy)-5-bromo-1-(chloromethyl)-3-methoxybenzene 27e (1.89 g, white solid), the total yield of the two-step reaction: 93%.

Step 5

Ethyl 3-(2-(benzyloxy)-5-bromo-3-methoxyphenyl)-2-((diphenylmethylene)amino)propionate Under the protection of argon gas, 2-(benzyloxy)-5-bromo-1-(chloromethyl)-3-methoxybenzene 27e (1.13 g, 3.31 mmol), diphenylmethyleneglycine ethyl ester (1.33 g, 4.96 mmol), cesium carbonate (2.16 g, 6.62 mmol) and potassium iodide (0.713 g, 4.3 mmol) were dissolved in 20 mL of acetonitrile, and the mixture was heated to 50° C. for 7 hours. After the reaction was completed, 30 mL ethyl acetate and 20 mL water were added to separate the layers. The organic phase was dried over anhydrous sodium sulfate, filtered, and concentrated under reduced pressure to obtain crude ethyl 3-(2-(benzyloxy)-5-bromo-3-methoxyphenyl)-2-((diphenylmethylene)amino)propionate 27f (2.1 g, yellow oil), which was used directly in the next step.

MS m/z(ESI): 571.8 [M+1]

Step 6

Ethyl 2-amino-3-(2-(benzyloxy)-5-bromo-3-methoxyphenyl)propionate

Ethyl 3-(2-(benzyloxy)-5-bromo-3-methoxyphenyl)-2-((diphenylmethylene)amino) propionate 27f (2.1 g, 3.7 mmol) was dissolved in 10 mL tetrahydrofuran, and 10 mL 3M hydrochloric acid solution was added. The mixture was reacted at room temperature for 4 hours. After the reaction was completed, saturated sodium carbonate solution was added so that the reaction solution was adjusted to pH=11. The resulting solution was extracted with 20 mL ethyl acetate. The organic phases were concentrated under reduced pressure. The obtained residue was purified by silica gel column chromatography (eluent: system B) to obtain ethyl 2-amino-3-(2-(benzyloxy)-5-bromo-3-methoxyphenyl)propionate 27g (1.1 g, yellow oil), the total yield of the two-step reaction: 79%.

MS m/z(ESI): 407.9 [M+1]

Step 7

Ethyl 5-(benzyloxy)-8-bromo-6-methoxy-1,2,3,4-tetrahydroisoquinoline-3-carboxylate hydrochloride Ethyl 2-amino-3-(2-(benzyloxy)-5-bromo-3-methoxyphenyl)propionate 27g (1.1 g, 2.7 mmol) was dissolved in 2N dilute hydrochloric acid (10 mL) and the mixture was stirred for 30 minutes at room temperature. Aqueous formaldehyde solution (12 mL, 37 wt. %) and tetrahydrofuran (5 mL) were added in sequence, and the mixture was reacted overnight at room temperature. After the reaction was completed, the resulting solution was directly concentrated under reduced pressure and dried to obtain ethyl 5-(benzyloxy)-8-bromo-6-methoxy-1,2,3,4-tetrahydroisoquinoline-3-carboxylate hydrochloride 27h (1.0 g), yield: 81%.

MS m/z(ESI): 419.9 [M+1]

Step 8

Ethyl 5-(benzyloxy)-8-bromo-2-(6-fluorobenzo[d]oxazol-2-yl)-6-methoxy-1,2,3,4-tetrahydroisoquinoline-3-carboxylate Ethyl 5-(benzyloxy)-8-bromo-6-methoxy-1,2,3,4-tetrahydroisoquinoline-3-carboxylate hydrochloride 27h (100 mg, 0.24 mmol), 2-chloro-6-fluorobenzoxazole 14f (41 mg, 0.24 mmol) and triethylamine (99 µL, 0.71 mmol) were dissolved in 3 mL of tetrahydrofuran, and the mixture was reacted at 50-60° C. for 5 hours. After the reaction was completed, the resulting solution was cooled to room temperature and concentrated under reduced pressure. The residue obtained was purified by thin layer chromatography (developer: system B) to obtain ethyl 5-(benzyloxy)-8-bromo-2-(6-fluorobenzo[d]oxazol-2-yl)-6-methoxy-1,2,3,4-tetrahydroisoquinoline-3-carboxylate 27i (10 mg), yield: 7.6%.

MS m/z(ESI): 554.8 [M+1]

Step 9

5-(Benzyloxy)-8-bromo-2-(6-fluorobenzo[d]oxazol-2-yl)-6-methoxy-1,2,3,4-tetrahydroisoquinoline-3-carboxylic acid Ethyl 5-(benzyloxy)-8-bromo-2-(6-fluorobenzo[d]oxazol-2-yl)-6-methoxy-1,2,3,4-tetrahydroisoquinoline-3-carboxylate 27i (10 mg, 0.018 mmol) was dissolved in 2 mL of tetrahydrofuran; lithium hydroxide (2 mg, 0.09 mmol) was dissolved in 0.5 mL of water, and the mixture was added dropwise to the above solution. The resulting solution was reacted overnight at room temperature. After the reaction was completed, the resulting solution was concentrated under reduced pressure, and 5 mL of dichloromethane was added. 1N dilute hydrochloric acid was added dropwise to neutralize. The resulting solution was extracted with dichloromethane (10 mL×2). The organic phases were combined, dried with anhydrous sodium sulfate, filtered, and concentrated under reduced pressure. The obtained residue was purified by thin layer chromatography (developer: system B) to obtain 5-(benzyloxy)-8-bromo-2-(6-fluorobenzo [d]oxazol-2-yl)-6-methoxy-1,2,3,4-tetrahydroisoquinoline-3-carboxylic acid 27 (3 mg), yield: 32%.

MS m/z(ESI): 526.8 [M+1]
$^1$H NMR (400 MHz, CDCl$_3$) δ 7.43-7.31 (m, 6H), 7.08 (m, 2H), 6.90 (t, J=8.4 Hz, 1H), 5.14 (d, J=3.2 Hz, 1H), 5.01 (d, J=10.8 Hz, 1H), 4.96 (d, J=10.4 Hz, 1H), 4.81 (d, J=16.4 Hz, 1H), 4.62 (d, J=16.4 Hz, 1H), 3.87 (s, 3H), 3.65 (d, J=16.8 Hz 1H), 2.86 (dd, J=16.2, 5.8 Hz, 1H).

Example 28

(S)-5-(Benzyloxy)-6-methoxy-2-(6-methoxybenzo[d]oxazol-2-yl)-1,2,3,4-tetrahydroisoquinoline-3-carboxylic acid

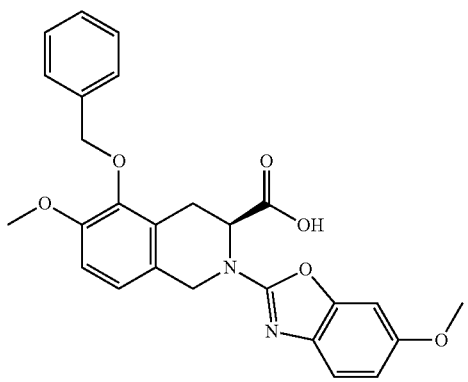

Step 1

Methyl (S)-5-(Benzyloxy)-6-methoxy-2-(6-methoxybenzo[d]oxazol-2-yl)-1,2,3,4-tetrahydroisoquinoline-3-carboxylate Methyl (S)-5-(benzyloxy)-6-methoxy-1,2,3,4-tetrahydroisoquinoline-3-carboxylate hydrochloride 14f (200 mg, 0.55 mmol), 2-chloro-6-methoxybenzo[d]oxazole 28a (121.1 mg, 0.66 mmol, prepared according to published patent WO 2011112602) and triethylamine (305 µL, 2.2 mmol) were dissolved in 3 mL of tetrahydrofuran, and the mixture was reacted at 60-70° C. for 5 hours. Trimethylamine (400 µL) was replenished and the reaction was continued at 60-70° C. for 3 days. After the reaction was completed, the resulting solution was cooled to room temperature and concentrated under reduced pressure to obtain crude product methyl (S)-5-(benzyloxy)-6-methoxy-2-(6-methoxybenzo[d]oxazol-2-yl)-1,2,3,4-tetrahydroisoquinoline-3-carboxylate 28b (260 mg), which was directly used in the next reaction, yield: 100%.

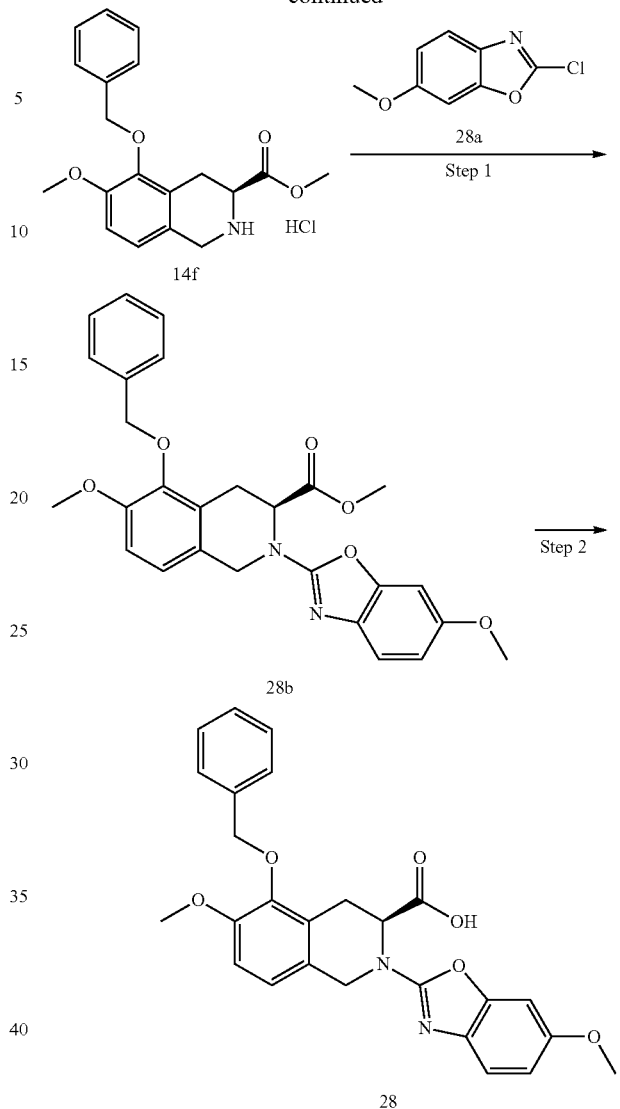

MS m/z(ESI): 474.9 [M+1]

Step 2

(S)-5-(Benzyloxy)-6-methoxy-2-(6-methoxybenzo[d]oxazol-2-yl)-1,2,3,4-tetrahydroisoquinoline-3-carboxylic acid Methyl (S)-5-(benzyloxy)-6-methoxy-2-(6-methoxybenzo[d]oxazol-2-yl)-1,2,3,4-tetrahydroisoquinoline-3-carboxylate 28b (260 mg, 0.55 mmol) and lithium hydroxide monohydrate (80 mg, 1.90 mmol) were dissolved in 4.5 mL of a mixed solvent of tetrahydrofuran and water (V:V=8:1). The mixture was stirred at room temperature for 1 day. 100 mg of lithium hydroxide monohydrate was replenished and the mixture was continued to be stirred at room temperature for 2 days. After the reaction was completed, 2M hydrochloric acid solution was added dropwise so that the reaction solution was adjusted to pH=1. 20 mL ethyl acetate and 10 mL water were added and the resulting solution was separated into layers. The water layer was removed and the organic phase was concentrated under reduced pressure. The obtained residue was separated and purified by a preparative column to obtain (S)-5-(benzyloxy)-6-methoxy-2-(6-methoxybenzo[d]oxazol-2-yl)-1,2,3,4-tetrahydroisoquinoline-3-carboxylic acid 28 (100 mg), yield: 40%.

MS m/z(ESI): 460.9 [M+1]

$^1$H NMR (400 MHz, DMSO-$d_6$) δ 12.99 (s, 1H), 7.48-7.36 (m, 5H), 7.24 (d, J=8.4 Hz, 1H), 7.16 (d, J=2.0 Hz, 1H), 7.06 (d, J=8.8 Hz, 1H), 7.01 (d, J=8.4 Hz, 1H), 6.79 (dd, J=8.4, 2.4 Hz, 1H), 5.06 (dd, J=6.2, 2.6 Hz, 1H), 4.98 (d, J=11.2 Hz, 1H), 4.86 (d, J=10.8 Hz, 1H), 4.76 (d, J=16.0 Hz, 1H), 4.64 (d, J=15.6 Hz, 1H), 3.84 (s, 3H), 3.76 (s, 3H), 3.50 (dd, J=15.8, 2.2 Hz, 1H), 2.99 (dd, J=16.6, 5.8 Hz, 1H).

Example 29

(S)-2-(6-fluorobenzo[d]oxazol-2-yl)-5-((4-fluorobenzyl)oxy)-6-methoxy-1,2,3,4-tetrahydroisoquinoline-3-carboxylic acid

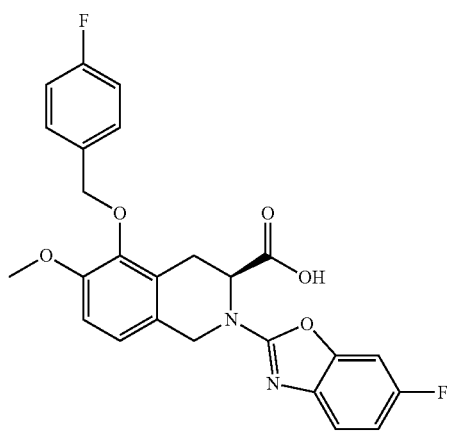

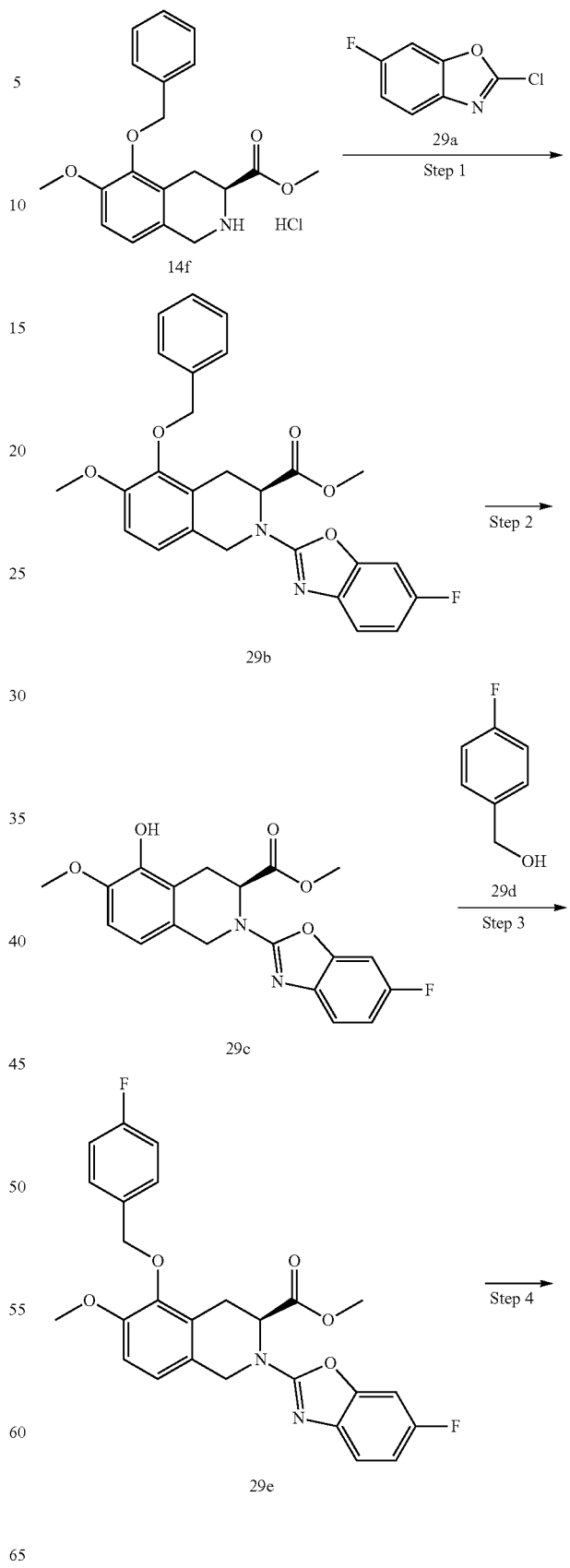

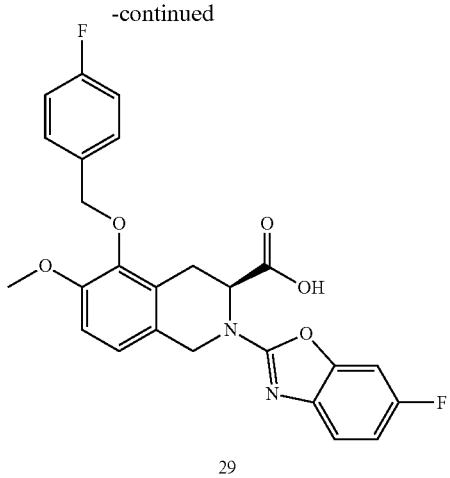

29

Step 1

Methyl (S)-5-(benzyloxy)-2-(6-fluorobenzo[d]oxa-zol-2-yl)-6-methoxy-1,2,3,4-tetrahydroisoquinoline-3-carboxylate Methyl (S)-5-(benzyloxy)-6-methoxy-1,2,3,4-tetrahydroisoquinoline-3-carboxylate hydrochloride14f (80 mg, 0.22 mmol), 2-chloro-6-fluorobenzo[d]oxazole 29a (37 mg, 0.22 mmol) and triethylamine (91 μL, 0.66 mmol) were dissolved in 2 mL of tetrahydrofuran, and the mixture was reacted at 50-60° C. for 5 hours. After the reaction was completed, the resulting solution was cooled to room temperature and concentrated under reduced pressure. The residue obtained was purified by thin layer chromatography (developer: system A) to obtain methyl (S)-5-(benzyloxy)-2-(6-fluorobenzo[d]oxazol-2-yl)-6-methoxy-1,2,3,4-tetrahydroisoquinoline-3-carboxylate 29b (60 mg), yield: 59%.

MS m/z(ESI): 462.9 [M+1]

$^1$H NMR (400 MHz, CDCl$_3$) δ 7.49-7.29 (m, 6H), 7.06 (dd, J=7.8, 2.2 Hz, 1H), 6.96-6.86 (m, 3H), 5.19 (dd, J=6.4, 2.4 Hz, 1H), 5.05 (d, J=10.8 Hz, 1H), 4.95 (d, J=11.2 Hz, 1H), 4.90 (d, J=15.6 Hz, 1H), 4.76 (d, J=15.2 Hz, 1H), 3.89 (s, 3H), 3.66-3.61 (m, 4H), 2.94 (dd, J=16.4, 6.4 Hz, 1H).

Step 2

Methyl (S)-2-(6-fluorobenzo[d]oxazol-2-yl)-5-hydroxy-6-methoxy-1,2,3,4-tetrahydroisoquinoline-3-carboxylate Methyl (S)-5-(benzyloxy)-2-(6-fluorobenzo[d]oxazol-2-yl)-6-methoxy-1,2,3,4-tetrahydroisoquinoline-3-carboxylate 29b (600 mg, 1.3 mmol) and 10% palladium-carbon (300 mg, 50% w) were dissolved in 10 mL methanol, and a hydrogen balloon was inserted, and the mixture was bubbled with hydrogen for 4 times. The resulting mixture was reacted overnight at room temperature. After the reaction was completed, the reaction solution was filtered with celite, and the celite was washed sequentially with a mixed solvent of ethyl acetate and methanol (V:V=1:1) (100 mL×3) and dichloromethane (100 mL×3). The filter liquor was concentrated under reduced pressure to obtain crude product methyl (S)-2-(6-fluorobenzo[d]oxazol-2-yl)-5-hydroxy-6-methoxy-1,2,3,4-tetrahydroisoquinoline-3-carboxylate 29c (500 mg), yield: 100%.

MS m/z(ESI): 372.9 [M+1]

$^1$H NMR (400 MHz, DMSO-d$_6$) δ 8.86 (br, 1H), 7.50 (dd, J=8.8, 2.4 Hz, 1H), 7.35 (dd, J=8.6, 5.4 Hz, 1H), 7.10-7.04 (m, 1H), 6.88 (d, J=8.4 Hz, 1H), 6.74 (d, J=8.4 Hz, 1H), 5.25 (dd, J=6.4, 2.4 Hz, 1H), 4.81 (d, J=15.2 Hz, 1H), 4.63 (d, J=15.6 Hz, 1H), 3.79 (s, 3H), 3.59 (s, 3H), 3.46 (dd, J=16.2, 1.8 Hz, 1H), 3.04 (dd, J=16.8, 6.4 Hz, 1H).

Step 3

Methyl (S)-2-(6-fluorobenzo[d]oxazol-2-yl)-5-((4-fluorobenzyl)oxy)-6-methoxy-1,2,3,4-tetrahydroisoquinoline-3-carboxylate Under the protection of argon gas, methyl (S)-2-(6-fluorobenzo[d]oxazol-2-yl)-5-hydroxy-6-methoxy-1,2,3,4-tetrahydroisoquinoline-3-carboxylate 29c (100 mg, 0.268 mmol), p-fluorobenzyl alcohol 29d (40.65 mg, 0.322 mmol) and triphenylphosphine (106 mg, 0.402 mmol) were dissolved in 4 mL tetrahydrofuran, and the mixture was stirred at room temperature for 15 minutes. Diisopropyl azodicarboxylate (DIAD) (81.4 mg, 0.402 mmol) was added dropwise, and the resulting solution was reacted overnight at room temperature. After the reaction was completed, the resulting solution was concentrated under reduced pressure, and the obtained residue was purified by silica gel column chromatography (eluent: system A) to obtain methyl (S)-2-(6-fluorobenzo[d]oxazol-2-yl)-5-((4-fluorobenzyl)oxy)-6-methoxy-1,2,3,4-tetrahydroisoquinoline-3-carboxylate 29e (100 mg), yield: 77%.

MS m/z(ESI): 480.9 [M+1]

Step 4

(S)-2-(6-Fluorobenzo[d]oxazol-2-yl)-5-((4-fluorobenzyl)oxy)-6-methoxy-1,2,3,4-tetrahydroisoquinoline-3-carboxylic acid Methyl (S)-2-(6-fluorobenzo[d]oxazol-2-yl)-5-((4-fluorobenzyl)oxy)-6-methoxy-1,2,3,4-tetrahydroisoquinoline-3-carboxylate 29e (100 mg, 0.21 mmol) and lithium hydroxide monohydrate (8.9 mg, 0.21 mmol) were dissolved in 3.5 mL of a mixed solvent of tetrahydrofuran and water (V:V=4:3). The resulting solution was reacted overnight at room temperature. After the reaction was completed, 100 mL ethyl acetate was added and 1M dilute hydrochloric acid was added so that the reaction solution was adjusted to pH=4-5. The resulting solution was extracted with ethyl acetate (50 mL×2). The organic phases were combined, washed with saturated brine (50 mL×2), dried with anhydrous sodium sulfate, filtered, and concentrated under reduced pressure. The obtained residue was separated and purified by a preparative column to obtain (S)-2-(6-fluorobenzo[d]oxazol-2-yl)-5-((4-fluorobenzyl)oxy)-6-methoxy-1,2,3,4-tetrahydroisoquinoline-3-carboxylic acid 29 (20 mg), yield: 21%.

MS m/z(ESI): 466.9 [M+1]

$^1$H NMR (400 MHz, DMSO-d6) δ 13.10 (s, 1H), 7.52-7.47 (m, 3H), 7.33 (dd, J=8.4, 5.2 Hz, 1H), 7.23 (t, J=8.8 Hz, 2H), 7.08-6.99 (m, 3H), 5.06 (d, J=4.0 Hz, 1H), 4.95 (d, J=10.8 Hz, 1H), 4.85 (d, J=10.8 Hz, 1H), 4.77 (d, J=16.0 Hz, 1H), 4.66 (d, J=16.0 Hz, 1H), 3.83 (s, 3H), 3.50 (dd, J=16.0, 2.4 Hz, 1H), 2.97 (dd, J=15.8, 6.6 Hz, 1H).

Example 30

(S)-2-(6-fluorobenzo[d]oxazol-2-yl)-6-methoxy-5-((4-methoxybenzyl)oxy)-1,2,3,4-tetrahydroisoquinoline-3-carboxylic acid

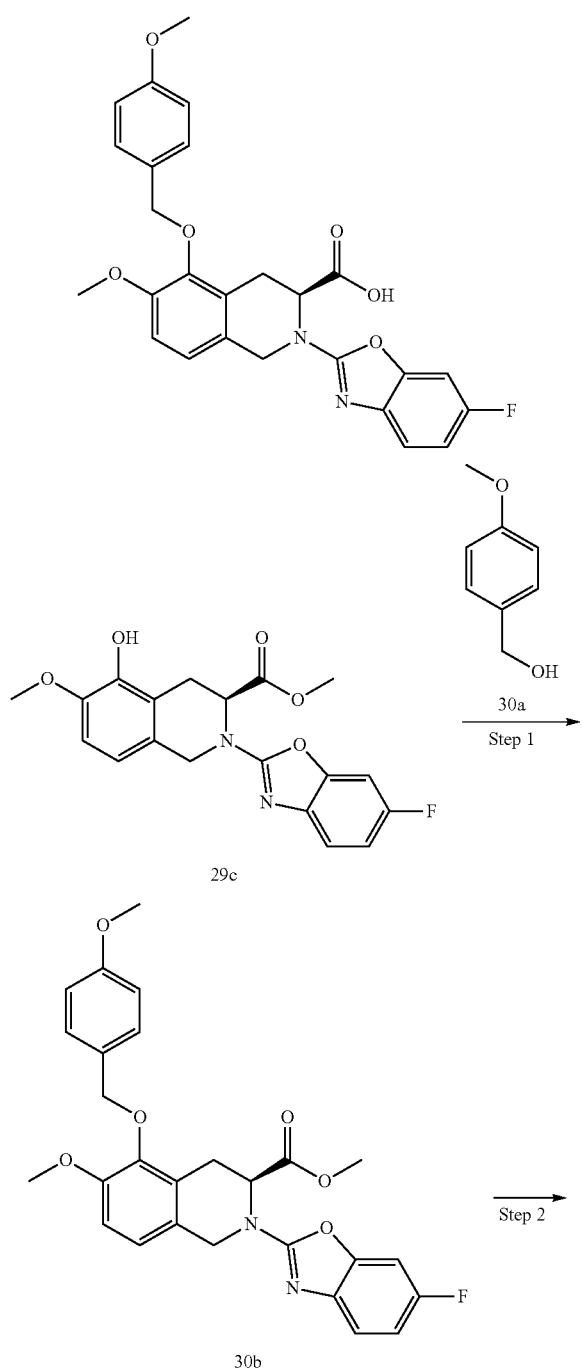

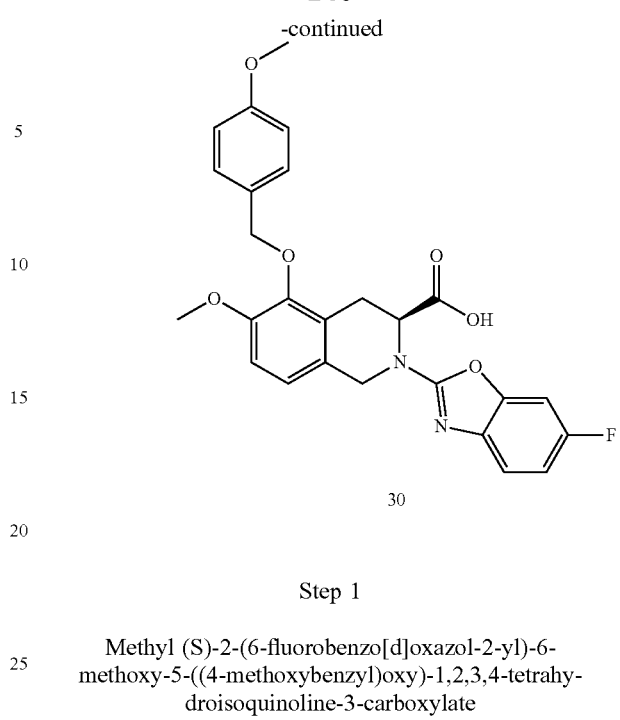

Step 1

Methyl (S)-2-(6-fluorobenzo[d]oxazol-2-yl)-6-methoxy-5-((4-methoxybenzyl)oxy)-1,2,3,4-tetrahydroisoquinoline-3-carboxylate Under the protection of argon gas, methyl (S)-2-(6-fluorobenzo[d]oxazol-2-yl)-5-hydroxy-6-methoxy-1,2,3,4-tetrahydroisoquinoline-3-carboxylate 29c (100 mg, 0.27 mmol), p-methoxybenzyl alcohol 30a (44.8 mg, 0.324 mmol) and triphenylphosphine (106 mg, 0.405 mmol) were dissolved in 4 mL tetrahydrofuran, and the mixture was stirred at room temperature for 15 minutes. Diisopropyl azodicarboxylate (DIAD) (81.9 mg, 0.405 mmol) was added dropwise, and the resulting solution was reacted overnight at room temperature. After the reaction was completed, the resulting solution was concentrated under reduced pressure, and the obtained residue was purified by silica gel column chromatography (eluent: system A) to obtain methyl (S)-2-(6-fluorobenzo[d]oxazol-2-yl)-6-methoxy-5-((4-methoxybenzyl)oxy)-1,2,3,4-tetrahydroisoquinoline-3-carboxylate 30b (100 mg), yield: 78%.

MS m/z(ESI): 492.9 [M+1]

$^1$H NMR (400 MHz, DMSO-$d_6$) δ 7.50 (dd, J=8.4, 2.8 Hz, 1H), 7.41-7.34 (m, 3H), 7.10-6.95 (m, 5H), 5.19 (dd, J=6.4, 2.8 Hz, 1H), 4.94 (d, J=10.8 Hz, 1H), 4.82-4.77 (m, 2H), 4.66 (d, J=15.6 Hz, 1H), 3.85 (s, 3H), 3.79-3.76 (m, 4H), 3.57 (s, 3H), 3.01 (dd, J=16.4, 6.4 Hz, 1H).

Step 2

(S)-2-(6-fluorobenzo[d]oxazol-2-yl)-6-methoxy-5-((4-methoxybenzyl)oxy)-1,2,3,4-tetrahydroisoquinoline-3-carboxylic acid Methyl (S)-2-(6-fluorobenzo[d]oxazol-2-yl)-6-methoxy-5-((4-methoxybenzyl)oxy)-1,2,3,4-tetrahydroisoquinoline-3-carboxylate 30b (100 mg, 0.20 mmol) and lithium hydroxide monohydrate (8.4 mg, 0.20 mmol) were dissolved in 3 mL of a mixed solvent of tetrahydrofuran and water (V:V=2:1). The resulting solution was reacted overnight at room temperature. After the reaction was completed, 100 mL ethyl acetate was added and 1M dilute hydrochloric acid was added so that the reaction solution was adjusted to pH=4-5. The resulting solution was extracted with ethyl acetate (50 mL×2). The organic phases were combined, washed with saturated brine (50 mL×2), dried with anhydrous sodium sulfate, filtered, and concentrated under reduced pressure. The obtained residue was separated and purified by a preparative column to obtain (S)-2-(6-fluorobenzo[d]oxazol-2-yl)-6-methoxy-5-((4-methoxybenzyl)oxy)-1,2,3,4-tetrahydroisoquinoline-3-carboxylic acid 30 (49 mg), yield: 52%.

MS m/z(ESI): 478.9 [M+1]

$^1$H NMR (400 MHz, DMSO-d6) δ 7.48 (dd, J=8.4, 2.0 Hz, 1H), 7.40-7.32 (m, 3H), 7.08-6.95 (m, 5H), 5.07 (d, J=3.6 Hz, 1H), 4.92 (d, J=10.8 Hz, 1H), 4.82-4.75 (m, 2H), 4.67 (d, J=16.0 Hz, 1H), 3.84 (s, 3H), 3.77 (s, 3H), 3.52 (d, J=14.4 Hz, 1H). 2.97 (dd, J=16.6, 6.2 Hz, 1H).

Example 31

(S)-5-((4-chlorobenzyl)oxy)-2-(6-fluorobenzo[d]oxazol-2-yl)-6-methoxy-1,2,3,4-tetrahydroisoquinoline-3-carboxylic acid

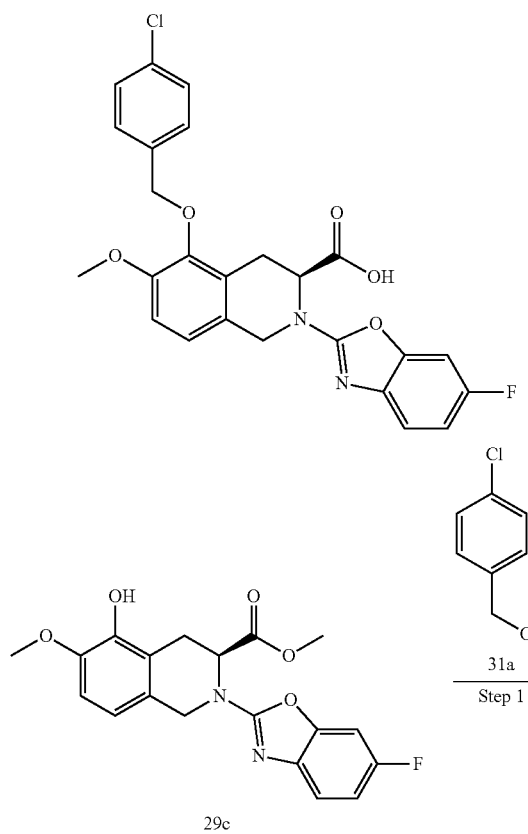

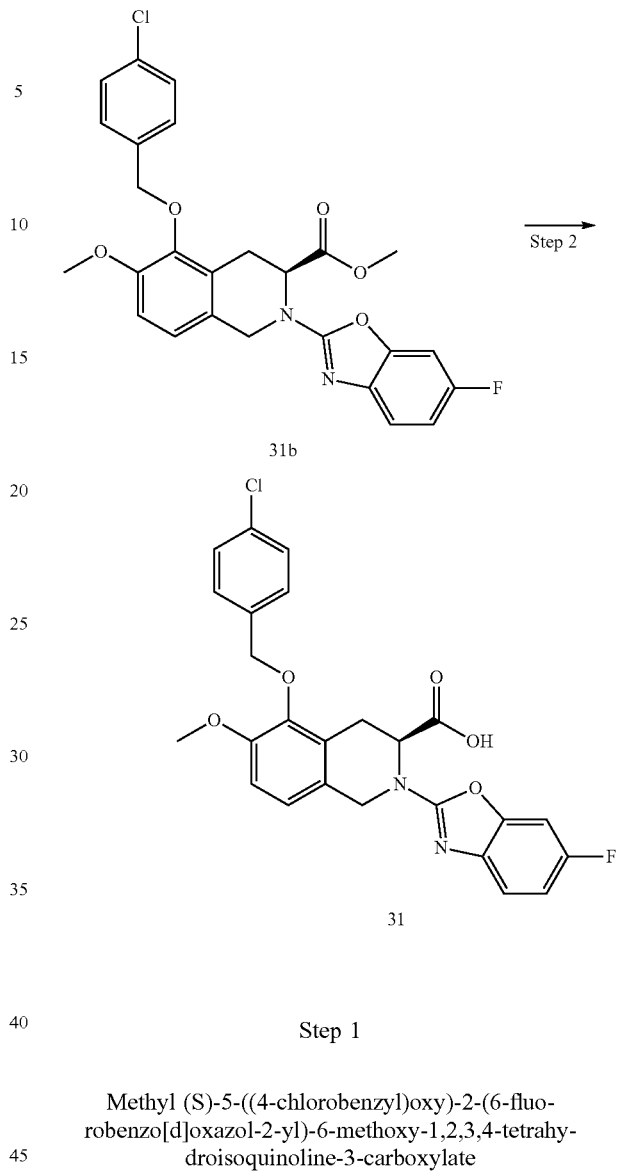

Step 1

Methyl (S)-5-((4-chlorobenzyl)oxy)-2-(6-fluorobenzo[d]oxazol-2-yl)-6-methoxy-1,2,3,4-tetrahydroisoquinoline-3-carboxylate Under the protection of argon, methyl (S)-2-(6-fluorobenzo[d]oxazol-2-yl)-5-hydroxy-6-methoxy-1,2,3,4-tetrahydroisoquinoline-3-carboxylate 29c (100 mg, 0.268 mmol), p-chlorobenzyl alcohol 31a (46.2 mg, 0.323 mmol) and triphenylphosphine (106 mg, 0.405 mmol) were dissolved in 5 mL tetrahydrofuran, and the mixture was stirred at room temperature for 15 minutes. Diisopropyl azodicarboxylate (DIAD) (81.4 mg, 0.405 mmol) was added dropwise, and the resulting solution was reacted overnight at room temperature. After the reaction was completed, the resulting solution was concentrated under reduced pressure, and the obtained residue was purified by silica gel column chromatography (eluent: system A) to obtain methyl (S)-5-((4-chlorobenzyl)oxy)-2-(6-fluorobenzo[d]oxazol-2-yl)-6-methoxy-1,2,3,4-tetrahydroisoquinoline-3-carboxylate 31b (130 mg), yield: 98%.

MS m/z(ESI): 496.9 [M+1]

Step 2

(S)-5-((4-chlorobenzyl)oxy)-2-(6-fluorobenzo[d]
oxazol-2-yl)-6-methoxy-1,2,3,4-tetrahydroisoquino-
line-3-carboxylic acid Methyl (S)-5-((4-chlorobenzyl)oxy)-2-(6-fluorobenzo[d]
oxazol-2-yl)-6-methoxy-1,2,3,4-tetrahydroisoquinoline-3-
carboxylate 31b (130 mg, 0.254 mmol) and lithium hydroxide monohydrate (10.7 mg, 0.254 mmol) were dissolved in 3.5 mL of a mixed solvent of tetrahydrofuran and water (V:V=4:3). The resulting solution was reacted overnight at room temperature. After the reaction was completed, 100 mL ethyl acetate was added and 1M dilute hydrochloric acid was added so that the reaction solution was adjusted to pH=4-5. The resulting solution was extracted with ethyl acetate (50 mL×2). The organic phases were combined, washed with saturated brine (50 mL×2), dried with anhydrous sodium sulfate, filtered, and concentrated under reduced pressure. The obtained residue was separated and purified by a preparative column to obtain (S)-5-((4-chlorobenzyl)oxy)-2-(6-fluorobenzo[d]oxazol-2-yl)-6-methoxy-1,2,3,4-tetrahydroisoquinoline-3-carboxylic acid 31 (18 mg), yield: 15%.

MS m/z(ESI): 482.9 [M+1]

$^1$H NMR (400 MHz, DMSO-$d_6$) δ 7.51-7.45 (m, 5H), 7.32 (dd, J=8.8, 5.2 Hz, 1H), 7.07-6.98 (m, 3H), 5.02 (d, J=4.0 Hz, 1H), 4.96 (d, J=10.8 Hz, 1H), 4.87 (d, J=11.2 Hz, 1H), 4.77 (d, J=15.2 Hz, 1H), 4.67 (d, J=16.0 Hz, 1H), 3.82 (s, 3H), 3.55 (m, 1H), 2.97 (dd, J=16.4, 6.4 Hz, 1H).

Example 32

(S)-5-((3-chlorobenzyl)oxy)-2-(6-fluorobenzo[d]
oxazol-2-yl)-6-methoxy-1,2,3,4-tetrahydroisoquino-
line-3-carboxylic acid

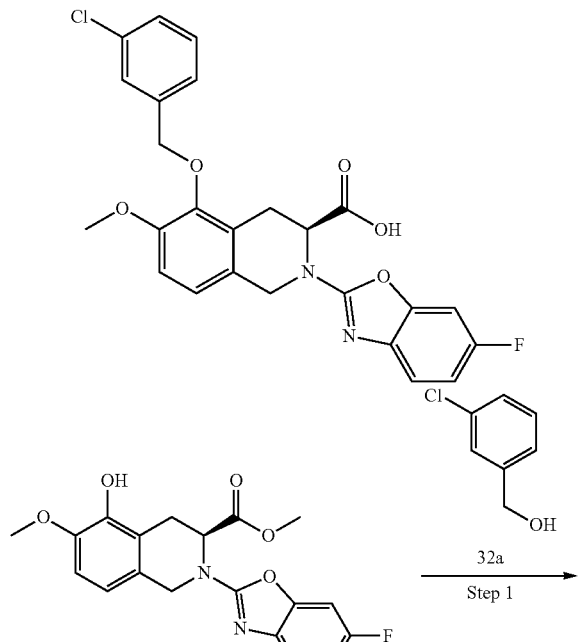

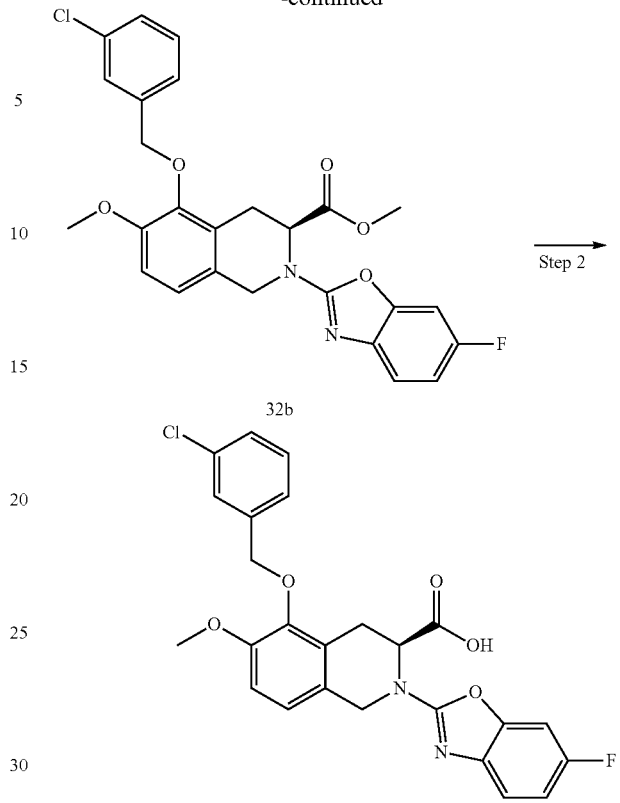

Step 1 methyl (S)-5-((3-chlorobenzyl)oxy)-2-(6-fluorobenzo[d]oxazol-2-yl)-6-methoxy-1,2,3,4-tetrahydroisoquinoline-3-carboxylate Under the protection of argon gas, methyl (S)-2-(6-fluorobenzo[d]oxazol-2-yl)-5-hydroxy-6-methoxy-1,2,3,4-tetrahydroisoquinoline-3-carboxylate 29c (100 mg, 0.268 mmol), 3-chlorobenzyl alcohol 32a (46.2 mg, 0.323 mmol) and triphenylphosphine (106 mg, 0.405 mmol) were dissolved in 5 mL tetrahydrofuran, and the mixture was stirred at room temperature for 15 minutes. Diisopropyl azodicarboxylate (DIAD) (81.4 mg, 0.405 mmol) was added dropwise, and the resulting solution was reacted overnight at room temperature. After the reaction was completed, the resulting solution was concentrated under reduced pressure, and the obtained residue was purified by silica gel column chromatography (eluent: system A) to obtain crude product methyl (S)-5-((3-chlorobenzyl)oxy)-2-(6-fluorobenzo[d]oxazol-2-yl)-6-methoxy-1,2,3,4-tetrahydroisoquinoline-3-carboxylate 32b (80 mg), yield: 60%.

MS m/z(ESI): 496.8 [M+1]

Step 2

(S)-5-((3-chlorobenzyl)oxy)-2-(6-fluorobenzo[d]
oxazol-2-yl)-6-methoxy-1,2,3,4-tetrahydroisoquino-
line-3-carboxylic acid Methyl (S)-5-((3-chlorobenzyl)oxy)-2-(6-fluorobenzo[d]oxazol-2-yl)-6-methoxy-1,2,3,4-tetrahydroisoquinoline-3- carboxylate 32b (80 mg, 0.16 mmol) and lithium hydroxide monohydrate (6.73 mg, 0.16 mmol) were dissolved in 6 mL of a mixed solvent of tetrahydrofuran and water (V:V=1:1). The resulting solution was reacted overnight at room temperature. After the reaction was completed, 50 mL ethyl acetate was added and 1M dilute hydrochloric acid was added so that the reaction solution was adjusted to pH=4-5. The resulting solution was extracted with ethyl acetate (50 mL×2). The organic phases were combined, washed with saturated brine (50 mL×2), dried with anhydrous sodium sulfate, filtered, and concentrated under reduced pressure. The obtained residue was separated and purified by a preparative column to obtain (S)-5-((3-chlorobenzyl)oxy)-2-(6-fluorobenzo[d]oxazol-2-yl)-6-methoxy-1,2,3,4-tetrahydroisoquinoline-3-carboxylic acid 32 (10 mg), yield: 11%.

MS m/z(ESI): 482.8 [M+1]

$^1$H NMR (400 MHz, DMSO-d$_6$) δ 7.55 (s, 1H), 7.49-7.43 (m, 4H), 7.32 (dd, J=8.4, 4.8 Hz, 1H), 7.07-7.00 (m, 3H), 5.03 (d, J=4.8 Hz, 1H), 4.98 (d, J=11.6 Hz, 1H), 4.88 (d, J=11.2 Hz, 1H), 4.79 (d, J=15.6 Hz, 1H), 4.69 (d, J=15.6 Hz, 1H), 3.83 (s, 3H), 3.56 (d, J=15.6 Hz, 1H), 3.00 (dd, J=15.8, 6.6 Hz, 1H)

Example 33

(S)-5-((2-chlorobenzyl)oxy)-2-(6-fluorobenzo[d]oxazol-2-yl)-6-methoxy-1,2,3,4-tetrahydroisoquinoline-3-carboxylic acid

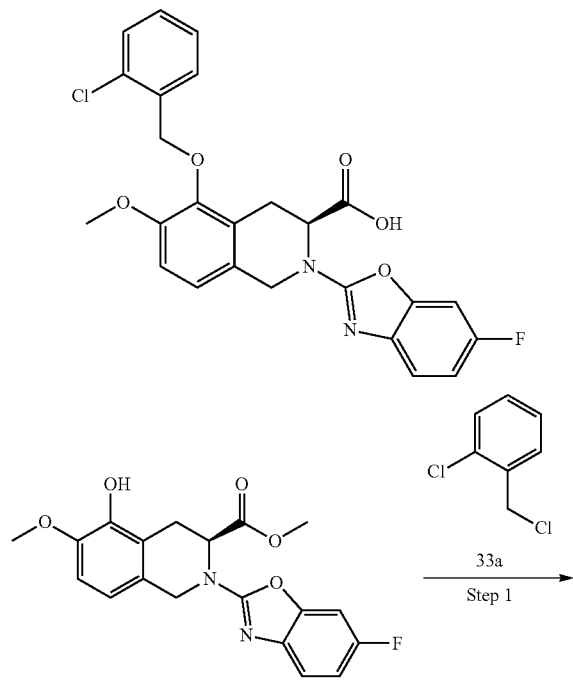

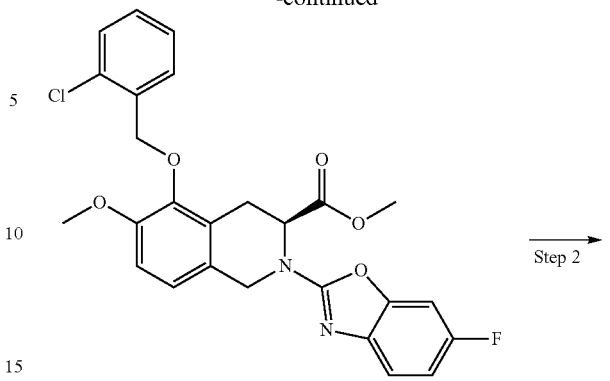

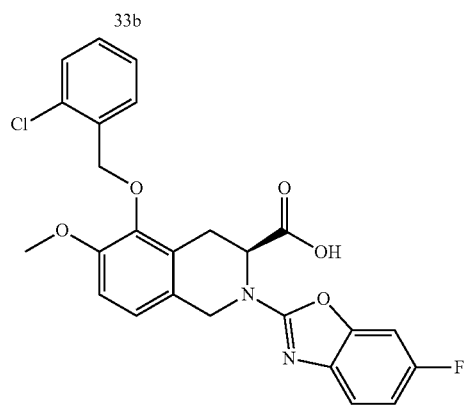

Step 1 methyl (S)-5-((2-chlorobenzyl)oxy)-2-(6-fluorobenzo[d]oxazol-2-yl)-6-methoxy-1,2,3,4-tetrahydroisoquinoline-3-carboxylate Methyl (S)-2-(6-fluorobenzo[d]oxazol-2-yl)-5-hydroxy-6-methoxy-1,2,3,4-tetrahydroisoquinoline-3-carboxylate 29c (60 mg, 0.16 mmol), o-chlorobenzyl chloride 33a (34 mg, 0.21 mmol), potassium carbonate (33.1 mg, 0.24 mmol) and sodium iodide (36 mg, 0.24 mmol) were dissolved in 5 mL N,N-dimethylformamide, and the mixture was reacted overnight at room temperature. After the reaction was completed, 100 mL ethyl acetate and 80 mL water were added and the resulting solution was separated into layers. The organic phase was collected, and the aqueous phase was extracted with ethyl acetate (100 mL×2). The organic phases were combined, washed with saturated brine (50 mL×2), dried with anhydrous sodium sulfate, filtered, and concentrated under reduced pressure to obtain crude product methyl (S)-5-((2-chlorobenzyl)oxy)-2-(6-fluorobenzo[d]oxazol-2-yl)-6-methoxy-1,2,3,4-tetrahydroisoquinoline-3-carboxylate 33b (70 mg), yield: 80%.

MS m/z(ESI): 496.9 [M+1]

Step 2

(S)-5-((2-chlorobenzyl)oxy)-2-(6-fluorobenzo[d]oxazol-2-yl)-6-methoxy-1,2,3,4-tetrahydroisoquinoline-3-carboxylic acid Methyl (S)-5-((2-chlorobenzyl)oxy)-2-(6-fluorobenzo[d]oxazol-2-yl)-6-methoxy-1,2,3,4-tetrahydroisoquinoline-3- carboxylate 33b (70 mg, 0.14 mmol) and lithium hydroxide monohydrate (6.0 mg, 0.14 mmol) were dissolved in 4 mL of a mixed solvent of tetrahydrofuran and water (V:V=3:1). The resulting solution was reacted overnight at room temperature. After the reaction was completed, 100 mL ethyl acetate and 50 mL water was added, and 1M dilute hydrochloric acid was added so that the reaction solution was adjusted to pH=4-5. The resulting solution was extracted with ethyl acetate (50 mL×2). The organic phases were combined, washed with saturated brine (50 mL×2), dried with anhydrous sodium sulfate, filtered, and concentrated under reduced pressure. The obtained residue was separated and purified by a preparative column to obtain (S)-5-((2-chlorobenzyl)oxy)-2-(6-fluorobenzo[d]oxazol-2-yl)-6-methoxy-1,2,3,4-tetrahydroisoquinoline-3-carboxylic acid 33 (10 mg), yield: 15%.

MS m/z(ESI): 482.9 [M+1]

¹H NMR (400 MHz, DMSO-d₆) δ 13.03 (br, 1H), 7.66-7.64 (m, 1H), 7.53-7.48 (m, 2H), 7.45-7.41 (m, 2H), 7.34 (dd, J=8.8, 4.8 Hz, 1H), 7.10-7.02 (m, 3H), 5.09-5.05 (m, 2H), 5.01 (d, J=11.6 Hz, 1H), 4.79 (d, J=15.6 Hz, 1H), 4.67 (d, J=15.6 Hz, 1H), 3.84 (s, 3H), 3.51 (dd, J=16.4, 2.8 Hz, 1H), 2.99 (dd, J=16.2, 6.6 Hz, 1H).

Example 34

(S)-2-(6-fluorobenzo[d]oxazol-2-yl)-6-methoxy-5-(pyridin-2-ylmethoxy)-1,2,3,4-tetrahydroisoquinoline-3-carboxylic acid

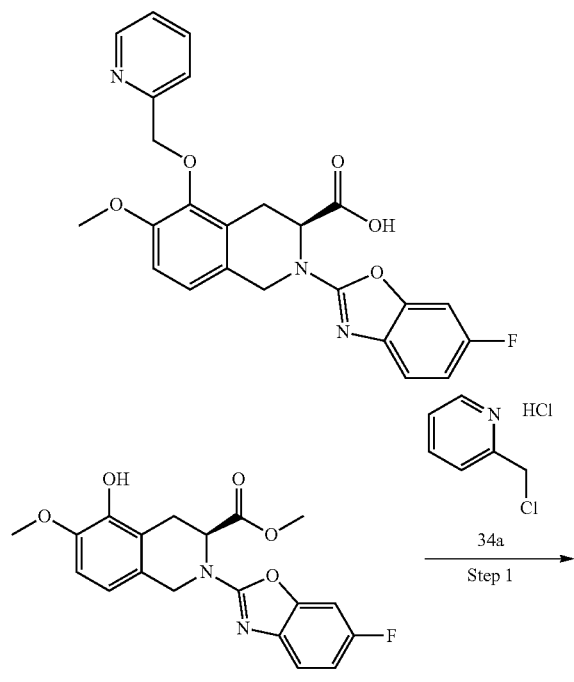

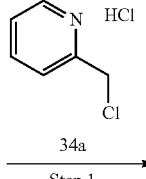

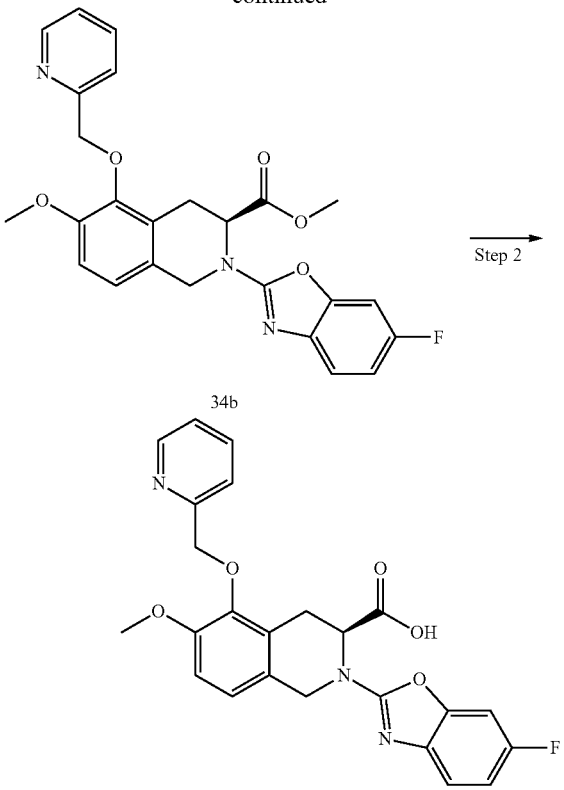

Step 1 methyl (S)-2-(6-fluorobenzo[d]oxazol-2-yl)-6-methoxy-5-(pyridin-2-ylmethoxy)-1,2,3,4-tetrahydroisoquinoline-3-carboxylate Methyl (S)-2-(6-fluorobenzo[d]oxazol-2-yl)-5-hydroxy-6-methoxy-1,2,3,4-tetrahydroisoquinoline-3-carboxylate 29c (80 mg, 0.22 mmol), 2-chloromethylpyridine hydrochloride 34a (280 mg, 1.7 mmol), potassium carbonate (121.5 mg, 0.88 mmol) and sodium iodide (132 mg, 0.88 mmol) were dissolved in 6 mL N,N-dimethylformamide, and the mixture was reacted overnight at room temperature. After the reaction was completed, 100 mL ethyl acetate and 50 mL water were added and the resulting solution was separated into layers. The organic phase was collected, and the aqueous phase was extracted with ethyl acetate (50 mL×2). The organic phases were combined, washed with saturated brine (20 mL×2), dried with anhydrous sodium sulfate, filtered, and concentrated under reduced pressure to obtain crude product methyl (S)-2-(6-fluorobenzo[d]oxazol-2-yl)-6-methoxy-5-(pyridin-2-ylmethoxy)-1,2,3,4-tetrahydroisoquinoline-3-carboxylate 34b (50 mg), yield: 50%.

MS m/z(ESI): 463.9 [M+1]

Step 2

(S)-2-(6-fluorobenzo[d]oxazol-2-yl)-6-methoxy-5-(pyridin-2-ylmethoxy)-1,2,3,4-tetrahydroisoquinoline-3-carboxylic acid Methyl (S)-2-(6-fluorobenzo[d]oxazol-2-yl)-6-methoxy-5-(pyridin-2-ylmethoxy)-1,2,3,4-tetrahydroisoquinoline-3- carboxylate 34b (50 mg, 0.11 mmol) and lithium hydroxide monohydrate (4.62 mg, 0.11 mmol) were dissolved in 7.5 mL of a mixed solvent of tetrahydrofuran and water (V:V=2:1). The resulting solution was reacted overnight at room temperature. After the reaction was completed, 100 mL ethyl acetate and 80 mL water were added, and 1M dilute hydrochloric acid was added so that the reaction solution was adjusted to pH=4-5. The resulting solution was separated into layers, the organic phase was collected, and the aqueous phase was extracted with ethyl acetate (60 mL×2). The organic phases were combined, washed with saturated brine (50 mL×2), dried with anhydrous sodium sulfate, filtered, and concentrated under reduced pressure. The obtained residue was separated and purified by a preparative column to obtain (S)-2-(6-fluorobenzo[d]oxazol-2-yl)-6-methoxy-5-(pyridin-2-ylmethoxy)-1,2,3,4-tetrahydroisoquinoline-3-carboxylic acid 34 (9 mg), yield: 18%.

MS m/z(ESI): 449.9 [M+1]

Example 35

(S)-2-(6-fluorobenzo[d]oxazol-2-yl)-6-methoxy-5-(pyridin-4-ylmethoxy)-1,2,3,4-tetrahydroisoquinoline-3-carboxylic acid

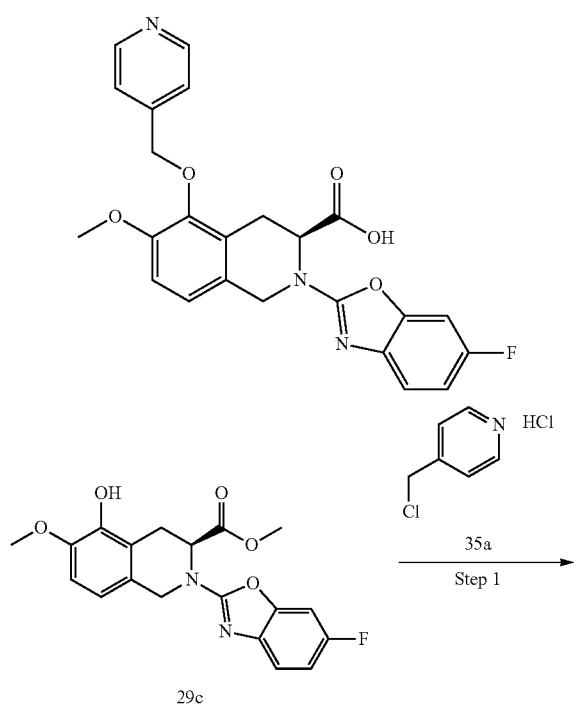

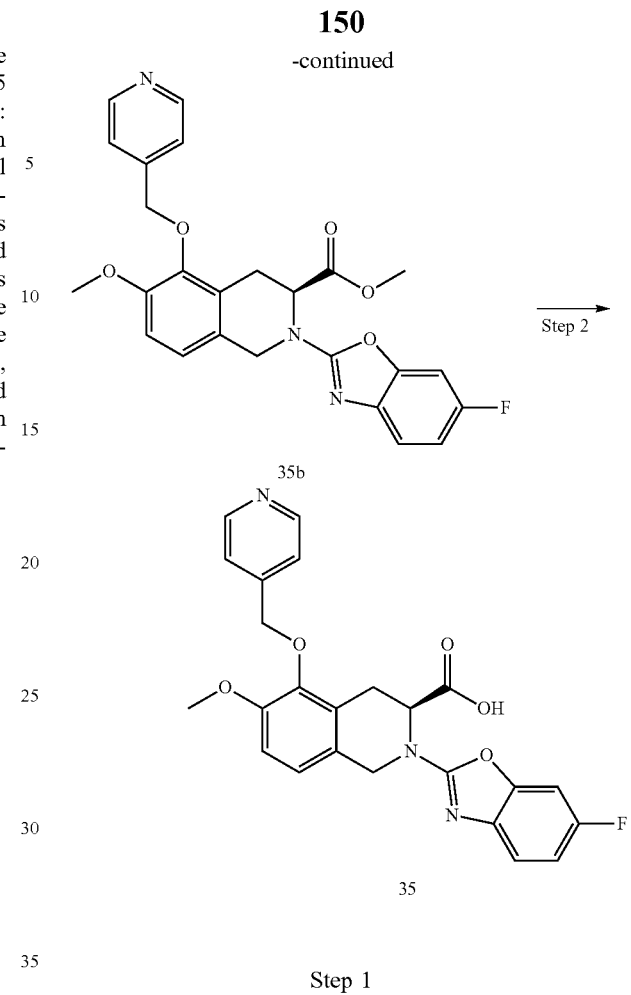

Step 1 methyl (S)-2-(6-fluorobenzo[d]oxazol-2-yl)-6-methoxy-5-(pyridin-4-ylmethoxy)-1,2,3,4-tetrahydroisoquinoline-3-carboxylate 4-Chloromethylpyridine hydrochloride 35a (128 mg, 1.0 mmol) and potassium carbonate (193.2 mg, 1.4 mmol) were dissolved in 5 mL N,N-dimethylformamide, and methyl (S)-2-(6-fluorobenzo[d]oxazol-2-yl)-5-hydroxy-6-methoxy-1,2,3,4-tetrahydroisoquinoline-3-carboxylate 29c (100 mg, 0.27 mmol) was added. The mixture was reacted at 75° C. for 4 hours. After the reaction was completed, 100 mL ethyl acetate and 100 mL water were added and the resulting solution was separated into layers. The organic phase was collected, and the aqueous phase was extracted with ethyl acetate (50 mL×2). The organic phases were combined, washed with saturated brine (20 mL×2), dried with anhydrous sodium sulfate, filtered, and concentrated under reduced pressure to obtain crude product methyl (S)-2-(6-fluorobenzo[d]oxazol-2-yl)-6-methoxy-5-(pyridin-4-ylmethoxy)-1,2,3,4-tetrahydroisoquinoline-3-carboxylate 35b (140 mg), yield: 100%.

MS m/z(ESI): 463.9 [M+1]

Step 2

(S)-2-(6-fluorobenzo[d]oxazol-2-yl)-6-methoxy-5-(pyridin-4-ylmethoxy)-1,2,3,4-tetrahydroisoquinoline-3-carboxylic acid Methyl (S)-2-(6-fluorobenzo[d]oxazol-2-yl)-6-methoxy-5-(pyridin-4-ylmethoxy)-1,2,3,4-tetrahydroisoquinoline-3- carboxylate 35b (125 mg, 0.27 mmol) was dissolved in 4 mL of tetrahydrofuran. 3 mL of a mixed solvent of calcium chloride (481.7 mg, 4.3 mmol) in isopropanol and water (V:V=2:1), and 3 mL of sodium hydroxide solution (56 mg, 1.4 mmol) were added. The resulting solution was reacted overnight at room temperature. After the reaction was completed, 80 mL ethyl acetate and 150 mL water were added, and 1M dilute hydrochloric acid was added so that the reaction solution was adjusted to pH=5-6. The resulting solution was separated into layers, the organic phase was collected, and the aqueous phase was extracted with ethyl acetate (50 mL×2). The organic phases were combined, washed with saturated brine (50 mL×2), dried with anhydrous sodium sulfate, filtered, and concentrated under reduced pressure. The obtained residue was separated and purified by a preparative column (elute: system D) to obtain (S)-2-(6-fluorobenzo[d]oxazol-2-yl)-6-methoxy-5-(pyridin-4-ylmethoxy)-1,2,3,4-tetrahydroisoquinoline-3-carboxylic acid 35 (20 mg), yield: 17%.

MS m/z(ESI): 450.0 [M+1]

Example 36

(S)-2-(6-fluorobenzo[d]oxazol-2-yl)-6-methoxy-5-((5-methoxypyridin-2-yl)methoxy)-1,2,3,4-tetrahydroisoquinoline-3-carboxylic acid

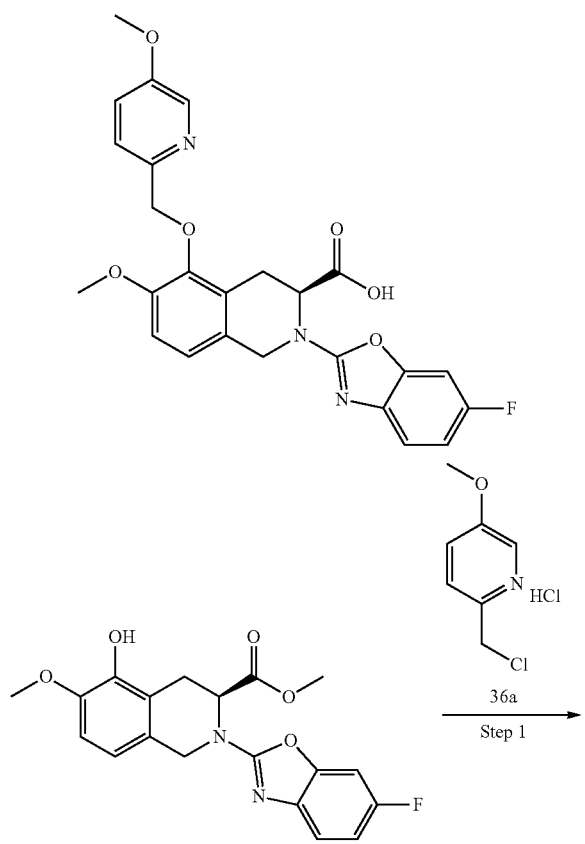

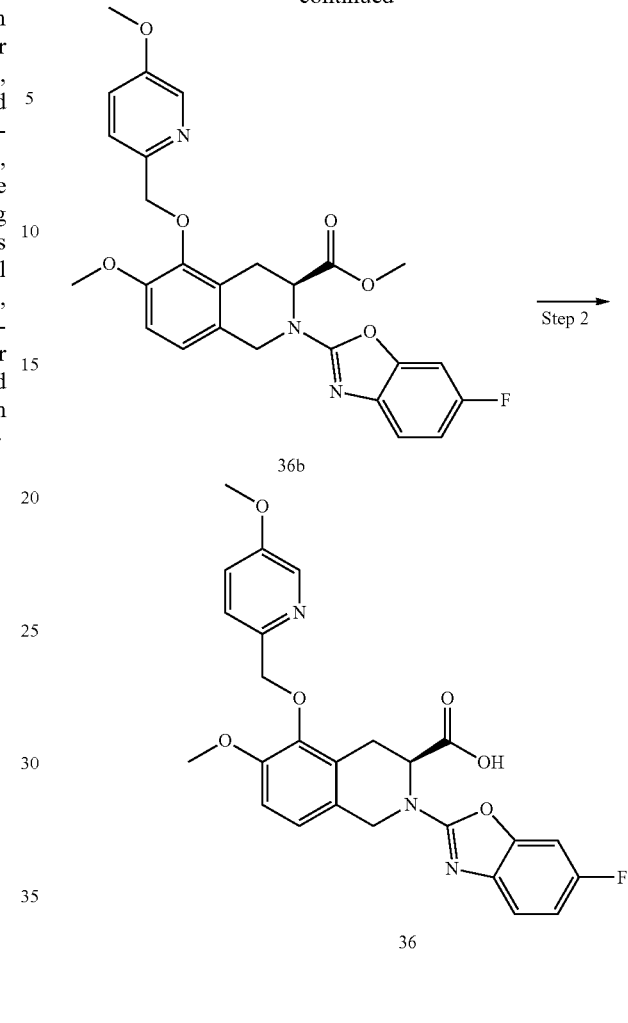

Step 1 methyl (S)-2-(6-fluorobenzo[d]oxazol-2-yl)-6-methoxy-5-((5-methoxypyridin-2-yl)methoxy)-1,2,3,4-tetrahydroisoquinoline-3-carboxylate 2-(Chloromethyl)-5-methoxypyridine hydrochloride 36a (113 mg, 0.72 mmol), potassium carbonate (149 mg, 1.08 mmol) and methyl (S)-2-(6-fluorobenzo[d]oxazol-2-yl)-5-hydroxy-6-methoxy-1,2,3,4-tetrahydroisoquinoline-3-carboxylate 29c (100 mg, 0.27 mmol) were successively dissolved in 6 mL N,N-dimethylformamide, and the mixture was reacted at 70° C. for 6 hours. After the reaction was completed, the mixture was cooled to room temperature, 100 mL ethyl acetate and 50 mL water were added and the resulting solution was separated into layers. The organic phase was collected, and the aqueous phase was extracted with ethyl acetate (50 mL×2). The organic phases were combined, washed with saturated brine (50 mL×2), dried with anhydrous sodium sulfate, filtered, and concentrated under reduced pressure to obtain crude product methyl (S)-2-(6-fluorobenzo[d]oxazol-2-yl)-6-methoxy-5-((5-methoxypyridin-2-yl)methoxy)-1,2,3,4-tetrahydroisoquinoline-3-carboxylate 36b (133 mg), yield: 100%. The crude product can be further separated and purified by column chromatography (eluent: system B) for characterization.

MS m/z(ESI): 493.9 [M+1]

¹H NMR (400 MHz, CDCl₃) δ 8.30 (d, J=2.4 Hz, 1H), 7.59 (d, J=8.8 Hz, 1H), 7.32-7.29 (m, 2H), 7.07 (dd, J=7.8, 2.2 Hz, 1H), 6.96-6.86 (m, 3H), 5.21 (dd, J=6.4, 2.4 Hz, 1H), 5.12 (d, J=12.0 Hz, 1H), 5.05 (d, J=11.6 Hz, 1H), 4.91 (d, J=15.6 Hz, 1H), 4.77 (d, J=15.6 Hz, 1H), 3.89 (s, 3H), 3.87 (s, 3H), 3.67 (dd, J=16.4, 2.4 Hz, 1H), 3.63 (s, 3H), 3.02 (dd, J=16.4, 6.4 Hz, 1H).

Step 2

(S)-2-(6-fluorobenzo[d]oxazol-2-yl)-6-methoxy-5-((5-methoxypyridin-2-yl)methoxy)-1,2,3,4-tetrahydroisoquinoline-3-carboxylic acid Methyl (S)-2-(6-fluorobenzo[d]oxazol-2-yl)-6-methoxy-5-((5-methoxypyridin-2-yl) methoxy)-1,2,3,4-tetrahydroisoquinoline-3-carboxylate 36b (133 mg, 0.27 mmol) was dissolved in 4 mL of tetrahydrofuran. 3 mL of a mixed solution of calcium chloride (481.74 mg, 4.34 mmol) in isopropanol and water (V:V=2:1), and 3 mL of sodium hydroxide solution (56 mg, 1.4 mmol) were added. The resulting solution was reacted overnight at room temperature. After the reaction was completed, 80 mL ethyl acetate and 100 mL water were added, and 1M dilute hydrochloric acid was added so that the reaction solution was adjusted to pH=5-6. The resulting solution was separated into layers, the organic phase was collected, and the aqueous phase was extracted with ethyl acetate (50 mL×2). The organic phases were combined, washed with saturated brine (50 mL×2), dried with anhydrous sodium sulfate, filtered, and concentrated under reduced pressure. The obtained residue was separated and purified by a preparative column to obtain (S)-2-(6-fluorobenzo[d]oxazol-2-yl)-6-methoxy-5-((5-methoxypyridin-2-yl)methoxy)-1,2,3,4-tetrahydroisoquinoline-3-carboxylic acid 36 (15 mg), yield: 12%.

MS m/z(ESI): 479.9 [M+1]

¹H NMR (400 MHz, DMSO-d₆) δ 8.30 (d, J=2.8 Hz, 1H), 7.58 (d, J=8.4 Hz, 1H), 7.52-7.48 (m, 2H), 7.34 (dd, J=8.6, 5.0 Hz, 1H), 7.09-7.01 (m, 3H), 5.07 (dd, J=6.2, 2.6 Hz, 1H), 5.00 (d, J=11.2 Hz, 1H), 4.93 (d, J=11.2 Hz, 1H), 4.79 (d, J=15.6 Hz, 1H), 4.66 (d, J=15.2 Hz, 1H), 3.87 (s, 3H), 3.83 (s, 3H), 3.51 (dd, J=16.0, 2.4 Hz, 1H), 3.00 (dd, J=16.2, 6.6 Hz, 1H).

Example 37

(S)-5-((4-cyanobenzyl)oxy)-2-(6-fluorobenzo[d]oxazol-2-yl)-6-methoxy-1,2,3,4-tetrahydroisoquinoline-3-carboxylic acid

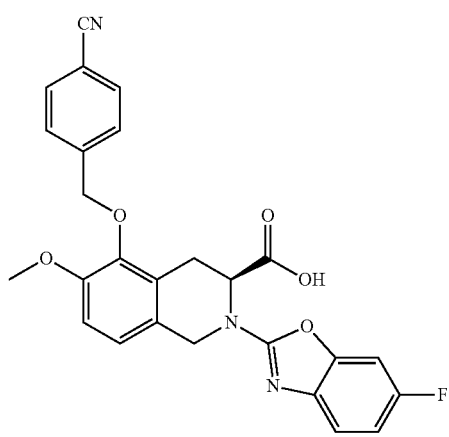

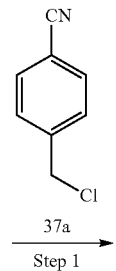

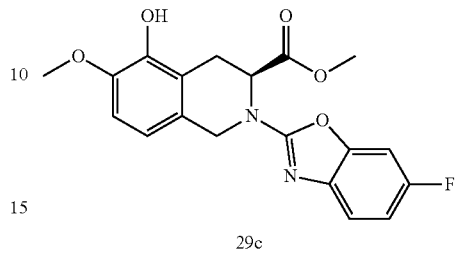

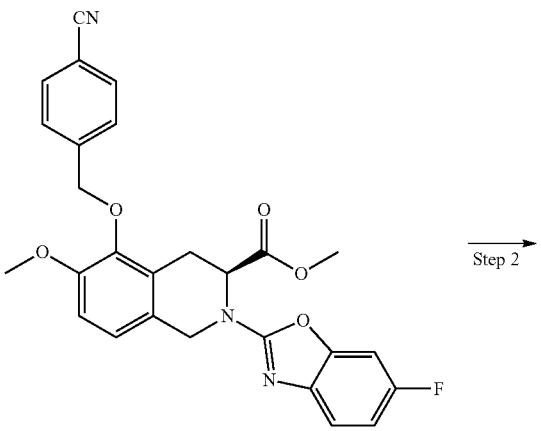

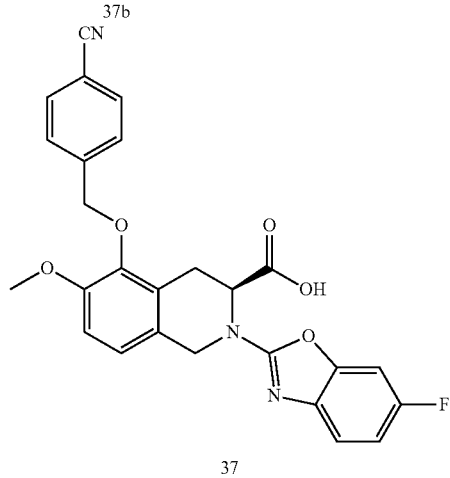

Step 1 methyl (S)-5-((4-cyanobenzyl)oxy)-2-(6-fluorobenzo[d]oxazol-2-yl)-6-methoxy-1,2,3,4-tetrahydroisoquinoline-3-carboxylate Methyl (S)-2-(6-fluorobenzo[d]oxazol-2-yl)-5-hydroxy-6-methoxy-1,2,3,4-tetrahydroisoquinoline-3-carboxylate 29c (100 mg, 0.27 mmol), p-cyanobenzyl chloride 37a (49.1 mg, 0.32 mmol) and potassium carbonate (111.8 mg, 0.81 mmol) were dissolved in 8 mL of N,N-dimethylformamide, and the mixture was reacted at 70° C. for 6 hours. After the reaction was completed, the resulting solution was cooled to room temperature. 80 mL ethyl acetate and 100 mL water were added and the resulting solution was separated into layers. The organic phase was collected, and the aqueous phase was extracted with ethyl acetate (80 mL×2). The organic phases were combined, washed with saturated brine (50 mL×2), dried with anhydrous sodium sulfate, filtered, and concentrated under reduced pressure to obtain crude product methyl (S)-5-((4-cyanobenzyl)oxy)-2-(6-fluorobenzo[d]oxazol-2-yl)-6-methoxy-1,2,3,4-tetrahydroisoquinoline-3-carboxylate 37b (130 mg), yield: 99%.

MS m/z(ESI): 487.9 [M+1]

Step 2

(S)-5-((4-cyanobenzyl)oxy)-2-(6-fluorobenzo[d]oxazol-2-yl)-6-methoxy-1,2,3,4-tetrahydroisoquinoline-3-carboxylic acid Methyl (S)-5-((4-cyanobenzyl)oxy)-2-(6-fluorobenzo[d]oxazol-2-yl)-6-methoxy-1,2,3,4-tetrahydroisoquinoline-3-carboxylate 37b (130 mg, 0.27 mmol) was dissolved in 4 mL of tetrahydrofuran. 3 mL of a mixed solution of calcium chloride (481.7 mg, 4.3 mmol) in isopropanol and water (V:V=2:1), and 3 mL of sodium hydroxide solution (56 mg, 1.4 mmol) were added. The resulting solution was reacted overnight at room temperature. After the reaction was completed, 100 mL ethyl acetate and 50 mL water were added, and 1M dilute hydrochloric acid was added so that the reaction solution was adjusted to pH=5-6. The resulting solution was separated into layers, the organic phase was collected, and the aqueous phase was extracted with ethyl acetate (50 mL×2). The organic phases were combined, washed with saturated brine (50 mL×2), dried with anhydrous sodium sulfate, filtered, and concentrated under reduced pressure. The obtained residue was separated and purified by a preparative column to obtain (S)-5-((4-cyanobenzyl)oxy)-2-(6-fluorobenzo[d]oxazol-2-yl)-6-methoxy-1,2,3,4-tetrahydroisoquinoline-3-carboxylic acid 37 (20 mg), yield: 16%.

MS m/z(ESI): 473.9 [M+1]

$^1$H NMR (400 MHz, DMSO-$d_6$) δ 7.89 (d, J=8.0 Hz, 2H), 7.68 (d, J=8.0 Hz, 2H), 7.49 (dd, J=8.4, 2.8 Hz, 1H), 7.34 (dd, J=8.6, 5.0 Hz, 1H), 7.09-7.01 (m, 3H), 5.11-5.07 (m, 2H), 4.98 (d, J=12.4 Hz, 1H), 4.79 (d, J=16.0 Hz, 1H), 4.67 (d, J=15.6 Hz, 1H), 3.82 (s, 3H), 3.51 (dd, J=16.6, 2.6 Hz, 1H), 3.04 (dd, J=16.4, 6.4 Hz, 1H).

Example 38

(S)-2-(6-fluorobenzo[d]oxazol-2-yl)-6-methoxy-5-((4-(trifluoromethyl)benzyl)oxy)-1,2,3,4-tetrahydroisoquinoline-3-carboxylic acid

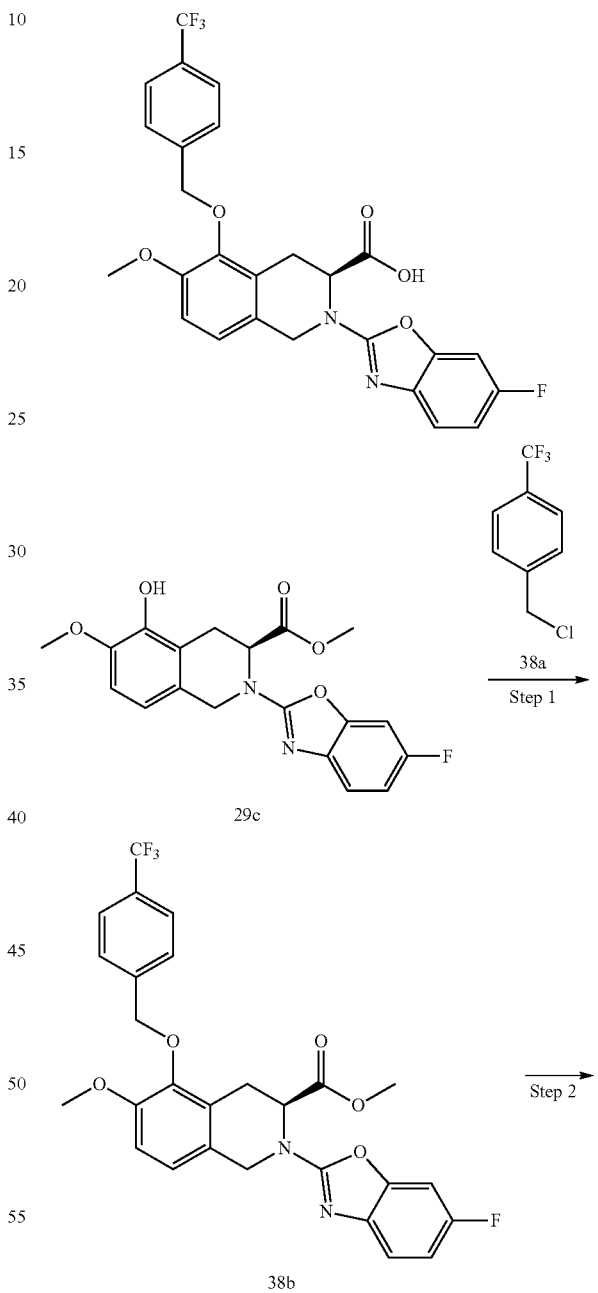

-continued

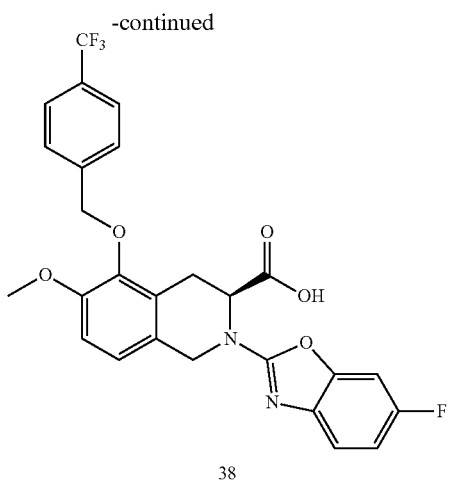

38

Step 1 methyl (S)-2-(6-fluorobenzo[d]oxazol-2-yl)-6-methoxy-5-((4-(trifluoromethyl) benzyl)oxy)-1,2,3,4-tetrahydroisoquinoline-3-carboxylate Methyl (S)-2-(6-fluorobenzo[d]oxazol-2-yl)-5-hydroxy-6-methoxy-1,2,3,4-tetrahydroisoquinoline-3-carboxylate 29c (100 mg, 0.27 mmol), 4-(trifluoromethyl)benzyl chloride 38a (58 mg, 0.3 mmol) and potassium carbonate (111.8 mg, 0.81 mmol) were dissolved in 8 mL of N,N-dimethylformamide, and the mixture was reacted at 70° C. for 3 hours. After the reaction was completed, the resulting solution was cooled to room temperature. 50 mL ethyl acetate and 100 mL water were added and the resulting solution was separated into layers. The organic phase was collected, and the aqueous phase was extracted with ethyl acetate (50 mL×2). The organic phases were combined, washed with saturated brine (30 mL×2), dried with anhydrous sodium sulfate, filtered, and concentrated under reduced pressure to obtain crude product methyl (S)-2-(6-fluorobenzo[d]oxazol-2-yl)-6-methoxy-5-((4-(trifluoromethyl)benzyl)oxy)-1,2,3,4-tetrahydroisoquinoline-3-carboxylate 38b (143 mg), yield: 100%.

MS m/z(ESI): 530.9 [M+1]

Step 2

(S)-2-(6-fluorobenzo[d]oxazol-2-yl)-6-methoxy-5-((4-(trifluoromethyl)benzyl)oxy)-1,2,3,4-tetrahydroisoquinoline-3-carboxylic acid Methyl (S)-2-(6-fluorobenzo[d]oxazol-2-yl)-6-methoxy-5-((4-(trifluoromethyl)benzyl) oxy)-1,2,3,4-tetrahydroisoquinoline-3-carboxylate 38b (143 mg, 0.27 mmol) was dissolved in 4 mL of tetrahydrofuran. 3 mL of a mixed solution of calcium chloride (481.7 mg, 4.3 mmol) in isopropanol and water (V:V=2:1), and 3 mL of sodium hydroxide solution (56 mg, 1.4 mmol) were added. The resulting solution was reacted overnight at room temperature. After the reaction was completed, 100 mL ethyl acetate and 50 mL water were added, and 1M dilute hydrochloric acid was added so that the reaction solution was adjusted to pH=5-6. The resulting solution was separated into layers, the organic phase was collected, and the aqueous phase was extracted with ethyl acetate (50 mL×2). The organic phases were combined, washed with saturated brine (50 mL×2), dried with anhydrous sodium sulfate, filtered, and concentrated under reduced pressure. The obtained residue was separated and purified by a preparative column to obtain (S)-2-(6-fluorobenzo[d]oxazol-2-yl)-6-methoxy-5-((4-(trifluoromethyl)benzyl)oxy)-1,2,3,4-tetrahydroisoquinoline-3-carboxylic acid 38 (60 mg), yield: 43%.

MS m/z(ESI): 516.8 [M+1]

$^1$H NMR (400 MHz, DMSO-$d_6$) δ 13.06 (br, 1H), 7.79 (d, J=8.4 Hz, 2H), 7.71 (d, J=8.0 Hz, 2H), 7.49 (dd, J=8.4, 2.4 Hz, 1H), 7.33 (dd, J=8.4, 5.2 Hz, 1H), 7.09-7.01 (m, 3H), 5.10-5.07 (m, 2H), 4.97 (d, J=11.6 Hz, 1H), 4.79 (d, J=15.2 Hz, 1H), 4.67 (d, J=15.6 Hz, 1H), 3.82 (s, 3H), 3.52 (dd, J=16.2, 2.2 Hz, 1H), 3.05 (dd, J=16.2, 6.2 Hz, 1H).

Example 39

(S)-2-(6-fluorobenzo[d]oxazol-2-yl)-6-methoxy-5-((6-methoxypyridin-3-yl)methoxy)-1,2,3,4-tetrahydroisoquinoline-3-carboxylic acid

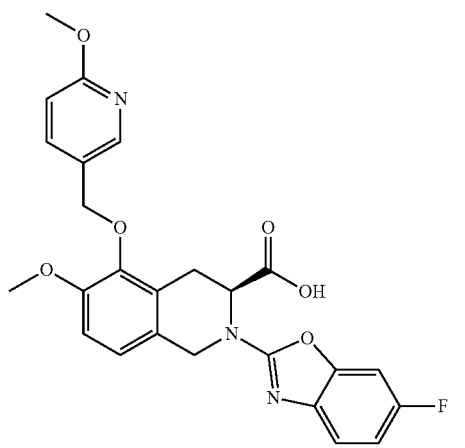

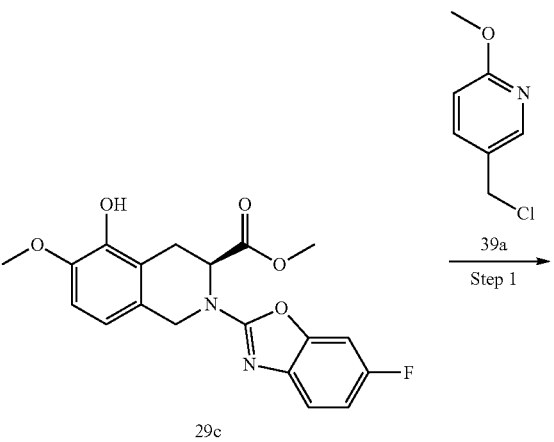

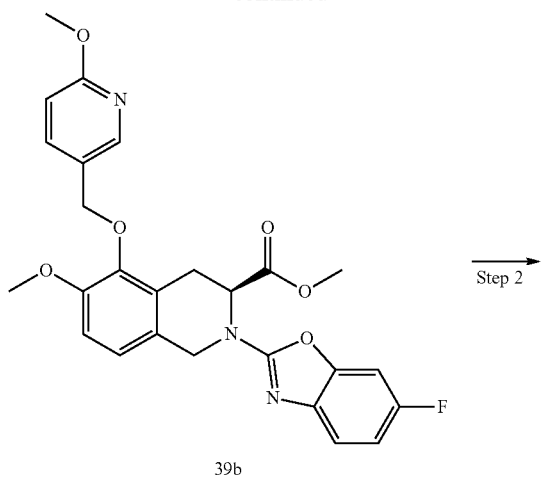

39b

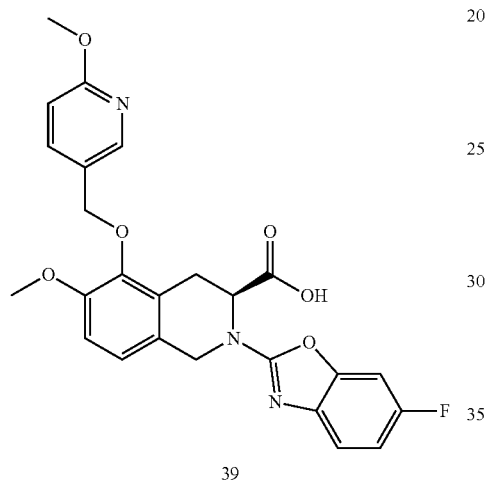

39

Step 1 methyl (S)-2-(6-fluorobenzo[d]oxazol-2-yl)-6-methoxy-5-((6-methoxypyridin-3-yl) methoxy)-1,2,3,4-tetrahydroisoquinoline-3-carboxylate Methyl (S)-2-(6-fluorobenzo[d]oxazol-2-yl)-5-hydroxy-6-methoxy-1,2,3,4-tetrahydroisoquinoline-3-carboxylate 29c (350 mg, 0.94 mmol), 5-chloromethyl-2-methoxypyridine 39a (500 mg, 3.16 mmol) and potassium carbonate (600 mg, 4.34 mmol) were dissolved in 8 mL of N,N-dimethylformamide, and the mixture was reacted at 80° C. for 4 hours, and then reacted overnight at room temperature. After the reaction was completed, 150 mL ethyl acetate and 150 mL saturated brine were added and the resulting solution was separated into layers. The organic phase was collected, and the aqueous phase was extracted with ethyl acetate (100 mL×2). The organic phases were combined, dried with anhydrous sodium sulfate, filtered, and concentrated under reduced pressure to obtain crude product methyl (S)-2-(6-fluorobenzo[d]oxazol-2-yl)-6-methoxy-5-((6-methoxypyridin-3-yl)methoxy)-1,2,3,4-tetrahydroisoquinoline-3-carboxylate 39b (450 mg), yield: 97%.

MS m/z(ESI): 493.9 [M+1]

Step 2

(S)-2-(6-fluorobenzo[d]oxazol-2-yl)-6-methoxy-5-((6-methoxypyridin-3-yl)methoxy)-1,2,3,4-tetrahydroisoquinoline-3-carboxylic acid Methyl (S)-2-(6-fluorobenzo[d]oxazol-2-yl)-6-methoxy-5-((6-methoxypyridin-2-yl) methoxy)-1,2,3,4-tetrahydroisoquinoline-3-carboxylate 39b (450 mg, 0.91 mmol) was dissolved in 8 mL of tetrahydrofuran. 9 mL of a mixed solution of calcium chloride (1.57 g, 14.1 mmol) in isopropanol and water (V:V=2:1), and 3 mL of sodium hydroxide solution (182 mg, 4.55 mmol) were added. The resulting solution was reacted overnight at room temperature. After the reaction was completed, 150 mL ethyl acetate was added, and 1M dilute hydrochloric acid was added so that the reaction solution was adjusted to pH=4-5, and 200 mL brine was added. The resulting solution was separated into layers, the organic phase was collected, and the aqueous phase was extracted with ethyl acetate (100 mL×2). The organic phases were combined, dried with anhydrous sodium sulfate, filtered, and concentrated under reduced pressure. The obtained residue was separated and purified by a preparative column to obtain (S)-2-(6-fluorobenzo[d]oxazol-2-yl)-6-methoxy-5-((6-methoxypyridin-3-yl)methoxy)-1,2,3,4-tetrahydroisoquinoline-3-carboxylic acid 39 (210 mg), yield: 48%.

MS m/z(ESI): 480.2 [M+1]

Example 40

(S)-2-(6-fluorobenzo[d]oxazol-2-yl)-6-methoxy-5-((4-methylbenzyl)oxy)-1,2,3,4-tetrahydroisoquinoline-3-carboxylic acid

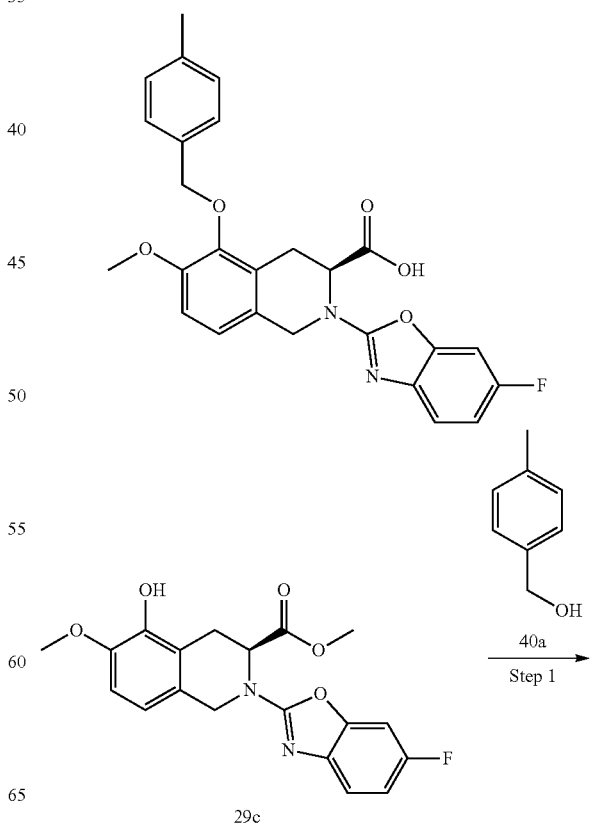

-continued

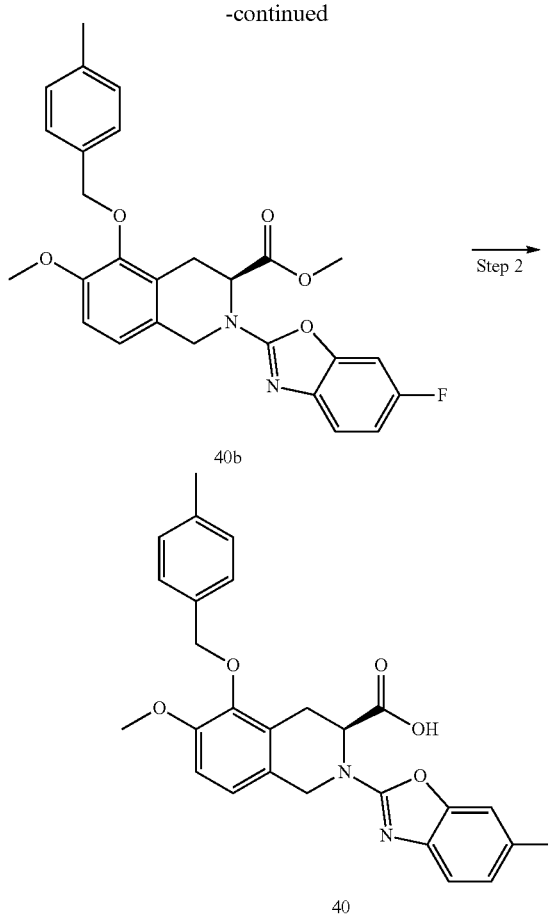

Step 1 methyl (S)-2-(6-fluorobenzo[d]oxazol-2-yl)-6-methoxy-5-((4-methylbenzyl)oxy)-1,2,3,4-tetrahydroisoquinoline-3-carboxylate Under the protection of argon gas, methyl (S)-2-(6-fluorobenzo[d]oxazol-2-yl)-5-hydroxy-6-methoxy-1,2,3,4-tetrahydroisoquinoline-3-carboxylate 29c (100 mg, 0.268 mmol), p-methylbenzyl alcohol 40a (36.1 mg, 0.295 mmol) and triphenylphosphine (106 mg, 0.402 mmol) were dissolved in 5 mL tetrahydrofuran, and the mixture was stirred at room temperature for 15 minutes. Dibenzyl azodicarboxylate (DBAD) (92.7 mg, 0.402 mmol) was added dropwise, and the resulting solution was reacted overnight at room temperature. After the reaction was completed, the resulting solution was concentrated under reduced pressure, and the obtained residue was purified by silica gel column chromatography (eluent: system A) to obtain methyl (S)-2-(6-fluorobenzo[d]oxazol-2-yl)-6-methoxy-5-((4-methylbenzyl)oxy)-1,2,3,4-tetrahydroisoquinoline-3-carboxylate 40b (120 mg), yield: 94%.

MS m/z(ESI): 476.9 [M+1]

Step 2

(S)-2-(6-fluorobenzo[d]oxazol-2-yl)-6-methoxy-5-((4-methylbenzyl)oxy)-1,2,3,4-tetrahydroisoquinoline-3-carboxylic acid Methyl (S)-2-(6-fluorobenzo[d]oxazol-2-yl)-6-methoxy-5-((4-methylbenzyl)oxy)-1,2,3,4-tetrahydroisoquinoline-3-carboxylate 40b (120 mg, 0.252 mmol) and lithium hydroxide monohydrate (10.6 mg, 0.252 mmol) were dissolved in 4 mL of a mixed solvent of tetrahydrofuran and water (V:V=1:1). The resulting solution was reacted overnight at room temperature. After the reaction was completed, 50 mL ethyl acetate was added and 1M dilute hydrochloric acid was added so that the reaction solution was adjusted to pH=4-5. The resulting solution was extracted with ethyl acetate (50 mL×2). The organic phases were combined, washed with saturated brine (50 mL×2), dried with anhydrous sodium sulfate, filtered, and concentrated under reduced pressure. The obtained residue was separated and purified by a preparative column to obtain (S)-2-(6-fluorobenzo[d]oxazol-2-yl)-6-methoxy-5-((4-methylbenzyl)oxy)-1,2,3,4-tetrahydroisoquinoline-3-carboxylic acid 40 (20 mg), yield: 17%.

MS m/z(ESI): 462.9 [M+1]

$^1$H NMR (400 MHz, DMSO-$d_6$) δ 13.05 (br, 1H), 7.49 (dd, J=8.4, 2.4 Hz, 1H), 7.36-7.31 (m, 3H), 7.21 (d, J=8.0 Hz, 2H), 7.08-6.99 (m, 3H), 5.06 (dd, J=6.0, 2.8 Hz, 1H), 4.93 (d, J=10.4 Hz, 1H), 4.81 (d, J=10.8 Hz, 1H), 4.77 (d, J=15.6 Hz, 1H), 4.65 (d, J=15.2 Hz, 1H), 3.83 (s, 3H), 3.50 (dd, J=16.2, 2.2 Hz, 1H), 2.97 (dd, J=16.2, 6.2 Hz, 1H), 2.32 (s, 3H).

Example 41

(S)-2-(6-fluorobenzo[d]oxazol-2-yl)-6-methoxy-5-((4-trifluoromethoxy)benzyl)oxy)-1,2,3,4-tetrahydroisoquinoline-3-carboxylic acid

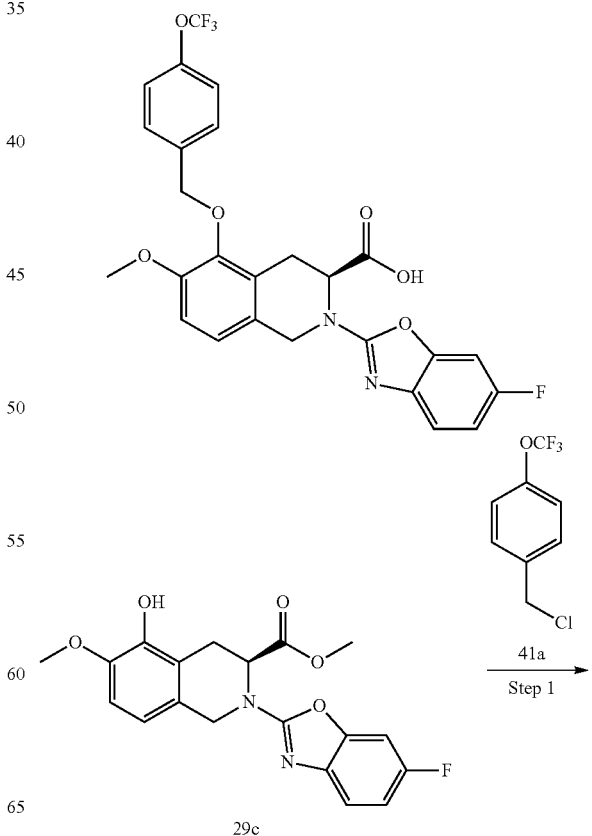

-continued

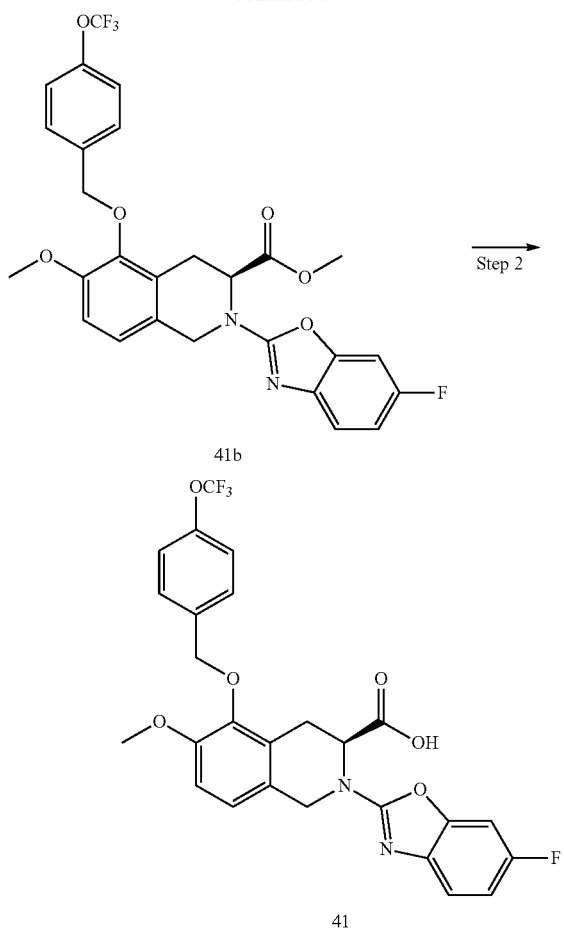

Step 1 methyl (S)-2-(6-fluorobenzo[d]oxazol-2-yl)-6-methoxy-5-((4-trifluoromethoxy)benzyl) oxy)-1,2,3,4-tetrahydroisoquinoline-3-carboxylate Methyl (S)-2-(6-fluorobenzo[d]oxazol-2-yl)-5-hydroxy-6-methoxy-1,2,3,4-tetrahydroisoquinoline-3-carboxylate 29c (100 mg, 0.27 mmol), 4-trifluoromethoxybenzyl chloride 41a (63.2 mg, 0.32 mmol) and potassium carbonate (111.8 mg, 0.81 mmol) were dissolved in 8 mL of N,N-dimethylformamide, and the mixture was reacted at 70° C. for 4 hours. After the reaction was completed, the resulting solution was cooled to room temperature. 50 mL ethyl acetate and 100 mL water were added and the resulting solution was separated into layers. The organic phase was collected, and the aqueous phase was extracted with ethyl acetate (50 mL×2). The organic phases were combined, washed with saturated brine (50 mL×2), dried with anhydrous sodium sulfate, filtered, and concentrated under reduced pressure to obtain crude product methyl (S)-2-(6-fluorobenzo[d]oxazol-2-yl)-6-methoxy-5-((4-trifluoromethoxy)benzyl)oxy)-1,2,3,4-tetrahydroisoquinoline-3-carboxylate 41b (147 mg), yield: 100%.

MS m/z(ESI): 546.9[M+1]

Step 2

(S)-2-(6-fluorobenzo[d]oxazol-2-yl)-6-methoxy-5-((4-trifluoromethoxy)benzyl)oxy)-1,2,3,4-tetrahydroisoquinoline-3-carboxylic acid Methyl (S)-2-(6-fluorobenzo[d]oxazol-2-yl)-6-methoxy-5-((4-trifluoromethoxy)benzyl) oxy)-1,2,3,4-tetrahydroisoquinoline-3-carboxylate 41b (147 mg, 0.27 mmol) was dissolved in 4 mL of tetrahydrofuran. 3 mL of a mixed solution of calcium chloride (481.7 mg, 4.3 mmol) in isopropanol and water (V:V=2:1), and 3 mL of sodium hydroxide solution (56 mg, 1.4 mmol) were added. The resulting solution was reacted overnight at room temperature. After the reaction was completed, 100 mL ethyl acetate was added, and 1M dilute hydrochloric acid was added so that the reaction solution was adjusted to pH=5-6 and 50 mL brine was added. The resulting solution was separated into layers, the organic phase was collected, and the aqueous phase was extracted with ethyl acetate (50 mL×2). The organic phases were combined, washed with saturated brine (50 mL×2), dried with anhydrous sodium sulfate, filtered, and concentrated under reduced pressure. The obtained residue was separated and purified by a preparative column to obtain (S)-2-(6-fluorobenzo[d]oxazol-2-yl)-6-methoxy-5-((4-trifluoromethoxy)benzyl)oxy)-1,2,3,4-tetrahydroisoquinoline-3-carboxylic acid 41 (60 mg), yield: 42%.

MS m/z(ESI): 532.8 [M+1]

$^1$H NMR (400 MHz, DMSO-$d_6$) δ 13.06 (br, 1H), 7.61 (d, J=8.4 Hz, 2H), 7.48 (dd, J=8.2, 2.2 Hz, 1H), 7.41 (d, J=8.0 Hz, 2H), 7.33 (dd, J=8.4, 4.8 Hz, 1H), 7.08-7.00 (m, 3H), 5.09 (dd, J=6.4, 2.8 Hz, 1H), 5.01 (d, J=11.2 Hz, 1H), 4.89 (d, J=11.6 Hz, 1H), 4.78 (d, J=16.0 Hz, 1H), 4.66 (d, J=15.6 Hz, 1H), 3.82 (s, 3H), 3.51 (dd, J=16.6, 2.2 Hz, 1H), 3.02 (dd, J=16.0, 6.4 Hz, 1H).

Example 42

(S)-2-(6-cyanobenzo[d]oxazol-2-yl)-6-methoxy-5-((4-methoxybenzyl)oxy)-1,2,3,4-tetrahydroisoquinoline-3-carboxylic acid

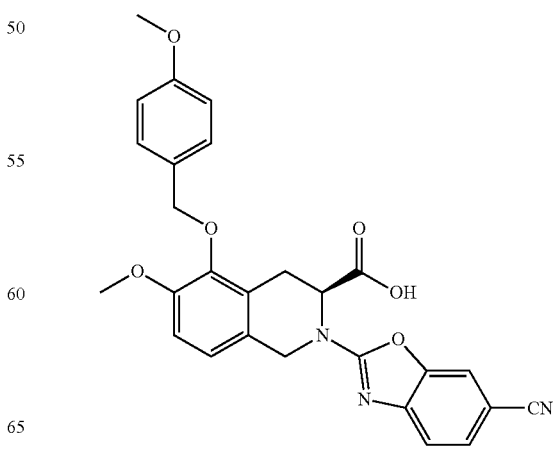

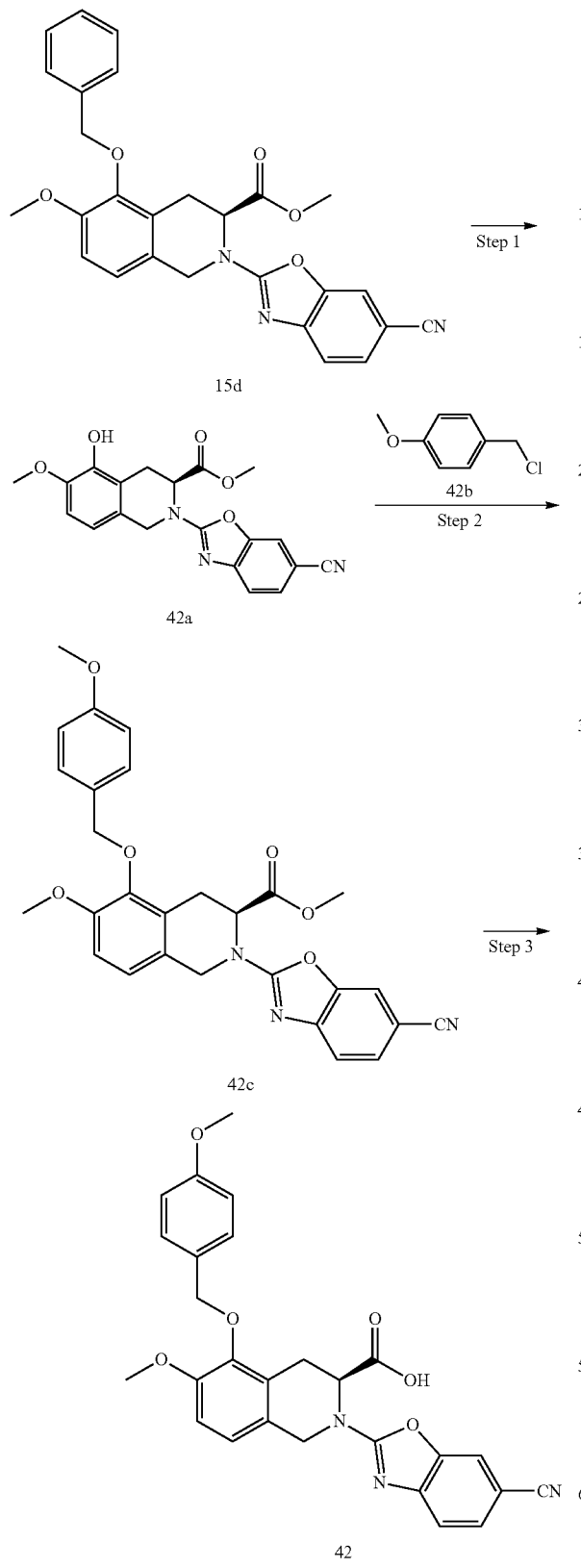

Step 1 methyl (S)-2-(6-cyanobenzo[d]oxazol-2-yl)-5-hydroxy-6-methoxy-1,2,3,4-tetrahydroisoquinoline-3-carboxylate Methyl (S)-5-(benzyloxy)-2-(6-cyanobenzo[d]oxazol-2-yl)-6-methoxy-1,2,3,4-tetrahydroisoquinoline-3-carboxylate 15d (1.9 g, 4.05 mmol) and 10 wt. % palladium-carbon (190 mg, 10%) were dissolved in 20 mL of tetrahydrofuran. The mixture was bubbled with hydrogen gas for three times, and a hydrogen balloon was inserted. The resulting mixture was reacted overnight at room temperature. After the reaction was completed, the resulting solution was filtered and the filter liquor was concentrated under reduced pressure to obtain methyl (S)-2-(6-cyanobenzo[d]oxazol-2-yl)-5-hydroxy-6-methoxy-1,2,3,4-tetrahydroisoquinoline-3-carboxylate 42a (1.5 g), yield: 98%.

MS m/z(ESI): 380.1 [M+1]

$^1$H NMR (400 MHz, CDCl$_3$) δ 7.56 (d, J=0.8 Hz, 1H), 7.51 (dd, J=8.4, 1.2 Hz, 1H), 7.41 (d, J=8.0 Hz, 1H), 6.80 (d, J=8.4 Hz, 1H), 6.72 (d, J=8.4 Hz, 1H), 5.88 (s, 1H), 5.32 (d, J=4.4 Hz, 1H), 4.97 (d, J=15.6 Hz, 1H), 4.81 (d, J=15.6 Hz, 1H), 3.88 (s, 3H), 3.67-3.63 (m, 4H), 3.13 (dd, J=16.6, 6.6 Hz, 1H).

Step 2 methyl (S)-2-(6-cyanobenzo[d]oxazol-2-yl)-6-methoxy-5-((4-methoxybenzyl)oxy)-1,2,3,4-tetrahydroisoquinoline-3-carboxylate Methyl (S)-2-(6-cyanobenzo[d]oxazol-2-yl)-5-hydroxy-6-methoxy-1,2,3,4-tetrahydroisoquinoline-3-carboxylate 42a (100 mg, 0.26 mmol), 4-methoxybenzyl chloride 42b (100 mg, 0.64 mmol) and potassium carbonate (150 mg, 1.08 mmol) were dissolved in 6 mL of N,N-dimethylformamide, and the mixture was reacted at 70° C. for 3 hours. After the reaction was completed, the resulting solution was cooled to room temperature. 30 mL ethyl acetate and 20 mL water were added and the resulting solution was separated into layers. The organic phase was collected, and the aqueous phase was extracted with ethyl acetate (10 mL×2). The organic phases were combined, washed with saturated brine (50 mL), dried with anhydrous sodium sulfate, filtered, and concentrated under reduced pressure. The obtained residue was separated and purified by a preparative column to obtain methyl (S)-2-(6-cyanobenzo[d]oxazol-2-yl)-6-methoxy-5-((4-methoxybenzyl)oxy)-1,2,3,4-tetrahydroisoquinoline-3-carboxylate 42c (120 mg), yield: 93%.

MS m/z(ESI): 500.1 [M+1]

$^1$H NMR (400 MHz, CDCl$_3$) δ 7.57 (s, 1H), 7.53 (d, J=8.4 Hz, 1H), 7.46 (d, J=7.6 Hz, 1H), 7.37 (d, J=8.4 Hz, 2H), 6.95-6.87 (m, 4H), 5.15 (s, 1H), 5.00 (d, J=10.8 Hz, 1H), 4.93-4.89 (m, 2H), 4.79 (d, J=15.6 Hz, 1H), 3.90 (s, 3H), 3.82 (s, 3H), 3.64-3.59 (m, 4H), 2.90 (dd, J=16.2, 6.6 Hz, 1H).

Step 3

(S)-2-(6-cyanobenzo[d]oxazol-2-yl)-6-methoxy-5-((4-methoxybenzyl)oxy)-1,2,3,4-tetrahydroisoquinoline-3-carboxylic acid Methyl (S)-2-(6-cyanobenzo[d]oxazol-2-yl)-6-methoxy-5-((4-methoxybenzyl)oxy)-1,2,3,4-tetrahydroisoquinoline-3-carboxylate 42c (129.8 mg, 0.26 mmol) was dissolved in 1.5 mL of tetrahydrofuran. 2.1 mL of a mixed solution of calcium chloride (453.5 mg, 4.08 mmol) in isopropanol and water (V:V=2:1), and 3 mL of sodium hydroxide solution (52.7 mg, 1.38 mmol) were added. The resulting solution was reacted overnight at room temperature. After the reaction was completed, 20 mL ethyl acetate was added, and 2M dilute hydrochloric acid was added so that the reaction solution was adjusted to pH=3 and 20 mL brine was added. The resulting solution was separated into layers, the organic phase was collected, and the aqueous phase was extracted with ethyl acetate (10 mL×2). The organic phases were combined, washed with saturated brine (20 mL), dried with anhydrous sodium sulfate, filtered, and concentrated under reduced pressure. The obtained residue was separated and purified by a preparative column to obtain (S)-2-(6-cyano-benzo[d]oxazol-2-yl)-6-methoxy-5-((4-methoxybenzyl)oxy)-1,2,3,4-tetrahydroisoquinoline-3-carboxylic acid 42 (60 mg), yield: 48%.

MS m/z(ESI): 486.1 [M+1]

¹H NMR (400 MHz, DMSO-d₆) δ 13.12 (s, 1H), 8.04 (s, 1H), 7.67 (d, J=8.0 Hz, 1H), 7.80 (d, J=8.4 Hz, 1H), 7.38 (d, J=8.4 Hz, 2H), 7.07 (d, J=8.4 Hz, 1H), 7.01 (d, J=8.4 Hz, 1H), 6.95 (d, J=8.8 Hz, 2H), 5.11 (dd, J=5.4, 2.2 Hz, 1H), 4.91 (d, J=10.0 Hz, 1H), 4.83-4.78 (m, 2H), 4.71 (d, J=15.6 Hz, 1H), 3.84 (s, 3H), 3.76 (s, 3H), 4.52 (dd, J=15.4, 1.8 Hz, 1H), 2.90 (dd, J=16.4, 6.8 Hz, 1H).

Example 43

(S)-2-(6-cyanobenzo[d]oxazol-2-yl)-6-methoxy-5-((6-methoxypyridin-3-yl)methoxy)-1,2,3,4-tetrahydroisoquinoline-3-carboxylic acid

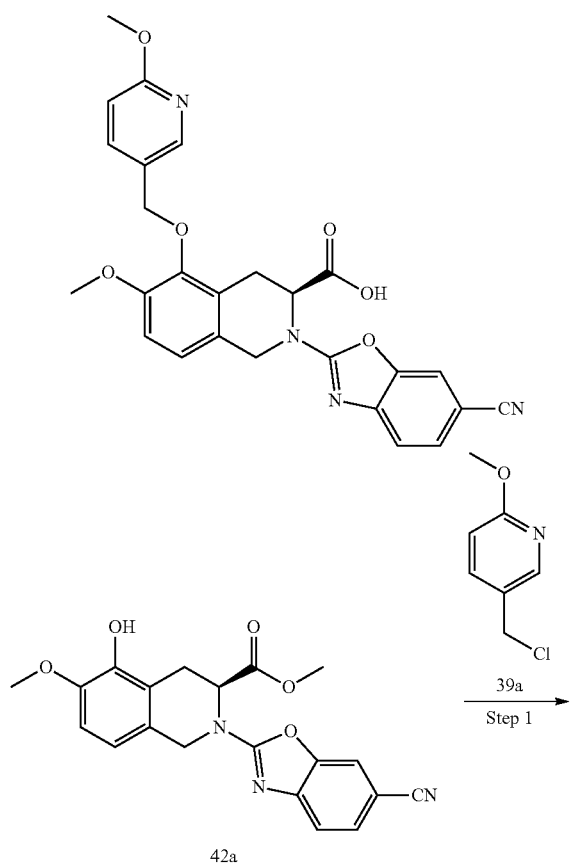

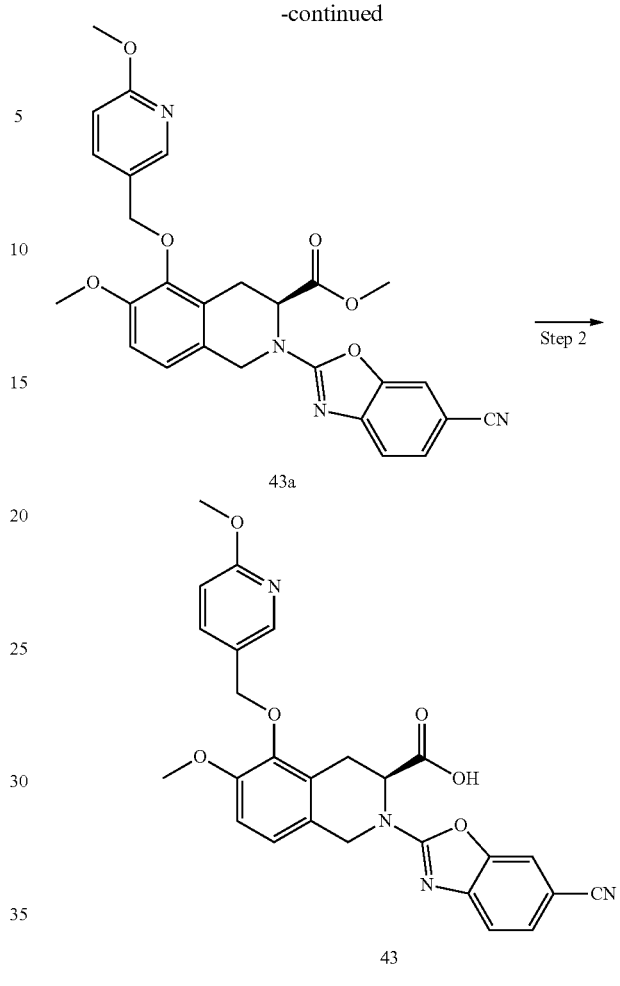

Step 1 methyl (S)-2-(6-cyanobenzo[d]oxazol-2-yl)-6-methoxy-5-((6-methoxypyridin-3-yl) methoxy)-1,2,3,4-tetrahydroisoquinoline-3-carboxylate Methyl (S)-2-(6-cyanobenzo[d]oxazol-2-yl)-5-hydroxy-6-methoxy-1,2,3,4-tetrahydroisoquinoline-3-carboxylate 42a (100 mg, 0.26 mmol), 5-chloromethyl-2-methoxypyridine 39a (100 mg, 0.63 mmol) and potassium carbonate (300 mg, 2.16 mmol) were dissolved in 6 mL of N,N-dimethylformamide, and the mixture was reacted at 70° C. for 6 hours. After the reaction was completed, the resulting solution was cooled to room temperature. 30 mL ethyl acetate and 20 mL water were added and the resulting solution was separated into layers. The organic phase was collected, and the aqueous phase was extracted with ethyl acetate (10 mL×2). The organic phases were combined, washed with saturated brine (50 mL×2), dried with anhydrous sodium sulfate, filtered, and concentrated under reduced pressure to obtain crude product methyl (S)-2-(6-cyanobenzo[d]oxazol-2-yl)-6-methoxy-5-((6-methoxypyridin-3-yl)methoxy)-1,2,3,4-tetrahydroisoquinoline-3-carboxylate 43a, which was directly used in the next reaction.

MS m/z(ESI): 500.9 [M+1]

¹H NMR (400 MHz, CDCl₃) δ 8.31 (s, 1H), 7.88 (d, J=8.4 Hz, 1H), 7.58 (s, 1H), 7.53 (d, J=8.0 Hz, 1H), 7.44 (d, J=8.0

Hz, 1H), 6.97-6.87 (m, 3H), 5.24 (s, 1H), 5.03 (d, J=10.8 Hz, 1H), 4.97-4.91 (m, 2H), 4.80 (d, J=15.2 Hz, 1H), 4.01 (s, 3H), 3.90 (s, 3H), 3.67-3.61 (m, 4H), 2.96 (dd, J=16.4, 6.0 Hz, 1H).

Step 2

(S)-2-(6-cyanobenzo[d]oxazol-2-yl)-6-methoxy-5-((6-methoxypyridin-3-yl)methoxy)-1,2,3,4-tetrahydroisoquinoline-3-carboxylic acid Methyl (S)-2-(6-cyanobenzo[d]oxazol-2-yl)-6-methoxy-5-((6-methoxypyridin-3-yl) methoxy)-1,2,3,4-tetrahydroisoquinoline-3-carboxylate 43a (130 mg, 0.26 mmol) was dissolved in 1.5 mL of tetrahydrofuran. 2.1 mL of a mixed solution of calcium chloride (453.5 mg, 4.08 mmol) in isopropanol and water (V:V=2:1), and 3 mL of sodium hydroxide solution (52.7 mg, 1.38 mmol) were added. The resulting solution was reacted overnight at room temperature. After the reaction was completed, 20 mL ethyl acetate was added, and 2M dilute hydrochloric acid was added so that the reaction solution was adjusted to pH=3 and 20 mL brine was added. The resulting solution was separated into layers, the organic phase was collected, and the aqueous phase was extracted with ethyl acetate (10 mL×2). The organic phases were combined, washed with saturated brine (20 mL), dried with anhydrous sodium sulfate, filtered, and concentrated under reduced pressure. The obtained residue was separated and purified by a preparative column to obtain (S)-2-(6-cyanobenzo[d]oxazol-2-yl)-6-methoxy-5-((6-methoxypyridin-3-yl) methoxy)-1,2,3,4-tetrahydroisoquinoline-3-carboxylic acid 43 (55 mg), yield: 44%.

MS m/z(ESI): 486.9 [M+1]

$^1$H NMR (400 MHz, DMSO-$d_6$) δ 13.12 (s, 1H), 8.21 (s, 1H), 8.05 (s, 1H), 7.81 (dd, J=8.6, 2.2 Hz, 1H), 7.67 (d, J=8.4 Hz, 1H), 7.48 (d, J=8.0 Hz, 1H), 7.08 (d, J=8.4 Hz, 1H), 7.01 (d, J=8.4 Hz, 1H), 6.86 (d, J=8.8 Hz, 1H), 5.13 (dd, J=6.0, 2.4 Hz, 1H), 4.95 (d, J=10.8 Hz, 1H), 4.85-4.80 (m, 2H), 4.72 (d, J=16.0 Hz, 1H), 3.86 (s, 3H), 3.84 (s, 3H), 3.50 (dd, J=16.6, 2.2 Hz, 1H), 2.96 (dd, J=16.6, 7.0 Hz, 1H).

Example 44

(S)-2-(6-cyanobenzo[d]oxazol-2-yl)-6-methoxy-5-((5-methoxypyridin-2-yl)methoxy)-1,2,3,4-tetrahydroisoquinoline-3-carboxylic acid

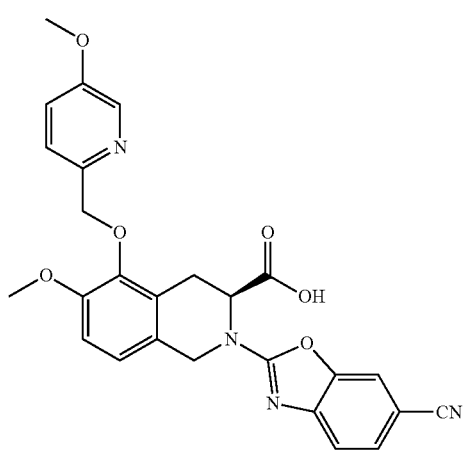

44

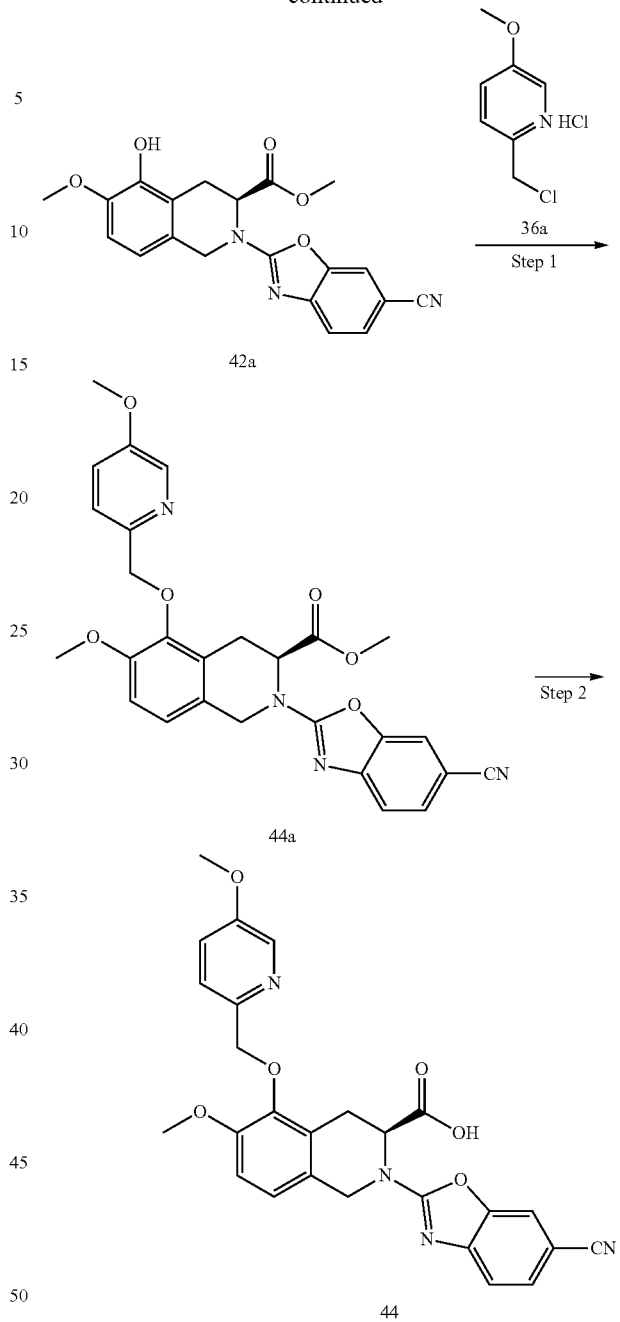

Step 1 methyl (S)-2-(6-cyanobenzo[d]oxazol-2-yl)-6-methoxy-5-((5-methoxypyridin-2-yl) methoxy)-1,2,3,4-tetrahydroisoquinoline-3-carboxylate Methyl (S)-2-(6-cyanobenzo[d]oxazol-2-yl)-5-hydroxy-6-methoxy-1,2,3,4-tetrahydroisoquinoline-3-carboxylate 42a (100 mg, 0.26 mmol), 2-(chloromethyl)-5-methoxypyridine hydrochloride 36a (122 mg, 0.63 mmol) and potassium carbonate (300 mg, 2.1 mmol) were dissolved in 6 mL of N,N-dimethylformamide, and the mixture was reacted at 70° C. for 6 hours. After the reaction was completed, the resulting solution was cooled to room temperature. 30 mL ethyl acetate and 20 mL water were added and the resulting solution was separated into layers. The organic phase was collected, and the aqueous phase was extracted with ethyl acetate (10 mL×2). The organic phases were combined, washed with saturated brine (15 mL), dried with anhydrous sodium sulfate, filtered, and concentrated under reduced pressure. The obtained residue was separated and purified by a preparative column to obtain methyl (S)-2-(6-cyanobenzo[d]oxazol-2-yl)-6-methoxy-5-((5-methoxypyridin-2-yl) methoxy)-1,2,3,4-tetrahydroisoquinoline-3-carboxylate 44a (100 mg), yield: 76%.

MS m/z(ESI): 500.9 [M+1]

$^1$H NMR (400 MHz, CDCl$_3$) δ 8.31 (d, J=2.4 Hz, 1H), 7.57-7.55 (m, 2H), 7.51 (d, J=8.4 Hz, 1H), 7.41 (d, J=8.0 Hz, 1H), 7.29-7.28 (m, 1H), 6.96 (d, J=8.8 Hz, 1H), 6.88 (d, J=8.8 Hz, 1H), 5.23 (br, 1H), 5.11 (d, J=12.0 Hz, 1H), 5.03 (d, J=11.6 Hz, 1H), 4.94 (d, J=15.6 Hz, 1H), 4.81 (d, J=15.6 Hz, 1H), 3.89 (s, 3H), 3.88 (s, 3H), 3.70-3.64 (m, 4H), 3.04 (dd, J=16.4, 6.0 Hz, 1H).

Step 2

(S)-2-(6-cyanobenzo[d]oxazol-2-yl)-6-methoxy-5-((5-methoxypyridin-2-yl)methoxy)-1,2,3,4-tetrahydroisoquinoline-3-carboxylic acid Methyl (S)-2-(6-cyanobenzo[d]oxazol-2-yl)-6-methoxy-5-((5-methoxypyridin-2-yl) methoxy)-1,2,3,4-tetrahydroisoquinoline-3-carboxylate 44a (130 mg, 0.26 mmol) was dissolved in 1.5 mL of tetrahydrofuran. 2.1 mL of a mixed solution of calcium chloride (453.5 mg, 4.08 mmol) in isopropanol and water (V:V=2:1), and 3 mL of sodium hydroxide solution (52.7 mg, 1.38 mmol) were added. The resulting solution was reacted overnight at room temperature. After the reaction was completed, 20 mL ethyl acetate was added, and 2M dilute hydrochloric acid was added so that the reaction solution was adjusted to pH=3 and 20 mL brine was added. The resulting solution was separated into layers, the organic phase was collected, and the aqueous phase was extracted with ethyl acetate (10 mL×2). The organic phases were combined, washed with saturated brine (20 mL), dried with anhydrous sodium sulfate, filtered, and concentrated under reduced pressure. The obtained residue was separated and purified by a preparative column to obtain (S)-2-(6-cyanobenzo[d]oxazol-2-yl)-6-methoxy-5-((5-methoxypyridin-2-yl) methoxy)-1,2,3,4-tetrahydroisoquinoline-3-carboxylic acid 44 (8 mg), yield: 6%.

MS m/z(ESI): 487.1 [M+1]

$^1$H NMR (400 MHz, DMSO-d$_6$) δ 8.28 (d, J=2.8 Hz, 1H), 8.04 (s, 1H), 7.66 (dd, J=8.0, 1.2 Hz, 1H), 7.55 (d, J=8.8 Hz, 1H), 7.49-7.46 (m, 2H), 7.09 (d, J=8.8 Hz, 1H), 7.02 (d, J=8.4 Hz, 1H), 5.12 (dd, J=6.4, 2.8 Hz, 1H), 4.99 (d, J=11.2 Hz, 1H), 4.91 (d, J=11.2 Hz, 1H), 4.83 (d, J=15.6 Hz, 1H), 4.72 (d, J=15.2 Hz, 1H), 3.85 (s, 3H), 3.83 (s, 3H), 3.55-3.50 (m, 1H), 3.00 (dd, J=17.2, 6.4 Hz, 1H).

Example 45

(S)—N-(ethylsulfonyl)-2-(6-fluorobenzo[d]oxazol-2-yl)-6-methoxy-5-((4-methoxybenzyl)oxy)-1,2,3,4-tetrahydroisoquinoline-3-carboxamide

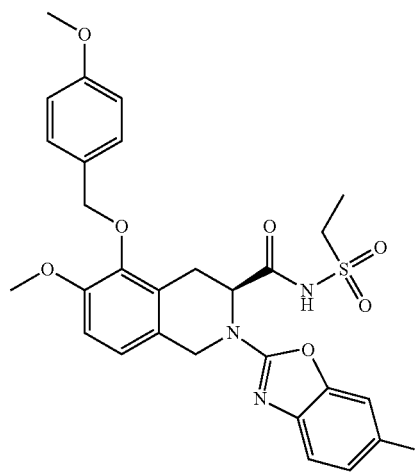

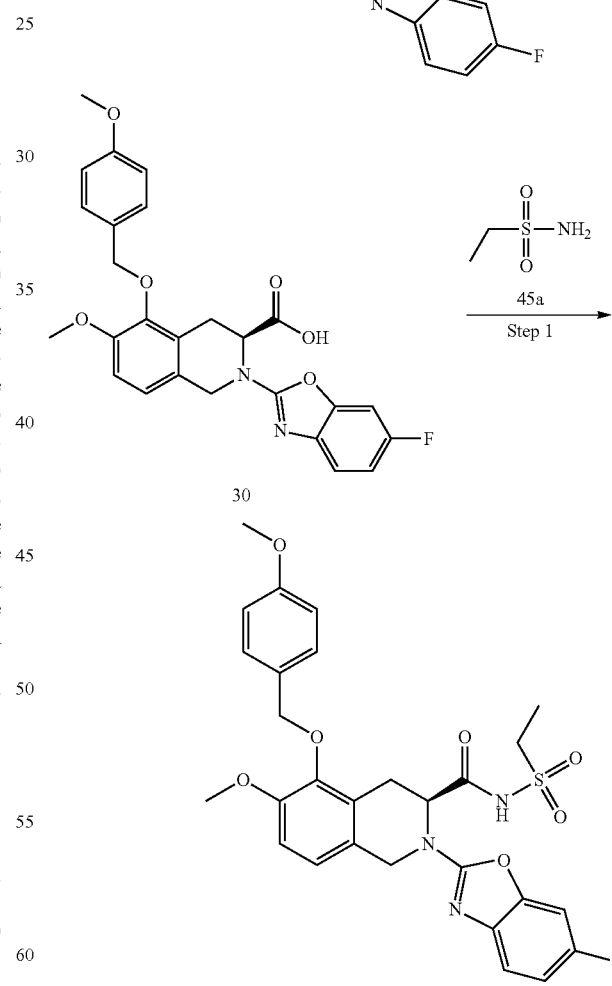

Step 1

(S)—N-(ethylsulfonyl)-2-(6-fluorobenzo[d]oxazol-2-yl)-6-methoxy-5-((4-methoxybenzyl)oxy)-1,2,3,4-tetrahydroisoquinoline-3-carboxamide (S)-2-(6-Fluorobenzo[d]oxazol-2-yl)-6-methoxy-5-((4-methoxybenzyl)oxy)-1,2,3,4-tetr ahydroisoquinoline-3-carboxylic acid 30 (50 mg, 0.104 mmol), ethylsulfonamide 45a (22 mg, 0.209 mmol), 2-(7-azobenzotriazole)-N,N,N',N'-tetramethylurea hexafluorophosphate (95.3 mg, 0.25 mmol) and 1-hydroxybenzotriazole (34 mg, 0.25 mmol) were dissolved in 8 mL of dichloromethane, and the mixture was stirred in an ice bath to lower the temperature. N,N-diisopropylethylamine (101 mg, 0.78 mmol) was slowly added dropwise. After the addition was completed, the resulting solution was reacted overnight at room temperature. After the reaction was completed, the resulting solution was concentrated under reduced pressure. The obtained residue was separated and purified by a preparative column to obtain (S)—N-(ethylsulfonyl)-2-(6-fluorobenzo[d]oxazol-2-yl)-6-methoxy-5-((4-methoxybenzyl)oxy)-1,2,3,4-tetrahydroisoquinoline-3-carboxamide 45 (4.05 mg), yield: 6.8%.

MS m/z(ESI): 570.2 [M+1]

$^1$H NMR (400 MHz, CDCl$_3$) δ 7.35-7.29 (m, 3H), 7.11 (d, J=6.0 Hz, 1H), 6.98-6.84 (m, 5H), 5.03 (d, J=10.4 Hz, 1H), 4.95 (d, J=10.8 Hz, 1H), 4.77 (d, J=14.8 Hz, 1H), 4.55 (d, J=14.8 Hz, 1H), 4.44 (t, J=6.0 Hz, 1H), 3.91 (s, 3H), 3.83 (s, 3H), 3.38-3.33 (m, 3H), 2.94 (dd, J=15.8, 6.2 Hz, 1H), 1.24 (t, J=7.4 Hz, 3H).

Example 46

(S)—N—(N,N-dimethylamino)-2-(6-fluorobenzo[d]oxazol-2-yl)-6-methoxy-5-((4-methoxybenzyl)oxy)-1,2,3,4-tetrahydroisoquinoline-3-carboxamide

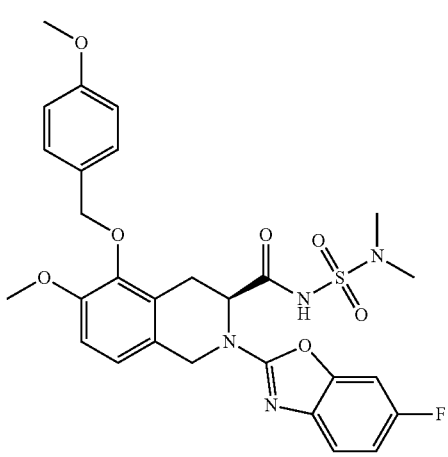

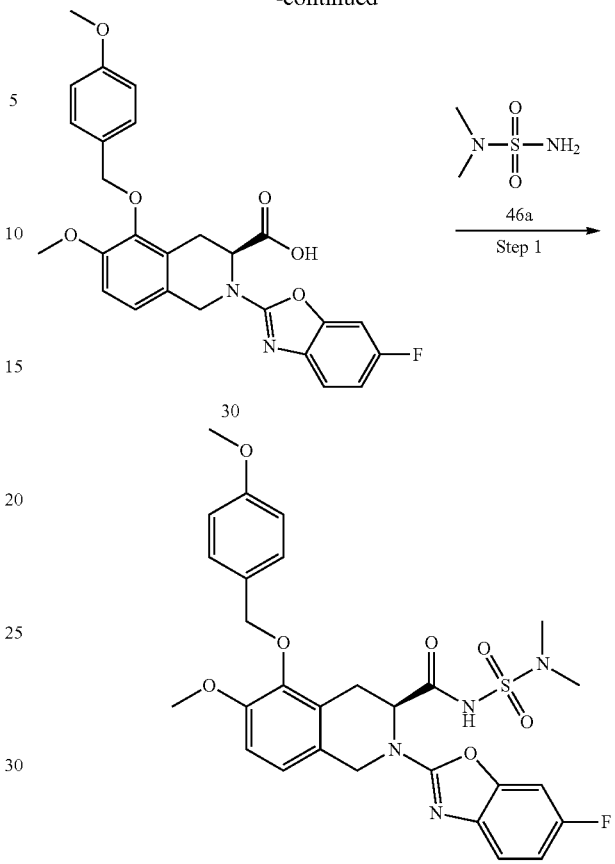

Step 1

(S)—N—(N,N-dimethylamino)-2-(6-fluorobenzo[d]oxazol-2-yl)-6-methoxy-5-((4-methoxybenzyl)oxy)-1,2,3,4-tetrahydroisoquinoline-3-carboxamide (S)-2-(6-Fluorobenzo[d]oxazol-2-yl)-6-methoxy-5-((4-methoxybenzyl)oxy)-1,2,3,4-tetr ahydroisoquinoline-3-carboxylic acid 30 (50 mg, 0.104 mmol), N,N-dimethylsulfonamide 46a (26 mg, 0.209 mmol), 2-(7-azobenzotriazole)-N,N,N',N'-tetramethylurea hexafluorophosphate (95.3 mg, 0.25 mmol) and 1-hydroxybenzotriazole (34 mg, 0.25 mmol) were dissolved in 8 mL of dichloromethane, and the mixture was stirred in an ice bath to lower the temperature. N,N-diisopropylethylamine (101 mg, 0.78 mmol) was slowly added dropwise. After the addition was completed, the resulting solution was reacted overnight at room temperature. After the reaction was completed, the resulting solution was concentrated under reduced pressure. The obtained residue was separated and purified by a preparative column to obtain (S)—N—(N,N-dimethylamino)-2-(6-fluorobenzo[d]oxazol-2-yl)-6-methoxy-5-((4-methoxybenzyl)oxy)-1,2,3,4-tetrahydroisoquinoline-3-carboxamide 46 (13.8 mg), yield: 22.6%.

MS m/z(ESI): 585.2 [M+1]

$^1$H NMR (400 MHz, CDCl$_3$) δ 9.20 (s, 1H), 7.35-7.30 (m, 3H), 7.10 (dd, J=8.0, 2.0 Hz, 1H), 7.00-6.84 (m, 5H), 5.02 (d, J=10.8 Hz, 1H), 4.94 (d, J=11.2 Hz, 1H), 4.77 (d, J=15.2 Hz, 1H), 4.60 (d, J=14.8 Hz, 1H), 4.49 (t, J=5.8 Hz, 1H), 3.90 (s, 3H), 3.83 (s, 3H), 3.36 (dd, J=15.6, 5.6 Hz, 1H), 2.92 (dd, J=16.4, 6.4 Hz, 1H), 2.81 (s, 6H).

Biological Evaluation

Test Example 1. Antagonistic Activity Assay of the Compound of the Present Disclosure on Human $AT_2R$ Ligand Binding Angiotensin II Type 2 Receptor ($AT_2R$) is involved in neuron differentiation and regeneration, cell proliferation and angiogenesis, and maintenance of bone mass. $AT_2R$ inhibitors can be used for treating pain and abnormal nerve regeneration diseases, inhibiting the proliferation of tumor cells and increase bone mass. The following method uses $AT_2$ ligand binding assay to study the antagonism of the compounds of the present disclosure on $AT_2R$.

1. Reagents and Consumables

| Materials and reagents | Manufacturer | Catalog No. |
|---|---|---|
| Tag-lite Angiotensin AT2 labeled Cells, ready-to-use (transformed & labeled), 200 tests* (384-well small volume white plate, 20 ul) | Cisbio | C1TT1AT2 |
| Angiotensin AT2 Receptor red agonist Fluorescent Ligand, 5000 test (384-well small volume plate, 20 ul) | Cisbio | L0007RED |
| Tag-lite Buffer (5X concentrate), 100 mL | Cisbio | LABMED |
| Angiotensin II human (CAS: 4474-91-3) DRVYIHPF, 10 mg, MW: 1046.18 | MedChem Express | HY-13948 |

| consumables | Manufacturer | Product No. |
|---|---|---|
| 384-well low volume plate (40 plates/box) | Greiner | 784075 |
| Echo qualified 384-well polypropylene microplate, clear, flat bottom (100 plates/case) | LABCYTE | P-05525 |
| 分装384-well round bottom, no lid, non-sterile, polypropylene (100 plates/case) | Corning | 3657 |
| 96-well conical btm PP Plt nature RNASE/Dnase-free plate (120 plates/case) | ThermoFisher | 249944 |

2. Preparation of Reagents (1) 10 mM Angiotensin II human: 10 mg Angiotensin II human (purity 99.09%) was dissolved in 0.947 mL deionized water, and the resulting mixture was stores at −80° C. after subpackaging;

(2) Preparation of Compound Stock Solution

According to standard methods, all compounds were dissolved in dimethyl sulfoxide and prepared as 10 mM stock solutions.

(3) Tag-lite angiotensin receptor red agonist: 8600 nM stock solution was aliquoted and stored at −80° C.;

(4) 1× Tag-Lite Buffer (TLB): 5×TLB was diluted with deionized water to 1×.

3. Experimental Steps (1) An appropriate amount of 1×TLB was prepared, which was mixed well for later use;

(2) The test compound was diluted 5 times, with a total of 10 concentration gradients;

(3) Each of the diluted compound in step (2) was transferred to a working plate (3657, Corning) at 160 nL/well, at 200 g, at room temperature for 1 minute;

(4) 40 μl 1×TLB was added to the above working plate, and it was centrifuged at 200 g (centrifugal force) at room temperature for 1 minute, shook on a shaker for 15 minutes to mix well, and centrifuged at 200 g (working concentration of the compound was 4×) at room temperature for 1 minute for later use;

(5) Tag-lite angiotensin receptor red agonist (8600 nM stock solution) was diluted to 12 nM with 1×TLB for later use;

(6) 5 mL 1×TLB was taken in a 15 mL centrifuge tube;

(7) a Tb-labeled-$AT_2R$ cells were frozen and thawed in a 37° C. water bath until the ice was completely melted (1-2 minutes);

(8) The frozen and thawed cells were rapidly transferred to the 1×TLB in step (6), and the resulting solution was mixed gently, and then centrifuged at 1200 g at room temperature for 5 minutes;

(9) The supernatant was gently aspirated, the cells were resuspended and mixed well with 1 mL of 1×TLB, and then 1.7 mL of 1×TLB was added. After being mixed well, the resulting mixture was placed at room temperature for late use;

(10) 10 μL of cells were added to all test wells, centrifuged at 200 g for 3 seconds at room temperature; 5 μL of the compound working solution 4× in step (4) was added to the corresponding wells; 5 μL of the 4× Tag-lite angiotensin receptor red agonist diluted in step (5) was added to all test wells.

(11) The reaction plate was centrifuged at 200 g at room temperature for 1 minute, and stood for 1 hour at room temperature of 25° C., and then it was centrifuged at 200 g at room temperature for 1 minute. The data was collected using Envision HTRF microplate reader, and $IC_{50}$ was calculated using a nonlinear fitting formula.

(12) In the same way, $IC_{50}$ of the antagonistic activity of the compounds of the present disclosure against $AT_1R$ was determined using the same method except that Tb-labeled-$AT_1R$ cells were used instead of Tb-labeled-$AT_2R$ cells.

4. Experimental Results

The $IC_{50}$ values of the antagonistic activity essay of the compounds of the examples of the present disclosure against $AT_2R$ are shown in the following table.

| Example number | $IC_{50}$ (nM)/$AT_2R$ |
|---|---|
| olodanrigan | 49 |
| 14 | 12 |
| 15 | 36 |
| 16 | 36 |
| 19 | 25 |
| 20 | 26 |
| 21 | 36 |
| 26 | 37 |
| 29 | 17 |
| 30 | 4 |
| 35 | 15 |
| 36 | 10 |
| 37 | 36 |
| 38 | 11 |
| 39 | 7 |
| 42 | 6 |
| 43 | 33 |
| 44 | 33 |
| 45 | 6 |
| 46 | 5 |

Conclusion:

(1) The compounds of the present disclosure have significant antagonistic activity against $AT_2R$;

(2) The compounds of the present disclosure have antagonistic $IC_{50}$ values of >10 μM against $AT_1R$, and have no antagonistic activity against $AT_1R$;

Therefore, the compounds of the present disclosure have a highly selectivity for the antagonistic effect against $AT_2R$.

Test Example 2. Study on the Metabolic Stability of the Compound of the Present Disclosure in Rat Liver Microsomes 1. The Purpose of the Experiment The purpose of this experiment is to study the metabolic stability of the compounds of the present disclosure in rat liver microsomes.

2. Reagent Information

| Name | Batch Number | Supplier |
|---|---|---|
| Rat liver microsomes | 5118007 | Corning, USA |
| Midazolam maleate | 171265-201402 | China Institute for Food and Drug Control |
| NADPH | 20595626 | Roche, Switzerland |
| Potassium dihydrogen phosphate | 20150428 | Sinopharm Chemical Reagent Co., Ltd. |
| Dipotassium hydrogen phosphate | 20150312 | Sinopharm Chemical Reagent Co., Ltd. |
| Magnesium chloride ($MgCl_2$) | F20090916 | Sinopharm Chemical Reagent Co., Ltd. |
| Verapamil Hydrochloride | 100223-200102 | China Institute for Food and Drug Control |
| Glibenclamide | 100135-201105 | China Institute for Food and Drug Control |
| DMSO | 1427C108 | Amresco, USA |
| Methanol | QADG3H | Honeywell, USA |
| Acetonitrile | S13A1H | Honeywell, USA |
| Formic acid | A1819048 | Shanghai Aladdin Biochemical Technology Co., Ltd. |

3. Experimental Scheme

The compounds were incubated with rat liver microsomes and coenzyme NADPH was added to initiate the reaction. At 0, 5, 15, 30 and 60 minutes, 20 μL of incubation solution was taken out and transferred to 200 μL of acetonitrile containing internal standard to stop the reaction. After protein precipitation, the resulting mixture was centrifuged at 3,700 rpm for 10 minutes, and the supernatant was taken. The supernatant was diluted 1:1 with water and analyzed by LC-MS/MS method. According to the elimination half-life of the test compound in the incubation system, the in vitro intrinsic clearance rate was calculated. Midazolam was used as the internal reference compound and all incubations were performed in duplicate in parallel. The incubation conditions are summarized in the following table:

| | |
|---|---|
| Liver microsomes | 0.5 mg · ml$^{-1}$ (test compound); 0.2 mg · mL$^{-1}$ (midazolam) |
| Incubation buffer | phosphate buffer (100 mM, pH 7.4) |
| Initial concentration of test compound for incubation | 1 μM |
| Final volume of incubation system | 0.2 mL |
| Incubation time | 0, 5, 15, 30, 60 min (compound of the present disclosure) 0, 5, 20 min (midazolam) |
| Magnesium chloride | 3 mM |
| NADPH | 1 mM |
| Parallel reaction | in duplicate in parallel |

4. Data Analysis

The peak area ratio analyte/internal standard ($A_{analyte}/A_{IS}$) is obtained by the instrument, and the remaining percentage (% Control) is calculated from the ratio $A_{analyte}/A_{IS}$ in the non-zero time point sample to the zero time point sample. Ln (% Control) against incubation time is plotted and a linear fit was performed. The clearance constant (k, min-) and clearance half-life ($T_{1/2}$, min) of the test compound are calculated by the following equations.

$k = -\text{slope}$ $T_{1/2} = 0.693/k$

5. Experimental Results

The relevant parameters of the stability of the compounds of the examples of the present disclosure in rat liver microsomes are shown in the following table:

| Example number | Half-life/($T_{1/2}$, min) |
|---|---|
| olodanrigan | 96.3 |
| 14 | 233 |
| 15 | 317 |
| 19 | 175 |
| 29 | 164 |
| 30 | 251 |
| 36 | 768 |
| 39 | 845 |
| 42 | 451 |

Among them, after the compound of Example 22 was incubated in rat liver microsomes for 60 minutes, the remaining original drug was close to 100%, indicating that compound of Example 22 was almost not metabolized in rat liver microsomes.

Conclusion: Compared with olodanrigan, the compounds of the examples of the present disclosure have a significantly prolonged half-life, and the stability in rat liver microsomes is significantly improved.

Test Example 3. Oral Pharmacokinetic Studies of the Compounds of the Present Disclosure in SD Rats 1. The Purpose of the Experiment SD rats were used as the experimental animal. The rats were intravenously injected or intragastrically administered with the compounds of the present disclosure, and the drug concentrations in plasma at different times were tested by LC/MS/MS methods, so as to research the pharmacokinetic characteristics of compounds of present disclosure in rats.

2. Experimental Scheme 2.1 Experimental Drugs and Animals

Olodanrigan, compounds 9, 14, 15, 22, 30, 36 and 39 of the present disclosure;

Forty-eight healthy adult Sprague Dawley (SD) male rats were purchased from Weitong Lihua Laboratory Animal Technology Co., Ltd., production license number: 11400700271077.

2.2 Drug Preparation and Drug Delivery

Intravenous Injection Group:

(1) 2.27 mg Olodanrigan was weighed, and dissolved in 1.135 mL dimethylacetamide (DMA). The resulting mixture was vortexed for 1 minute and sonicated for 1 minute, and then dissolved in 1.35 mL solutol HS 15 (30%, w/v). The resulting mixture was vortexed for 1 minute and sonicated for 1 minute. 9.08 mL of normal saline was added and the resulting mixture was vortexed for 1 minute. The solution was filtered through a PTEE membrane to finally formulate a concentration of 0.2 mg/mL. 100 μL of the solution was placed into a 1.5 mL EP tube.

(2) 2.46 mg compound 9 was weighed, and dissolved in 1.21 mL DMA. The resulting mixture was vortexed for 1 minute and sonicated for 1 minute, and then dissolved in 1.21 mL solutol HS 15 (30%, w/v). The resulting mixture was vortexed for 1 minute and sonicated for 1 minute. 9.862 mL of normal saline was added and the resulting mixture was vortexed for 1 minute. The solution was filtered through a PTEE membrane to finally formulate a concentration of 0.2 mg/mL. 100 μL of the solution was placed into a 1.5 mL EP tube.

(3) 2.21 mg compound 14 was weighed, and dissolved in 1.05 mL DMA. The resulting mixture was vortexed and shaken until the solid was completely dissolved, and then the resulting mixture was dissolved in 1.05 mL solutol HS 15 (30%, w/v). The resulting mixture was vortexed evenly. 8.398 mL of normal saline was added and the resulting mixture was vortexed evenly. The solution was filtered through a filter membrane (PALL, Nylon, 0.45p M) to finally formulate a concentration of 0.2 mg/mL. 100 μL×2 of the filtered preparation was placed into a 1.5 mL EP tube.

(4) 3.32 mg compound 15 was weighed, and dissolved in 3.303 mL DMA. The resulting mixture was vortexed evenly, and then the resulting mixture was dissolved in 3.303 mL solutol HS 15 (30%, w/v). The resulting mixture was vortexed evenly. 9.910 mL of normal saline was added and the resulting mixture was vortexed evenly. The solution was filtered through a PTEE membrane to finally formulate a concentration of 0.2 mg/mL. 100 μL×2 of the solution was placed into a 1.5 mL EP tube.

(5) 2.36 mg compound 22 was weighed, and dissolved in 0.906 mL DMA. The resulting mixture was vortexed and shaken until the solid was completely dissolved, and then the resulting mixture was dissolved in 0.906 mL solutol HS 15 (30%, w/v). The resulting mixture was vortexed evenly. 7.25 mL of normal saline was added and the resulting mixture was vortexed evenly. The solution was filtered through a PTEE membrane to finally formulate a concentration of 0.2 mg/mL. 100 μL×2 of the filtered preparation was placed into a 1.5 mL EP tube.

(6) 2.25 mg compound 30 was weighed, and dissolved in 0.898 mL DMA. The resulting mixture was vortexed and shaken until the solid was completely dissolved, and then the resulting mixture was dissolved in 0.898 mL solutol HS 15 (30%, w/v). The resulting mixture was vortexed evenly. 2.695 mL of normal saline was added and the resulting mixture was vortexed evenly. The solution was filtered through a PTEE membrane to finally formulate a concentration of 0.5 mg/mL. 100 μL×2 of the filtered preparation was placed into a 1.5 mL EP tube.

(7) 2.0 mg compound 36 was weighed, and dissolved in 0.391 mL DMA. The resulting mixture was vortexed and shaken until the solid was completely dissolved, and then the resulting mixture was dissolved in 0.391 mL solutol HS 15 (30%, w/v). The resulting mixture was vortexed evenly. 3.124 mL of normal saline was added and the resulting mixture was vortexed evenly. The solution was filtered through a PTEE membrane to finally formulate a concentration of 0.5 mg/mL. 100 μL×2 of the filtered preparation was placed into a 1.5 mL EP tube.

(8) 2.0 mg compound 39 was weighed, and dissolved in 0.793 mL DMA. The resulting mixture was vortexed and shaken until the solid was completely dissolved, and then the resulting mixture was dissolved in 0.793 mL solutol HS 15 (30%, w/v). The resulting mixture was vortexed evenly. 2.378 mL of normal saline was added and the resulting mixture was vortexed evenly. The solution was filtered through a PTEE membrane to finally formulate a concentration of 0.5 mg/mL. 100 μL×2 of the filtered preparation was placed into a 1.5 mL EP tube.

Oral Gavage Group:

(1) 10.42 mg Olodanrigan was weighed, and dissolved in 10.42 mL 0.5% sodium carboxymethyl cellulose (CMC-Na) (containing 0.5% Tween 80). The resulting mixture was vortexed for 1 minute, and sonicated for 1 minute until the compound was completely suspended, to finally formulate a concentration of 1 mg/mL. 100 μL of the preparation was placed into a 1.5 mL EP tube.

(2) 10.29 mg compound 9 was weighed, and dissolved in 10.125 mL 0.5% sodium carboxymethyl cellulose (CMC-Na) (containing 0.5% Tween 80). The resulting mixture was vortexed for 1 minute, and sonicated for 1 minute until the compound was completely suspended, to finally formulate a concentration of 1 mg/mL. 100 μL of the preparation was placed into a 1.5 mL EP tube.

(3) 10.11 mg compound 14 was weighed, and dissolved in 9.605 mL 0.5% CMC-Na (containing 0.5% Tween 80). The resulting mixture was vortexed and shaken, and sonicated until the compound was completely suspended, to finally formulate a concentration of 1 mg/mL. 100 μL×2 of the preparation was placed into a 1.5 mL EP tube.

(4) 10.19 mg compound 15 was weighed, and dissolved in 10.139 mL 0.5% CMC-Na (containing 0.5% Tween 80). The resulting mixture was vortexed and shaken, and sonicated until the compound was completely suspended, to finally formulate a concentration of 1 mg/mL. 100 μL×2 of the preparation was placed into a 1.5 mL EP tube.

(5) 10.02 mg compound 22 was weighed, and dissolved in 7.695 mL 0.5% CMC-Na (containing 0.5% Tween 80). The resulting mixture was vortexed and shaken, and sonicated until the compound was completely suspended, to finally formulate a concentration of 1 mg/mL. 100 μL×2 of the preparation was placed into a 1.5 mL EP tube.

(6) 10.29 mg compound 30 was weighed, and dissolved in 10.271 mL 0.5% CMC-Na (containing 0.5% Tween 80). The resulting mixture was vortexed and shaken, and sonicated until the compound was completely suspended, to finally formulate a concentration of 1 mg/mL. 100 μL×2 of the preparation was placed into a 1.5 mL EP tube.

(7) 10.03 mg compound 36 was weighed, and dissolved in 9.791 mL 0.5% CMC-Na (containing 0.5% Tween 80). The resulting mixture was vortexed and shaken, and sonicated until the compound was completely suspended, to finally formulate a concentration of 1 mg/mL. 100 μL×2 of the preparation was placed into a 1.5 mL EP tube.

(8) 10.01 mg compound 39 was weighed, and dissolved in 9.92 mL 0.5% CMC-Na (containing 0.5% Tween 80). The resulting mixture was vortexed and shaken, and sonicated until the compound was completely suspended, to finally formulate a concentration of 1 mg/mL. 100 μL×2 of the preparation was placed into a 1.5 mL EP tube.

48 healthy adult male SD rats were fasted overnight and administered via tail vein injection (at a dosage of 1 mg/kg)

and intragastrically administered (at a dosage of 10 mg/kg), respectively. The rats were fed 4 h after the administration.

2.3 Sample Collection

About 0.2 mL of blood was collected from the jugular vein before administering and at 0.083 hours, 0.25 hours, 0.5 hours, 1 hour, 2 hours, 4 hours, 8 hours, 12 hours, and 24 hours after administering, and heparin sodium was used for anticoagulation. Blood samples were collected and placed on ice, and plasma was separated by centrifugation (centrifugation conditions: 1500 g, 10 min). The collected plasma was stored at −40° C.-20° C. before analysis.

2.4 Sample Pretreatment

10 μL of plasma sample was taken and 400 μL of acetonitrile (containing internal standard working solution, comprising 5 ng/mL verapamil and 50 ng/mL glibenclamide) was added. The resulting mixture was vortexed for 10 minutes, and centrifuged at 3700 rpm for 10 minutes. 70 μL of the supernatant was taken, and 70 NL of water was added. The resulting mixture was vortexed for 10 minutes, and 2 μL of the mixture was transferred to the LC-MS/MS for sample analysis.

3. Results of Pharmacokinetic Parameters

The pharmacokinetic parameters of the compounds of the present disclosure and the positive control are shown in the following table.

| Example Number | Mode of administration Dosage | blood concentration Cmax (ng/mL) | area under curve $AUC_{0-\infty}$ (ng·h/mL) | Half-life T1/2 (h) | residence time MRT(h) | Bioavailability F(%) |
|---|---|---|---|---|---|---|
| olodanrigan | Oral (10 mg/kg) | 470 ± 197 | 1483 ± 715 | 1.5 ± 0.3 | 2.6 ± 1.0 | 12.1 |
|  | Injection (1 mg/kg) | N/A | 1230 ± 96 | 1.6 ± 0.3 | 0.92 ± 0.16 |  |
| 9 | Oral (10 mg/kg) | 9470 ± 5890 | 18133 ± 5398 | 2.1 ± 1.6 | 2.2 ± 0.8 | 71.1 |
|  | Injection (1 mg/kg) | N/A | 2550 ± 720 | 1.3 ± 0.1 | 1.3 ± 0.2 |  |
| 14 | Oral (10 mg/kg) | 5280 ± 72 | 29633 ± 4670 | 3.6 ± 0.2 | 5.3 ± 0.4 | 36.0 |
|  | Injection (1 mg/kg) | N/A | 8230 ± 1087 | 3.5 ± 0.3 | 1.9 ± 0.4 |  |
| 15 | Oral (10 mg/kg) | 6657 ± 1745 | 45367 ± 11909 | 4.7 ± 1.3 | 6.3 ± 1.1 | 47.3 |
|  | Injection (1 mg/kg) | N/A | 9587 ± 579 | 4.2 ± 1.2 | 2.0 ± 0.6 |  |
| 22 | Oral (10 mg/kg) | 15933 ± 10951 | 35733 ± 6093 | 3.9 ± 0.8 | 3.7 ± 0.8 | 44.6 |
|  | Injection (1 mg/kg) | N/A | 8020 ± 635 | 2.0 ± 0.6 | 1.2 ± 0.3 |  |
| 30 | Oral (10 mg/kg) | 2370 ± 182 | 7130 ± 1632 | 3.3 ± 0.5 | 3.6 ± 0.4 | 22.1 |
|  | Injection (1 mg/kg) | N/A | 3230 ± 659 | 2.4 ± 0.8 | 1.2 ± 0.4 |  |
| 36 | Oral (10 mg/kg) | 4740 ± 662 | 24700 ± 9396 | 3.8 ± 1.0 | 5.4 ± 1.3 | 53.7 |
|  | Injection (1 mg/kg) | N/A | 4600 ± 240 | 4.8 ± 2.6 | 2.3 ± 0.6 |  |
| 39 | Oral (10 mg/kg) | 5490 ± 1311 | 15300 ± 2261 | 3.6 ± 0.3 | 4.3 ± 0.6 | 45.3 |
|  | Injection (1 mg/kg) | N/A | 3380 ± 405 | 2.3 ± 0.4 | 1.9 ± 0.3 |  |

Conclusion: Compared with olodanrigan, the compounds of the present disclosure have good pharmacokinetic absorption, significantly improved bioavailability, and better pharmacokinetic properties.

Note: N/A means no relevant results

The invention claimed is:

1. A compound represented by formula (I) or a stereoisomer, a tautomer or a pharmaceutically acceptable salt thereof:

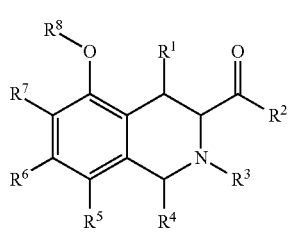

wherein $R^1$, $R^4$, $R^5$ and $R^6$ are each independently selected from hydrogen, hydroxyl, halogen, nitro, cyano, alkyl, alkoxy, cycloalkyl, heterocyclyl, aryl and heteroaryl, wherein the alkyl, alkoxy, cycloalkyl, heterocyclyl, aryl or heteroaryl is optionally further substituted by one or more substituents selected from hydroxyl, halogen, nitro, cyano, alkyl, alkoxy, cycloalkyl, heterocyclyl, aryl, heteroaryl, —C(O)$R^9$, —C(O)O$R^9$, —OC(O)$R^9$, —N$R^{10}R^{11}$, —C(O)N$R^{10}R^{11}$, —S(O)$_n R^{10}R^{11}$ and —N$R^{10}$C(O)$R^{11}$;

$R^2$ is selected from —O$R^a$ and —N$R^b$S(O)$_n R^c$;

$R^a$ is selected from hydrogen and alkyl;

$R^b$ is selected from hydrogen and alkyl;

$R^c$ is selected from hydrogen, alkyl, cycloalkyl and —NR$^d$R$^e$;

$R^d$ is selected from hydrogen and alkyl;

$R^e$ is selected from alkyl, wherein the alkyl is optionally further substituted by one or more substituents selected from hydroxyl, halogen, nitro, cyano, alkoxy, cycloalkyl, heterocyclyl, aryl, heteroaryl, —C(O)R$^9$, —C(O)OR$^9$, —OC(O)R$^9$, —NR$^{10}$R$^{11}$, —C(O)NR$^{10}$R$^{11}$, —S(O)$_n$NR$^{10}$R$^{11}$ and —NR$^{10}$C(O)R$^{11}$;

or $R^d$ and $R^e$ together with the N to which they are attached form a 4 to 8-membered heterocyclyl, wherein the 4 to 8-membered heterocyclyl contains one or more N, O or S(O)$_n$, and the 4 to 8-membered heterocyclyl is optionally further substituted by one or more substituents selected from hydroxyl, halogen, nitro, cyano, alkyl, alkoxy, cycloalkyl, heterocyclyl, aryl, heteroaryl, =O, —C(O)R$^{12}$, —C(O)OR$^{12}$, —OC(O)R$^{12}$, —NR$^{13}$R$^{14}$, —C(O)NR$^{13}$R$^{14}$, —S(O)$_n$NR$^{13}$R$^{14}$ and —NR$^{13}$C(O)R$^{14}$;

$R^3$ is selected from heteroaryl, wherein the heteroaryl is optionally further substituted by one or more substituents selected from $R^f$;

$R^f$ is selected from hydroxyl, halogen, nitro, cyano, alkyl, alkoxy, cycloalkyl, heterocyclyl, aryl, heteroaryl, —C(O)R$^9$, —C(O)OR$^9$, —OC(O)R$^9$, —NR$^{10}$R$^{11}$, —C(O)NR$^{10}$R$^{11}$, —S(O)$_n$NR$^{10}$R$^{11}$ and —NR$^{10}$C(O)R$^{11}$, wherein the alkyl, alkoxy, cycloalkyl, heterocyclyl, aryl or heteroaryl is optionally further substituted by one or more substituents selected from hydroxyl, halogen, nitro, cyano, alkoxy, cycloalkyl, heterocyclyl, aryl, heteroaryl, —C(O)R$^9$, —C(O)OR$^9$, —OC(O)R$^9$, —NR$^{10}$R$^{11}$, —C(O)NR$^{10}$R$^{11}$, —S(O)$_n$NR$^{10}$R$^{11}$ and —NR$^{10}$C(O)R$^{11}$;

$R^7$ is selected from hydrogen, halogen, alkyl, cycloalkyl, cyano and —OR$^g$, wherein the alkyl or cycloalkyl is optionally further substituted by one or more substituents selected from hydroxyl, halogen, nitro and cyano;

$R^g$ is selected from alkyl, cycloalkyl, heterocyclyl, aryl and heteroaryl, wherein the alkyl, cycloalkyl, heterocyclyl, aryl or heteroaryl is optionally further substituted by one or more substituents selected from hydroxyl, halogen, nitro, cyano, alkyl, alkoxy, cycloalkyl, heterocyclyl, aryl, heteroaryl, —C(O)R$^9$, —C(O)OR$^9$, —OC(O)R$^9$, —NR$^{10}$R$^{11}$, —C(O)NR$^{10}$R$^{11}$, —S(O)$_n$NR$^{10}$R$^{11}$ and —NR$^{10}$C(O)R$^{11}$;

$R^8$ is alkyl, wherein the alkyl is further substituted by aryl or heteroaryl, wherein the aryl or heteroaryl is optionally further substituted by one or more substituents selected from $R^h$; the aryl is C$_6$-C$_{10}$ aryl; the heteroaryl is preferably 5 to 6-membered heteroaryl;

$R^h$ is selected from hydroxyl, halogen, nitro, cyano, alkyl, alkoxy, cycloalkyl, heterocyclyl, aryl, heteroaryl, —C(O)R$^9$, —C(O)OR$^9$, —OC(O)R$^9$, —NR$^{10}$R$^{11}$, —C(O)NR$^{10}$R$^{11}$, —S(O)$_n$NR$^{10}$R$^{11}$ and —NR$^{10}$C(O)R$^{11}$; wherein the alkyl, alkoxy, cycloalkyl, heterocyclyl, aryl or heteroaryl is optionally further substituted by one or more substituents selected from hydroxyl, halogen, nitro, cyano, alkoxy, cycloalkyl, heterocyclyl, aryl, heteroaryl, —C(O)R$^9$, —C(O)OR$^9$, —OC(O)R$^9$, —NR$^{10}$R$^{11}$, —C(O)NR$^{10}$R$^{11}$, —S(O)$_n$NR$^{10}$R$^{11}$ and —NR$^{10}$C(O)R$^{11}$;

$R^9$, $R^{10}$ and $R^{11}$ are each independently selected from hydrogen, hydroxyl, halogen, nitro, cyano, alkyl, alkoxy, cycloalkyl, heterocyclyl, aryl and heteroaryl, wherein the alkyl, alkoxy, cycloalkyl, heterocyclyl, aryl or heteroaryl is optionally further substituted by one or more substituents selected from hydroxyl, halogen, nitro, cyano, alkyl, alkoxy, cycloalkyl, heterocyclyl, aryl, heteroaryl, —C(O)R$^{12}$, —C(O)OR$^{12}$, —OC(O)R$^{12}$, —NR$^{13}$R$^{14}$, —C(O)NR$^{13}$R$^{14}$, —S(O)$_n$NR$^{13}$R$^{14}$ and —NR$^{13}$C(O)R$^{14}$;

or $R^{10}$ and $R^{11}$ together with the N to which they are attached form a 4 to 8-membered heterocyclyl, wherein the 4 to 8-membered heterocyclyl contains one or more N, O or S(O)$_n$, and the 4 to 8-membered heterocyclyl is optionally further substituted by one or more substituents selected from hydroxyl, halogen, nitro, cyano, alkyl, alkoxy, cycloalkyl, heterocyclyl, aryl, heteroaryl, =O, —C(O)R$^{12}$, —C(O)OR$^{12}$, —OC(O)R$^{12}$, —NR$^{13}$R$^{14}$, —C(O)NR$^{13}$R$^{14}$, —S(O)$_n$NR$^{13}$R$^{14}$ and —NR$^{13}$C(O)R$^{14}$;

$R^{12}$, $R^{13}$ and $R^{14}$ are each independently selected from hydrogen, alkyl, cycloalkyl, heterocyclyl, aryl and heteroaryl, wherein the alkyl, cycloalkyl, heterocyclyl, aryl or heteroaryl is optionally further substituted by one or more substituents selected from hydroxyl, halogen, nitro, cyano, alkyl, alkoxy, cycloalkyl, heterocyclyl, aryl, heteroaryl, carboxyl and carboxylate ester group; and n is selected from 0, 1 and 2.

2. The compound according to claim 1 or a stereoisomer, a tautomer, or a pharmaceutically acceptable salt thereof, which is a compound of formula (II) or a stereoisomer, a tautomer, or a pharmaceutically acceptable salt thereof,

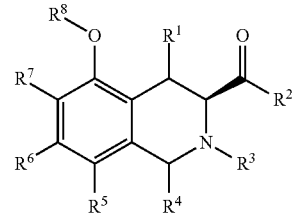

(II)

wherein $R^1$ to $R^8$ are as defined in claim 1.

3. The compound or a stereoisomer, a tautomer, or a pharmaceutically acceptable salt thereof according to claim 1, which is a compound of formula (III) or a stereoisomer, a tautomer, or a pharmaceutically acceptable salt thereof,

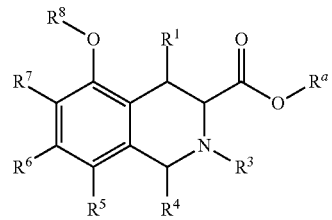

(III)

wherein $R^1$, $R^3$ to $R^8$ and $R^a$ are as defined in claim 1.

4. The compound or a stereoisomer, a tautomer, or a pharmaceutically acceptable salt thereof according to claim 1, which is a compound of formula (IV) or a stereoisomer, a tautomer, or a pharmaceutically acceptable salt thereof,

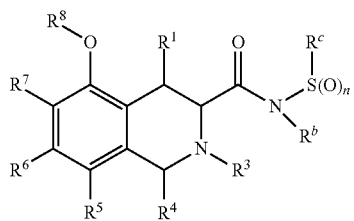

(IV)

wherein R¹, R³ to R⁸, R^b, R^c and n are as defined in claim 1.

5. The compound or a stereoisomer, a tautomer, or a pharmaceutically acceptable salt thereof according to claim 3, which is a compound of formula (V) or a stereoisomer, a tautomer, or a pharmaceutically acceptable salt thereof,

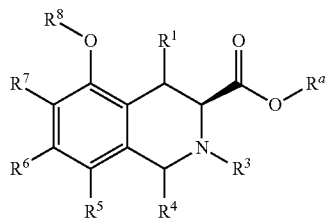

(V)

wherein R¹, R³ to R⁸ and R^a are as defined in claim 3.

6. The compound or a stereoisomer, a tautomer, or a pharmaceutically acceptable salt thereof according to claim 4, which is a compound of formula (VI) or a stereoisomer, a tautomer, or a pharmaceutically acceptable salt thereof,

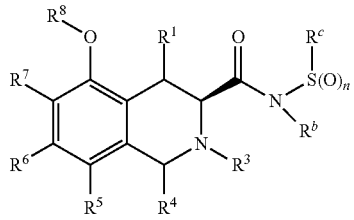

(VI)

wherein R¹, R³ to R⁸, R^b, R^c and n are as defined in claim 4.

7. The compound or a stereoisomer, a tautomer, or a pharmaceutically acceptable salt thereof according to claim 1, wherein R³ is selected from

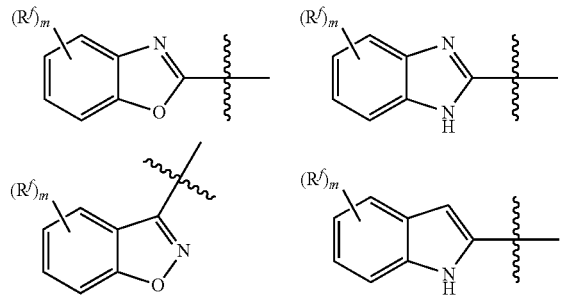

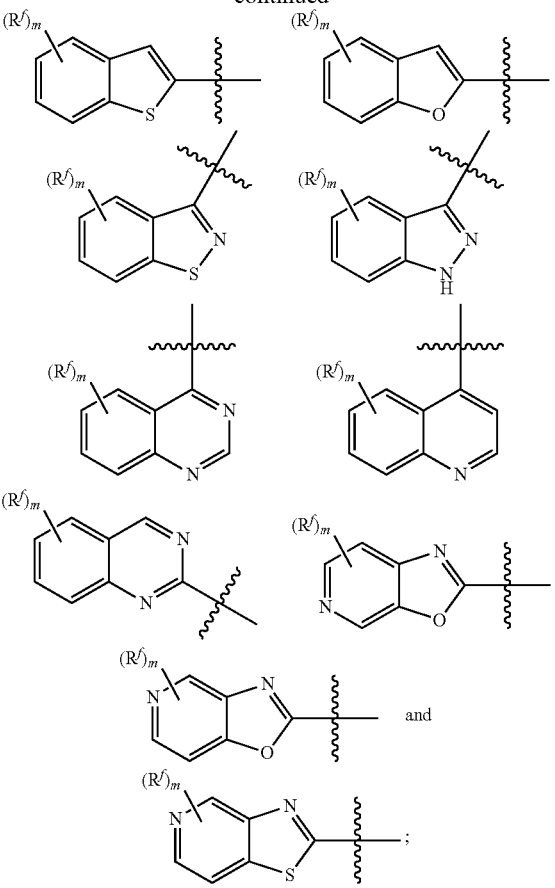

m is 0, 1, 2, 3 or 4; and $R^f$ is selected from $C_{1-6}$ alkyl, $C_{1-6}$ alkoxy, halogen and cyano, wherein $C_{1-6}$ alkyl or $C_{1-6}$ alkoxy is optionally further substituted by one or more halogens.

8. The compound or a stereoisomer, a tautomer, or a pharmaceutically acceptable salt thereof according to claim 1, wherein R³ is selected from

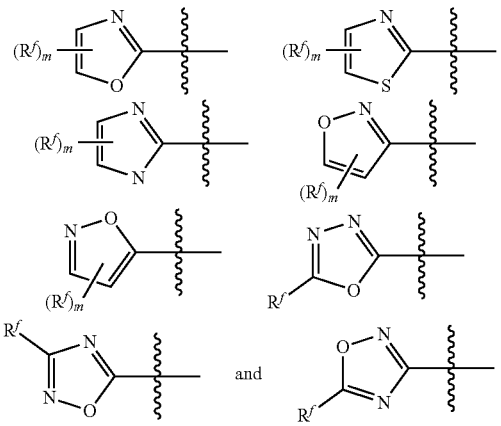

m is 0, 1 or 2; and $R^f$ is selected from $C_{1-6}$ alkyl, $C_{1-6}$ alkoxy, halogen and cyano, wherein $C_{1-6}$ alkyl or $C_{1-6}$ alkoxy is optionally further substituted by one or more halogens.

9. The compound or a stereoisomer, a tautomer, or a pharmaceutically acceptable salt thereof according to claim 7, wherein $R^3$ is selected from

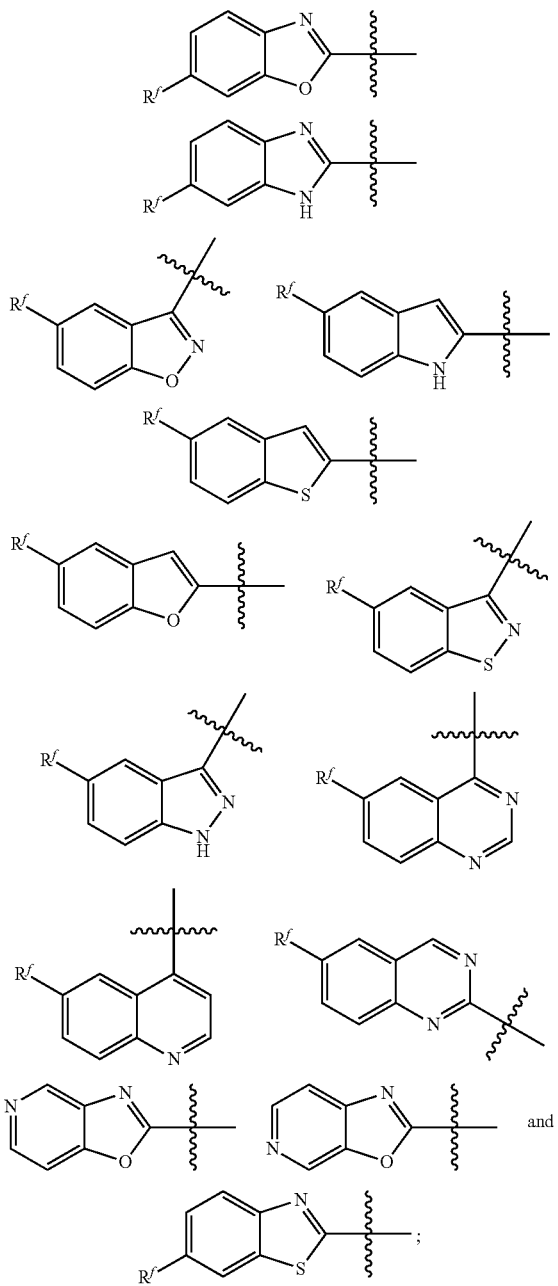

$R^f$ is selected from fluorine, chlorine, cyano, methyl, methoxy, ethyl, isopropyl, difluoromethyl, trifluoromethyl and trifluoromethoxy.

10. The compound or a stereoisomer, a tautomer, or a pharmaceutically acceptable salt thereof according to claim 1, wherein $R^8$ is selected from

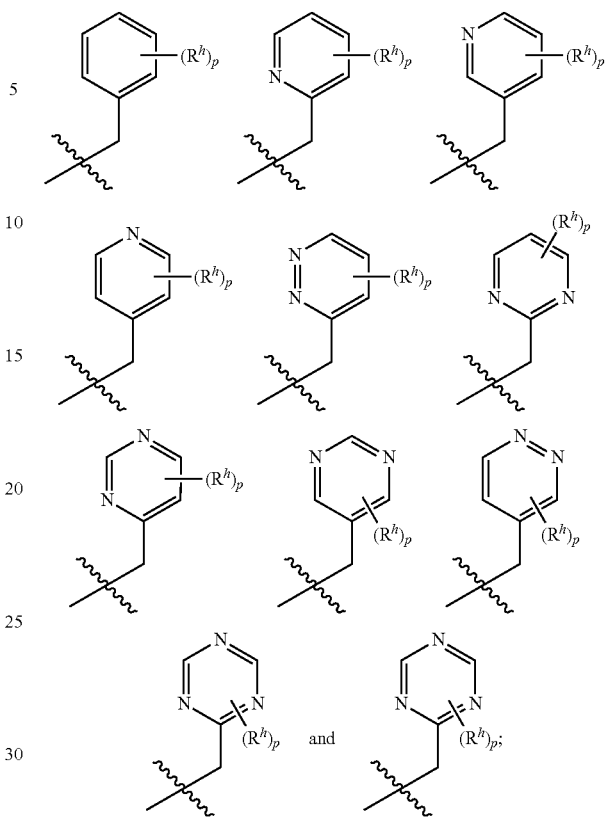

p is 0, 1, 2, 3 or 4; and $R^h$ is selected from $C_{1-6}$ alkyl, $C_{1-6}$ alkoxy, halogen and cyano, wherein $C_{1-6}$ alkyl or $C_{1-6}$ alkoxy is optionally further substituted by one or more halogens.

11. The compound or a stereoisomer, a tautomer, or a pharmaceutically acceptable salt thereof according to claim 1, wherein the compound is selected from

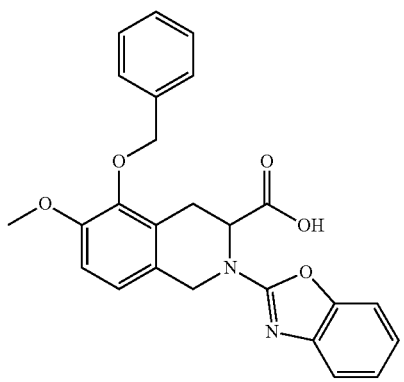

189
-continued
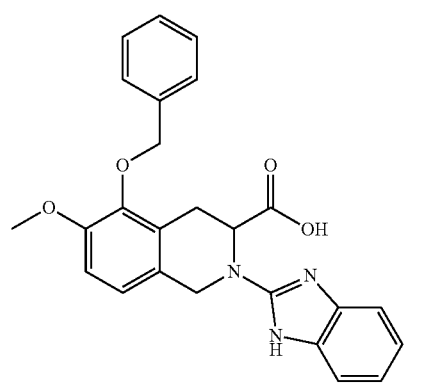
190
-continued
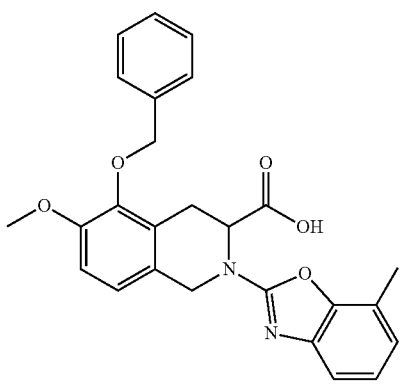
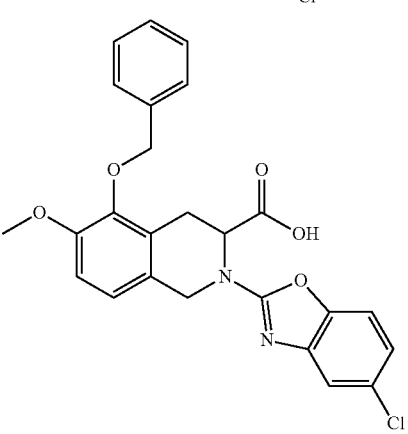
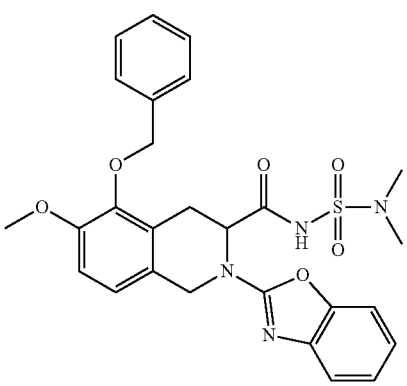

191
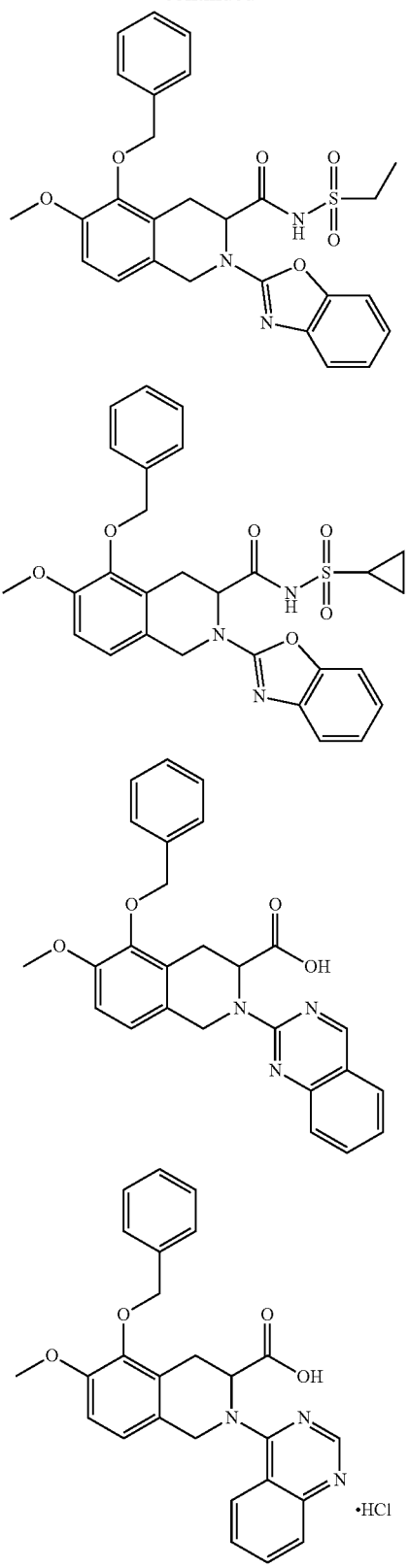
192
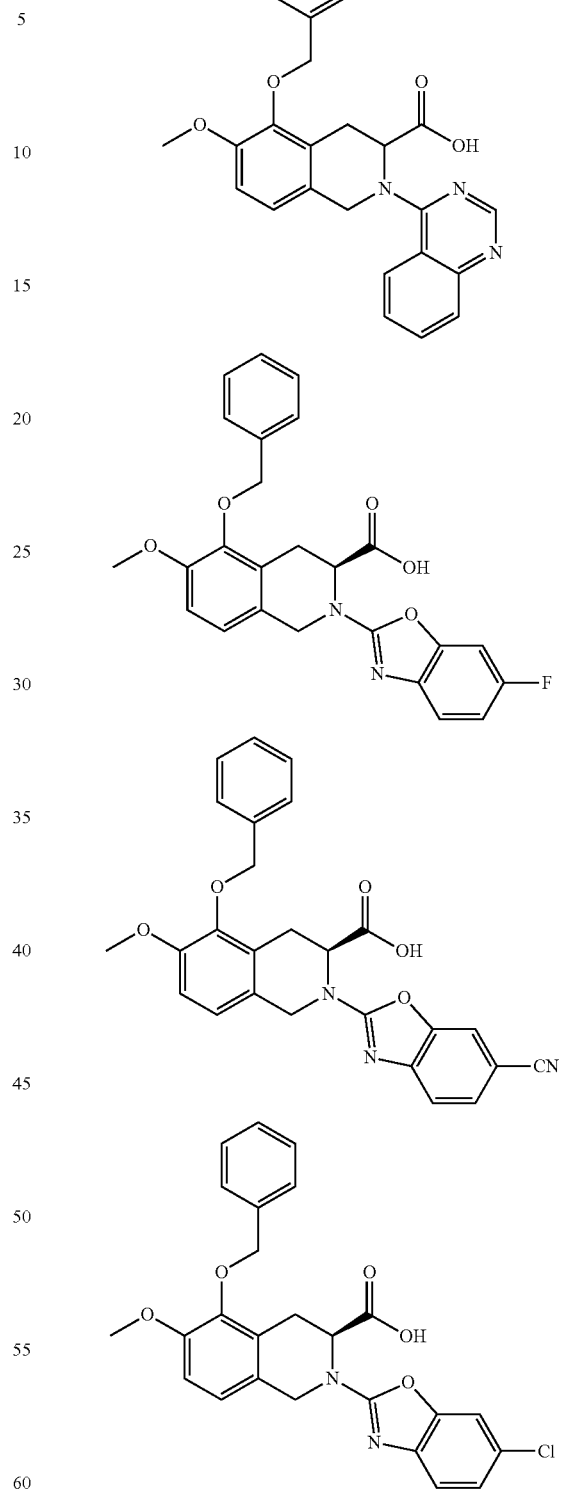

193
-continued
194
-continued
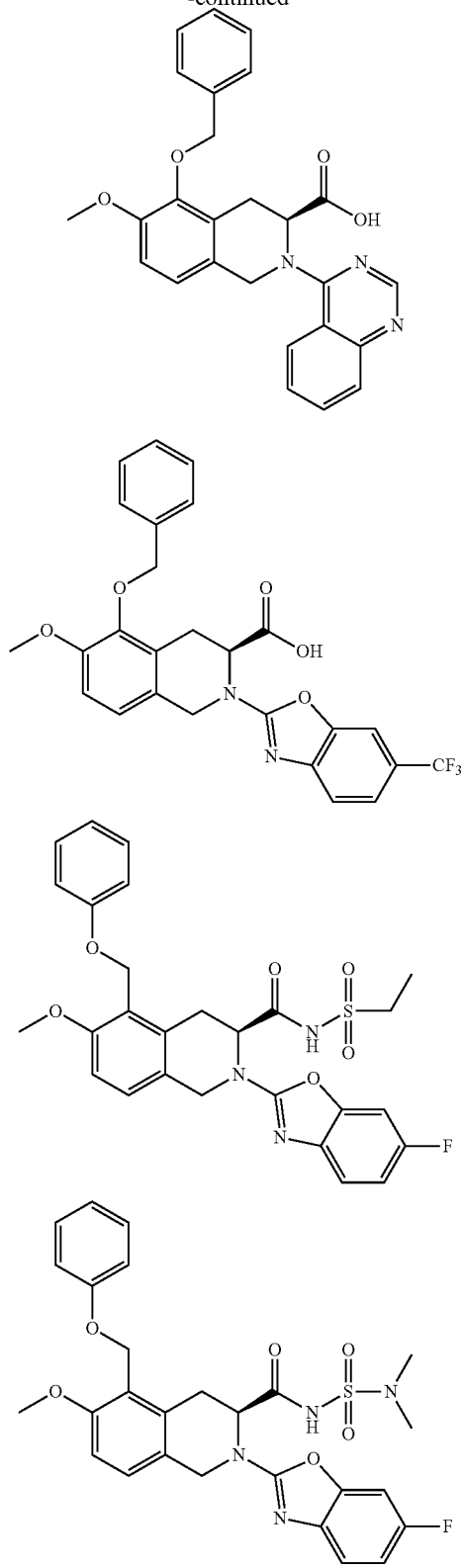
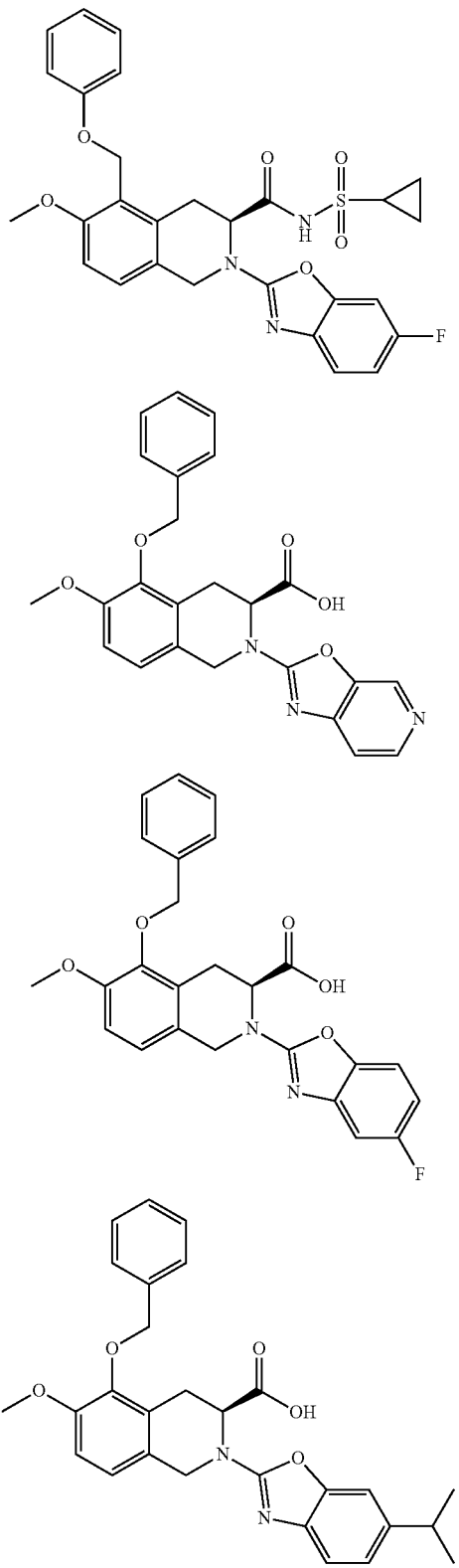

195
-continued
196
-continued
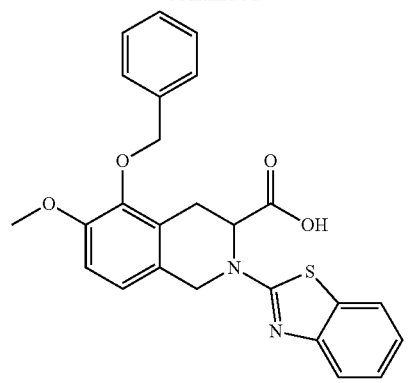
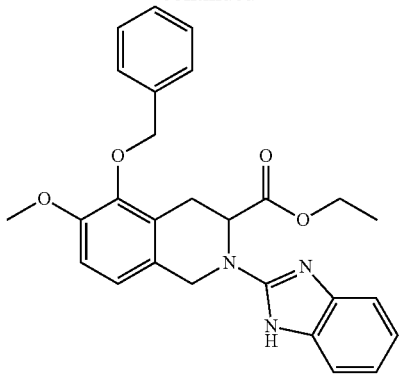

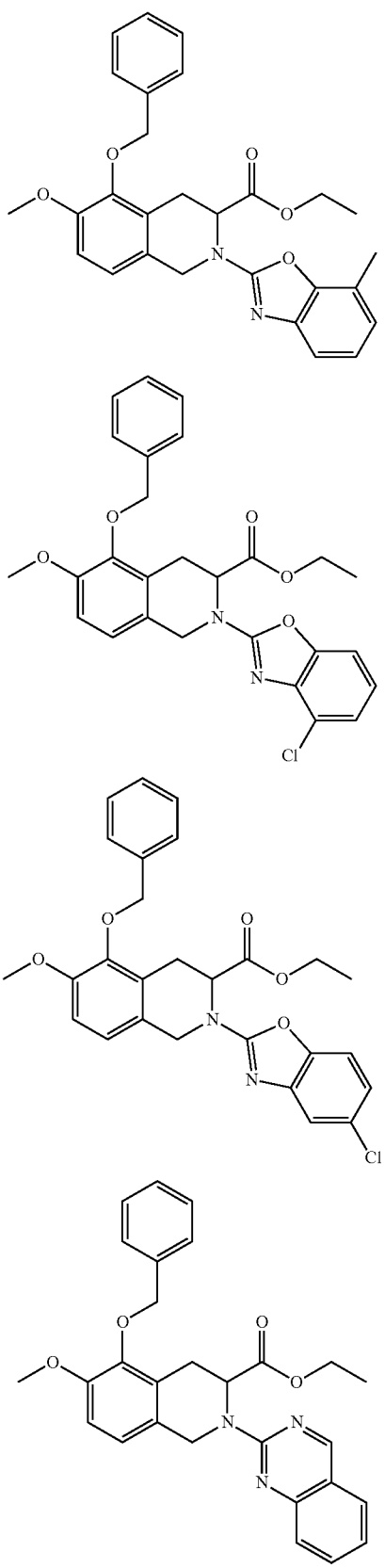
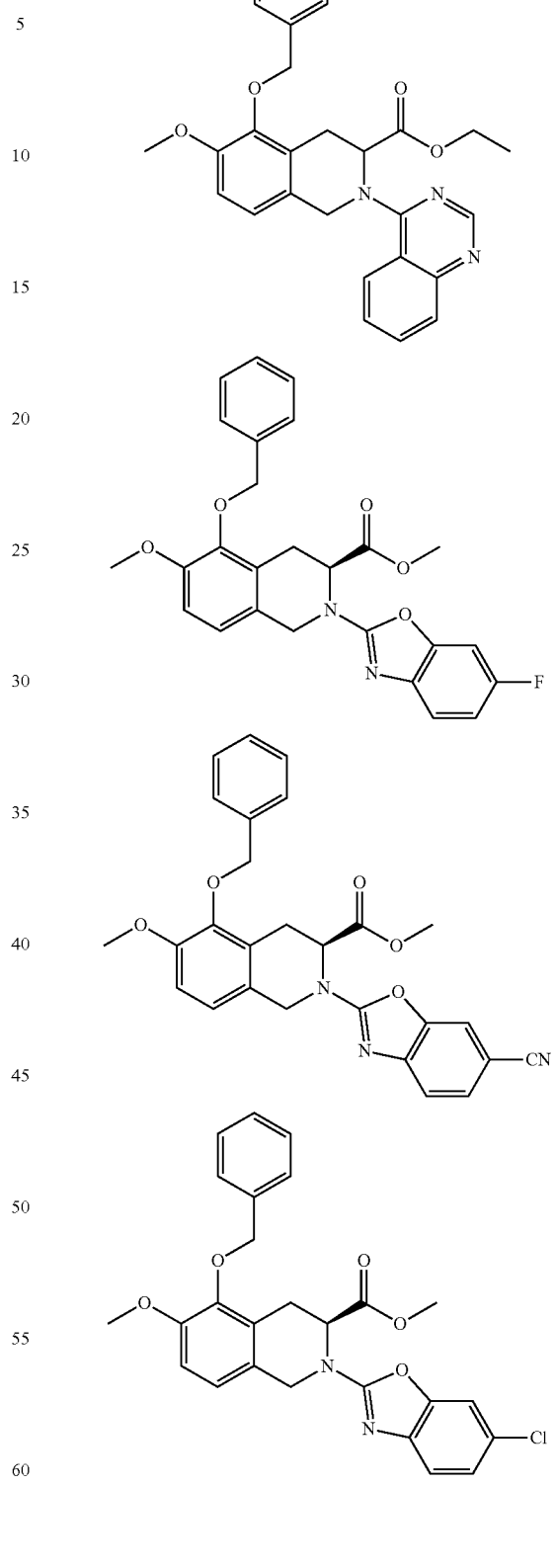

199
-continued
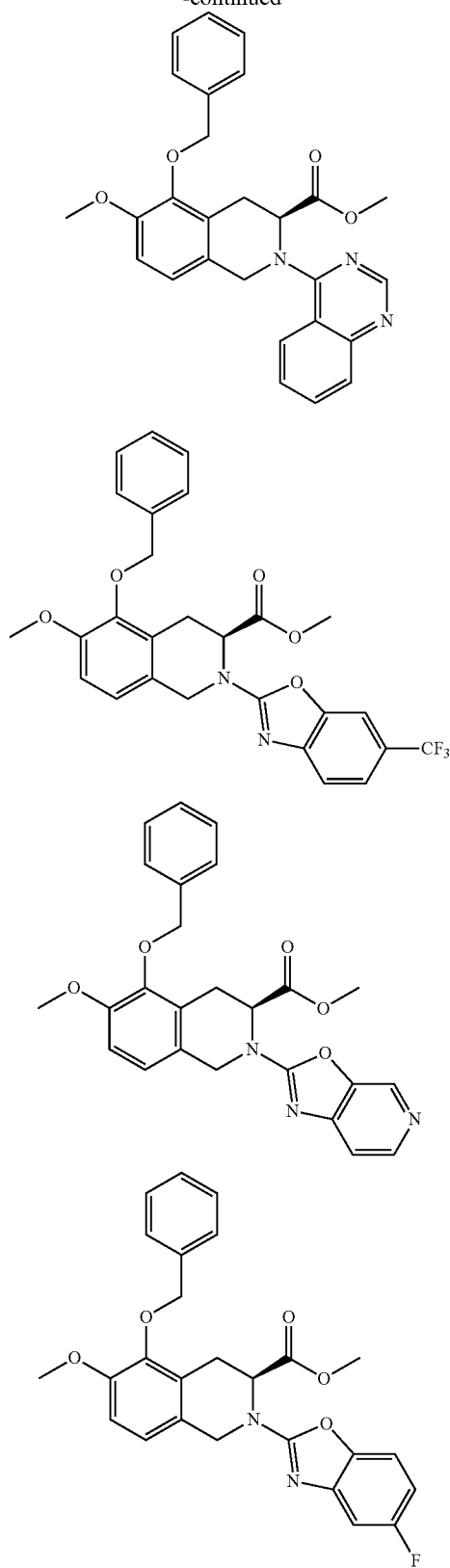
200
-continued
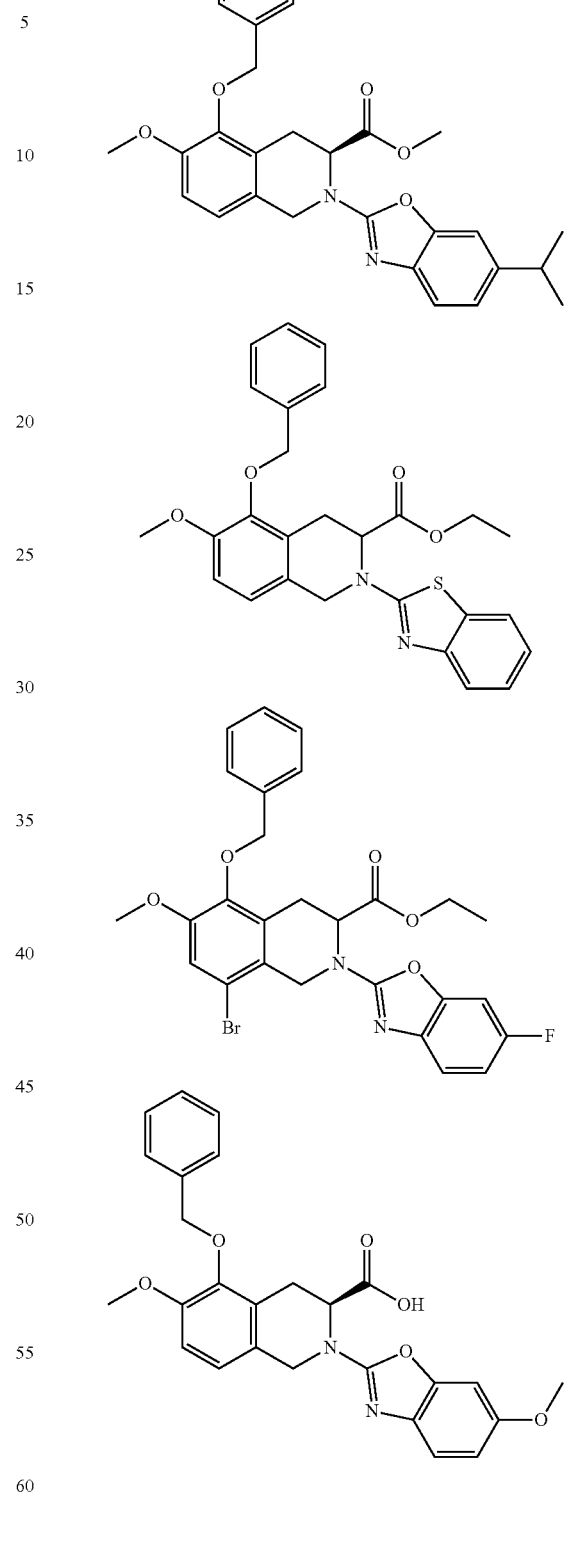

201
-continued
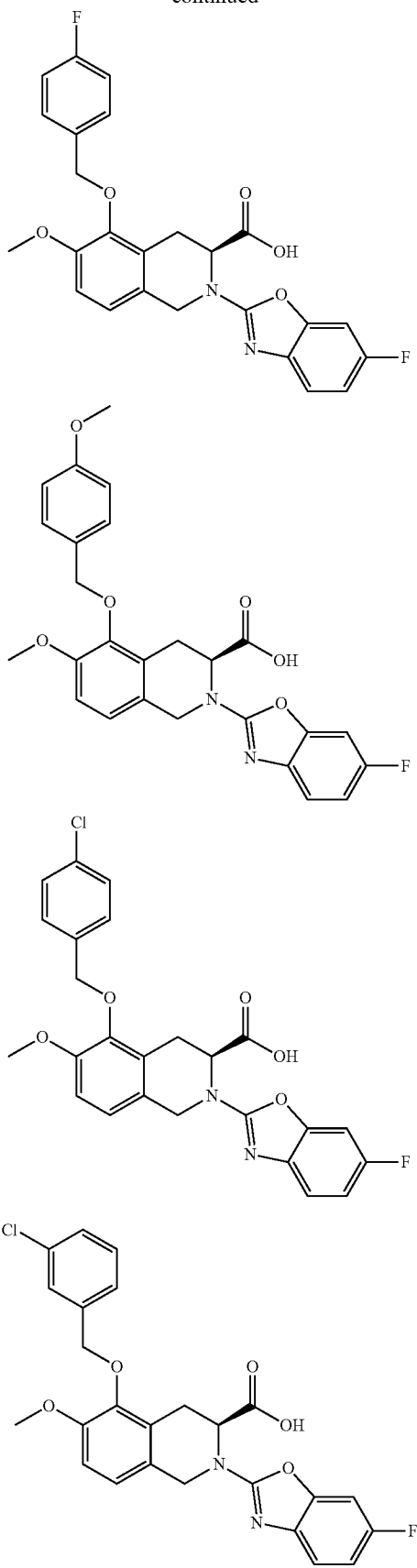
202
-continued
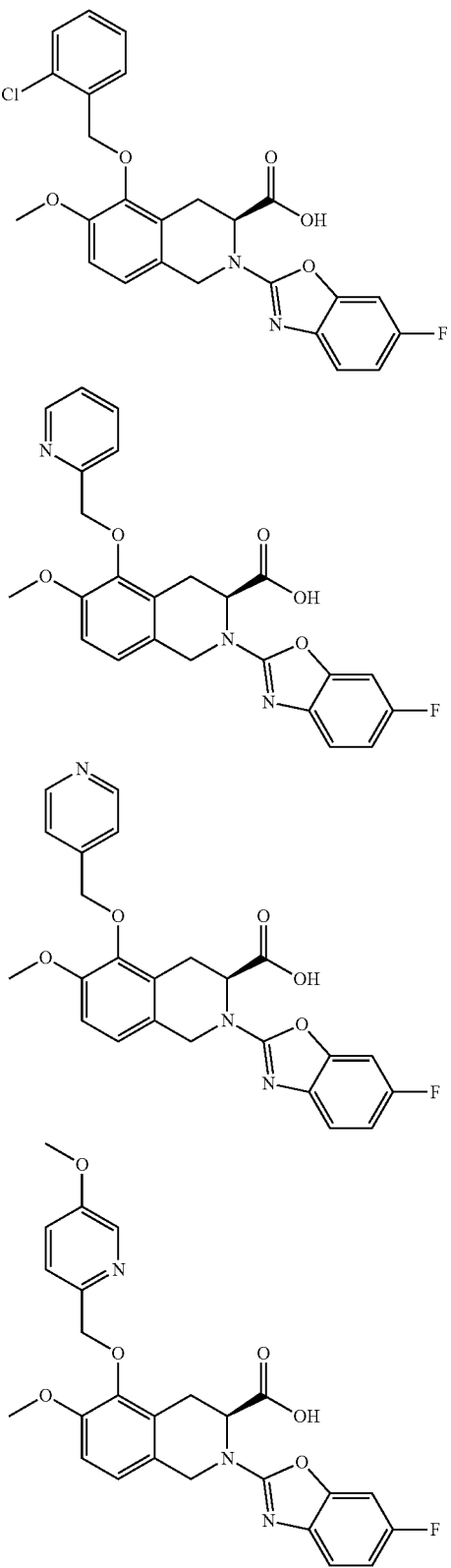

203
-continued
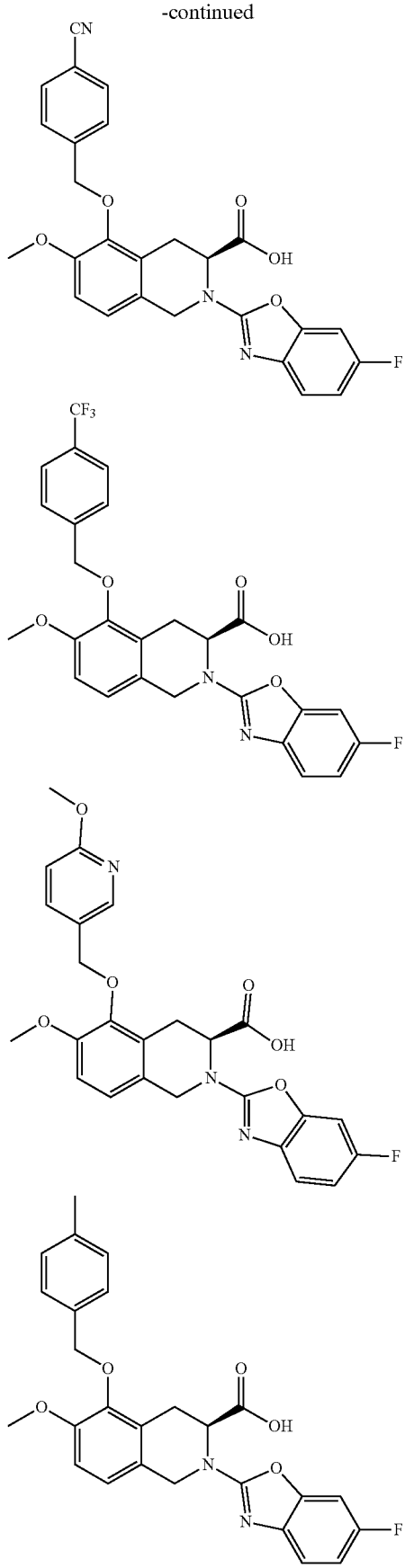
204
-continued
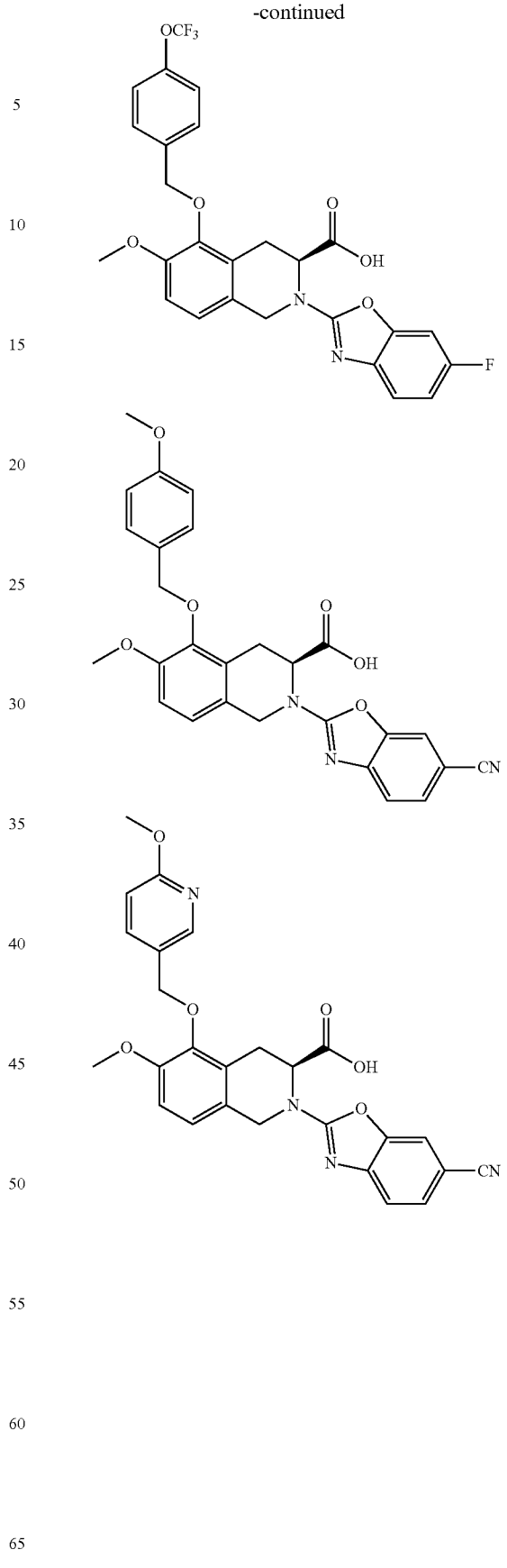

205
-continued
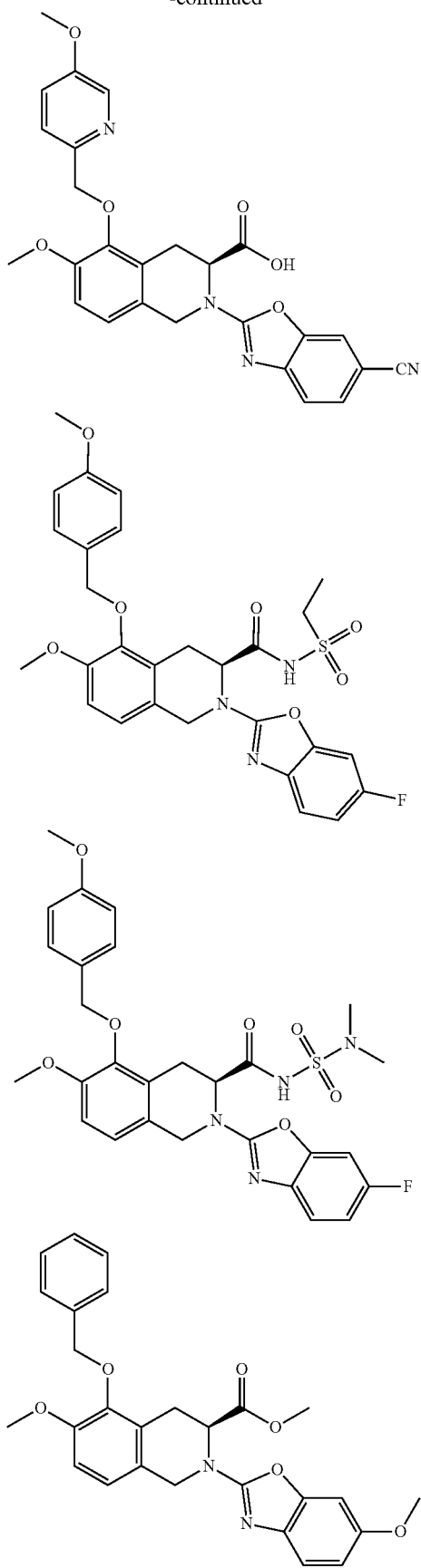
206
-continued
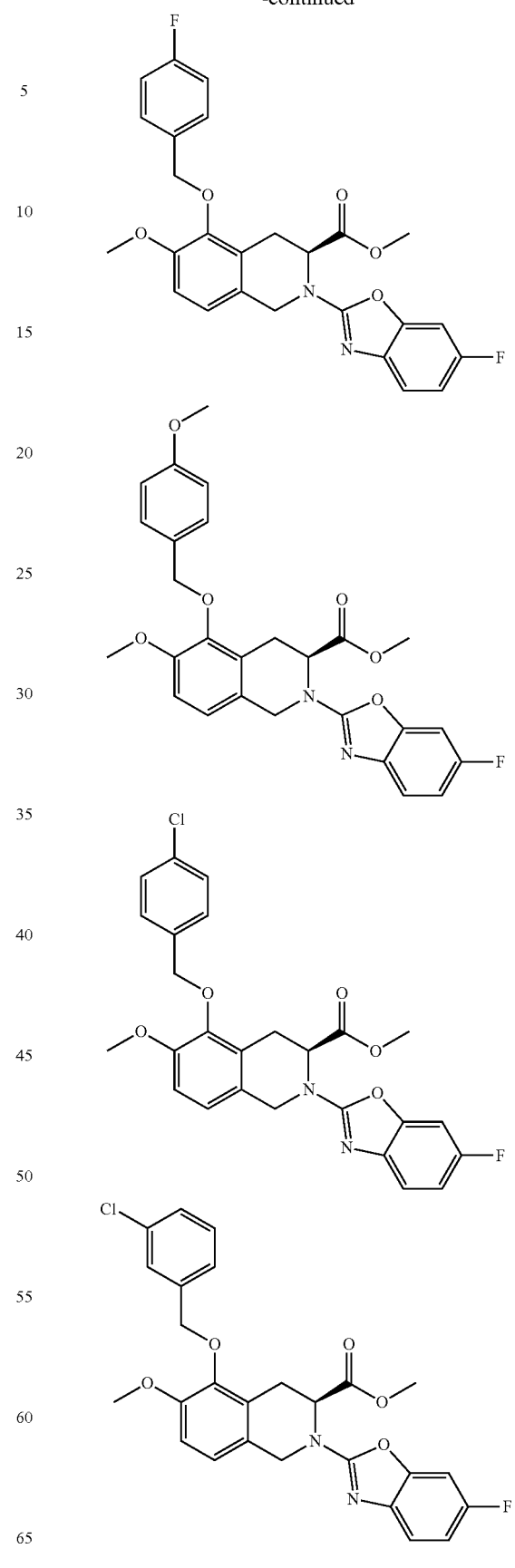

207
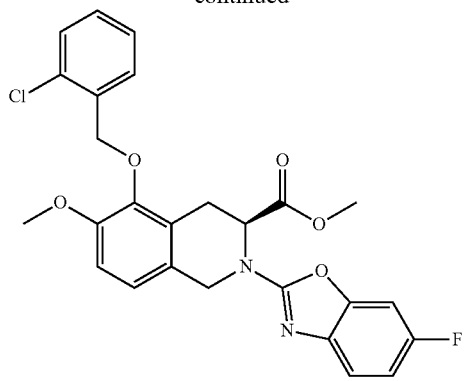
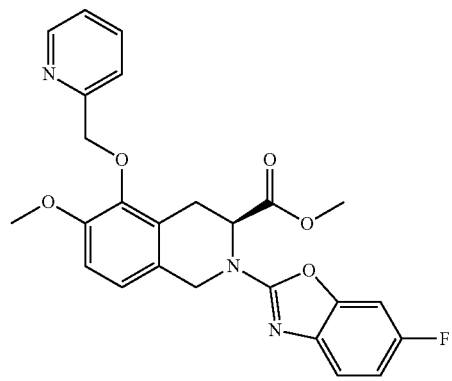
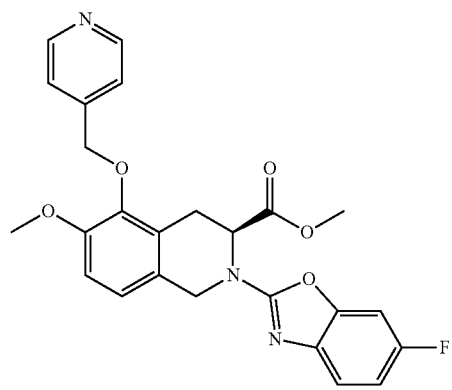
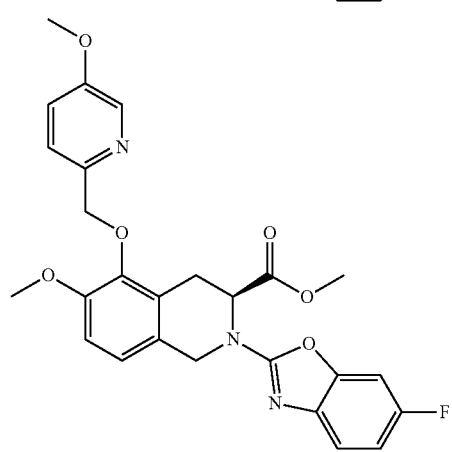
208
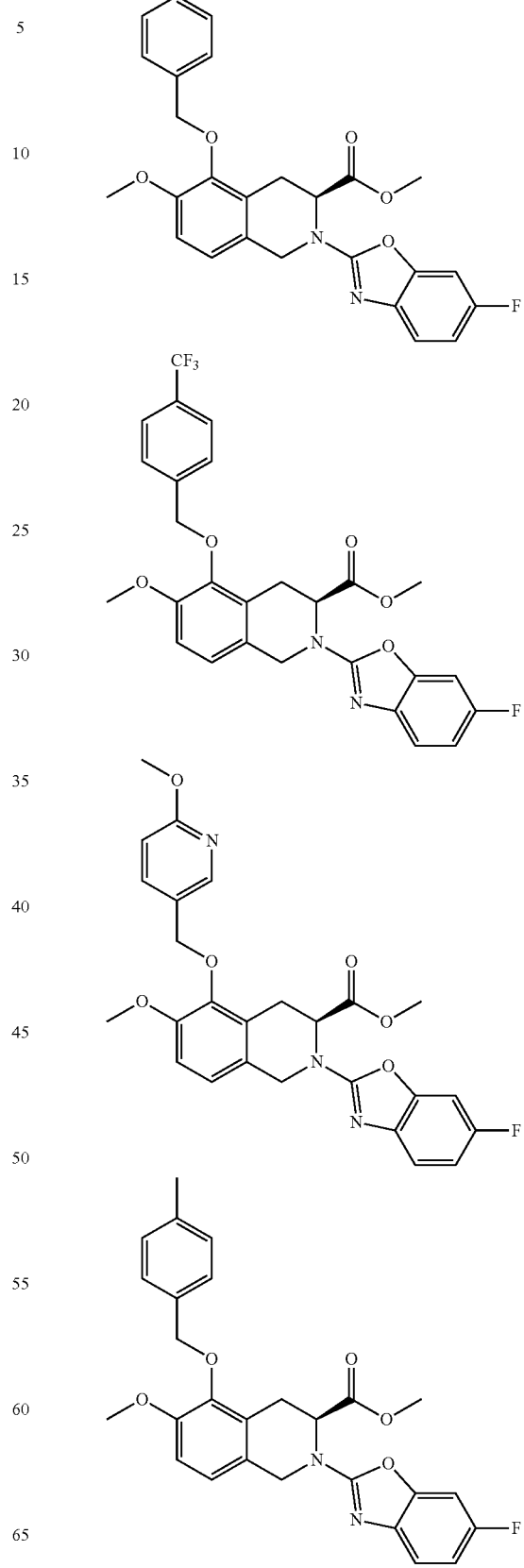

-continued

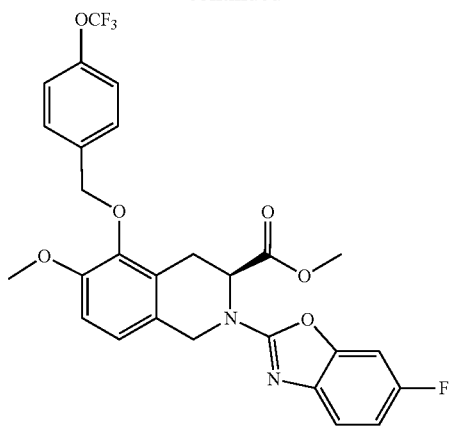

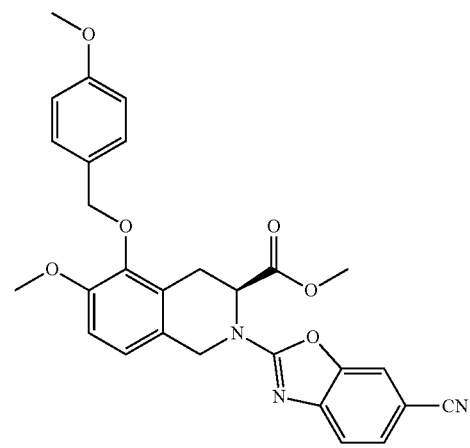 [SMILES: COC(=O)[C@@H]1Cc2c(ccc(OC)c2OCc2ccc(OC)cc2)CN1c1nc2ccc(C#N)cc2o1]

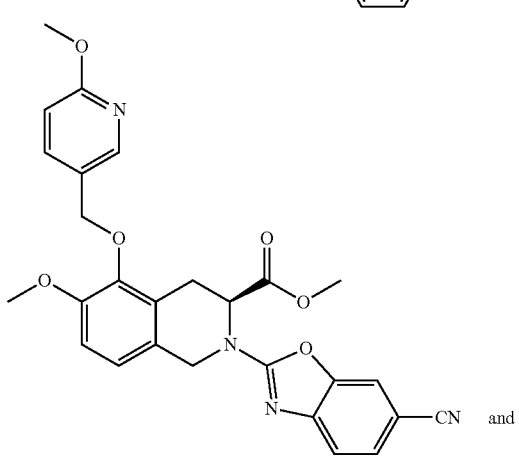

-continued

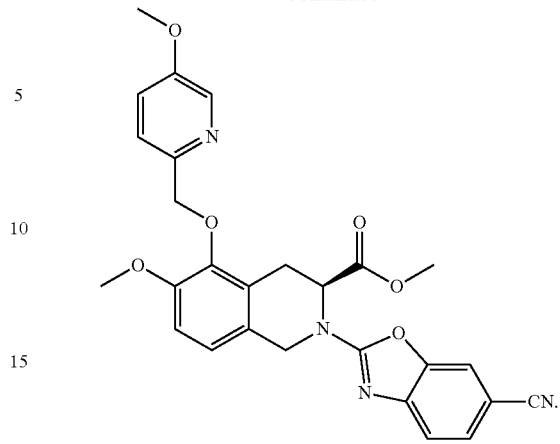

12. A method of preparing the compound of formula (III) or a stereoisomer, a tautomer, or a pharmaceutically acceptable salt thereof according to claim 3, comprising

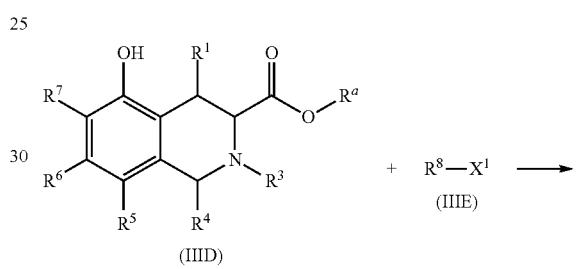

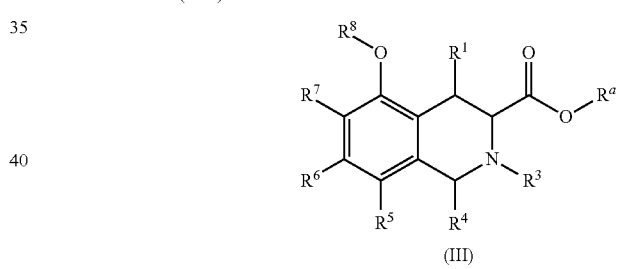

when $R^a$ is an alkyl, reacting a compound of formula (IIID) with a compound of formula (IIIE), to obtain a compound of formula (III) in which $R^a$ is an alkyl;

optionally further performing a hydrolysis reaction of the compound of formula (III) in which $R^a$ is an alkyl to obtain a compound of formula (III) in which $R^a$ is hydrogen;

wherein:

$X^1$ is a leaving group selected from chlorine and hydroxy; and $R^1$ and $R^3$ to $R^8$ are as defined in claim 3.

13. A method of preparing the compound of formula (V) or a stereoisomer, a tautomer, or a pharmaceutically acceptable salt thereof according to claim 5, comprising

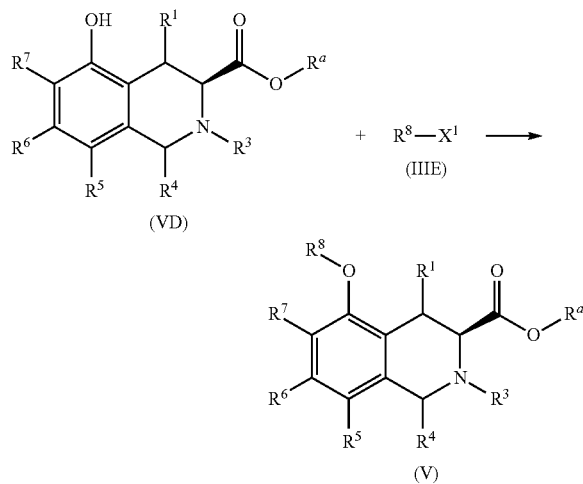

when $R^a$ is an alkyl, reacting a compound of formula (VD) with a compound of formula (IIIE), to obtain a compound of formula (V) in which $R^a$ is an alkyl;

optionally further performing a hydrolysis reaction of the compound of formula (V) in which $R^a$ is an alkyl to obtain a compound of formula (V) in which $R^a$ is hydrogen;

wherein:

$X^1$ is a leaving group selected from chlorine and hydroxy; and $R^1$ and $R^3$ to $R^8$ are as defined in claim 5.

14. A pharmaceutical composition comprising an effective amount of the compound, or a stereoisomer, a tautomer or a pharmaceutically acceptable salt thereof according to claim 1, and pharmaceutically acceptable carriers, excipients, or combinations thereof.

15. A method of treating diseases or disorders mediated by angiotensin II type 2 receptor, comprising administering to a patient in need thereof a therapeutically effective amount of the compound, or a stereoisomer, a tautomer or a pharmaceutically acceptable salt thereof according to claim 1, wherein the diseases or disorders mediated by angiotensin II type 2 receptor are neuropathy or neuropathic pain, wherein the neuropathy or neuropathic pain is primary neuropathy, secondary neuropathy, peripheral neuropathy, neuropathy caused by mechanical nerve injury or biochemical nerve injury, postherpetic neuralgia, diabetic neuralgia or related neurological diseases.

16. The compound according to claim 1 or a stereoisomer, a tautomer, or a pharmaceutically acceptable salt thereof, wherein $R^1$, $R^4$, $R^5$ and $R^6$ are each independently selected from hydrogen, alkyl, halogen and cyano.

17. The compound according to claim 1 or a stereoisomer, a tautomer, or a pharmaceutically acceptable salt thereof, wherein $R^3$ is selected from a 5-6 membered heteroaryl and a 8-10 membered heteroaryl.

18. The compound according to claim 1 or a stereoisomer, a tautomer, or a pharmaceutically acceptable salt thereof, wherein $R^g$ is methyl.

19. The compound according to claim 1 or a stereoisomer, a tautomer, or a pharmaceutically acceptable salt thereof, wherein $R^8$ is selected from benzyl, pyridylmethylene, pyrimidylmethylene and pyridazinylmethylene, wherein the benzyl, pyridylmethylene, pyrimidylmethylene or pyridazinylmethylene is optionally further substituted by one or more substituents selected from fluorine, chlorine, cyano, methyl, trifluoromethyl, methoxy and trifluoromethoxy.

* * * * *